(12) United States Patent
Shin et al.

(10) Patent No.: US 6,492,416 B1
(45) Date of Patent: Dec. 10, 2002

(54) 4,5-DIARYL-3(2H)-FURANONE DERIVATIVES AS CYCLOOXYGENASE-2 INHIBITORS

(75) Inventors: Song Seok Shin, Kyunggi-do (KR); Min-Soo Noh, Kyunggi-do (KR); Young Joo Byun, Kyunggi-do (KR); Jin Kyu Choi, Kyunggi-do (KR); Jin Kwan Kim, Seoul (KR); Kyung Min Lim, Kyunggi-do (KR); Ji Young Kim, Kyunggi-do (KR); Young Hoon Choi, Kyunggi-do (KR); Jun-Yong Ha, Kyunggki-do (KR); Ki-Wha Lee, Seoul (KR); Joo Hyun Moh, Cholanam-do (KR); Yeon Su Jeong, Kyunggi-do (KR); Shin Chung, Kyunggi-do (KR); Yung Hyup Joo, Seoul (KR); Chang Hoon Lee, Kyunggi-do (KR); Seon Hwa Kang, Seoul (KR); Young-Ho Park, Seoul (KR); Jung Bum Yi, Kyunggi-do (KR)

(73) Assignee: Pacific Corporation, Seoul (KR)

( * ) Notice: Subject to any disclaimer, the term of this patent is extended or adjusted under 35 U.S.C. 154(b) by 0 days.

(21) Appl. No.: 09/744,762

(22) PCT Filed: Apr. 12, 2000

(86) PCT No.: PCT/KR00/00339

§ 371 (c)(1),
(2), (4) Date: Nov. 27, 2001

(87) PCT Pub. No.: WO00/61571

PCT Pub. Date: Oct. 19, 2000

(30) Foreign Application Priority Data

Apr. 14, 1999 (KR) ......................... 1999 13170
Jul. 22, 1999 (KR) ......................... 1999 29779
Sep. 13, 1999 (KR) ......................... 1999 39043
Mar. 31, 2000 (KR) ......................... 2000 16866
Apr. 4, 2000 (KR) ......................... 2000 17647

(51) Int. Cl.[7] ............... A61K 31/341; C07D 307/58
(52) U.S. Cl. ............ 514/473; 549/479; 549/472; 549/465; 549/60; 549/58; 548/365.7; 546/284.4; 544/333; 514/469; 514/444; 514/443; 514/406; 514/336; 514/256

(58) Field of Search ............ 514/473, 256, 514/336, 406, 443, 444, 469; 549/479, 58, 60, 465, 472; 544/333; 546/284.4; 548/365.7

(56) References Cited

FOREIGN PATENT DOCUMENTS

| EP | 0 737 476 | 10/1996 |
|----|-----------|---------|
| EP | 0 822 190 | 2/1998 |
| JP | 63 313719 | 12/1988 |
| JP | 68 83075 | 3/1989 |
| JP | 02 164817 | 6/1990 |

OTHER PUBLICATIONS

Hongmiao Sheng et al., The Journal of Clinical Investigation, vol. 99, No. 9, 5/97, pp. 2254–2259.
Walter F. Steward et al., Neurology 1997; 48: pp. 626–632.
Shigeru Nogawa et al., The Journal of Neuroscience, vol. 17, No. 8, Apr. 15, 1997, pp. 2746–2755.
Petpiboon Prasit et al., Annual Reports in Medicinal Chemistry, 32, Chap. 21, pp. 211–220, 1997.
Jane A. Mitchell et al., Proc. Natl. Acad. Sci., USA, vol. 90, pp. 11693–11697, 12/94.
Roger Wrigglesworth et al., J. Med. Chem. 1996, vol. 39, No. 25, pp. 4942–4951.
Gideon Shapiro et al., J. Org. Chem. 1994, vol. 59, No. 19, pp. 5524–5526.
K. Hargreaves et al., Pain, 32 (1988), pp. 77–88.
Philippe Pradelles et al., Methods in Enzymology, vol. 187, pp. 24–34, (1990).
Fernand Dray et al., Methods in Enzymology, vol. 86, pp. 258–269, (1982).
Ann Y. Green et al., Br. J. Pharmac. (1971), 41, pp. 132–139.
W. Parker et al., J. Chem. Soc., Chap. 787, pp. 3871–3875, (Jun., 1958).
Norman Kharasch et al., J. Am. Chem. Soc., vol. 73, pp. 3240–3244 (Jul., 1951).
Tsuneo Imamoto et al., Tetrahedron Letters, vol. 25, No. 38, pp. 4233–4246.

*Primary Examiner*—Charanjits S. Aulakh
(74) *Attorney, Agent, or Firm*—Finnegan, Henderson, Farabow, Garrett & Dunner LLP

(57) ABSTRACT

The present invention provides a novel class of 4,5-diaryl-3(2H)-furanone derivatives, which inhibit strongly and selectively COX-2 over COX-1. They are useful to treat inflammation, inflammation-associated disorders, and COX-2 mediated diseases.

21 Claims, 1 Drawing Sheet

4,5-DIARYL-3(2H)-FURANONE DERIVATIVES AS CYCLOOXYGENASE-2 INHIBITORS

Figure 1:
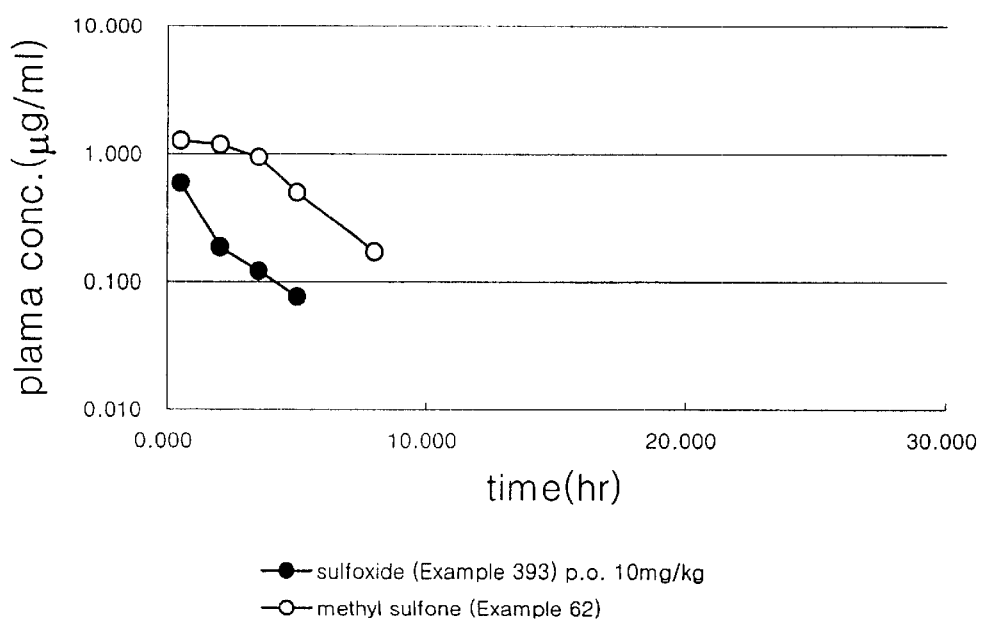

This application is a 371 of PCT/KR00/00339 filed Apr. 12, 2000, now WO 00/61571 Oct. 19, 2000.

FIELD OF INVENTION

The present invention relates generally to 4,5-diaryl-3(2H)-furanone derivatives, methods of preparation therefor, and their use for the treatment of inflammation and inflammation-associated disorders as selective cyclooxygenase-2 inhibitors.

BACKGROUND OF THE INVENTION

Prostaglandins are known to play an important roles in the inflammation. Since prostaglandins are produced from arachidonic acid by cyclooxygenases, inhibition of prostagalndin synthesis by cyclooxygenases, especially synthesis of $PGE_2$, $PGG_2$, and $PGH_2$, leads to the treatment of inflammation.

There are at least two kinds of cyclooxygenases, cyclooxygenase-1 (abbreviated as COX-1) and cyclooxygenase-2 (abbreviated as COX-2). COX-1 is constitutively present in the gastrointestinal tract and the kidney, and is implicated to be responsible for the maintenance of the physiological homeostasis, such as gastrointestinal integrity and renal function. Interruption of COX-1 activity can lead to life-threatening toxicities to the gastrointestinal tract, such as ulceration and bleeding. In the meantime, COX-2 is induced upon inflammatory stimuli and known to be responsible for progression of inflammation. Thus, selective inhibition of COX-2 over COX-1 is useful for the treatment of inflammation and inflammation-associated disorders without incurring gastrointestinal toxicities.

Conventional non-steroidal anti-inflammatory drugs (NSAIDs), such as indomethacin, naproxen, ketoprofen, ibuprofen, piroxicam, diclofenac etc, inhibit both COX-1 and COX-2, which would demonstrate their gastrointestinal toxicities as well as anti-inflammatory potency. However, they possess serious life-threatening gastrointestinal toxicities of bleeding and ulceration arising from their inhibition of COX-1, which limit their clinical use. Thus, a selective inhibitor of COX-2 can be useful as an anti-inflammatory therapeutic agent without the gastrointestinal toxicities, frequently occurring upon chronic use of conventional NSAIDs.

COX-2 inhibitors are implicated to possess a broad therapeutic spectrum besides anti-inflammatory, analgesic, and antipyretic activity. For example inhibition of COX-2 can prevent growth of certain types of cancer, especially colon cancer [J. Clin. Invest. 99, 2254 (1997)]. Another application of a COX-2 inhibitor can be found in the treatment of degenerative chronic neurological disorders, such as Alzheimer's disease [Neurology 48, 626 (1997)]. COX-2 inhibition would be useful in reducing the infarct volume accompanying the stroke [J. Neuroscience 17, 2746 (1997)].

Recently two of COX-2 selective antiinflammatory drugs, celecoxib and rofecoxib, were introduced into the clinic for arthritic indications. Celecoxib and rofecoxib show anti-inflammatory potency comparable to conventional NSAIDs without COX-2 selectivity. In the meantime, these drugs show appreciably lower gastro-intestinal toxicities than conventional NSAIDs without COX-2 selectivity over COX-1. Thus, COX-2 selective inhibition itself can be enough for anti-arthritic potency and the inhibition of COX-1 is largely responsible for the gastrointestinal toxicities associated with conventional NSAIDs without COX-2 selectivity.

cis-1,2-Diaryl-alkenes or its structural-equivalents are known to be a pharmacophore for achieving selective COX-2 inhibition over COX-1 [Ann. Rep. Med. Chem. 32, 211 (1997)]. In case of celecoxib and rofecoxib, pyrazole and 2(5H)-furanone correspond to the scaffold, respectively.

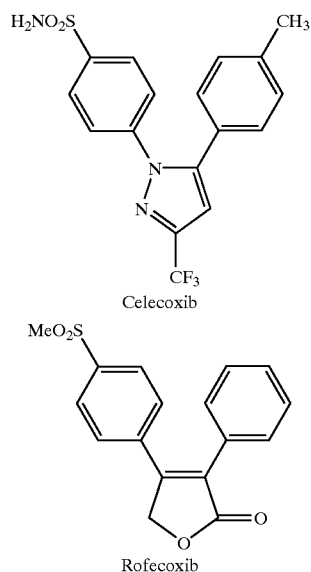

Celecoxib

Rofecoxib

By adopting an appropriate scaffold for the cis-alkene pharmacophore, it would be possible to modulate both in vitro and in vivo characteristics of such inhibitors, such as dosing regimen, daily dose, clinical indications arising from tissue distribution characteristics, safety profile, and so on.

In this invention, 3(2H)-furanone is adopted as a scaffold for COX-2 inhibitors. 3(2H)-furanone derivatives were prepared for use in the treatment of glaucoma [EP 0 737 476 A2]. However, there is no precedent case that 3(2H)-furanone derivatives have been ever used as COX-2 inhibitors. There is no reported case of 4,5-diaryl-3(2H)-furanone derivatives, either.

The 4,5-diaryl-3(2H)-furanone derivatives disclosed herein selectively inhibit COX-2 over COX-1 and relieve the effects of inflammation. 4,5-Diaryl-3(2H)-furanone derivatives of this invention do not show substantial inhibition of COX-1 and consequently show reduced gastrointestinal side effects. Thus, 4,5-diaryl-3(2H)-furanone derivatives of this invention are found useful as anti-inflammatory agents with significantly reduced gastrointestinal side effects, when compared with conventional NSAIDs.

SUMMARY OF INVENTION

The present invention provides a novel class of potent selective COX-2 inhibitors.

The present invention provides a novel class of 3(2H)-furanone derivatives as selective COX-2 inhibitors, which are represented by Formula I:

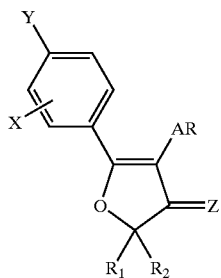

or a pharmaceutically-acceptable salt thereof, wherein:

X represents halo, hydrido, or alkyl;

Y represents alkylsulfonyl, aminosulfonyl, alkylsulfinyl, (N-acylamino)-sulfonyl, (N-alkylamino)sulfonyl, or alkylthio;

Z represents oxygen or sulfur atom;

$R_1$ and $R_2$ are selected independently from lower alkyl radicals, or form a 4- to 6-membered aliphatic or hetero cyclic group, taken together with the 2-position carbon atom of the 3(2H)-furanone ring;

and AR represents a substituted or non-substituted aromatic group of 5 to 10 atoms.

The present invention further provides methods for preparing 3(2H)-furanone derivatives of Formula I.

BRIEF DISCRIPTION THE DRAWINGS

FIG. 1 is a graph showing pharmacokinetics for orally administered Example 393 at 10 mg/kg body weight.

DESCRIPTION OF INVENTION

A novel class of 4,5-diaryl-3(2H)-furanone derivatives useful in treating inflammation and inflammation-associated disorders is defined by Formula I:

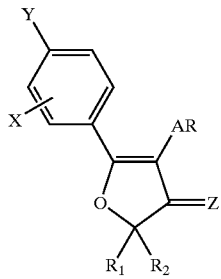

or a pharmaceutically-acceptable salt thereof, wherein:

X represents halo, hydrido, or alkyl;

Y represents alkylsulfonyl, aminosulfonyl, alkylsulfinyl, (N-acylamino)-sulfonyl, (N-alkylamino)sulfonyl, or alkylthio;

Z represents oxygen or sulfur atom;

$R_1$ and $R_2$ are selected independently from lower alkyl radicals, or form a 4- to 6-membered aliphatic or hetero cyclic group, taken together with the 2-position carbon atom of 3(2H)-furanone ring;

and AR represents a substituted or non-substituted aromatic group of 5 to 10 atoms.

4,5-diaryl-3(2H)-furanone derivatives of this invention selectively inhibit COX-2 over COX-1, and thus can be useful for the treatment of inflammation and inflammation-associated disorders but with reduced gastrointestinal toxicities when compared with conventional NSAIDs.

Compounds of Formula I would be useful for, but not limited to, the relief of inflammation, pain and fever. For example, compounds of Formula I would be useful to treat inflammation and pain from arthritis, including but not limited to rheumatoid arthritis, spondyloarthopathies, gout, oesteoarthritis, systemic lupus erythematosus and juvenile arthritis. Compounds of Formula I would be useful for the relief of pain associated with, including but not limited to, headache, toothache, dysmenorrhea, neuralgia, and bodily pain such as in the neck and in the low back. Compounds of Formula I would be useful to relieve symptoms associated with common cold, viral infections including but not limited to influenza. Compounds of Formula I would be useful for the treatment of inflammatory conditions, including but not limited to, myositis, gingivitis, synovitis, ankylosing spondylitis, burstitis, burns, injury, and so on. Compounds of Formula I would be useful in the relief of inflammation and pain after surgical and dental operation. Such compounds are useful to treat psoriasis, eczema, and dermatitis. Compounds of Formula I would be useful for the treatment of inflammatory conditions associated with, including but not limited to, inflammatory bowel disease, Crohn's disease, type I diabetes, and the like. Such compounds may be useful to inhibit cyclooxygenase-mediated growth of certain types of cancer, including but not limited to colon cancer. Compounds of Formula I would be useful to reduce the infarct volume of reperfusion injury following stroke. Such compounds would be useful to alleviate inflammatory conditions in, including but not limited to, asthma and bronchitis. Compounds of Formula I would be useful in the treatment of degenerative neurological disorders including Alzheimer's disease. Such compounds would be useful in the treatment of retinopathy associated with diabetes, which involves cyclooxygenase-mediated angiogenesis.

Considering their high COX-2 selectivity over COX-1, compounds of Formula I would show significantly reduced gastrointestinal side effects such as ulceration and bleeding, when compared with conventional NSAIDs. Thus, compounds of Formula I may be useful as a far safer alternative to conventional NSAIDs. Compounds of Formula I may be useful in the treatment of humans as well as animals, including but not limited to, cattle, sheep, dogs, horses, and the like.

Compounds of Formula I may be used with other anti-inflammatories, including but not limited to, steroids, conventional NSAIDs such as aspirin, acetaminophen, diclofenac, indomethacin, ibuprofen, and the like. Compounds of Formula I can be used with a variety of therapeutics, including but not limited to, a $H_2$-antagonist, an anti-hypertensive including but not limited to an ACE inhibitor, a prostaglandin, an anti-histamine, an immuno-modulator including methotrexate, an anti-coagulant, and the like.

Compounds of Formula I can be administered by various methods, including but not limited to, oral, intravenous, subcutaneous, topical administration, and the like. Compounds of Formula I can be administered along with various pharmaceutically-acceptable adjuvant ingredients, including but not limited to, citric acid, hydrochloric acid, sodium chloride, tartaric acid, stearic acid, starch, gelatin, talc, sesame oil, ascorbic acid, olive oil, palm oil, methylcellulose, sodium carboxymethylcelluose, polyethyleneglycol (PEG), polypropyleneglycol, sweeteners, preservatives, ethanol, titanium oxide, sodium bicarbonate, soybean lecithin, and the like. Compounds of Formula I can be formulated in a variety of dosage forms, including but not limited to, tablet, powder, granule, hard capsule, soft capsule, oral suspension, spray solution for inhalation, injectable solution, and the like.

A compound of Formula I can be converted into the pharmaceutically-acceptable salt by neutralizing the compound, depending on the presence of an acidic group or a basic group in the compound, with an equivalent amount of an appropriate pharmaceutically-acceptable acid or base, such as potassium hydroxide, sodium hydroxide, hydrochloric acid, methansulfonic acid, citric acid, and the like.

Compounds of Formula I can be administered to humans at daily doses of 0.1 to 100 mg/kg body weight depending on indications, symptoms, or condition of a patient. Preferred daily doses of the compound of Formula I, however, may be between 0.1 and 10 mg/kg bodyweight for inflammatory indications such as rheumatoid arthritis. Compounds of Formula I can be administered according to various schedules, including but not limited to, daily once, daily twice, three times a day, and the like.

A preferred class of compounds encompasses those compounds of Formula I, wherein X is selected from halo, hydrido and lower alkyl; wherein Y is selected from (lower alkyl)sulfonyl, aminosulfonyl, (lower alkyl)sulfinyl, (lower N-acylamino)-sulfonyl, (lower N-alkylamino)sulfonyl and (lower alkyl)thio; wherein Z is selected from oxygen and sulfur atom; wherein $R_1$ and $R_2$ are selected independently from lower alkyl radicals, or $R_1$ and $R_2$ represent pentylidenyl (—$CH_2$—$CH_2$—$CH_2$—$CH_2$—), hexylidenyl (—$CH_2$—$CH_2$—$CH_2$—$CH_2$—$CH_2$—), 4-tetrahydro-(4H)-pyranylidenyl (—$CH_2$—$CH_2$—O—$CH_2$—$CH_2$—), 3-tetrahydrofuranylidenyl (—$CH_2$—O—$CH_2$—$CH_2$—) or 3-oxetanylidenyl (—$CH_2$—O—$CH_2$—) to form a cycle taken together with the 2-position carbon atom of the 3(2H)-furanone ring; and wherein AR represents a substituted or non-substituted aromatic group of 5 to 10 atoms, which is selected from, but not limited to, the aromatic groups encompassing

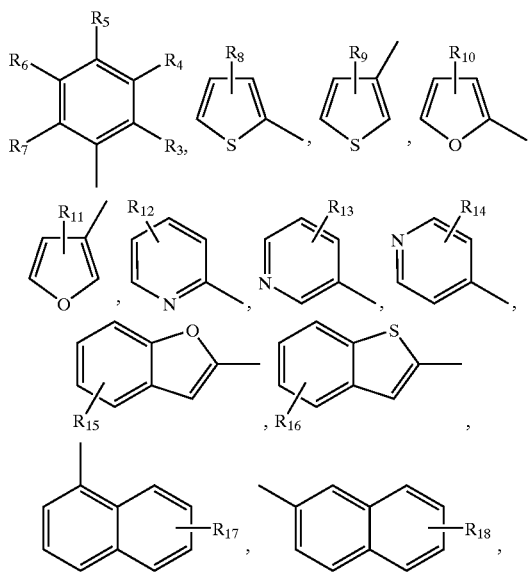

-continued

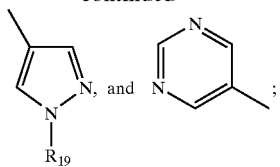

wherein, each of $R_3$ to $R_7$, if present, is independently selected from hydrido, halo, alkyl, haloalkyl, alkoxy, haloalkoxy, acyl, nitro, amino, N-alkylamino, N,N-dialkylamino, N-acylamino, (haloacyl)amino, formyl, cyano, azido, hydroxy, alkylthio, alkylsulfonyl, phenyl, alkoxyalkyl and hydroxyalkyl, or adjacent two groups of $R_3$ to $R_7$ form, taken together, methylenedioxy; and wherein each of $R_8$ to $R_{19}$, if present, is selected from hydrido, halo, alkyl, acyl, haloalkyl, alkoxy, formyl, cyano, nitro, amino, azido and N-acylamino; or a pharmaceutically-acceptable salt thereof.

A class of compounds of particular interest encompasses those compounds of Formula I, wherein X is selected from fluoro, chloro, bromo, hydrido, methyl, ethyl, and n-propyl; wherein Y is selected from methylsulfonyl, ethylsulfonyl, n-propylsulfonyl, aminosulfonyl, methylsulfonyl, ethylsulfonyl, n-propylsulfonyl, (N-acetylamino)sulfonyl, (N-propionylamino)sulfonyl, (N-butyrylamino)sulfonyl, (N-methylamino)sulfonyl, (N-ethylamino)sulfonyl, methylthio, ethylthio, and n-propylthio; wherein Z is selected from oxygen and sulfur atom; wherein $R_1$ and $R_2$ are selected independently from methyl and ethyl, or $R_1$ and $R_2$ represent, taken together, pentylidenyl (—$CH_2$—$CH_2$—$CH_2$—$CH_2$—), hexylidenyl (—$CH_2$—$CH_2$—$CH_2$—$CH_2$—$CH_2$—), 4-tetrahydro-(4H)-pyranylidenyl (—CH2—$CH_2$—O—$CH_2$—$CH_2$—), 3-tetrahydrofuranylidenyl (—$CH_2$—O—$CH_2$—$CH_2$—), and 3-oxetanylidenyl (—$CH_2$—O—$CH_2$—) to form a cycle with the 2-position carbon atom of the 3(2H)-furanone ring; wherein each of $R_3$ to $R_7$, if present, is independently selected from hydrido, fluoro, chloro, bromo, methyl, ethyl, n-propyl, iso-propyl, n-butyl, iso-butyl, t-butyl, n-pentyl, iso-pentyl, fluoromethyl, difluoromethyl, trifluoromethyl, 2-fluoroethyl, 1-fluoroethyl, 2,2-difluoroethyl, 1,2-difluoroethyl, 1,1-difluoroethyl, 2,2,2-trifluoroethyl, methoxy, ethoxy, n-propyloxy, iso-propyloxy, n-butoxy, trifluoromethoxy, difluoromethoxy, fluoromethoxy, acetyl, propionyl, n-butanoyl, iso-butanoyl, n-pentanoyl, nitro, amino, N-methylamino, N-ethylamino, N-n-propylamino, N,N-dimethylamino, N-acetylamino, N-propionylamino, N-(trifluoroacetyl)amino, formyl, hydroxy, methylthio, ethylthio, n-propylthio, methylsulfonyl, ethylsulfonyl, n-propylsulfonyl, phenyl, hydroxymethyl, 1-hydroxyethyl and 2-hydroxyethyl, or adjacent two groups of $R_3$ to $R_7$ form, taken together, methylenedioxy; and wherein each of $R_8$ to $R_{19}$, if present, is selected from hydrido, fluoro, chloro, bromo, methyl, ethyl, n-propyl, isopropyl, acetyl, propionyl, methoxy, ethoxy, iso-propyloxy, n-propyloxy and formyl; or a pharmaceutically acceptable salt thereof.

Within Formula I there is a subclass of compounds of high interest represented by Formula II:

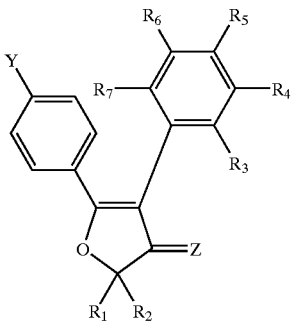

II wherein Y represents alkylsulfonyl, aminosulfonyl, alkylsulfonyl, (N-acylamino)sulfonyl, (N-alkylamino)sulfonyl, or alkylthio; wherein Z represents oxygen or sulfur atom; $R_1$ and $R_2$ are selected independently from lower alkyl radicals; and wherein each of $R_3$ to $R_7$, if present, is independently selected from hydrido, halo, alkyl, haloalkyl, alkoxy, haloalkoxy, acyl, nitro, amino, N-alkylamino, N,N-dialkylamino, N-acylamino, N-(haloacyl)amino, formyl, cyano, azido, hydroxy, alkylthio, alkylsulfonyl, phenyl, alkoxyalkyl and hydroxyalkyl, or two adjacent groups of $R_3$ and $R_7$ form, taken together, methylenedioxy; or a pharmaceutically-acceptable salt thereof.

A preferred class of compounds comprises those compounds of Formula II, wherein Y is selected from (lower alkyl)sulfonyl, aminosulfonyl, (lower alkyl)sulfonyl, (lower N-acylamino)sulfonyl, (lower N-alkylamino)sulfonyl, and (lower alkyl)thio; wherein Z is selected from oxygen and sulfur atom; wherein $R_1$ and $R_2$ are independently selected from methyl and ethyl radical; and wherein each of $R_3$ to $R_7$, if present, is independently selected from hydrido, halo, lower alkyl, lower haloalkyl, lower alkoxy, lower haloalkoxy, lower acyl, nitro, amino, lower N-alkylamino, lower N,N-dialkylamino, lower N-acylamino, (lower haloacyl)amino, formyl, cyano, azido, hydroxy, lower alkylthio, lower alkylsulfonyl, phenyl, lower alkoxyalkyl and lower hydroxyalkyl, or two adjacent groups of $R_3$ to $R_7$ form, taken together, methylenedioxy; or a pharmaceutically-acceptable salt thereof.

A class of compounds of particular interest encompasses those compounds of Formula II, wherein Y is selected from methylsulfonyl, aminosulfonyl, methylsulfonyl, (N-acetylamino)sulfonyl, (N-propionylamino)sulfonyl, (N-butyrylamino)sulfonyl, (N-methylamino)sulfonyl, (N-ethylamino)sulfonyl, and methylthio; wherein Z is selected from oxygen and sulfur atom; wherein $R_1$ and $R_2$ are independently selected from methyl and ethyl radical; and wherein each of $R_3$ to $R_7$, if present, is independently selected from hydrido, fluoro, chloro, bromo, methyl, ethyl, n-propyl, iso-propyl, n-butyl, iso-butyl, t-butyl, n-pentyl, iso-pentyl, fluoromethyl, difluoromethyl, trifluoromethyl, 1-fluoroethyl, 2,2,2-trifluoroethyl, methoxy, trifluoromethoxy, difluoromethoxy, fluoromethoxy, acetyl, propionyl, n-butanoyl, iso-butanoyl, n-pentanoyl, nitro, amino, N,N-dimethylamino, N-acetylamino, N-propionylamino, formyl, hydroxy, methylthio, ethylthio, n-propylthio, methylsulfonyl, ethylsulfonyl, n-propylsulfonyl, phenyl, hydroxymethyl, 1-hydroxyethyl and 2-hydroxyethyl, or adjacent two groups of $R_3$ to $R_7$ form, taken together, methylenedioxy; or a pharmaceutically-acceptable salt thereof.

A family of specific compounds of particular interest within Formula II comprises the compounds and pharmaceutically acceptable salts thereof as follows:

2,2-Dimethyl-5-{4-(methylsulfonyl)phenyl}-4-phenyl-3(2H)-furanone;
2,2-Dimethyl-4-(2-fluorophenyl)-5-{4-(methylsulfonyl)phenyl}-3(2H)-furanone;
2,2-Dimethyl-4-(3-fluorophenyl)-5-{4-(methylsulfonyl)phenyl}-3(2H)-furanone;
2,2-Dimethyl-4-(4-fluorophenyl)-5-{4-(methylsulfonyl)phenyl}-3(2H)-furanone;
2,2-Dimethyl-4-(3-fluoro-4-phenylphenyl)-5-{4-(methylsulfonyl)phenyl}-3(2H)-furanone;
4-(2,4-Difluorophenyl)-2,2-dimethyl-5-{4-(methylsulfonyl)phenyl}-3(2H)-furanone;
4-(2,5-Difluorophenyl)-2,2-dimethyl-5-{4-(methylsulfonyl)phenyl}-3(2H)-furanone;
4-(3,4-Difluorophenyl)-2,2-dimethyl-5-{4-(methylsulfonyl)phenyl}-3(2H)-furanone;
4-(3,5-Difluorophenyl)-2,2-dimethyl-5-{4-(methylsulfonyl)phenyl}-3(2H)-furanone;
4-(2-Chlorophenyl)-2,2-dimethyl-5-{4-(methylsulfonyl)phenyl}-3(2H)-furanone;
4-(3-Chlorophenyl)-2,2-dimethyl-5-{4-(methylsulfonyl)phenyl}-3(2H)-furanone;
4-(4-Chlorophenyl)-2,2-dimethyl-5-{4-(methylsulfonyl)phenyl}-3(2H)-furanone;
4-(3-Chloro-4-fluorophenyl)-2,2-dimethyl-5-{4-(methylsulfonyl)phenyl}-3(2H)-furanone;
4-(3-Chloro-5-fluorophenyl)-2,2-dimethyl-5-{4-(methylsulfonyl)phenyl}-3(2H)-furanone;
4-(4-Chloro-3-fluorophenyl)-2,2-dimethyl-5-{4-(methylsulfonyl)phenyl}-3(2H)-furanone;
4-(2,4-Dichlorophenyl)-2,2-dimethyl-5-{4-(methylsulfonyl)phenyl}-3(2H)-furanone;
4-(3,4-Dichlorophenyl)-2,2-dimethyl-5-{4-(methylsulfonyl)phenyl}-3(2H)-furanone;
4-(3,5-Dichlorophenyl)-2,2-dimethyl-5-{4-(methylsulfonyl)phenyl}-3(2H)-furanone;
4-(4-Bromophenyl)-2,2-dimethyl-5-{4-(methylsulfonyl)phenyl}-3(2H)-furanone;
4-(3-Bromophenyl)-2,2-dimethyl-5-{4-(methylsulfonyl)phenyl}-3(2H)-furanone;
2,2-Dimethyl-4-(2-methylphenyl)-5-{4-(methylsulfonyl)phenyl}-3(2H)-furanone;
2,2-Dimethyl-4-(3-methylphenyl)-5-{4-(methylsulfonyl)phenyl}-3(2H)-furanone;
2,2-Dimethyl-4-(4-methylphenyl)-5-{4-(methylsulfonyl)phenyl}-3(2H)-furanone;
2,2-Dimethyl-4-(4-ethylphenyl)-5-{4-(methylsulfonyl)phenyl}-3(2H)-furanone;
2,2-Dimethyl-5-{4-(methylsulfonyl)phenyl}-4-(4-n-propylphenyl)-3(2H)-furanone;
2,2-Dimethyl-4-(3-iso-propylphenyl)-5-{4-(methylsulfonyl)phenyl}-3(2H)-furanone,
2,2-Dimethyl-4-(4-iso-propylphenyl)-5-{4-(methylsulfonyl)phenyl}-3(2H)-furanone:
2,2-Dimethyl-4-(3-fluoro-4-iso-propylphenyl)-5-{4-(methylsulfonyl)phenyl}-3(2H)-furanone;
4-(3-Chloro-4-iso-propylphenyl)-2,2-dimethyl-5-{4-(methylsulfonyl)phenyl}-3(2H)-furanone;
2,2-Dimethyl-4-(4-n-butylphenyl)-5-{4-(methylsulfonyl)phenyl}-3(2H)-furanone;
2,2-Dimethyl-4-(4-t-butylphenyl)-5-{4-(methylsulfonyl)phenyl}-3(2H)-furanone;
2,2-Dimethyl-4-(4-fluoro-2-methylphenyl)-5-{4-(methylsulfonyl)phenyl}-3(2H)-furanone;
2,2-Dimethyl-4-(5-fluoro-2-methylphenyl)-5-{4-(methylsulfonyl)phenyl}-3(2H)-furanone;

2,2-Dimethyl-4-(3-fluoro-4-methylphenyl)-5-{4-(methylsulfonyl)phenyl}-3(2H)-furanone;

2,2-Dimethyl-4-(2-methoxyphenyl)-5-{4-(methylsulfonyl)phenyl}-3(2H)-furanone;

2,2-Dimethyl-4-(3-methoxyphenyl)-5-{4-(methylsulfonyl)phenyl}-3(2H)-furanone;

2,2-Dimethyl-4-(4-methoxyphenyl)-5-{4-(methylsulfonyl)phenyl}-3(2H)-furanone;

2,2-Dimethyl-4-(2-hydroxyphenyl)-5-{4-(methylsulfonyl)phenyl}-3(2H)-furanone;

2,2-Dimethyl-4-(3-hydroxyphenyl)-5-{4-(methylsulfonyl)phenyl}-3(2H)-furanone;

2,2-Dimethyl-4-(4-hydroxyphenyl)-5-{4-(methylsulfonyl)phenyl}-3(2H)-furanone;

4-(2,4-Dimethoxyphenyl)-2,2-dimethyl-5-{4-(methylsulfonyl)phenyl}-3(2H)-furanone;

4-(3,4-Dimethoxyphenyl)-2,2-dimethyl-5-{4-(methylsulfonyl)phenyl}-3(2H)-furanone;

2,2-Dimethyl-4-(3,4-methylenedioxyphenyl)-5-{4-(methylsulfonyl)phenyl}-3(2H)-furanone;

2,2-Dimethyl-4-(3,5-dimethyl-4-methoxyphenyl)-5-{4-(methylsulfonyl)-phenyl}-3(2H)-furanone;

2,2-Dimethyl-4-(3,4-dimethylphenyl)-5-{4-(methylsulfonyl)phenyl}-3(2H)-furanone;

2,2-Dimethyl-4-(3-fluoro-4-methoxyphenyl)-5-{4-(methylsulfonyl)phenyl}-3(2H)-furanone;

2,2-Dimethyl-4-(3-fluoro-4-hydroxyphenyl)-5-{4-(methylsulfonyl)phenyl}-3(2H)-furanone;

2,2-Dimethyl-5-{4-(methylsulfonyl)phenyl}-4-{4-(methylthio)phenyl}-3(2H)-furanone;

2,2-Dimethyl-4-{4-(ethylthio)phenyl}-5-{4-(methylsulfonyl)phenyl}-3(2H)-furanone;

2,2-Dimethyl-4,5-di-{4-(methylsulfonyl)phenyl}-3(2H)-furanone;

2,2-Dimethyl-4-{4-(ethylsulfonyl)phenyl}-5-{4-(methylsulfonyl)phenyl}-3(2H)-furanone;

2,2-Dimethyl-4-{3-(fluoromethyl)phenyl}-5-{4-(methylsulfonyl)phenyl}-3(2H)-furanone;

2,2-Dimethyl-4-{4-(fluoromethyl)phenyl}-5-{4-(methylsulfonyl)phenyl}-3(2H)-furanone;

4-{3-(Difluoromethyl)phenyl}-2,2-dimethyl-5-{4-(methylsulfonyl)phenyl}-3(2H)-furanone;

4-{4-(Difluoromethyl)phenyl}-2,2-dimethyl-5-{4-(methylsulfonyl)phenyl}-3(2H)-furanone;

2,2-Dimethyl-5-{4-(methylsulfonyl)phenyl}-4-{2-(trifluoromethyl)phenyl}-3(2H)-furanone;

2,2-Dimethyl-5-{4-(methylsulfonyl)phenyl}-4-{3-(trifluoromethyl)phenyl}-3(2H)-furanone;

2,2-Dimethyl-4-{3-fluoro-5-(trifluoromethyl)phenyl}-5-{4-(methylsulfonyl)phenyl}-3(2H)-furanone;

4-{3-Chloro-5-(trifluoromethyl)phenyl}-2,2-dimethyl-5-{4-(methylsulfonyl)phenyl}-3(2H)-furanone;

4-{4-Acetyl-3-(trifluoromethyl)phenyl}-2,2-dimethyl-5-{4-(methylsulfonyl)phenyl}-3(2H)-furanone;

4-{3-Acetyl-5-(trifluoromethyl)phenyl}-2,2-dimethyl-5-{4-(methylsulfonyl)phenyl}-3(2H)-furanone;

2,2-Dimethyl-5-{4-(methylsulfonyl)phenyl}-4-{4-(trifluoromethyl)phenyl}-3(2H)-furanone;

2,2-Dimethyl-4-{3,5-di-(trifluoromethyl)phenyl}-5-{4-(methylsulfonyl)phenyl}-3(2H)-furanone;

4-{4-Chloro-3-(trifluoromethyl)phenyl}-2,2-dimethyl-5-{4-(methylsulfonyl)phenyl}-3(2H)-furanone;

2,2-Dimethyl-5-{4-(methylsulfonyl)phenyl}-4-(3-nitrophenyl)-3(2H)-furanone;

4-(3-Aminophenyl)-2,2-Dimethyl-5-{4-(methylsulfonyl)phenyl}-3(2H)-furanone;

2,2-Dimethyl-4-{4-(N,N-dimethylamino)phenyl}-5-{4-(methylsulfonyl)phenyl}-3(2H)-furanone;

2,2-Dimethyl-4-(2-formylphenyl)-5-{4-(methylsulfonyl)phenyl}-3(2H)-furanone;

2,2-Dimethyl-4-(3-formylphenyl)-5-{4-(methylsulfonyl)phenyl}-3(2H)-furanone;

2,2-Dimethyl-4-(4-formylphenyl)-5-{4-(methylsulfonyl)phenyl}-3(2H)-furanone;

4-{3-(Acetylamino)phenyl}-2,2-dimethyl-5-{4-(methylsulfonyl)phenyl}-3(2H)-furanone;

4-(3-Acetylphenyl)-2,2-dimethyl-5-{4-(methylsulfonyl)phenyl}-3(2H)-furanone;

4-(4-Acetylphenyl)-2,2-dimethyl-5-{4-(methylsulfonyl)phenyl}-3(2H)-furanone;

4-(4-Biphenyl)-2,2-dimethyl-5-{4-(methylsulfonyl)phenyl}-3(2H)-furanone;

2,2-Dimethyl-4-[4-(1-hydroxyethyl)phenyl]-5-{4-(methylsulfonyl)phenyl}-3(2H)-furanone;

2,2-Dimethyl-4-[4-(hydroxymethyl)phenyl]-5-{4-(methylsulfonyl)phenyl}-3(2H)-furanone;

2,2-Dimethyl-5-{4-(methylsulfinyl)phenyl}-4-phenyl-3(2H)-furanone;

2,2-Dimethyl-4-(3-fluorophenyl)-5-{4-(methylsulfinyl)phenyl}-3(2H)-furanone;

2,2-Dimethyl-4-(4-fluorophenyl)-5-{4-(methylsulfinyl)phenyl}-3(2H)-furanone;

2,2-Dimethyl-4-(3,5-difluorophenyl)-5-{4-(methylsulfinyl)phenyl}-3(2H)-furanone;

4-(3-Chloro-4-fluorophenyl)-2,2-dimethyl-5-{4-(methylsulfinyl)phenyl}-3(2H)-furanone;

4-(3-Chloro-5-fluorophenyl)-2,2-dimethyl-5-{4-(methylsulfinyl)phenyl}-3(2H)-furanone;

4-(3-Chlorophenyl)-2,2-dimethyl-5-{4-(methylsulfinyl)phenyl}-3(2H)-furanone;

4(4-t-Butylphenyl)-2,2-dimethyl-5-{4-(methylsulfinyl)phenyl}-3(2H)-furanone;

2,2-Dimethyl-4-(2-fluorophenyl)-5-{4-(methylsulfinyl)phenyl}-3(2H)-furanone;

2,2-Dimethyl-4-(3-fluorophenyl)-5-{4-(methylthio)phenyl}-3(2H)-furanone;

2,2-Dimethyl-5-{4-(methylthio)phenyl}-4-phenyl-3(2H)-furanone;

4-(3-Chlorophenyl)-2,2-dimethyl-5-{4-(methylthio)phenyl}-3(2H)-furanone;

2,2-Dimethyl-5-{4-(methylthio)phenyl}-4-{3-(trifluoromethyl)phenyl}-3(2H)-furanone;

2,2-Dimethyl-5-{4-(methylsulfinyl)phenyl}-4-{3-(trifluoromethyl)phenyl}-3(2H)-furanone;

2,2-Dimethyl-4-{3-fluoro-5-(trifluoromethyl)phenyl}-5-{4-(methylsulfinyl)phenyl}-3(2H)-furanone;

4-{3-Chloro-5-(trifluoromethyl)phenyl}-2,2-dimethyl-5-{4-(methylsulfinyl)phenyl}-3(2H)-furanone;

4-{3-Acetyl-5-(trifluoromethyl)phenyl}-2,2-dimethyl-5-{4-(methylsulfinyl)phenyl}-3(2H)-furanone;

4-{4-Acetyl-3-(trifluoromethyl)phenyl}-2,2-dimethyl-5-{4-(methylsulfinyl)phenyl}-3(2H)-furanone;

2,2-Dimethyl-5-{4-(methylthio)phenyl}-4-(4-nitrophenyl)-3(2H)-furanone;

2,2-Dimethyl-4-(4-methoxyphenyl)-5-{4-(methylthio)phenyl}-3(2H)-furanone;

4-(2,5-Difluorophenyl)-2,2-dimethyl-5-{4-(methylthio)phenyl}-3(2H)-furanone;

4-(3,5-Difluorophenyl)-2,2-dimethyl-5-{4-(methylthio)phenyl}-3(2H)-furanone;

5-{4-(Aminosulfonyl)phenyl}-2,2-dimethyl-4-(4-fluorophenyl)-3(2H)-furanone;

5-{4-(Aminosulfonyl)phenyl}-4-(3,5-difluorophenyl)-2,2-dimethyl-3(2H)-furanone;

5-{4-(Aminosulfonyl)phenyl}-4-(3-chloro-5-fluorophenyl)-2,2-dimethyl-3(2H)-furanone;

5-{4-(Aminosulfonyl)phenyl}-4-(3-chlorophenyl)-2,2-dimethyl-3(2H)-furanone;
5-{4-(Aminosulfonyl)phenyl}-4-(3,4-dichlorophenyl)-2,2-dimethyl-3(2H)-furanone;
5-{4-(Aminosulfonyl)phenyl}-4-(3,5-dichlorophenyl)-2,2-dimethyl-3(2H)-furanone;
5-{4-(Aminosulfonyl)phenyl}-2,2-dimethyl-4-{3-(trifluoromethyl)phenyl}-3(2H)-furanone;
5-{4-(Aminosulfonyl)phenyl}-2,2-dimethyl-4-{3-fluoro-5-(trifluoromethyl)phenyl}-3(2H)-furanone;
5-{4-(Aminosulfonyl)phenyl}-4-{3-chloro-5-(trifluoromethyl)phenyl}-2,2-dimethyl 3(2H)-furanone;
4-{3-Acetyl-5-(trifluoromethyl)phenyl}-5-{4-(aminosulfonyl)phenyl}-2,2-dimethyl 3(2H)-furanone;
4-{4-Acetyl-5-(trifluoromethyl)phenyl}-5-{4-(aminosulfonyl)phenyl}-2,2-dimethyl 3(2H)-furanone;
5-{4-(Aminosulfonyl)phenyl}-2,2-dimethyl-4-(3-methylphenyl)-3(2H)-furanone;
5-{4-(Aminosulfonyl)phenyl}-2,2-dimethyl-4-(3-fluorophenyl)-3(2H)-furanone;
5-{4-(Aminosulfonyl)phenyl}-4-(2,4-difluorophenyl)-2,2-dimethyl-3(2H)-furanone;
5-{4-(Aminosulfonyl)phenyl}-2,2-dimethyl-4-(3,4-dimethylphenyl)-3(2H)-furanone;
5-{4-(Aminosulfonyl)phenyl}-4-(2,4-dimethoxyphenyl)-2,2-dimethyl-3(2H)-furanone;
5-{4-(Aminosulfonyl)phenyl}-4-(3,4-dimethoxyphenyl)-2,2-dimethyl-3(2H)-furanone;
4-(3-Acetylphenyl)-5-{4-(aminosulfonyl)phenyl}-2,2-dimethyl-3(2H)-furanone;
4-(3-Acetyl-5-chlorophenyl)-5-{4-(aminosulfonyl)phenyl}-2,2-dimethyl-3(2H)-furanone;
4-(3-Acetyl-4-chlorophenyl)-5-{4-(aminosulfonyl)phenyl}-2,2-dimethyl-3(2H)-furanone;
4-(3-Acetyl-4-fluorophenyl)-5-{4-(aminosulfonyl)phenyl}-2,2-dimethyl-3(2H)-furanone;
4-(3-Acetyl-5-fluorophenyl)-5-{4-(aminosulfonyl)phenyl}-2,2-dimethyl-3(2H)-furanone;
5-{4-(Aminosulfonyl)phenyl}-2,2-dimethyl-4-phenyl-3(2H)-furanone;
5-{4-(Aminosulfonyl)phenyl}-4-(3-chloro-4-fluorophenyl)-2,2-dimethyl-3(2H)-furanone;
5-{4-(Aminosulfonyl)phenyl}-2,2-dimethyl-4-(3-methoxyphenyl)-3(2H)-furanone;
4-(4-Acetylphenyl)-5-{4-(aminosulfonyl)phenyl}-2,2-dimethyl-3(2H)-furanone;
4-(4-Acetyl-3-chlorophenyl)-5-{4-(aminosulfonyl)phenyl}-2,2-dimethyl-3(2H)-furanone;
4-(4-Acetyl-3-fluorophenyl)-5-{4-(aminosulfonyl)phenyl}-2,2-dimethyl-3(2H)-furanone;
4-(4-Acetyl-3-bromophenyl)-5-{4-(aminosulfonyl)phenyl}-2,2-dimethyl-3(2H)-furanone;
4-{4-(Acetylamino)phenyl}-5-{4-(Aminosulfonyl)phenyl}-2,2-dimethyl-3(2H)-furanone;
5-{4-(Aminosulfonyl)phenyl}-2,2-dimethyl-4-(2-methylphenyl)-3(2H)-furanone;
5-{4-(Aminosulfonyl)phenyl}-4-(3,4-difluorophenyl)-2,2-dimethyl-3(2H)-furanone;
5-{4-(Aminosulfonyl)phenyl}-2,2-dimethyl-4-(4-methylphenyl)-3(2H)-furanone;
5-{4-(Aminosulfonyl)phenyl}-2,2-dimethyl-4-{3,4-methylenedioxy)phenyl}-3(2H)-furanone;
5-{4-(Aminosulfonyl)phenyl}-4-(4-chlorophenyl)-2,2-dimethyl-3(2H)-furanone;
5-{4-(Aminosulfonyl)phenyl}-2,2-dimethyl-4-{4-(methylthio)phenyl}-3(2H)-furanone;
5-{4-(Aminosulfonyl)phenyl}-2,2-dimethyl-4-(3-fluoro-4-phenylphenyl)-3(2H)-furanone;
5-{4-(Aminosulfonyl)phenyl}-4-(4-bromophenyl)-2,2-dimethyl-3(2H)-furanone;
5-{4-(Aminosulfonyl)phenyl}-2,2-dimethyl-4-(5-isopropyl-2-methoxyphenyl)-3(2H)-furanone;
5-{4-(Aminosulfonyl)phenyl}-2,2-dimethyl-4-(5-isopropylphenyl)-3(2H)-furanone;
5-{4-(Aminosulfonyl)phenyl}-2,2-dimethyl-4-{4-(ethylthio)phenyl}-3(2H)-furanone;
5-{4-(Aminosulfonyl)phenyl}-2,2-dimethyl-4-(2-methoxyphenyl)-3(2H)-furanone;
5-{4-(Aminosulfonyl)phenyl}-4-(4-n-butylphenyl)-2,2-dimethyl-3(2H)-furanone;
5-{4-(Aminosulfonyl)phenyl}-4-(3,5-dichlorophenyl)-2,2-dimethyl-3(2H)-furanone;
5-{4-(Aminosulfonyl)phenyl}-2,2-dimethyl-4-(3,4,5-trimethoxyphenyl)-3(2H)-furanone;
5-{4-(Aminosulfonyl)phenyl}-2,2-dimethyl-4-(4-hydroxyphenyl)-3(2H)-furanone;
5-{4-(Aminosulfonyl)phenyl}-2,2-dimethyl-4-(4-fluoro-3-methoxyphenyl)-3(2H)-furanone;
5-{4-(Aminosulfonyl)phenyl}-2,2-dimethyl-4-(3,5-dimethyl-4-methoxyphenyl)-3(2H)-furanone;
5-{4-(Aminosulfonyl)phenyl}-2,2-dimethyl-4-(4-ethylphenyl)-3(2H)-furanone;
5-{4-(Aminosulfonyl)phenyl}-2,2-dimethyl-4-(3-phenylphenyl)-3(2H)-furanone;
5-{4-(Aminosulfonyl)phenyl}-2,2-dimethyl-4-(2-fluorophenyl)-3(2H)-furanone;
4-(3-Aminophenyl)-5-{4-(aminosulfonyl)phenyl}-2,2-dimethyl-3(2H)-furanone;
5-{4-(Aminosulfonyl)phenyl}-4-(2,5-difluorophenyl)-2,2-dimethyl-3(2H)-furanone;
5-{4-(Aminosulfonyl)phenyl}-2,2-dimethyl-4-(3-nitrophenyl)-3(2H)-furanone;
5-{4-(Aminosulfonyl)phenyl}-2,2-dimethyl-4-(5-fluoro-2-methylphenyl)-3(2H)-furanone;
2-Ethyl-2-methyl-5-{4-(methylsulfonyl)phenyl)}-4-phenyl-3(2H)-furanone;
2-Ethyl-4-(4-fluorophenyl)-2-methyl-5-{4-(methylsulfonyl)phenyl}-3(2H)-furanone;
2-Ethyl-4-(3-fluorophenyl)-2-methyl-5-{4-(methylsulfonyl)phenyl}-3(2H)-furanone;
4-(3-Chlorophenyl)-2-ethyl-2-methyl-5-{4-(methylsulfonyl)phenyl}-3(2H)-furanone;
2-Ethyl-4-(2-fluorophenyl)-2-methyl-5-{4-(methylsulfonyl)phenyl}-3(2H)-furanone;
4-(4-Acetylphenyl)-2-ethyl-2-methyl-5-{4-(methylsulfonyl)phenyl}-3(2H)-furanone;
4-(4-Acetyl-3-chlorophenyl)-2-ethyl-2-methyl-5-{4-(methylsulfonyl)phenyl}-3(2H)-furanone;
4-(4-Acetyl-3-fluorophenyl)-2-ethyl-2-methyl-5-{4-(methylsulfonyl)phenyl}-3(2H)-furanone;
4-{4-Acetyl-3-(trifluoromethyl)phenyl}-2-ethyl-2-methyl-5-{4-(methylsulfonyl-phenyl}-3(2H)-furanone;
4-(3,5-Difluorophenyl)-2-ethyl-2-methyl-5-{4-(methylsulfonyl)phenyl}-3(2H)-furanone;
4-(3,4-Difluorophenyl)-2-ethyl-2-methyl-5-{4-(methylsulfonyl)phenyl}-3(2H)-furanone;
4-(3-Chloro-4-fluorophenyl)-2-ethyl-2-methyl-5-{4-(methylsulfonyl)phenyl}-3(2H)-furanone;
4-(3-Chloro-5-fluorophenyl)-2-ethyl-2-methyl-5-{4-(methylsulfonyl)phenyl}-3(2H)-furanone;
4-(3,5-Dichlorophenyl)-2-ethyl-2-methyl-5-{4-(methylsulfonyl)phenyl}-3(2H)-furanone;
2-Ethyl-4-(4-methoxyphenyl)-2-methyl-5-{4-(methylsulfonyl)phenyl}-3(2H)-furanone;
2-Ethyl-2-methyl-4-(4-methylphenyl)-5-{4-(methylsulfonyl)phenyl}-3(2H)-furanone;

2-Ethyl-2-methyl-4-(3-methylphenyl)-5-{4-(methylsulfonyl)phenyl}-3(2H)-furanone;
2-Ethyl-2-methyl-5-{4-(methylsulfonyl)phenyl}-4-(3-trifluoromethylphenyl)-3(2H)-furanone;
4-(3-Acetylphenyl)-2-ethyl-2-methyl-5-{4-(methylsulfonyl)phenyl}-3(2H)-furanone;
4-(3-Acetyl-4-fluorophenyl)-2-ethyl-2-methyl-5-{4-(methylsulfonyl)phenyl}-3(2H)-furanone;
4-(3-Acetyl-4-chlorophenyl)-2-ethyl-2-methyl-5-{4-(methylsulfonyl)phenyl}-3(2H)-furanone;
4-{3-(Acetylamino)phenyl}-2-ethyl-2-methyl-5-{4-(methylsulfonyl)phenyl}-3(2H)-furanone;
2-Ethyl-2-methyl-4-{3,4-(methylenedioxy)phenyl}-5-{4-(methylsulfonyl)phenyl}-3(2H)-furanone;
4-{4-Chloro-3-(trifluoromethyl)phenyl}-2-ethyl-2-methyl-5-{4-(methylsulfonyl)-phenyl}-3(2H)-furanone;
4-{5-Chloro-3-(trifluoromethyl)phenyl}-2-ethyl-2-methyl-5-{4-(methylsulfonyl)-phenyl}-3(2H)-furanone;
2-Ethyl-4-{5-fluoro-3-(trifluoromethyl)phenyl}-2-ethyl-2-methyl-5-{4-(methylsulfonyl)phenyl}3(2H)-furanone;
2-Ethyl-4-(4-ethylphenyl)-2-methyl-5-{4-(methylsulfonyl)phenyl}-3(2H)-furanone;
2-Ethyl-4-(3-methoxyphenyl)-2-methyl-5-{4-(methylsulfonyl)phenyl}-3(2H)-furanone;
2-Ethyl-4-(3-iso-propylphenyl)-2-methyl-5-{4-(methylsulfonyl)phenyl}-3(2H)-furanone;
2-Ethyl-4-(4-iso-propylphenyl)-2-methyl-5-{4-(methylsulfonyl)phenyl}-3(2H)-furanone;
2-Ethyl-4-(3-fluoro-4-iso-propylphenyl)-2-methyl-5-{4-(methylsulfonyl)phenyl}-3(2H)-furanone;
2-Ethyl-4-(5-fluoro-4-iso-propylphenyl)-2-methyl-5-{4-(methylsulfonyl)phenyl}-3(2H)-furanone;
4-(3-Chloro-4-iso-propylphenyl)-2-ethyl-2-methyl-5-{4-(methylsulfonyl)phenyl}-3(2H)-furanone;
4-(4-t-Butylphenyl)-2-ethyl-2-methyl-5-{4-(methylsulfonyl)phenyl}-3(2H)-furanone;
2-Ethyl-2-methyl-5-{4-(methylsulfonyl)phenyl}4-(4-n-propylphenyl)-3(2H)-furanone;
4-(4-n-Butylphenyl)-2-ethyl-2-methyl-5-{4-(methylsulfonyl)phenyl}-3(2H)-furanone;
4-(3,4-Dimethylphenyl)-2-ethyl-2-methyl-5-{4-(methylsulfonyl)phenyl}-3(2H)-furanone;
4-(3,4-Dichlorophenyl)-2-ethyl-2-methyl-5-{4-(methylsulfonyl)phenyl}-3(2H)-furanone;
4-(3-Aminophenyl)-2-ethyl-2-methyl-5-{4-(methylsulfonyl)phenyl}-3(2H)-furanone;
4-{3-(Difluoromethyl)phenyl}-2-ethyl-2-methyl-5-{4-(methylsulfonyl)phenyl}-3(2H)-furanone;
2-Ethyl-4-{4-(fluoromethyl)phenyl}-2-methyl-5-{4-(methylsulfonyl)phenyl}-3(2H)-furanone;
4-(4-Chlorophenyl)-2-ethyl-2-methyl-5-{4-(methylsulfonyl)phenyl}-3(2H)-furanone;
2-Ethyl-2-methyl-5-{4-(methylsulfonyl)phenyl}-4-{4-(trifluoromethyl)phenyl}-3(2H)-furanone;
2-Ethyl-2-methyl-5-{4-(methylsulfonyl)phenyl}-4-{4-(trifluoromethoxy)phenyl}-3(2H)-furanone;
4-(4-Chloro-3-fluorophenyl)-2-ethyl-2-methyl-5-{4-(methylsulfonyl)phenyl}-3(2H)-furanone;
2-Ethyl-4-(4-fluoro-2-methylphenyl)-2-methyl-5-{4-(methylsulfonyl)phenyl}-3(2H)-furanone;
2-Ethyl-4-(5-fluoro-2-methylphenyl)-2-methyl-5-{4-(methylsulfonyl)phenyl}-3(2H)-furanone;
4-(3,4-Dimethoxyphenyl)-2-ethyl-2-methyl-5-{4-(methylsulfonyl)phenyl}-3(2H)-furanone;
4-(3,5-Dimethoxyphenyl)-2-ethyl-2-methyl-5-{4-(methylsulfonyl)phenyl}-3(2H)-furanone;
2-Ethyl-4-(5-fluoro-2-methylphenyl)-2-methyl-5-{4-(methylsulfonyl)phenyl}-3(2H)-furanone;
2-Ethyl-4-(3-fluoro-4-methoxyphenyl)-2-methyl-5-{4-(methylsulfonyl)phenyl}-3(2H)-furanone;
4-(3,5-Difluorophenyl)-2-ethyl-2-methyl-5-{4-(methylsulfonyl)phenyl}-3(2H)-furanone;
4-(3,5-Dichlorophenyl)-2-ethyl-2-methyl-5-{4-(methylsulfonyl)phenyl}-3(2H)-furanone;
4-(3,5-Dimethyl-4-methoxyphenyl)-2-ethyl-2-methyl-5-{4-(methylsulfonyl)phenyl}-3(2H)-furanone;
2-Ethyl-2-methyl-5-{4-(methylsulfonyl)phenyl}-4-(3,4,5-trimethoxyphenyl)-3(2H)-furanone;
5-{4-(Aminosulfonyl)phenyl}-2-ethyl-2-methyl-4-phenyl-3(2H)-furanone;
5-{4-(Aminosulfonyl)phenyl}-2-ethyl-4-(4-fluorophenyl)-2-methyl-3(2H)-furanone;
5-{4-(Aminosulfonyl)phenyl}-2-ethyl-4-(3-fluorophenyl)-2-methyl-3(2H)-furanone;
5-{4-(Aminosulfonyl)phenyl}-2-ethyl-2-methyl-4-(3-methylphenyl)-3(2H)-furanone;
5-{4-(Aminosulfonyl)phenyl}-4-(3-chlorophenyl)-2-ethyl-2-methyl-3(2H)-furanone;
5-{4-(Aminosulfonyl)phenyl}-4-(4-chlorophenyl)-2-ethyl-2-methyl-3(2H)-furanone;
5-(4-Aminosulfonylphenyl)-2-ethyl-2-methyl-4-{3-(trifluoromethyl)phenyl}-3(2H)-furanone;
5-(4-Aminosulfonylphenyl)-2-ethyl-2-methyl-4-{3-fluoro-5-(trifluoromethyl)phenyl}-3(2H)-furanone;
5-(4-Aminosulfonylphenyl)-4-{3-chloro-5-(trifluoromethyl)phenyl}-2-ethyl-2-methyl-3(2H)-furanone;
5-{4-(Aminosulfonyl)phenyl}-2-ethyl-2-methyl-4-{4-(trifluoromethyl)phenyl}-3(2H)-furanone;
5-{4-(Aminosulfonyl)phenyl}-4-(3,5-difluorophenyl)-2-ethyl-2-methyl-3(2H)-furanone;
5-{4-(Aminosulfonyl)phenyl}-4-(3,5-dichlorophenyl)-2-ethyl-2-methyl-3(2H)-furanone;
5-{4-(Aminosulfonyl)phenyl}-4-(3,4-difluorophenyl)-2-ethyl-2-methyl-3(2H)-furanone;
5-{4-(Aminosulfonyl)phenyl}-2-ethyl-4-(3-methoxyphenyl)-2-methyl-3(2H)-furanone;
4-(4-Acetylphenyl)-5-{4-(aminosulfonyl)phenyl}-2-ethyl-2-methyl-3(2H)-furanone;
4-(4-Acetyl-3-chlorophenyl)-5-{4-(aminosulfonyl)phenyl}-2-ethyl-2-methyl-3(2H)-furanone;
4-(4-Acetyl-3-fluorophenyl)-5-{4-(aminosulfonyl)phenyl}-2-ethyl-2-methyl-3(2H)-furanone;
4-{4-Acetyl-4-(trifluoromethyl)phenyl}-5-{4-(aminosulfonyl)phenyl}-2-ethyl-2-methyl-3(2H)-furanone;
5-{4-(Aminosulfonyl)phenyl}-2-ethyl-4-(4-fluoro-3-methoxyphenyl)-2-methyl-3(2H)-furanone;
2,2-Diethyl-5-{4-(methylsulfonyl)phenyl}-4-phenyl-3(2H)-furanone;
2,2-Diethyl-4-(3-fluorophenyl)-5-{4-(methylsulfonyl)phenyl}-3(2H)-furanone;
4-(3-Chlorophenyl)-2,2-diethyl-5-{4-(methylsulfonyl)phenyl}-3(2H)-furanone;
2,2-Diethyl-4-(3-methylphenyl)-5-{4-(methylsulfonyl)phenyl}-3(2H)-furanone;
2,2-Diethyl-4-(3-methoxyphenyl)-5-{4-(methylsulfonyl)phenyl}-3(2H)-furanone;
2,2-Diethyl-5-{4-(methylsulfonyl)phenyl}-4-{3-(trifluoromethyl)phenyl}-3(2H)-furanone;
2,2-Diethyl-4-{3-fluoro-5-(trifluoromethyl)phenyl}-5-{4-(methylsulfonyl)phenyl}-3(2H)-furanone;
4-{3-Chloro-5-(trifluoromethyl)phenyl}-2,2-diethyl-5-{4-(methylsulfonyl)phenyl}-3(2H)-furanone;
2,2-Diethyl-4-(4-fluorophenyl)-5-{4-(methylsulfonyl)phenyl}-3(2H)-furanone;

4-(4-Chlorophenyl)-2,2-diethyl-5-{4-(methylsulfonyl)
phenyl}-3(2H)-furanone;
2,2-Diethyl-4-(4-methylphenyl)-5-{4-(methylsulfonyl)
phenyl}-3(2H)-furanone;
2,2-Diethyl-4-(4-methoxyphenyl)-5-{4-(methylsulfonyl)
phenyl}-3(2H)-furanone;
2,2-Diethyl-5-{4-(methylsulfonyl)phenyl}-4-{4-
(trifluoromethyl)phenyl}-3(2H)-furanone;
4-(4-Acetyl-3-chlorophenyl)-2,2-diethyl-5-{4-
(methylsulfonyl)phenyl}-3(2H)-furanone;
4-(4-Acetylphenyl)-2,2-diethyl-5-{4-(methylsulfonyl)
phenyl}-3(2H)-furanone;
4-(4-Acetyl-3-fluorophenyl)-2,2-diethyl-5-{4-
(methylsulfonyl)phenyl}-3(2H)-furanone;
4-(4-Acetyl-2-chlorophenyl)-2,2-diethyl-5-{4-
(methylsulfonyl)phenyl}-3(2H)-furanone;
4-(4-Acetyl-2-fluorophenyl)-2,2-diethyl-5-{4-
(methylsulfonyl)phenyl}-3(2H)-furanone;
2,2-Diethyl-4-(3,4-difluorophenyl)-5-{4-(methylsulfonyl)
phenyl}-3(2H)-furanone;
2,2-Diethyl-4-(3,5-difluorophenyl)-5-{4-(methylsulfonyl)
phenyl}-3(2H)-furanone;
2,2-Diethyl-4-(2,5-difluorophenyl)-5-{4-(methylsulfonyl)
phenyl}-3(2H)-furanone;
4-(3-Chloro-5-fluorophenyl)-2,2-diethyl-5-{4-
(methylsulfonyl)phenyl}-3(2H)-furanone;
2,2-Diethyl-4-(3,4-dimethoxyphenyl)-5-{4-
(methylsulfonyl)phenyl}-3(2H)-furanone;
2,2-Diethyl-5-{4-(methylsulfonyl)phenyl}-4-(4-n-
propylphenyl)-3(2H)-furanone;
2,2-Diethyl-4-(2,4-difluorophenyl)-5-{4-(methylsulfonyl)
phenyl}-3(2H)-furanone;
4-(4-t-Butylphenyl)-2,2-diethyl-5-{4-(methylsulfonyl)
phenyl}-3(2H)-furanone;
2,2-Diethyl-4-(3,4-dimethylphenyl)-5-{4-(methylsulfonyl)
phenyl}-3(2H)-furanone;
2,2-Diethyl-4-(4-iso-propylphenyl)-5-{4-(methylsulfonyl)
phenyl}-3(2H)-furanone;
4-(3-Acetylphenyl)-2,2-diethyl-5-{4-(methylsulfonyl)
phenyl}-3(2H)-furanone;
4-(3-Chloro-4-fluorophenyl)-2,2-diethyl-5-{4-
(methylsulfonyl)phenyl}-3-(2H)-furanone;
2,2-Diethyl-4-(3-fluoro-4-methoxyphenyl)-5-{4-
(methylsulfonyl)phenyl}-3(2H)-furanone;
4-(3-Chloro-4-fluorophenyl)-2,2-dimethyl-5-{4-
(methylsulfonyl)phenyl}-(2H)-furan-3-thione;
2,2-Dimethyl-4-(4-fluorophenyl)-5-{4-(methylsulfonyl)
phenyl}-(2H)-furan-3-thione;
2,2-Dimethyl-4-(3-fluorophenyl)-5-{4-(methylsulfonyl)
phenyl}-(2H)-furan-3-thione;
4-(3,5-Difluorophenyl)-2,2-dimethyl-5-{4-(methylsulfonyl)
phenyl}-(2H)-furan-3-thione;
5-[4-{(Acetylamino)sulfonyl}phenyl]-2,2-dimethyl-4-(3-
fluorophenyl)-3(2H)-furanone;
5-[4-{(Butyrylamino)sulfonyl}phenyl]-2,2-dimethyl-4-(3-
fluorophenyl)-3(2H)-furanone;
2,2-Dimethyl-5-[4-{(N-methylamino)sulfonyl}phenyl]-4-
(3-fluorophenyl)-3(2,H)-furanone;
2,2-Dimethyl-5-[4-{(N-ethylamino)sulfonyl}phenyl]-4-(3-
fluorophenyl)-3(2H)-furanone.

Within Formula I there is a subclass of compounds of high interest represented by Formula III:

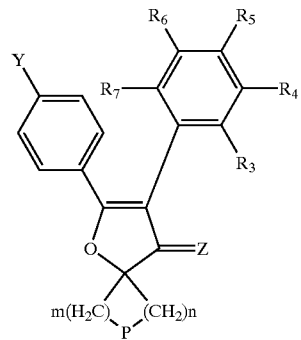

III wherein Y represents alkylsulfonyl, aminosulfonyl, alkylsulfinyl, (N-acylamino)sulfonyl, (N-alkylamino) sulfonyl, or alkylthio; wherein Z represents oxygen or sulfur atom; wherein m and n are integers from 1 to 3 inclusive, with proviso that (m+n)$\leq$4; wherein P is selected from oxygen atom and methylene radical (—$CH_2$—); and wherein each of $R_3$ to $R_7$, if present, is independently selected from hydrido, halo, alkyl, haloalkyl, alkoxy, haloalkoxy, acyl, nitro, amino, N-alkylamino, N,N-dialkylamino, N-acylamino, N-(haloacyl)amino, formyl, cyano, azido, hydroxy, alkylthio, alkylsulfonyl, phenyl, alkoxyallkyl and hydroxyallkyl, or two adjacent groups of $R_3$ to $R_7$, form, taken together, methylenedioxy; or a pharmaceutically-acceptable salt thereof.

A preferred class of compounds comprises those compounds of Formula III; wherein Y is selected from (lower alkyl)sulfonyl, aminosulfonyl, (lower alkyl)sulfinyl, (lower N-acylamino)sulfonyl, (lower N-alkylamino)sulfonyl, and (lower alkyl)thio; wherein Z is selected from oxygen and sulfur atom; wherein m and n are integers from 1 to 3 inclusive, with proviso that (m+n)$\leq$4; wherein P is selected from oxygen atom and methylene radical (—$CH_2$—); and wherein each of $R_3$ to $R_7$, if present, is independently selected from hydrido, halo, alkyl, haloalkyl, alkoxy, haloalkoxy, acyl, nitro, amino, N-alkylamino, N,N-dialkylamino, N-acylamino, N-(haloacyl)amino, formyl, cyano, azido, hydroxy, alkylthio, alkylsulfonyl, phenyl, lower alkoxyalkyl and lower hydroxyalkyl, or adjacent two groups of $R_3$ to $R_7$ form, taken together, methylenedioxy; or a pharmaceutically acceptable salt thereof.

A class of compounds of particular interest encompasses those compounds of Formula III, wherein Y is selected from methylsulfonyl, aminosulfonyl, methylsulfinyl, (N-acetylamino)sulfonyl, (N-propionylamino)sulfonyl, (N-butyrylamino)sulfonyl, (N-methylamino)sulfonyl, (N-ethylamino)sulfonyl, and methylthio; wherein Z is selected from oxygen and sulfur atom; wherein m and n are integers from 1 to 3 inclusive, with proviso that (m+n)$\leq$4; wherein P is oxygen atom or methylene radical (—$CH_2$—); and wherein each of $R_3$ to $R_7$, if present, is independently selected from hydrido, fluoro, chloro, bromo, methyl, ethyl, n-propyl, iso-propyl, n-butyl, iso-butyl, t-butyl, acetyl, and propionyl; or a pharmaceutically-acceptable salt thereof.

A family of specific compounds of particular interest within Formula III comprises compounds and pharmaceutically acceptable salts thereof as follows:

2-{4-(Methylsulfonyl)phenyl}-3-phenyl-1-oxa-spiro[4,4]
non-2-en-4-one;
3-(3-Methylphenyl)-2-{4-(methylsulfonyl)phenyl}-1-oxa-
spiro[4,4]non-2-en-4-one;
3-(4-iso-Propylphenyl)-2-{4-(methylsulfonyl)phenyl}-1-
oxa-spiro[4,4]non-2-ene-4-one;

3-(3,5-Difluorophenyl)-2-{4-(methylsulfonyl)phenyl}-1-oxa-spiro[4,4]non-2-ene-4-one;
3-(2-Fluorophenyl)-2-{4-(methylsulfonyl)phenyl}-1-oxa-spiro[4,4]non-2-ene-4-one;
3-(3-Fluorophenyl)-2-{4-(methylsulfonyl)phenyl}-1-oxa-spiro[4,4]non-2-ene-4-one;
3-(3-Chlorophenyl)-2-{4-(methylsulfonyl)phenyl}-1-oxa-spiro[4,4]non-2-ene-4-one;
3-(4-Fluorophenyl)-2-{4-(methylsulfonyl)phenyl}-1-oxa-spiro[4,4]non-2-ene-4-one;
3-(4-Acetylphenyl)-2-{4-(methylsulfonyl)phenyl}-1-oxa-spiro[4,4]non-2-ene-4-one;
3-(4-Acetyl-3-fluorophenyl)-2-{4-(methylsulfonyl)phenyl}-1-oxa-spiro[4,4]non-2-ene-4-one;
3-(4-Acetyl-3-chlorophenyl)-2-{4-(methylsulfonyl)phenyl}-1-oxa-spiro[4,4]non-2-ene-4-one;
2-{4-(Methylsulfonyl)phenyl}-3-phenyl-1-oxa-spiro[4,5]dec-2-en-4-one;
2-{4-(Methylsulfonyl)phenyl}-3-{3-(trifluoromethyl)phenyl}-1-oxa-spiro[4,5]dec-2-en-4-one;
3-(3-Methylphenyl)-2-{4-(methylsulfonyl)phenyl}-1-oxa-spiro[4,5]dec-2-en-4-one;
3-(4-Acetylphenyl)-2-{4-(methylsulfonyl)phenyl}-1-oxa-spiro[4,5]dec-2-en-4-one;
3-(3-Fluorophenyl)-2-{4-(methylsulfonyl)phenyl}-1,8-dioxa-spiro[4.5]dec-2-en-4-one;
3-(3,5-difluorophenyl)-2-{4-(methylsulfonyl)phenyl}-1,8-dioxa-spiro[4.5]dec-2-en-4-one;
3-(3-Chlorophenyl)-2-{4-(methylsulfonyl)phenyl}-1,8-dioxa-spiro[4.5]dec-2-en-4-one;
3-(4-Acetylphenyl)-2-{4-(methylsulfonyl)phenyl}-1,8-dioxa-spiro[4.5]dec-2-en-4-one;
2-{4-(Methylsulfonyl)phenyl}-3-phenyl-1,8-dioxa-spiro[4.5]dec-2-en-4-one;
3-(3-Chlorophenyl)-2-{4-(methylsulfonyl)phenyl}-1,8-dioxa-spiro[4.5]dec-2-en-4-one.

Within Formula I there is a subclass of compounds of high interest represented by Formula IV:

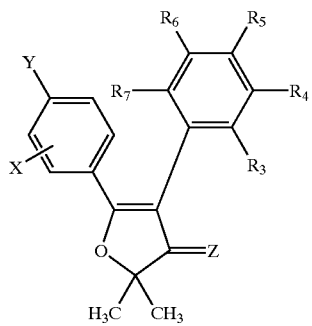

IV wherein X represents halo or alkyl; wherein Y represents alkylsulfonyl, aminosulfonyl, alkylsulfonyl, (N-acylamino)sulfonyl, (N-alkylamino)sulfonyl, or alkylthio; wherein Z represents oxygen or sulfur atom; and wherein each of $R_3$ to $R_7$, if present, is independently selected from hydrido, halo, alkyl, haloalkyl, alkyloxy, nitro, amino, N-acylamino, acyl, formyl, hydroxyalkyl, phenyl, and cyano, or two adjacent groups of $R_3$ to $R_7$ form, taken together, methylenedioxy; or a pharmaceutically-acceptable salt thereof.

A preferred class of compounds comprises those compounds of Formula IV, wherein X represents halo or lower alkyl; wherein Y is selected from (lower alkyl)sulfonyl, aminosulfonyl, (lower alkyl)sulfinyl, (lower N-acylamino) sulfonyl, (lower N-alkylamino)sulfonyl, and (lower alkyl) thio; wherein Z is selected from oxygen and sulfur atom; and wherein each of $R_3$ to $R_7$, if present, is independently selected from hydrido, halo, lower alkyl, lower haloalkyl, lower alkyloxy, nitro, amino, and N-(lower acyl)amino; or a pharmaceutically acceptable salt thereof.

A class of compounds of particular interest encompasses those compounds of Formula IV, wherein X represents fluoro, chloro, bromo or methyl; wherein Y is selected from methylsulfonyl, ethylsulfonyl, aminosulfonyl, methylsulfinyl, ethylsulfinyl, (N-acetylamino)sulfonyl, (N-propionylamino)sulfonyl, (N-butyrylamino)-sulfonyl, (N-methylamino)sulfonyl, (N-ethylamino)sulfonyl, methylthio, and ethylthio; wherein Z is selected from oxygen and sulfur atom; and wherein each of $R_3$ to $R_7$, if present, is independently selected from hydrido, fluoro, chloro, bromo, methyl, ethyl, iso-propyl, fluoromethyl, difluoromethyl, trifluoromethyl, methoxy, ethoxy, n-propyloxy, iso-propyloxy, n-butoxy, nitro, amino, N-acetylamino, and N-propionylamino; or a pharmaceutically-acceptable salt thereof.

A family of specific compounds of particular interest within Formula IV comprises compounds and pharmaceutically acceptable salts thereof as follows:

2,2-Dimethyl-5-{3-fluoro-4-(methylthio)phenyl}-4-phenyl-3(2H)-furanone;
2,2-Dimethyl-5-{3-fluoro-4-(methylsulfinyl)phenyl}-4-phenyl-3(2H)-furanone;
2,2-Dimethyl-5-{3-fluoro-4-(methylsulfonyl)phenyl}-4-phenyl-3(2H)-furanone;
5-{4-(Aminosulfonyl)-3-fluorophenyl}-2,2-dimethyl-4-phenyl-3(2H)-furanone;
4-(2-Chlorophenyl)-2,2-dimethyl-5-{3-fluoro-4-(methylthio)phenyl}-3(2H)-furanone;
4-(2-Chlorophenyl)-2,2-dimethyl-5-{3-fluoro-4-(methylsulfinyl)phenyl}-3(2H)-furanone;
4-(2-Chlorophenyl)-2,2-dimethyl-5-{3-fluoro-4-(methylsulfonyl)phenyl}-3(2H)-furanone;
5-{4-(Aminosulfonyl)-3-fluorophenyl}-4-(2-chlorophenyl)-2,2-dimethyl-3(2H)-furanone;
4-(3-Chlorophenyl)-2,2-dimethyl-5-{3-fluoro-4-(methylthio)phenyl}-3(2H)-furanone;
4-(3-Chlorophenyl)-2,2-dimethyl-5-{3-fluoro-4-(methylsulfinyl)phenyl}-3(2H)-furanone;
4-(3-Chlorophenyl)-2,2-dimethyl-5-{3-fluoro-4-(methylsulfonyl)phenyl}-3(2H)-furanone;
5-{4Aminosulfonyl)-3-fluorophenyl}-4-(3-chlorophenyl)-2,2-dimethyl-3(2H)-furanone;
4-(4-Chlorophenyl)-2,2-dimethyl-5-{3-fluoro-4-(methylthio)phenyl}-3(2H)-furanone;
4-(4-Chlorophenyl)-2,2-dimethyl-5-{3-fluoro-4-(methylsulfinyl)phenyl}-3(2H)-furanone;
4-(4-Chlorophenyl)-2,2-dimethyl-5-{3-fluoro-4-(methylsulfonyl)phenyl}-3(2H)-furanone;
5-{4-(Aminosulfonyl)-3-fluorophenyl}-4-(4-chlorophenyl)-2,2-dimethyl-3(2H)-furanone;
4-(3,4-Dichlorophenyl)-2,2-dimethyl-5-{3-fluoro-4-(methylthio)phenyl}-3(2H)-furanone;
4-(3,4-Dichlorophenyl)-2,2-dimethyl-5-{3-fluoro-4-(methylsulfinyl)phenyl}-3(2H)-furanone;
4-(3,4-Dichlorophenyl)-2,2-dimethyl-5-{3-fluoro4-(methylsulfonyl)phenyl}-3(2H)-furanone;
5-{4-(Aminosulfonyl)-3-fluorophenyl}-4-(3,4-dichlorophenyl)-2,2-dimethyl-3(2H)-furanone;
2,2-Dimethyl-5-{3-fluoro-4-(methylthio)phenyl}-4-(2-fluorophenyl)-3(2H)-furanone;

2,2-Dimethyl-5-{3-fluoro-4-(methylsulfinyl)phenyl}-4-(2-fluorophenyl)-3(2H)-furanone;
2,2-Dimethyl-5-{3-fluoro-4-(methylsulfonyl)phenyl}-4-(2-fluorophenyl)-3(2H)-furanone;
5-{4-(Aminosulfonyl)-3-fluorophenyl}-2,2-dimethyl-4-(2-fluorophenyl)-3(2H)-furanone;
2,2-Dimethyl-5-{3-fluoro-4-(methylthio)phenyl}-4-(3-fluorophenyl)-3(2H)-furanone;
2,2-Dimethyl-5-{3-fluoro-4-(methylsulfinyl)phenyl}-4-(3-fluorophenyl)-3(2H)-furanone;
2,2-Dimethyl-5-{3-fluoro-4-(methylsulfonyl)phenyl}-4-(3-fluorophenyl)-3(2H)-furanone;
5-{4-(Aminosulfonyl)-3-fluorophenyl}-2,2-dimethyl-4-(3-fluorophenyl)-3(2H)-furanone;
2,2-Dimethyl-5-{3-fluoro-4-(methylthio)phenyl}-4-(4-fluorophenyl)-3(2H)-furanone;
2,2-Dimethyl-5-{3-fluoro-4-(methylsulfinyl)phenyl}-4-(4-fluorophenyl)-3(2H)-furanone;
2,2-Dimethyl-5-{3-fluoro-4-(methylsulfonyl)phenyl}-4-(4-fluorophenyl)-3(2H)-furanone;
5-{4-(Aminosulfonyl)-3-fluorophenyl}-2,2-dimethyl-4-(4-fluorophenyl)-3(2H)-furanone;
4-(2,4-Difluorophenyl)-2,2-dimethyl-5-{3-fluoro-4-(methylthio)phenyl}-3(2H)-furanone;
4-(2,4-Difluorophenyl)-2,2-dimethyl-5-{3-fluoro-4-(methylsulfinyl)phenyl}-3(2H)-furanone;
4-(2,4-Difluorophenyl)-2,2-dimethyl-5-{3-fluoro-4-(methylsulfonyl)phenyl}-3(2H)-furanone;
5-{4-(Aminosulfonyl)-3-fluorophenyl}-4-(2,4-difluorophenyl)-2,2-dimethyl-3(2H)-furanone;
4-(2,5-Difluorophenyl)-2,2-dimethyl-5-{3-fluoro-4-(methylthio)phenyl}-3(2H)-furanone;
4-(2,5-Difluorophenyl)-2,2-dimethyl-5-{3-fluoro-4-(methylsulfinyl)phenyl}-3(2H)-furanone;
4-(2,5-Difluorophenyl)-2,2-dimethyl-5-{3-fluoro-4-(methylsulfonyl)phenyl}-3(2H)-furanone;
5-{4-(Aminosulfonyl)-3-fluorophenyl}-4-(2,5-difluorophenyl)-2,2-dimethyl-3(2H)-furanone;
4-(2,6-Difluorophenyl)-2,2-dimethyl-5-{3-fluoro-4-(methylthio)phenyl}-3(2H)-furanone;
4-(2,6-Difluorophenyl)-2,2-dimethyl-5-{3-fluoro-4-(methylsulfinyl)phenyl}-3(2H)-furanone;
4-(2,6-Difluorophenyl)-2,2-dimethyl-5-{3-fluoro-4-(methylsulfonyl)phenyl}-3(2H)-furanone;
5-{4-(Aminosulfonyl)-3-fluorophenyl}-4-(2,6-difluorophenyl)-2,2-dimethyl-3(2H)-furanone;
4-(3,4-Difluorophenyl)-2,2-dimethyl-5-{3-fluoro-4-(methylthio)phenyl}-3(2H)-furanone;
4-(3,4-Difluorophenyl)-2,2-dimethyl-5-{3-fluoro-4-(methylsulfinyl)phenyl}-3(2H)-furanone;
4-(3,4-Difluorophenyl)-2,2-dimethyl-5-{3-fluoro-4-(methylsulfonyl)phenyl}-3(2H)-furanone;
5-{4-(Aminosulfonyl)-3-fluorophenyl}-4-(3,4-difluorophenyl)-2,2-dimethyl-3(2H)-furanone;
4-(3,5-Difluorophenyl)-2,2-dimethyl-5-{3-fluoro-4-(methylthio)phenyl}-3(2H)-furanone;
4-(3,5-Difluorophenyl)-2,2-dimethyl-5-{3-fluoro-4-(methylsulfinyl)phenyl}-3(2H)-furanone;
4-(3,5-Difluorophenyl)-2,2-dimethyl-5-{3-fluoro-4-(methylsulfonyl)phenyl}-3(2H)-furanone;
5-{4-(Aminosulfonyl)-3-fluorophenyl}-4-(3,5-difluorophenyl)-2,2-dimethyl-3(2H)-furanone;
2,2-Dimethyl-5-{3-fluoro-4-(methylthio)phenyl}-4-(2-trifluoromethylphenyl)-3(2H)-furanone;
2,2-Dimethyl-5-{3-fluoro-4-(methylsulfinyl)phenyl}-4-(2-trifluoromethylphenyl)-3(2H)-furanone;
2,2-Dimethyl-5-{3-fluoro-4-(methylsulfonyl)phenyl}-4-(2-trifluoromethylphenyl)-3(2H)-furanone;
5-{4-(Aminosulfonyl)-3-fluorophenyl}-2,2-dimethyl-4-(2-trifuoromethylphenyl)-3(2H)-furanone;
2,2-Dimethyl-5-{3-fluoro-4-(methylthio)phenyl}-4-(3-trifluoromethylphenyl)-3(2H)-furanone;
2,2-Dimethyl-5-{3-fluoro-4-(methylsulfinyl)phenyl}-4-(3-trifluoromethylphenyl)-3(2H)-furanone;
2,2-Dimethyl-5-{3-fluoro-4-(methylsulfonyl)phenyl}-4-(3-trifluoromethylphenyl)-3(2H)-furanone;
5-{4-(Aminosulfonyl)-3-fluorophenyl}-2,2-dimethyl-4-(3-trifluoromethylphenyl)-3(2H)-furanone;
2,2-Dimethyl-5-{3-fluoro-4-(methylthio)phenyl}-4-(4-trifluoromethylphenyl)-3(2H)-furanone;
2,2-Dimethyl-5-{3-fluoro-4-(methylsulfinyl)phenyl}-4-(4-trifluoromethylphenyl)-3(2H)-furanone;
2,2-Dimethyl-5-{3-fluoro-4-(methylsulfonyl)phenyl}-4-(4-trifluoromethylphenyl)-3(2H)-furanone;
5-{4-(Aminosulfonyl)-3-fluorophenyl}-2,2-dimethyl-4-(4-trifluoromethylphenyl)-3(2H)-furanone;
2,2-Dimethyl-5-{3-fluoro-4-(methylthio)phenyl}-4-(4-nitrophenyl)-3(2H)-furanone;
2,2-Dimethyl-5-{3-fluoro-4-(methylsulfinyl)phenyl}-4-(4-nitrophenyl)-3(2H)-furanone;
2,2-Dimethyl-5-{3-fluoro-4-(methylsulfonyl)phenyl}-4-(4-nitrophenyl)-3(2H)-furanone;
5-{4-(Aminosulfonyl)-3-fluorophenyl}-2,2-dimethyl-4-(4-nitrophenyl)-3(2H)-furanone;
4-(4-Aminophenyl)-2,2-dimethyl-5-{3-fluoro-4-(methylthio)phenyl}-3(2H)-furanone;
4-(4-Aminophenyl)-2,2-dimethyl-5-{3-fluoro 4-(methylsulfinyl)phenyl}-3(2H)-furanone;
4-(4-Aminophenyl)-2,2-dimethyl-5-{3-fluoro-4-(methylsulfonyl)phenyl}-3(2H)-furanone;
4(4-Aminophenyl)-5-{4-(aminosulfonyl)-3-fluorophenyl}-2,2-dimethyl-3(2H)-furanone;
4-{4-(Acetylamino)phenyl}-2,2-dimethyl-5-{3-fluoro-4-(methylthio)phenyl}-3(2H)-furanone;
4-{4-(Acetylamino)phenyl}-2,2-dimethyl-5-{3-fluoro-4-(methylsulfinyl)phenyl}-3(2H)-furanone;
4-{4-(Acetylamino)phenyl}-2,2-dimethyl-5-{3-fluoro-4-(methylsulfonyl)phenyl}-3(2H) furanone;
4-{4-(Acetylamino)phenyl}-5-{4-(aminosulfonyl)-3-fluorophenyl}-2,2-dimethyl-3(2H)-furanone;
2,2-Dimethyl-5-{3-fluoro-4-(methylthio)phenyl}-4-(3-methoxyphenyl)-3(2H)-furanone;
2,2-Dimethyl-5-{3-fluoro-4-(methylsulfonyl)phenyl}-4-(3-methoxyphenyl)-3(2H)-furanone;
2,2-Dimethyl-5-{2-fluoro-4-(methylthio)phenyl}-4-phenyl-3(2H)-furanone;
2,2-Dimethyl-5-{2-fluoro-4-(methylsulfinyl)phenyl}-4-phenyl-3(2H)-furanone;
2,2-Dimethyl-5-{2-fluoro-4-(methylsulfonyl)phenyl}-4-phenyl-3(2H)-furanone;
5-{4-(Aminosulfonyl)-2-fluorophenyl}-2,2-dimethyl-4-phenyl-3(2H)-furanone;
4-(2-Chlorophenyl)-2,2-dimethyl-5-{2-fluoro-4-(methylthio)phenyl}-3(2H)-furanone;
4-(2-Chlorophenyl)-2,2-dimethyl-5-{2-fluoro-4-(methylsulfinyl)phenyl}-3(2H)-furanone;
4-(2-Chlorophenyl)-2,2-dimethyl-5-{2-fluoro-4-(methylsulfonyl)phenyl}-3(2H)-furanone;
5-{4-(Aminosulfonyl)-2-fluorophenyl}-4-(2-chlorophenyl)-2,2-dimethyl-3(2H)-furanone;
4-(3-Chlorophenyl)-2,2-Dimethyl-5-{2-fluoro-4-(methylthio)phenyl}-3(2H)-furanone;
4-(3-Chlorophenyl)-2,2-dimethyl-5-{2-fluoro-4-(methylsulfinyl)phenyl}-3(2H)-furanone;
4-(3-Chlorophenyl)-2,2-Dimethyl-5-{2-fluoro-4-(methylsulfonyl)phenyl}-3(2H)-furanone;

5-{4-(Aminosulfonyl)-2-fluorophenyl}-4-(3-chlorophenyl)-2,2-dimethyl-3(2H)-furanone;
2,2-Dimethyl-5-{2-fluoro-4-(methylthio)phenyl}-4-(2-fluorophenyl)-3(2H)-furanone;
2,2-Dimethyl-5-{2-fluoro-4-(methylsulfinyl)phenyl}-4-(2-fluorophenyl)-3(2H)-furanone;
2,2-Dimethyl-5-{2-fluoro-4-(methylsulfonyl)phenyl}-4-(2-fluorophenyl)-3(2H)-furanone;
5-{4-(Aminosulfonyl)-2-fluorophenyl}-2,2-dimethyl-4-(2-fluorophenyl)-3(2H)-furanone;
2,2-Dimethyl-5-{2-fluoro-4-(methylthio)phenyl}-4-(3-fluorophenyl)-3(2H)-furanone;
2,2-Dimethyl-5-{2-fluoro-4-(methylsulfinyl)phenyl}-4-(3-fluorophenyl)-3(2H)-furanone;
2,2-Dimethyl-5-{2-fluoro-4-(methylsulfonyl)phenyl}-4-(3-fluorophenyl)-3(2H)-furanone;
5-{4-(Aminosulfonyl)-2-fluorophenyl}-2,2-dimethyl-4-(3-fluorophenyl)-3(2H)-furanone;
2,2-Dimethyl-5-{2-fluoro-4-(methylthio)phenyl}-4-(4-fluorophenyl)-3(2H)-furanone;
2,2-Dimethyl-5-{2-fluoro-4-(methylsulfinyl)phenyl}-4-(4-fluorophenyl)-3(2H)-furanone;
2,2-Dimethyl-5-{2-fluoro-4-(methylsulfonyl)phenyl}-4-(4-fluorophenyl)-3(2H)-furanone;
5-{4-(Aminosulfonyl)-2-fluorophenyl}-2,2-dimethyl-4-(4-fluorophenyl)-3(2H)-furanone;
4-(2,4-Difluorophenyl)-2,2-dimethyl-5-{2-fluoro-4-(methylthio)phenyl}-3(2H)-furanone;
4-(2,4-Difluorophenyl)-2,2-dimethyl-5-{2-fluoro-4-(methylsulfinyl)phenyl}-3(2H)-furanone;
4-(2,4-Difluorophenyl)-2,2-dimethyl-5-{2-fluoro-4-(methylsulfonyl)phenyl}-3(2H)-furanone;
5-{4-(Aminosulfonyl)-2-fluorophenyl}-4-(2,4-difluorophenyl)2,2-dimethyl-3(2H)-furanone;
4-(2,5-Difluorophenyl)-2,2-dimethyl-5-{2-fluoro-4-(methylthio)phenyl}-3(2H)-furanone;
4-(2,5-Difluorophenyl)-2,2-dimethyl-5-{2-fluoro-4-(methylsulfinyl)phenyl}-3(2H)-furanone;
4-(2,5-Difluorophenyl)-2,2-dimethyl-5-{2-fluoro-4-(methylsulfonyl)phenyl}-3(2H)-furanone;
5-{4-(Aminosulfonyl)-2-fluoropheny}-4-(2,5-difluorophenyl)-2,2-dimethyl-3(2H)-furanone;
4-(3,4-Difluorophenyl)-2,2-dimethyl-5-{2-fluoro-4-(methylthio)phenyl}-3(2H)-furanone;
4-(3,4-Difluorophenyl)-2,2-dimethyl-5-{2-fluoro-4-(methylsulfinyl)phenyl}-3(2H)-furanone;
4-(3,4-Difluorophenyl)-2,2-dimethyl-5-{2-fluoro-4-(methylsulfonyl)phenyl}-3(2H)-furanone;
5-{4-(Aminosulfonyl)-2-fluorophenyl}-4-(3,4-difluorophenyl)-2,2-dimethyl-3(2H)-furanone;
4-(3,5-Difluorophenyl)-2,2-dimethyl-5-{2-fluoro-4-(methylthio)phenyl}-3(2H)-furanone;
4-(3,5-Difluorophenyl)-2,2-dimethyl-5-{2-fluoro-4-(methylsulfinyl)phenyl}-3(2H)-furanone;
4-(3,5-Difluorophenyl)-2,2-dimethyl-5-{2-fluoro-4-(methylsulfonyl)phenyl}-3(2H)-furanone;
5-{4-(Aminosulfonyl)-2-fluorophenyl}-4-(3,5-difluorophenyl)-2,2-dimethyl-3(2H)-furanone;
2,2-Dimethyl-5-{2-fluoro-4-(methylthio)phenyl}-4-(3-trifluoromethylphenyl)-3(2H)-furanone;
2,2-Dimethyl-5-{2-fluoro-4-(methylsulfinyl)phenyl}-4-(3-trifluoromethylphenyl)-3(2H)-furanone;
2,2-Dimethyl-5-{2-fluoro-4-(methylsulfonyl)phenyl}-4-(3-trifluoromethylphenyl)-3(2H)-furanone;
5-{4-(Aminosulfonyl)-2-fluorophenyl}-2,2-dimethyl-4-(3-trifluoromethylphenyl)-3(2H)-furanone;
5-{3-Bromo-4-(methylthio)phenyl}-2,2-dimethyl-4-phenyl-3(2H)-furanone;
5-{3-Bromo-4-(methylsulfonyl)phenyl}-2,2-dimethyl-4-phenyl-3(2H)-furanone;
5-{3-Bromo-4-(methylsulfinyl)phenyl}-2,2-dimethyl-4-phenyl-3(2H)-furanone;
5-{4-(Aminosulfonyl)-3-bromophenyl}-2,2-dimethyl-4-phenyl-3(2H)-furanone;
5-{3-Bromo-4-(methylthio)phenyl}-4-(3-chlorophenyl)-2,2dimethyl-3(2H)-furanone;
5-{3-Bromo-4-(methylsulfonyl)phenyl}-4-(3-chlorophenyl)-2,2-dimethyl-3(2H)-furanone;
5-{3-Bromo-4-(methylsulfinyl)phenyl}-4-(3-chlorophenyl)-2,2-dimethyl-3(2H)-furanone;
5-{4-(Aminosulfonyl)-3-bromophenyl}-4-(3-chlorophenyl)-2,2-dimethyl-3(2H)-furanone;
5-{3-Bromo-4-(methylthio)phenyl}-4-(4-chlorophenyl)-2,2-dimethyl-3(2H)-furanone;
5-{3-Bromo-4-(methylsulfonyl)phenyl}-4-(4-chlorophenyl)-2,2-dimethyl-3(2H)-furanone;
5-{3-Bromo-4-(methylsulfinyl)phenyl}-4-(4-chlorophenyl)-2,2-dimethyl-3(2H)-furanone;
5-{4-(Aminosulfonyl)-3-bromophenyl}-4-(4-chlorophenyl)-2,2-dimethyl-3(2H)-furanone;
5-{3-Bromo-4-(methylthio)phenyl}-2,2-dimethyl-4-(3-fluorophenyl)-3(2H)-furanone;
5-{3-Bromo-4-(methylsulfonyl)phenyl}-2,2-dimethyl-4-(3-fluorophenyl)-3(2H)-furanone;
5-{3-Bromo-4-(methylsulfinyl)phenyl}-2,2-dimethyl-4-(3-fluorophenyl)-3(2H)-furanone;
5-{4-(Aminosulfonyl)-3-bromophenyl}-2,2-dimethyl-4-(3-fluorophenyl)-3(2H)-furanone;
5-{3-Bromo-4-(methylthio)phenyl}-2,2-dimethyl-4-(4-fluorophenyl)-3(2H)-furanone;
5-{3-Bromo-4-(methylsulfonyl)phenyl}-2,2-dimethyl-4-(4-fluorophenyl)-3(2H)-furanone;
5-{3-Bromo-4-(methylsulfinyl)phenyl}-2,2-dimethyl-4-(4-fluorophenyl)-3(2H)-furanone;
5-{4-(Aminosulfonyl)-3-bromophenyl}-2,2-dimethyl-4-(4-fluorophenyl)-3(2H)-furanone;
5-{3-Bromo-4-(methylthio)phenyl}-4-(2,4-difluorophenyl)-2,2-dimethyl-3(2H)-furanone;
5-{3-Bromo-4(methylsulfonyl)phenyl}-4-(2,4-difluorophenyl)-2,2-dimethyl-3(2H)-furanone;
5-{3-Bromo-4-(methylsulfinyl)phenyl}-4-(2,4-difluorophenyl)-2,2-dimethyl-3(2H)-furanone;
5-{4-(Aminosulfonyl)-3-bromophenyl}-4-(2,4-difluorophenyl)-2,2-dimethyl-3(2H)-furanone;
5-{3-Bromo-4-(methylthio)phenyl}-4-(2,5-difluorophenyl)-2,2-dimethyl-3(2H)-furanone;
5-{3-Bromo-4-(methylsulfonyl)phenyl}-4-(2,5-difluorophenyl)-2,2-dimethyl-3(2H)-furanone;
5-{3-Bromo-4-(methylsulfinyl)phenyl}-4-(2,5-difluorophenyl)-2,2-dimethyl-3(2H)-furanone;
5-{4-(Aminosulfonyl)-3-bromophenyl}-4-(2,5-difluorophenyl)-2,2-dimethyl-3(2H)-furanone;
5-{3-Bromo-4-(methylthio)phenyl}-4-(3,5-difluorophenyl)-2,2-dimethyl-3(2H)-furanone;
5-{3-Bromo-4-(methylsulfonyl)phenyl}-4-(3,5-difluorophenyl)-2,2-dimethyl-3(2H)-furanone;
5-{3-Bromo-4-(methylsulfinyl)phenyl}-4-(3,5-difluorophenyl)-2,2-dimethyl-3(2H)-furanone;
5-{4-(Aminosulfonyl)-3-bromophenyl}-4-(3,5-difluorophenyl)-2,2-dimethyl-3(2H)-furanone;
5-{3-Bromo-4-(methylthio)phenyl}-2,2-dimethyl-4-(3-trifluoromethylphenyl)-3(2H)-furanone;
5-{3-Bromo-4-(methylsulfonyl)phenyl}-2,2-dimethyl-4-(3-trifluoromethylphenyl)-3(2H)-furanone;
5-{3-Bromo-4-(methylsulfinyl)phenyl}-2,2-dimethyl-4-(3-trifluoromethylphenyl)-3(2H)-furanone;

5-{4-(Aminosulfonyl)-3-bromophenyl}-2,2-dimethyl-4-(3-trifluoromethylphenyl)-3(2H)-furanone;
5-{3-Chloro-4-(methylthio)phenyl}-2,2-dimethyl-4-phenyl-3(2H)-furanone;
5-{3-Chloro-4-(methylsulfonyl)phenyl}-2,2-dimethyl-4-phenyl-3(2H)-furanone;
5-{3-Chloro-4-(methylsulfinyl)phenyl}-2,2-dimethyl-4-phenyl-3(2H)-furanone;
5-{4-(Aminosulfonyl)-3-chlorophenyl}-2,2-dimethyl-4-phenyl-3(2H)-furanone;
5-{3-Chloro-4-(methylthio)phenyl}-4-(3-chlorophenyl)-2,2-dimethyl-3(2H)-furanone:
5-{3-Chloro-4-(methylsulfonyl)phenyl}-4-(3-chlorophenyl)-2,2-dimethyl-3(2H)-furanone;
5-{3-Chloro-4-(methylsulfinyl)phenyl}-4-(3-chlorophenyl)-2,2-dimethyl-3(2H)-furanone;
5-{4-(Aminosulfonyl)-3-chlorophenyl}-4-(3-chlorophenyl)-2,2-dimethyl-3(2H)-furanone;
5-{3-Chloro-4-(methylthio)phenyl}-4-(4-chlorophenyl)-2,2-dimethyl-3(2H)-furanone;
5-{3-Chloro-4-(methylsulfonyl)phenyl}-4-(4-chlorophenyl)-2,2-dimethyl-3(2H)-furanone;
5-{3-Chloro-4-(methylsulfinyl)phenyl}-4-(4-chlorophenyl)-2,2-dimethyl-3(2H)-furanone;
5-{4-(Aminosulfonyl)-3-chlorophenyl}-4-(4-chlorophenyl)-2,2-dimethyl-3(2H)-furanone;
5-{3-Chloro-4-(methylthio)phenyl}-4-(3-fluorophenyl)-2,2-dimethyl-3(2H)-furanone;
5-{3-Chloro-4-(methylsulfonyl)phenyl}-4-(3-fluorophenyl)-2,2-dimethyl-3(2H)-furanone;
5-{3-Chloro-4-(methylsulfinyl)phenyl}-4-(3-fluorophenyl)-2,2-dimethyl-3(2H)-furanone;
5-{4-(Aminosulfonyl)-3-chlorophenyl}-4-(3-fluorophenyl)-2,2-dimethyl-3(2H)-furanone;
5-{3-Chloro-4-(methylthio)phenyl}-4-(4-fluorophenyl)-2,2-dimethyl-3(2H)-furanone;
5-{3-Chloro-4-(methylsulfonyl)phenyl}-4-(4-fluorophenyl)-2,2-dimethyl-3(2H)-furanone;
5-{3-Chloro-4-(methylsulfinyl)phenyl}-4-(4-fluorophenyl)-2,2-dimethyl-3(2H)-furanone;
5-{4-(Aminosulfonyl)-3-chlorophenyl}-4-(4-fluorophenyl)-2,2-dimethyl-3(2H)-furanone;
5-{3-Chloro-4-(methylthio)phenyl}-4-(2,4-difluorophenyl)-2,2-dimethyl-3(2H)-furanone;
5-{3-Chloro-4-(methylsulfonyl)phenyl}-4-(2,4-difluorophenyl)-2,2-dimethyl-3(2H)-furanone;
5-{3-Chloro-4-(methylsulfinyl)phenyl}-4-(2,4-difluorophenyl)-2,2-dimethyl-3(2H)-furanone;
5-{4-(Aminosulfonyl)-3-chlorophenyl}-4-(2,4-difluorophenyl)-2,2-dimethyl-3(2H)-furanone;
5-{3-Chloro-4-(methylthio)phenyl}-4-(2,5-difluorophenyl)-2,2-dimethyl-3(2H)-furanone;
5-{3-Chloro-4-(methylsulfonyl)phenyl}-4-(2,5-difluorophenyl)-2,2-dimethyl-3(2H)-furanone;
5-{3-Chloro-4-(methylsulfinyl)phenyl}-4-(2,5-difluorophenyl)-2,2-dimethyl-3(2H)-furanone;
5-{4-(Aminosulfonyl)-3-chlorophenyl}-4-(2,5-difluorophenyl)-2,2-dimethyl-3(2H)-furanone;
5-{3-Chloro-4-(methylthio)phenyl}-4-(3,4-difluorophenyl)-2,2-dimethyl-3(2H)-furanone;
5-{3-Chloro-4-(methylsulfonyl)phenyl}-4-(3,4-difluorophenyl)-2,2-dimethyl-3(2H)-furanone;
5-{3-Chloro-4-(methylsulfinyl)phenyl}-4-(3,4-difluorophenyl)-2,2-dimethyl-3(2H)-furanone;
5-{4-(Aminosulfonyl)-3-chlorophenyl}-4-(3,4-difluorophenyl)-2,2-dimethyl-3(2H)-furanone;
5-{3-Chloro-4-(methylthio)phenyl}-4-(3,5-difluorophenyl)-2,2-dimethyl-3(2H)-furanone;
5-{3-Chloro-4-(methylsulfonyl)phenyl}-4-(3,5-difluorophenyl)-2,2-dimethyl-3(2H)-furanone;
5-{3-Chloro-4-(methylsulfinyl)phenyl}-4-(3,5-difluorophenyl)-2,2-dimethyl-3(2H)-furanone;
5-{4-(Aminosulfonyl)-3-chlorophenyl}-4-(3,5-difluorophenyl)-2,2-dimethyl-3(2H)-furanone;
4-(3,5-Difluorophenyl)-2,2-dimethyl-5-{3-methyl-4-(methylthio)phenyl}-3(2H)-furanone;
4-(3,5-Difluorophenyl)-2,2-dimethyl-5-{3-methyl-4-(methylsulfinyl)phenyl}-3(2H)-furanone;
4-(3,5-Difluorophenyl)-2,2-dimethyl-5-{3-methyl-4-(methylsulfonyl)phenyl}-3(2H)-furanone;
5-{4-(Aminosulfonyl)-3-methylphenyl}-4-(3,5-difluorophenyl)-2,2-dimethyl-3(2H)-furanone;
5-{3-Chloro-4-(methylthio)phenyl}-2,2-dimethyl-4-(3-trifluoromethylphenyl)-3(2H)-furanone;
5-{3-Chloro-4-(methylsulfonyl)phenyl}-2,2-dimethyl-4-(3-trifluoromethylphenyl)-3(2H)-furanone;
5-{3-Chloro-4-(methylsulfinyl)phenyl}-2,2-dimethyl-4-(3-trifluoromethylphenyl)-3(2H)-furanone;
5-{4-(Aminosulfonyl)-3-chlorophenyl}-2,2-dimethyl-4-(3-trifluoromethylphenyl)-3(2H)-furanone;
5-{2-Chloro-4-(methylthio)phenyl}-2,2-dimethyl-4-phenyl-3(2H)-furanone;
5-{2-Chloro-4-(methylsulfinyl)phenyl}-2,2-dimethyl-4-phenyl-3(2H)-furanone;
5-{2-Chloro-4-(methylsulfonyl)phenyl}-2,2-dimethyl-4-phenyl-3(2H)-furanone;
5-{4-(Aminosulfonyl)-2-chlorophenyl}-2,2-dimethyl-4-phenyl-3(2H)-furanone;
5-{2-Chloro-4-(methylthio)phenyl}-4-(3-chlorophenyl)-2,2-dimethyl-3(2H)-furanone;
5-{2-Chloro-4-(methylsulfonyl)phenyl}-4-(3-chlorophenyl)-2,2-dimethyl-3(2H)-furanone;
5-{2-Chloro-4-(methylsulfinyl)phenyl}-4-(3-chlorophenyl)-2,2-dimethyl-3(2H)-furanone;
5-{4-(Aminosulfonyl)-2-chlorophenyl}-4-(3chlorophenyl)-2,2-dimethyl-3(2H)-furanone;
5-{2-Chloro-4-(methylthio)phenyl}-2,2-dimethyl-4-(3-fluorophenyl)-3(2H)-furanone;
5-{2-Chloro-4-(methylsulfinyl)phenyl}-2,2-dimethyl-4-(3-fluorophenyl)-3(2H)-furanone;
5-{2-Chloro-4-(methylsulfonyl)phenyl}-2,2-dimethyl-4-(3-fluorophenyl)-3(2H)-furanone;
5-{4-(Aminosulfonyl)-2-chlorophenyl}-2,2-dimethyl-4-(3-fluorophenyl)-3(2H)-furanone;
5-{2-Chloro-4-(methylthio)phenyl}-2,2-dimethyl-4-(4-fluorophenyl)-3(2H)-furanone;
5-{2-Chloro-4-(methylsulfinyl)phenyl}-2,2-dimethyl-4-(4-fluorophenyl)-3(2H)-furanone;
5-{2-Chloro-4-(methylsulfonyl)phenyl}-2,2-dimethyl-4-(4-fluorophenyl)-3(2H)-furanone;
5-{4-(Aminosulfonyl)-2-chlorophenyl}-2,2-dimethyl-4-(4-fluorophenyl)-3(2H)-furanone;
5-{2-Chloro-4-(methylthio)phenyl}-4-(2,5-difluorophenyl)-2,2-dimethyl-3(2H)-furanone;
5-{2-Chloro-4-(methylsulfonyl)phenyl}-4-(2,5-difluorophenyl)-2,2-dimethyl-3(2H)-furanone;
5-{2-Chloro-4-(methylsulfinyl)phenyl}-4(2,5-difluorophenyl)-2,2-dimethyl-3(2H)-furanone;
5-{4-(Aminosulfonyl)-2-chlorophenyl}-4-(2,5-difluorophenyl)-2,2-dimethyl-3(2H)-furanone;
5-{2-Chloro-4-(methylthio)phenyl}-4-(3,5-difluorophenyl)-2,2-dimethyl-3(2H)-furanone;
5-{2-Chloro-4-(methylsulfonyl)phenyl}-4-(3,5-difluorophenyl)-2,2-dimethyl-3(2H)-furanone;
5-{2-Chloro-4-(methylsulfinyl)phenyl}-4-(3,5-difluorophenyl)-2,2-dimethyl-3(2H)-furanone;

5-{4-(Aminosulfonyl)-2-chlorophenyl}-4-(3,5-difluorophenyl)-2,2-dimethyl-3(2H)-furanone;

2,2-Dimethyl-5-{3-methyl-4-(methylthio)phenyl}-4-phenyl-3(2H)-furanone 2,2-Dimethyl-5-{3-methyl-4-(methylsulfinyl)phenyl}-4-phenyl-3(2H)-furanone;

2,2-Dimethyl-5-{3-methyl 4-(methylsulfonyl)phenyl}-4-phenyl-3(2H)-furanone;

5-{4-(Aminosulfonyl)-3-methylphenyl}-2,2-dimethyl-4-phenyl-3(2H)-furanone;

2,2-Dimethyl-4-(3-fluorophenyl)-5-{3-methyl-4-(methylthio)phenyl}-3(2H)-furanone;

2,2-Dimethyl-4-(3-fluorophenyl)-5-{3-methyl-4-(methylsulfinyl)phenyl}-3(2H)-furanone;

2,2-Dimethyl-4-(3-fluorophenyl)-5-{3-methyl-4-(methylsulfonyl)phenyl}-3(2H)-furanone;

5-{4-(Aminosulfonyl)-3-methylphenyl}-2,2-dimethyl-4-(3-fluorophenyl)-3(2H)-furanone;

4-(3,5-Difluorophenyl)-2,2-dimethyl-5-{3-methyl 4 (methylthio)phenyl}-3(2H)-furanone 4-(3,5-Difluorophenyl)-2,2-dimethyl-5-{3-methyl-4-(methylsulfinyl)phenyl}-3(2H)-furanone;

4-(3,5-Difluorophenyl)-2,2-dimethyl-5-{3-methyl-4-(methylsulfonyl)phenyl}-3(2H)-furanone;

5-{4-(Aminosulfonyl)-3-methylphenyl}-4-(3,5-difluorophenyl)-2,2-dimethyl-3(2H)-furanone;

5-{3-Chloro-4-(N-methylaminosulfonyl)phenyl}-2,2-dimethyl-4-phenyl-3(2H)-furanone 5-{3-Chloro-4-(N-ethylaminosulfonyl)phenyl}-2,2-dimethyl-4-phenyl-3(2H)-furanone 5-[4-{(Acetylamino)sulfonyl}-3-chlorophenyl]-2,2-dimethyl-4-phenyl-3(2H)-furanone;

5-[3-Chloro-4-{(N-n-propionylamino)sulfonyl}phenyl]-2,2-dimethyl-4-phenyl-3(2H)-furanone;

5-[3-Chloro-4-{(N-n-butyrylamino)sulfonyl}phenyl]-2,2-dimethyl-4-phenyl-3(2H)-furanone;

4-(3-Chlorophenyl)-2,2-dimethyl-5-{3-fluoro-4-(methylthio)phenyl}-(2H)-furan-3-thion 4-(3-Chlorophenyl)-2,2-dimethyl-5-{3-fluoro-4-(methylsulfonyl)phenyl}-(2H)-furan-3-thion 4-(3-Chlorophenyl)-2,2-dimethyl-5-{3-fluoro-4-(methylsulfinyl)phenyl}-(2H)-furan-3-thion 5-{4-(Aminosulfonyl)-3-fluorophenyl}-4-(3-chlorophenyl)-2,2-dimethyl-(2H)-furan-3-thion 4-(3,5-Difluorophenyl)-2,2-dimethyl-5-{3-fluoro-(4-methylthio)phenyl}-(2H)-furan-3-thione;

4-(3,5-Difluorophenyl)-2,2-dimethyl-5-{3-fluoro-(4-methylsulfonyl)phenyl}-(2H)-furan-3-thione;

4-(3,5-Difluorophenyl)-2,2-dimethyl-5-{3-fluoro-(4-methylsulfinyl)phenyl}-(2H)-furan-3-thione;

5-{(4-Aminosulfonyl)-3-fluorophenyl}-4-(3,5-difluorophenyl)-2,2dimethyl-(2H)-furan-3-thione.

Within Formula I there is a subclass of compounds of high interest represented by Formula V:

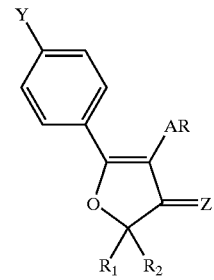

V wherein Y represents alkylsulfonyl, aminosulfonyl, alkylsulfinyl, (N-acylamino)sulfonyl, (N-alkylamino) sulfonyl, or alkylthio; wherein Z represents oxygen or sulfur atom; wherein $R_1$ and $R_2$ are independently selected from methyl and ethyl radical; and wherein AR is a substituted or non-substituted aromatic group of 5 to 10 atoms excluding substituted or non-substituted phenyl group; or a pharmaceutically-acceptable salt thereof.

A preferred class of compounds comprises those compounds of Formula V, wherein Y is selected from (lower alkyl)sulfonyl, aminosulfonyl, and (lower N-acylamino) sulfonyl; wherein Z is selected from oxygen and sulfur atom; wherein $R_1$ and $R_2$ are independently selected from methyl and ethyl radical; and wherein AR is selected from the following specific aromatic groups:

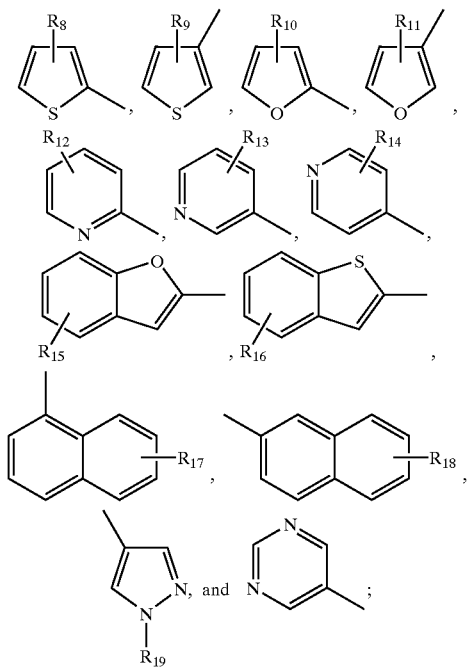

wherein, each of $R_8$ to $R_{19}$, if present, is selected from hydrido, halo, lower alkyl, lower acyl, lower haloalkyl, lower alkoxy, formyl, cyano, nitro, amino, azido, and N-acylamino; or a pharmaceutically acceptable salt thereof.

A class of compounds of particular interest encompasses those compounds of Formula V, wherein Y is selected from methylsulfonyl, ethylsulfonyl, aminosulfonyl, (N-acetylamino)sulfonyl, and (N-propionylamino)sulfonyl; wherein Z is selected from oxygen and sulfur atom; wherein $R_1$ and $R_2$ are independently selected from methyl and ethyl radical; and wherein each of $R_8$ to $R_{19}$, if present, is selected from hydrido, fluoro, chloro, bromo, methyl, ethyl, isopropyl, acetyl, n-proionyl, trifluoromethyl, methoxy, ethoxy, and formyl; or a pharmaceutically acceptable salt thereof.

A family of specific compounds of particular interest within Formula V comprises compounds and pharmaceutically-acceptable salts thereof as follows:

2,2-Dimethyl-5-{4-(methylthio)phenyl}-4-(3-thienyl)-3(2H)-furanone;
2,2-Dimethyl-4-{2-(3-methylthienyl)}-5-{4-(methylsulfonyl)phenyl}-3(2H)-furanone;
2,2-Dimethyl-4-{2-(5-formylthienyl)}-5-{4-(methylsulfonyl)phenyl}-3(2H)-furanone;
4-(2-Benzo[b]thienyl)-2,2-dimethyl-5-{4-(methylsulfonyl)phenyl}-3(2H)-furanone;
2,2-Dimethyl-5-{4-(methylsulfonyl)phenyl}-4-(1-naphthyl)-3(2H)-furanone;
2,2-Dimethyl-5-{4-(methylsulfonyl)phenyl}-4-(3-pyridyl)-3(2H)-furanone;
2,2-Dimethyl-5-{4-(methylsulfonyl)phenyl}-4-(2-pyridyl)-3(2H)-furanone;
4-(2-Benzo[b]furanyl)-2,2-dimethyl-5-{4-(methylsulfonyl)phenyl}-3(2H)-furanone;
2,2-Dimethyl-5-{4-(methylsulfonyl)phenyl}-4(2-naphthyl)-3(2H)-furanone;
2,2-Dimethyl-4-{5-(2-fluorothienyl)-5-{4-(methylsulfonyl)phenyl}-3(2H)-furanone;
2,2-Dimethyl-4-{5-(3-fluorothienyl)-5-{4-(methylsulfonyl)phenyl}-3(2H)-furanone;
2,2-Dimethyl-4-{4-(2-fluorothienyl)-5-{4-(methylsulfonyl)phenyl}-3(2H)-furanone;
2,2-Dimethyl-5-{4-(methylsulfonyl)phenyl}-4-(2-thienyl)-3(2H)-furanone;
2,2-Dimethyl-5-{4-(methylsulfonyl)phenyl}-4-(3-thienyl)-3(2H)-furanone;
4-{2-(5-Acetylthienyl)}-2,2-dimethyl-5-{4-(methylsulfonyl)phenyl}-3(2H)-furanone;
2,2-Dimethyl-4-(2-furanyl)-5-{4-(methylsulfonyl)phenyl}-3(2H)-furanone;
2,2-Dimethyl-4-(3-furanyl)-5-{4-(methylsulfonyl)phenyl}-3(2H)-furanone;
2,2-Dimethyl-4-{5-(3-fluorofuranyl)}-5-{4-(methylsulfonyl)phenyl}-3(2H)-furanone;
2,2-Dimethyl-4-{5-(2-fluorofuranyl)}-5-{4-(methylsulfonyl)phenyl}-3(2H)-furanone;
2,2-Dimethyl-4-{4-(2-fluorofuranyl)}-5-{4-(methylsulfonyl)phenyl}-3(2H)-furanone;
2,2-Dimethyl-4-{4-(1-N-methylpyrazolyl)}-5-{4-(methylsulfonyl)phenyl}-3(2H)-furanone;
2,2-Dimethyl-4-{4-(1-N-ethylpyrazolyl)}-5-{4-(methylsulfonyl)phenyl}-3(2H)-furanone;
2,2-Dimethyl-5-{4-(methylsulfonyl)phenyl}-4-(4-pyridyl)-3(2H)-furanone;
2,2-Dimethyl-4-{3-(6-methoxypyridyl)}-5-{4-(methylsulfonyl)phenyl}-3(2H)-furanone;
2,2-Dimethyl-4-{4-(1-N-iso-propylpyrazolyl)}-5-{4-(methylsulfonyl)phenyl}-3(2H)-furanone;
2,2-Dimethyl-5-{4-(methylsulfonyl)phenyl)}-4-(5-pyrimidinyl)-3(2H)-furanone;
2,2-Dimethyl-4-{3-(6-methylpyridyl)}-5-{4-(methylsulfonyl)phenyl}-3(2H)-furanone;
2,2-Dimethyl-4-{2-(5-formyl-4-methylthienyl)}-5-{4-(methylsulfonyl)phenyl}-3(2H)-furanone;
2,2-Dimethyl-4-[2-{5-(1,3-dioxolan)-2-yl}thienyl]-5-{4-(methylsulfonyl)phenyl}-3(2H)-furanone;
4-{2-(5-Bromothienyl)}-2,2-dimethyl-5-{4-(methylsulfonyl)phenyl}-3(2H)-furanone;
2,2-Dimethyl-5-{4-(methylsulfonyl)phenyl}-4-(4-pyrazolyl)-3(2H)-furanone;
5-{4-(Aminosulfonyl)phenyl}-2-ethyl-2-methyl-4-(2-pyridyl)-3(2H)-furanone;
5-{4-(Aminosulfonyl)phenyl}-2-ethyl-2-methyl-4-(3-pyridyl)-3(2H)-furanone;
5-{4-(Aminosulfonyl)phenyl}-2-ethyl-2-methyl-4-(4-pyridyl)-3(2H)-furanone;
5-{4-(Aminosulfonyl)phenyl}-2-ethyl-2-methyl-4-{4-(1-N-methylpyrazolyl)}-3(2H)-furanone;
5-{4-(Aminosulfonyl)phenyl}-2-ethyl-4-{4-(1-N-ethylpyrazolyl)}-2-methyl-3(2H)-furanone;
5-{4-(Aminosulfonyl)phenyl}-2-ethyl-2-methyl-4-{4-(1-N-iso-propylpyrazolyl)}-3(2H)-furanone;
5-{4-(Aminosulfonyl)phenyl}-2-ethyl-2-methyl-4-(3-thienyl)-3(2H)-furanone;
5-{4-(Aminosulfonyl)phenyl}-2-ethyl-4-{4-(2-fluorothienyl)}-2-methyl-3(2H)-furanone;
5-{4-(Aminosulfonyl)phenyl}-2-ethyl-4-{5-(2-fluorothienyl)}-2-methyl-3(2H)-furanone;
5-{4-(Aminosulfonyl)phenyl}-2-ethyl-4-{5-(3-fluorothienyl)}-2-methyl-3(2H)-furanone;
5-{4-(Aminosulfonyl)phenyl}-2-ethyl-4-(2-furanyl)-2-methyl-3(2H)-furanone;
5-{4-(Aminosulfonyl)phenyl}-2-ethyl-4-(3-furanyl)-2-methyl-3(2H)-furanone;
5-{4-(Aminosulfonyl)phenyl}-2-ethyl-4-{5-(3-fluorofuranyl)}-2-methyl-3(2H)-furanone;
5-{4-(Aminosulfonyl)phenyl}-2-ethyl-4-{4-(2-fluorofuranyl)}-2-methyl-3(2H)-furanone;
5-{4-(Aminosulfonyl)phenyl}-2-ethyl-4-{5-(2-fluorofuranyl)}-2-methyl-3(2H)-furanone;
2,2-Diethyl-5-{4-(methylsulfonyl)phenyl}-4-(3-thienyl)-3(2H)-furanone;
2,2-Diethyl-5-{4-(methylsulfonyl)phenyl}-4-(2-thienyl)-3(2H)-furanone;
2,2-Diethyl-5-{4-(methylsulfonyl)phenyl}-4-(2-pyridyl)-3(2H)-furanone;
2,2-Diethyl-5-{4-(methylsulfonyl)phenyl}-4-(4-pyridyl)-3(2H)-furanone;
2,2-Diethyl-4-{4-(1-N-methylpyrazolyl)}-5-{4-(methylsulfonyl)phenyl}-3(2H)-furanone;
2-Ethyl-2-methyl-5-{4-(methylsulfonyl)phenyl}-4-(3-pyridyl)-3(2H)-furanone;
2-Ethyl-2-methyl-4-{4-(1-N-methylpyrazolyl)}-5-{4-(methylsulfonyl)phenyl}-3(2H)-furanone;
2-Ethyl-2-methyl-5-{4-(methylsulfonyl)phenyl}-4-(4-pyrazolyl)-3(2H)-furanone;
2-Ethyl-4-{4-(1-N-ethylpyrazolyl)}-2-methyl-5-{4-(methylsulfonyl)phenyl}-3(2H)-furanone;
2-Ethyl-2-methyl-5-{4-(methylsulfonyl)phenyl}-4-{4-(1-N-iso-propylpyrazolyl)}-3(2H)-furanone;
2-Ethyl-2-methyl-4-{3-(6methoxypyridyl)}-5-{4-(methylsulfonyl)phenyl}-3(2H)-furanone;
2-Ethyl-2-methyl-4-{3-(6-methylpyridyl)}-5-{4-(methylsulfonyl)phenyl}-3(2H)-furanone;
2-Ethyl-2-methyl-5-{4-(methylsulfonyl)phenyl}-4-(3-thienyl)-3(2H)-furanone;
2-Ethyl-2-methyl-5-{4-(methylsulfonyl)phenyl}-4-{4-(2-fluorothienyl)}-3(2H)-furanone;
2-Ethyl-4-(2-furanyl)-2-methyl-5-{4-(methylsulfonyl)phenyl}-3(2H)-furanone;
2-Ethyl-4-(3-furanyl)-2-methyl-5-{4-(methylsulfonyl)phenyl}-3(2H)-furanone;
2-Ethyl-4-{5-(3-fluorofuranyl)}-2-methyl-5-{4-(methylsulfonyl)phenyl}-3(2H)-furanone;
2-Ethyl-4-{5-(2-fluorofuranyl)}-2-methyl-5-{4-(methylsulfonyl)phenyl}-3(2H)-furanone;

2-Ethyl-4-{4-(2-fluorofuranyl}-2-methyl-5-{4-(methylsulfonyl)phenyl}-3(2H)-furanone;
4-(2-Benzo[b]thienyl)-2-ethyl-2-methyl-5-{4-(methylsulfonyl)phenyl}-3(2H)-furanone;
4-(2-Benzo[b]furanyl)-2-ethyl-2-methyl-5-{4-(methylsulfonyl)phenyl}-3(2H)-furanone;
2-Ethyl-2-methyl-5-{4-(methylsulfonyl)phenyl}-4-(2-thienyl)-3(2H)-furanone;
2-Ethyl-4-{5-(fluorothienyl)}-2-methyl-5-{4-(methylsulfonyl)phenyl}-3(2H)-furanone;
4-{2-(5-Acetylthienyl)}-2-ethyl-2-methyl-5-{4-(methylsulfonyl)phenyl}-3(2H)-furanone;
2-Ethyl-2-methyl-5-{4-(methylsulfonyl)phenyl}-4-{2-(5-methylthienyl)}-3(2H)-furanone;
2-Ethyl-2-methyl-5-{4-(methylsulfonyl)phenyl}-4-{2-(3-methylthienyl)}-3(2H)-furanone;
5-{4-(Aminosulfonyl)phenyl}-2,2-dimethyl-4-(2-furanyl)-3(2H)-furanone;
5-{4-(Aminosulfonyl)phenyl}-2,2-dimethyl-4-(3-furanyl)-3(2H)-furanone;
5-{4-(Aminosulfonyl)phenyl}-2,2-dimethyl-4-{5-(3-fluorofuranyl)}-3(2H)-furanone;
5-{4-(Aminosulfonyl)phenyl}-2,2-dimethyl-4-{5-(2-fluorofuranyl)}-3(2H)-furanone;
5-{4-(Aminosulfonyl)phenyl}-2,2-dimethyl-4-{4-(2-fluorofuranyl)}-3(2H)-furanone;
5-{4-(Aminosulfonyl)phenyl}-2,2-dimethyl-4-(3-thienyl)-3(2H)-furanone;
5-{4-(Aminosulfonyl)phenyl}-2,2-dimethyl-4-(2-thienyl)-3(2H)-furanone;
5-{4-(Aminosulfonyl)phenyl}-2,2-dimethyl-4-{4-(2-fluorothienyl)}-3(2H)-furanone;
5-{4-(Aminosulfonyl)phenyl}-2,2-dimethyl-4-{5-(2-fluorothienyl)}-3(2H)-furanone;
5-{4-(Aminosulfonyl)phenyl}-2,2-dimethyl-4-{5-(3-fluorothienyl}-3(2H)-furanone;
5-{4-(Aminosulfonyl)phenyl}-4-(2-benzo[b]thienyl)-2,2-dimethyl-3(2H)-furanone;
5-{4-(Aminosulfonyl)phenyl}-4-(2-benzo[b]furanyl)-2,2-dimethyl-3(2H)-furanone;
5-{4-(Aminosulfonyl)phenyl}-2,2dimethyl-4-(2-naphthyl)-3(2H)-furanone;
5-{4-(Aminosulfonyl)phenyl}-2,2-dimethyl-4-(1-naphthyl)-3(2H)-furanone;
5-{4-(Aminosulfonyl)phenyl}-2,2-dimethyl-4-(2-pyridyl)-3(2H)-furanone;
5-{4-(Aminosulfonyl)phenyl}-2,2-dimethyl-4-(3-pyridyl)-3(2H)-furanone;
5-{4-(Aminosulfonyl)phenyl}-2,2-dimethyl-4-(4-pyridyl)-3(2H)-furanone;
5-{4-(Aminosulfonyl)phenyl}-2,2-dimethyl-4-{4-(1-N-methylpyrazolyl)}-3(2H)-furanone;
5-{4-(Aminosulfonyl)phenyl}-2,2-dimethyl-4-{4-(1-N-ethylpyrazolyl)}-3(2H)-furanone;
5-{4-(Aminosulfonyl)phenyl}-2,2-dimethyl-4-{4-(1-N-iso-propylpyrazolyl)}-3(2H)-furanone;
5-{4-(Aminosulfonyl)phenyl}-2,2-dimethyl-4-(4-pyrazolyl)-3(2H)-furanone.

The above used terms and abbreviations are illustrated in the following table.

| Term/Abbreviation | Illustration |
| --- | --- |
| Alkyl | Linear or branched alkyl radical having 1~10 carbon atom(s). |
| Haloalkyl | Alkyl radical substituted with one or more halogen atoms. Examples are fluoromethyl (F—$CH_2$—), 1-chloroethyl ($CH_3$—CHCl—), trifluoromethyl ($CF_3$—), and the like. |
| Hydroxyalkyl | Alkyl radical substituted with one or more hydroxyl radicals. Examples are hydroxymethyl (HO—$CH_2$—), 2-hydroxyethyl (HO—$CH_2CH_2$—), and the like. |
| Hydrido | Single hydrogen atom. |
| Halo | Halogen atom such as fluorine, chlorine, bromine or iodine. |
| Alkyloxy | Alkyloxy radical with an alkyl radical having 1~10 carbon atom(s). Examples are methoxy, ethoxy, propoxy, iso-propoxy, t-butoxy, and the like. Alkyloxy is the same as "alkoxy". |
| Lower | Denoting an alkyl radical of 1~5 carbon atom(s), when used with alkyl, haloalkyl, hydroxyalkyl, N-alkylamino, N-acylamino and the like. For example, "lower haloalkyl" denotes "alkyl radical having 1~5 carbon atom(s) substituted with one or more halogen atom(s). |
| Alkylthio | Alkyl radical substituted with a sulfur atom. Examples are methylthio ($CH_3$—S—), ethylthio ($CH_3CH_2$—S—), and the like. |
| Alkylsulfonyl | "—$SO_2$—" substituted with an alkyl radical. Examples are methylsulfonyl ($CH_3$—$SO_2$—), ethylsulfonyl ($CH_3CH_2$—$SO_2$—), and the like. |
| Aminosulfonyl | "—$SO_2$—" substituted with an amino (—$NH_2$) radical ($NH_2$—$SO_2$—). |
| (N-Alkylamino)-sulfonyl | "—$SO_2$—" substituted with an N-alkylamino radical. Examples are (N-methylamino)sulfonyl ($CH_3$—NH—$SO_2$—), (N-ethylamino)sulfonyl, ($CH_3CH_2$—NH—$SO_2$—), and the like. |
| (N-Acylamino)-sulfonyl | Aminosulfonyl radical substituted with an acyl group at the nitrogen atom. Examples are (N-acetylamino)sulfonyl [$CH_3C(O)$—NH—$SO_2$—], (N-propionylamino)sulfonyl [$CH_3CH_2C(O)$—NH—$SO_2$—], and the like. |
| Haloalkoxy | Alkoxy radical substituted with one or more halogen atom(s). Examples are fluoromethoxy ($FCH_2O$—), 2-Chloroethoxy ($ClCH_2$—$CH_2$—O—), trifluoromethoxy ($CF_3O$—), and the like. |
| Alkoxyalkyl | Alkyl radical substituted with an alkoxy radical. Examples are methoxymethyl ($CH_3$—O—$CH_2$—), 1-methoxy-n-propyl- [$CH_3$—$CH_2$—$CH(OCH_3)$—], and the like. |
| Formyl | "CHO—" radical. |
| Acyl | "—C(O)—" substituted with an alkyl radical. Examples are acetyl [$CH_3$—C(O)—], propionyl [$CH_3CH_2$—C(O)—], and the like. |
| N-Acylamino | "—NH—" substituted with an acyl radical. Examples are N-acetylamino [$CH_3C(O)$—NH—], N-propionylamino [$CH_3CH_2C(O)$—NH—], and the like. |
| Alkylsulfinyl | "—S(O)—" substituted with an alkyl radical. Examples are methylsulfinyl [$CH_3$—S(O)—], ethylsulfinyl [$CH_3CH_2S(O)$—], and the like. |
| Methylenedioxy | "—O—$CH_2$—O—" radical. |
| N,N-dialkylamino | Amino radical substituted with two alkyl radicals. Examples are N,N-dimethylamino [$(CH_3)_2N$—], N,N-methyl-ethylamino [$CH_3$—N—$CH_2CH_3$—], and the like. |

General Synthetic Procedures

Most of the compounds of the present invention can be synthesized according to the following procedures of Schemes I~VIII, wherein substituents $R_1$~$R_{19}$, X, Y, Z, and AR are as defined for Formula I, unless noted otherwise. Several compounds of this invention can be prepared by following procedures of Schemes I~VIII with minor modifications, such as used reagents, solvents, and change in the sequence of reactions. Some compounds in this invention were synthesized by following procedures which do not fall into the categories of Schemes I~VIII, and the synthetic details for those compounds are described in their individual preparation examples.

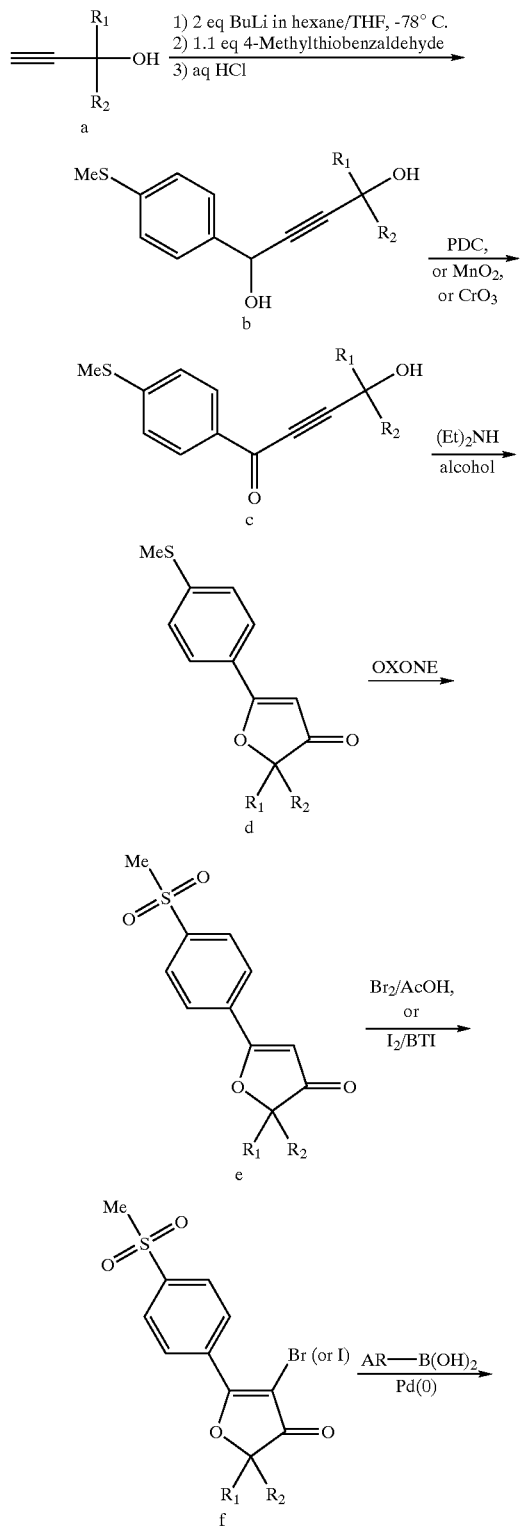

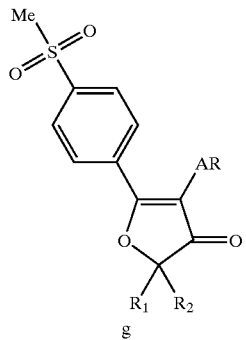

Scheme I shows the six step procedures used to prepare 2,2-dialkyl-4-aryl-5-{4-(methylsulfonyl)phenyl}-3(2H)-furanone (g) from commercially or easily available starting material 1,1-dialkyl-2-propyn-1-ol (a). In step one, the lithium acetylenide of a, which is generated in situ at −78° C. by adding n-BuLi to the THF solution of the starting material a, is reacted with 4-(methylthio)benzaldehyde to afford the diol b. In step two, the benzylic hydroxyl group of b is oxidized to the corresponding carbonyl of c by using an oxidizing agent such as pyridinium dichromate, manganese dioxide, chromium trioxide, and the like. In step three, the acyclic ketone c is cyclized to give 3(2H)-furanone d by using diethylamine as a catalyst in alcoholic solvent [J. Chem. Soc. 3871 (1958)]. In step four, the sulfide d is oxidized to the corresponding sulfone e by reacting with OXONE. In step five, halogenation of 5-aryl-2,2-dialkyl-3(2H)-furanone e is carried out to afford f by reacting e either with bromine in acetic acid or with iodine, in the presence of a catalytic amount of BTI [{bis(trifluoroacetoxy)iodo}benzene]. In step six, halide f is subjected to palladium (0)-mediated aromatic coupling to afford diaryl compound g, by using a proper aryl boronic acid [Suzuki Coupling: J. Org. Chem. 59, 5524 (1994)]. The order of the reactions in individual steps in all the reaction schemes may be changed as long as the overall process can give the desired compound. For example, in Scheme I, the halogenation step five may be carried out first and then the oxidation step four is performed instead of carrying out oxidation step four and then the halogenation step five.

Scheme II

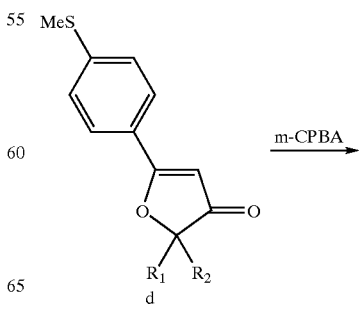

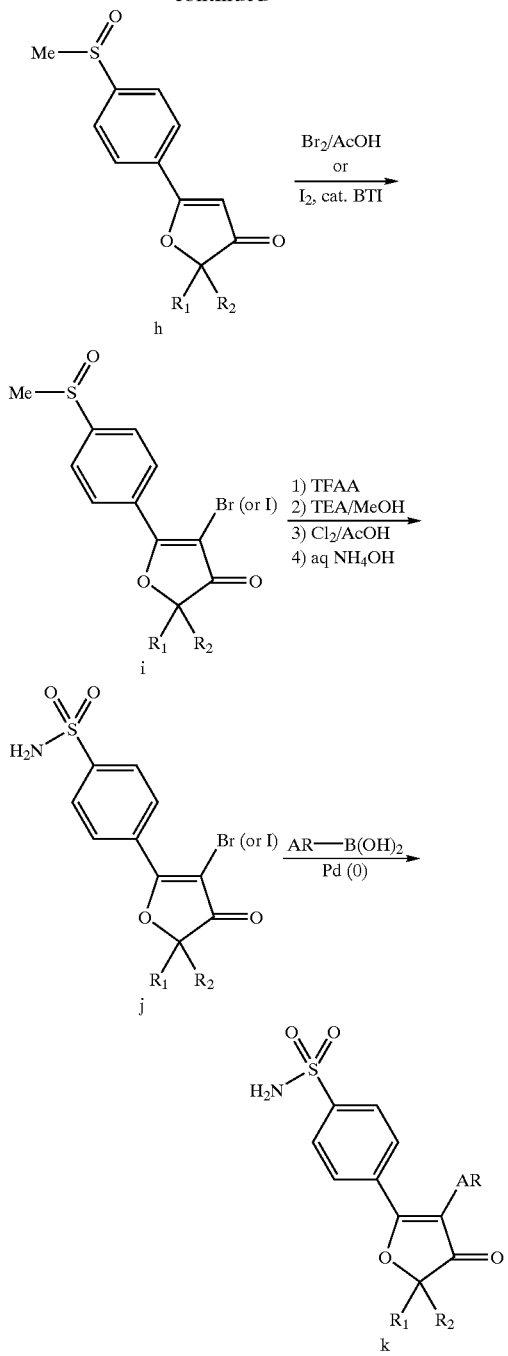

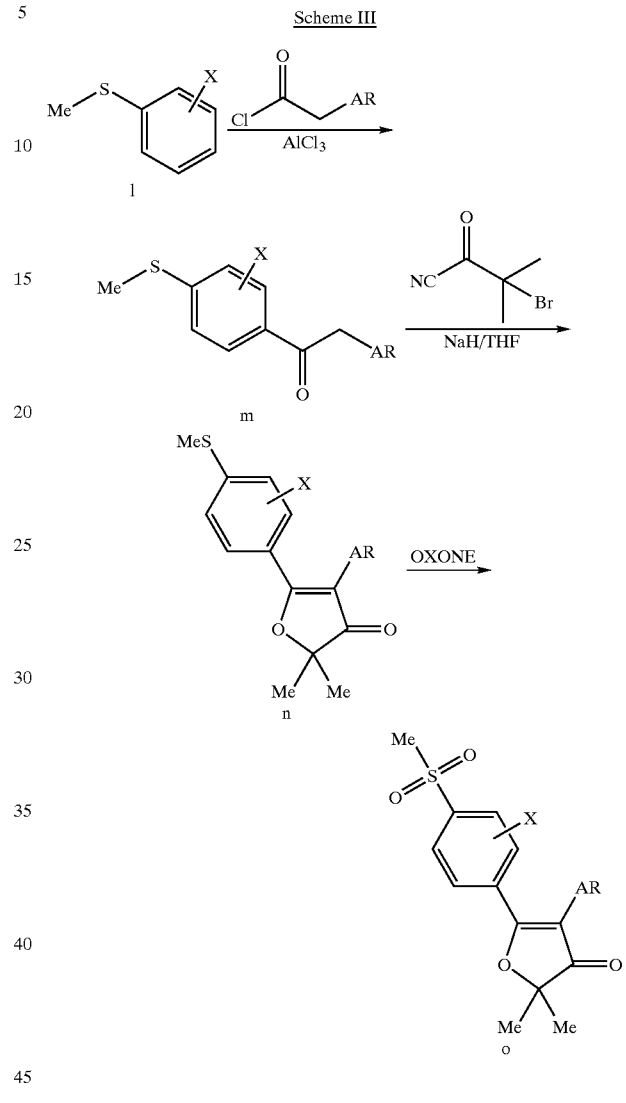

a proper aromatic boronic acid in the presence of a palladium(0) catalyst (Suzuki coupling) to afford 4,5-diaryl-3(2H)-furanone k.

Scheme II shows the four step procedures to prepare 4-aryl)-5-{4-(aminosulfonyl)phenyl}-3(2H)-furanone (k) from the sulfide intermediate d synthesized in Scheme I. In step one, partial oxidation of the sulfide d to the sulfoxide h is achieved by using m-chloroperbenzoic acid (m-CPBA). In step two, the sulfoxide h is subjected to halogenation reaction by using either bromine in acetic acid or iodine in the presence of a catalytic amount of BTI as in Scheme I to give halide i. In step three, the halide i is then transformed into sulfonamide j by sequential treatments of i with 1) trifluoroacetic anhydride (TFAA), 2) triethylamine (TEA) in methanol, 3) chlorine in acetic acid, and then 4) ammonia water, according to the literature [J. Am. Chem. Soc. 73, 3240 (1951)]. In step four, the sulfonamide j is coupled with Scheme III illustrates the three step procedures to synthesize 4,5-diaryl-3(2H)-furanone (o), wherein 5-{4-(methylsulfonyl)phenyl} group is substituted with "X". In step one, substituted thioanisole l is reacted with aromatic acetylchloride to afford the ketone m in the presence of aluminum chloride (Friedel-Craft acylation). In step two, the ketone m is subjected to "C-acylation" with α-bromoisobutyryl cyanide using sodium hydride as a base. The acylation further proceeds to give the intramolecular cyclization product n. In step three, the sulfide n is oxidized by using OXONE to yield the methylsulfone o. Thioanisole I can be replaced with an (alkylthio)benzene derivative to expand the scope of Scheme III to synthesize an alkylsulfone compound analogous to compound o. Furthermore the reaction sequence of Scheme III can be changed, where the oxidation of the methylthio group (step 3) is performed ahead of the reaction with α-bromoisobutyryl cyanide (step 2) to give the same target product o. Thus, several variations are possible with Scheme III to prepare compounds of this invention.

Scheme IV

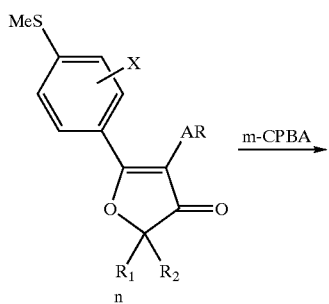

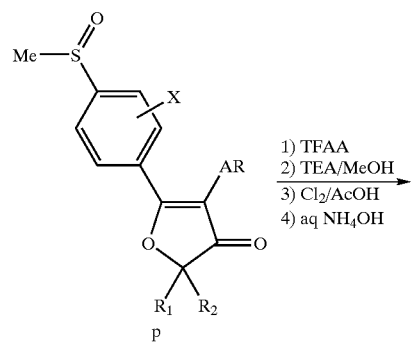

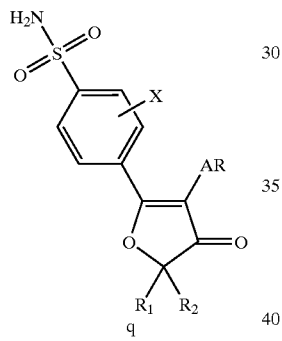

Scheme IV shows the two step procedures to synthesize sulfonamide q. In step one, the methylsulfide n is reacted with m-CPBA to obtain the sulfoxide p. In step two, the sulfoxide p is converted into the sulfonamide q by reacting p sequentially with 1) trifluoroacetic anhydride, 2) triethylamine in methanol, 3) chlorine in acetic acid, and then 4) ammonia water.

Scheme V

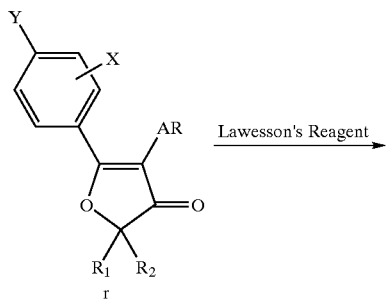

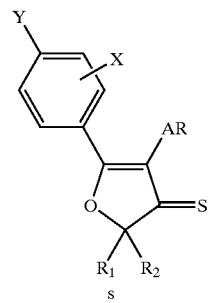

Scheme V illustrates the one step procedure to prepare the thiocarbonyl compound s. In Scheme V, the 4,5-diaryl-3 (2H)-furanone r is reacted with Lawesson's reagent to give the corresponding thiocarbonyl compound s.

Scheme VI

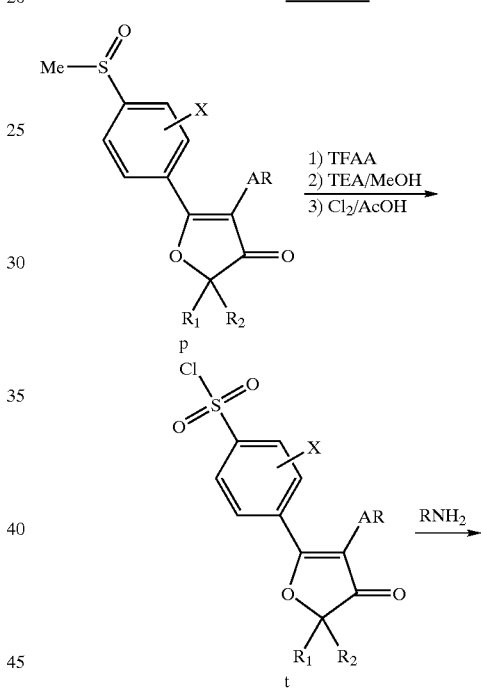

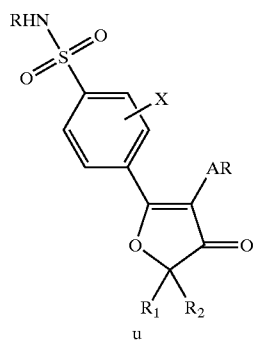

Scheme VI shows the two step procedures to synthesize N-alkylsulfonamide u from the sulfoxide p. In step one, the sulfoxide p is converted into the corresponding sulfonylchloride by reacting sequentially with 1) trifluoroacetic anhydride, 2) triethylamine in methanol, and then 3) chlorine in acetic acid. In step two, the reaction of the sulfonyl chloride t with alkylamine yields the N-alkylsulfonamide u.

Scheme VII

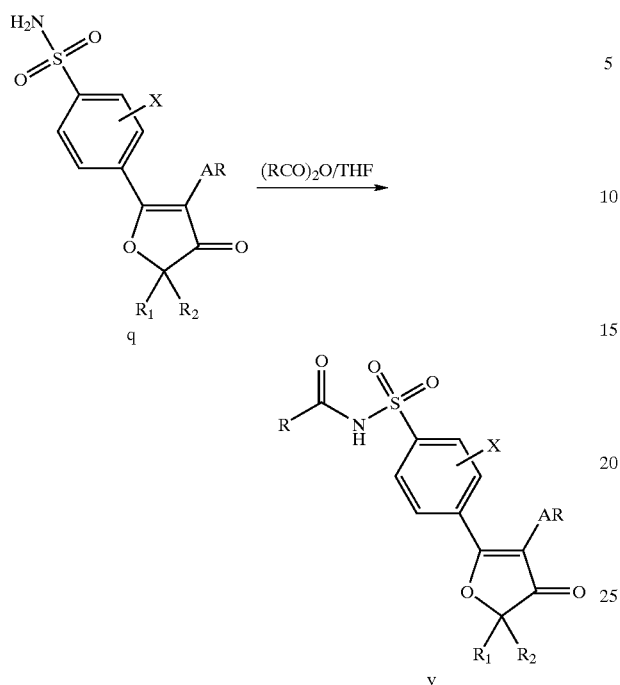

Scheme VII illustrates the one step procedure to synthesize the N-acylsulfonamide v. The sulfonamide q is reacted with an alkanoic anhydride in tetrahydrofuran to give v.

The reaction sequence of Scheme I can be modified to prepare 5-{4-(methylthio)phenyl}-3(2H)-furanone x and 5-{4-(methylsulfonyl)phenyl}-3(2H)-furanone y, as described in the following Scheme VIII.

Scheme VIII

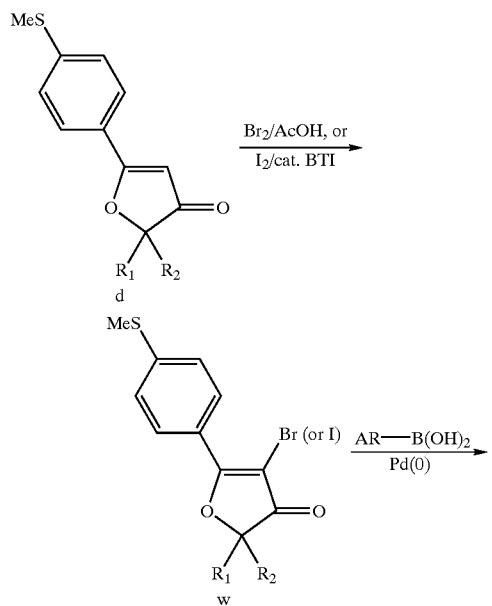

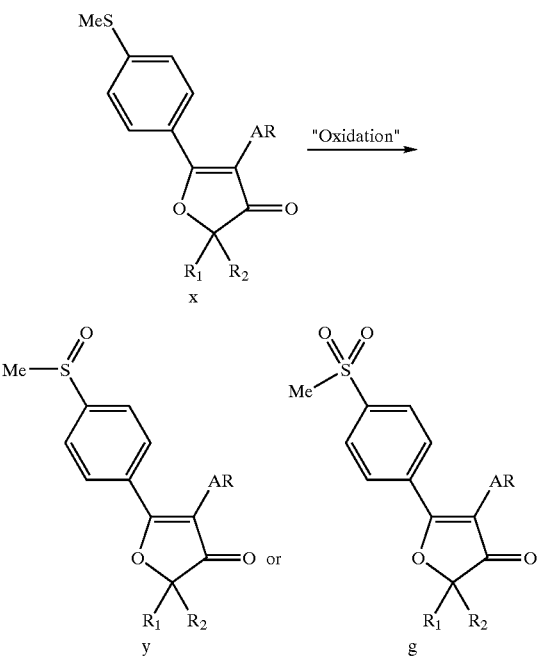

The following examples contain detailed descriptions of the preparation methods for compounds of Formula I–V. The detailed descriptions of these examples are presented illustrative purposes only and should not be interpreted as a restriction to the present invention. Most of these detailed descriptions fall within the scope, and serve to exemplify, the above described GENERAL SYNTHETIC PROCEDURES which form a part of the invention. All the chromatographic separations in the presented examples were performed using silica gel unless noted otherwise. The abbreviations used in the following examples are defined as in the following table.

| Abbreviation | Denotation |
|---|---|
| ° C. | Degree in Celcious. |
| mp | Melting point. Uncorrected value. |
| NMR | Proton nuclear magnetic resonance. All the NMR spectra were taken with a 300 MHz NMR. The NMR solvent in this invention is $CDCl_3$, unless noted otherwise. In presenting the NMR data of this invention, widely-accepted abbreviations were used as follows: s for singlet, d for doublet, t for triplet, q for quartet, br s for broad singlet, and so on. |
| IR | Infrared spectroscopy. All the IR spectra were taken for the neat form on a KBr window and the unit is in $cm^{-1}$ unless noted otherwise. |
| MS | Mass spectroscopy. All the MS data are presented in the m/e unit. |
| FAB | Fast atom bombardment. |
| EI | Electron ionization. |
| THF | Tetrahydrofuran |
| m | Ion peak for molecular weight in the MS data. Thus (m + 1) corresponds to the peak of parent molecule with one proton. |

EXAMPLE 1

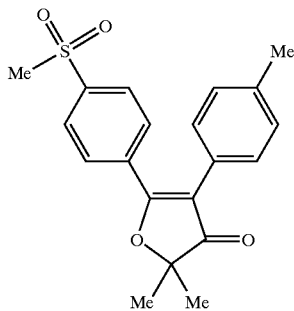

2,2-Dimethyl-4-(4methylphenyl)-5-{4-(methylsulfonyl)phenyl}-3(2H)-furanone

Step 1: Preparation of 1-{4-(methylthio)phenyl}-4-hydroxy-4-methyl-2-pentyn-1-ol

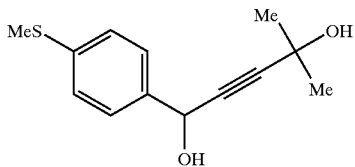

To a stirred solution of 2-methyl-3-butyn-2-ol (416 mg) and dry THF (30 ml) under argon and at −78° C., was added 1.6 M butyllithium in hexane (5 ml) dropwise over 10 minutes. 20 minutes later, p-methylthiobenzaldehyde (0.5 ml) was added dropwise to the reaction solution. Then the reaction solution was allowed to warm up to the ambient temperature by removing the cold bath. After stirring the reaction mixture for 2 hours, the reaction solvent was removed in vacuo, which was followed by neutralization with dilute aqueous HCl solution. The reaction mixture was then extracted with dichloromethane (50 ml×3), and the dichloromethane layer was washed with water (50 ml×1). The dichlomethane layer was concentrated in vacuo and the resulting residue was subjected to column chromatographic separation (hexane/ethyl acetate=1:1) to yield 724 mg of 1-{4-(methylthio)phenyl}-4-hydroxy-4-methyl-2-pentyn-1-ol. NMR: δ1.54 (s, 6H), 2.36 (s, 1H), 2.48 (s, 3H), 2.62 (d, 1H), 5.43(d, J=5.4 Hz, 1H), 7.25 (d, J=6.9 Hz, 2H), 7.43 (d, J=6.9 Hz, 2H).

Step 2: Preparation of 1-{(4-methylthio)phenyl}-4-hydroxy-4-methyl-2-pentyn-1-one

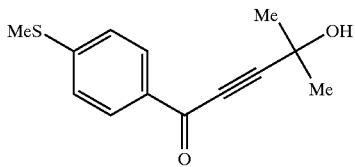

To 724 mg of 1-{4-(methylthio)phenyl}-4-hydroxy-4methyl-2-pentyn-1-ol dissolved in 30 ml acetone, was slowly added dropwise 451 mg of chromium trioxide dissolved in 10 ml water and 0.25 ml concentrated sulfuric acid. After stirring the reaction solution overnight at the ambient temperature, the reaction solution was concentrated in vacuo. The resulting aqueous residue was extracted with 50 ml water and dichloromethane (50 ml×3). The organic layer was concentrated in vacuo and the resulting residue was subjected to column chromatographic separation hexane/ethyl acetate=1:1) to yield 200 mg of 1-{(4-methylthio)phenyl}-4-hydroxy-4-methyl-2-pentyn-1-one as a solid. mp: 102–103° C. NMR: δ1.67(s, 6H), 2.41 (s, 1H), 2.54 (s, 3H), 7.28 (d, J=8.7 Hz, 2H), 8.02 (d, J=8.7 Hz, 2H). IR (cm$^{-1}$): 3404, 1613, 1176, 747.

Alternatively, 1-{(4-methylthio)phenyl}-4-hydroxy-4-methyl-2-pentyn-1-one was prepared by using PDC (pyridinium dichromate) in place of chromium trioxide as follows: To a stirred suspension of 1-{4-(methylthio)phenyl}-4-hydroxy-4-methyl-2-pentyn-1-ol (20 g) and celite (30 g) in 500 ml dichloromethane, was added PDC (40 g) portion-wise over 10 minutes. The reaction mixture was stirred for 12 hours at room temperature. The suspension was then filtered through Florisil pad (150 g) and the Florisil pad was washed with 500 ml methylene chloride. The filtrate was washed with dilute aqueous HCl (200 ml×1) and the organic layer was concentrated in vacuo. The resulting residue was chromatographed as above to afford 12.3 g of 1-{(4-methylthio)phenyl}-4-hydroxy-4-methyl-2-pentyn-1-one.

Another variation of oxidation reaction to prepare 1-{(4-methylthio)phenyl}-4-hydroxy-4-methyl-2-pentyn-1-one from 1-{4-(methylthio)phenyl}-4-hydroxy-4-methyl-2-pentyn-1-ol was performed as follows: A suspension of 1-{4-(methylthio)phenyl}-4-hydroxy-4-methyl-2-pentyn-1-ol (150 g) and activated manganese dioxide (200 g) in methylene chloride (2 L) was stirred using an overhead stirrer for 20 hours at room temperature. Then the suspension was filtered through celite (300 g) and the filtrate was concentrated under reduced pressure. The resulting crude solid was recrystallized from ethylacetate/hexane to afford 120 g of 1-{(4methylthio)phenyl}-4-hydroxy-4-methyl-2-pentyn-1-one.

Step 3: Preparation of 2,2-dimethyl-5-{4-(methylthio)phenyl}-3(2H)-furanone

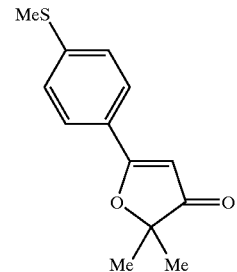

To a stirred solution of 1-{(4-methylthio)phenyl}-4-hydroxy-4-methyl-2-pentyn-1-one (120 mg) in 20 ml ethanol, was added dropwise diethylamine (0.08 ml) diluted in 7 ml ethanol over 5 minutes at room temperature. The reaction solution was stirred for another one hour and then the solvent was removed in vacuo. The resulting residue was diluted with 50 ml water and then extracted with diclomethane (30 ml×3). The organic layer was concentrated in vacuo and the resulting residue was subjected to column chromatographic separation (hexane/ethylacetate=4:1) to give 90 mg of 2.2-dimethyl-5-{4-(methylthio)phenyl}-3 (2H)-furanone as a solid. mp: 107–109° C. NMR: δ1.48 (s, 6H), 2.54 (s, 3H), 5.91 (s, 1H), 7.30 (d, J=8.4 Hz, 2H), 7.72 (d, J=8.4 Hz, 2H). IR (cm$^{-1}$): 1676, 1579, 1485, 1376, 1174, 1095, 1050, 809.

Step 4: Preparation of 4-bromo-2,2-dimethyl-5-{4-(methylthio)phenyl}-3(2H)-furanone

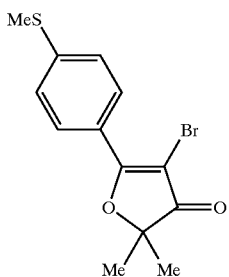

To a stirred solution of 2,2-dimethyl-5-{4-(methylthio)phenyl}-3(2H)-furanone (45 mg) in 20 ml carbon tetrachloride, were added acetic acid (0.5 ml) and bromine (0.1 ml). The reaction solution was stirred at room temperature for one hour. Then the reaction was quenched by adding 20 ml of saturated aqueous sodium thiosulfate solution to the reaction solution. After removing the carbon tetrachloride in vacuo, the resulting aqueous layer was extracted with dichloromethane (50 ml×3) and the organic layer was then washed with water (50 ml×1). The organic layer was concentrated in vacuo and the resulting residue was chromatographed (hexane/ethylacetate=2:1) to yield 69 mg of 4-bromo-2,2-dimethyl-5-{4-(methylthio)phenyl}-3(2H)-furanone as a solid. NMR: δ1.52 (s, 6H), 2.55 (s, 3H), 7.33 (d, J=9.3 Hz, 2H), 8.15 (d, J=9.0 Hz, 2H); IR (cm$^{-1}$): 1704, 1594, 1574, 1486, 1348, 1184, 1069.

Step 5: Preparation of 4-bromo-2,2-dimethyl-5-{4-(4-methylsulfonyl)phenyl}-3(2H)-furanone

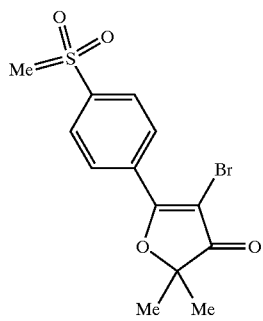

42 mg of 4-bromo-2,2-dimethyl-5-{4-(methylthio)phenyl}-3(2H)-furanone was dissolved in 15 ml THF and 15 ml ethanol, to which was added 178 mg of OXONE. The mixture was stirred overnight at room temperature. Then the solvent was removed in vacuo. The resulting residue was extracted with 50 ml water and methylene chloride (50 ml×3). The organic layer was concentrated under reduced pressure and the resulting residue was subjected to column chromatographic separation (hexane/ethylacetate=2:1) to afford 45 mg of desired 4-bromo-2,2-dimethyl-5-{4-(methylsulfonyl)phenyl}-3(2H)-furanone as a solid. mp: 196–196.5° C. NMR: δ1.57 (s, 6H), 3.11 (s, 3H), 8.11 (d, J=8.7 Hz, 2H), 8.40 (d, J=8.7 Hz, 2H). IR (cm$^{-1}$): 2928, 1703, 1559, 1270, 1148, 1076, 847. MS (EI): 346 (m).

Step 6: Preparation of 2,2-dimethyl-4-(4-methylphenyl)-5-{4-(methylsulfonyl)phenyl}-3(2H)-furanone To a stirred solution of 4-bromo-2,2-dimethyl-5-{4-(methylsulfonyl)phenyl}-3(2H)-furanone (110 mg) and tetrakis(triphenylpalladium(0) (54 mg) in 30 ml benzene, were added 2 M aqueous sodium carbonate (0.22 ml) and 4-methyl-benzeneboronic acid (60 mg). The reaction solution was stirred at reflux for 24 hours. Then the solvent was evaporated off under reduced pressure. The resulting residue was extracted with 50 ml water and dichloromethane (50 ml×3). The organic layer was concentrated in vacuo and the resulting residue was separated by column chromatography (hexane/ethylacetate=2:1) to give 76 mg of 2,2-dimethyl-4-(4-methylphenyl)-5-{4-(methylsulfonyl)phenyl}-3(2H)-furanone as a solid. mp: 167–168° C. NMR: δ1.57 (s, 6H), 2.38 (s, 3H), 3.07 (s, 3H), 7.17 (m, 4H), 7.89 (m, 4H). IR (cm$^{-1}$): 1707, 1660, 1531, 1289, 1230. MS (EI): 356 (m).

EXAMPLE 2

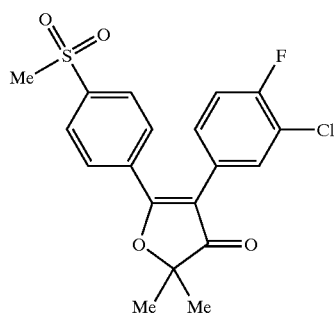

4-(3-Chloro-4-fluorophenyl)-2,2-dimethyl-5-{4-(methylsulfonyl)phenyl}-3(2H)-furanone To a stirred solution of 4-bromo-2,2-dimethyl-5-{4-(methylsulfonyl)phenyl}-3(2H)-furanone (112 mg) and tetrakis(triphenylphosphine)palladium(0) (54 mg) in 7 ml benzene and 1 ml ethanol, were added 2 M aqueous sodium carbonate (0.22 ml) and (3-chloro-4-fluorophenyl)boronic acid (82 mg). The reaction solution was kept at reflux for 24 hours. Then the solvent was evaporated off under reduced pressure. The resulting residue was extracted with 50 ml water and dichloromethane (50 ml×3). The organic layer was concentrated in vacuo and the resulting residue was separated by column chromatography (hexane/ethylacetate) to yield 32 mg of 4-(3-chloro-4-fluorophenyl)-2,2-dimethyl-5-{4-(methylsulfonyl)phenyl}-3(2H)-furanone as a solid. mp: 162–164° C. NMR: δ1.58 (s, 6H), 3.09 (s, 3H), 7.13 (m, 2H), 7.40 (d, J=6.6 Hz, 1H), 7.83 (d, J=8.1 Hz, 2H), 7.97 (d, J=8.1 Hz, 2H). IR (cm$^{-1}$): 2930, 1700, 1587, 1503, 1404, 1317, 1150, 1068, 913, 771, 744.

EXAMPLE 3

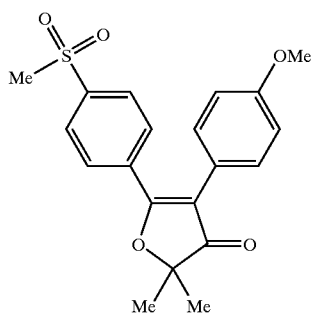

2,2-Dimethyl-4-(4-methoxyphenyl)-5-{4-(methylsulfonyl)phenyl}-3(2H)-furanone To a stirred solution of 4-bromo-2,2-dimethyl-5-{4-(methylsulfonyl)phenyl}-3(2H)-furanone (220 mg), 1,3-bis(diphenylphosphino)propane (24 mg) and palladium(II) acetate (6.1 mg) in 30 ml benzene, were added 2 M aqueous sodium carbonate (0.22 ml) and 4-methoxybenzeneboronic acid (90 mg). The reaction solution was kept at reflux for 24 hours. Then the solvent was removed under reduced pressure. The resulting residue was purified by a procedure similar to the purification method in Example 2 to yield 55 mg of 2,2-dimethyl-4-(4-methoxyphenyl)-5-{4-(methylsulfonyl)phenyl}-3(2H)-furanone as a solid. NMR: δ1.56 (s, 6H), 3.07 (s, 3H), 3.83 (s, 3H), 6.92 (d, J=8.7 Hz, 2H), 7.23 (d, J=9.0 Hz, 2H), 7.89(dd, J=8.7, 8.7 Hz, 4H). IR (cm$^{-1}$): 2925, 1697, 1592, 1149, 1031, 912, 745.

EXAMPLE 4

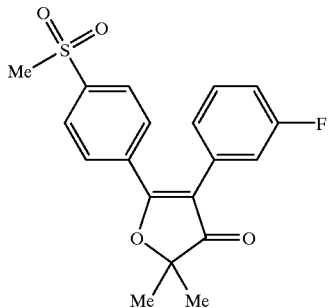

2,2-Dimethyl-4-(3-fluorophenyl)-5-{4-(methylsulfonyl)phenyl}-3(2H)-furanone

To a stirred solution of 4-bromo-2,2-dimethyl-5-{4-(methylsulfonyl)phenyl}-3(2H)-furanone (170 mg) in 30 ml toluene and 10 ml ethanol, were added 25 mg of tetrakis(triphenylphosphine)palladium(0), 10 ml of saturated aqueous sodium bicarbonate, and 100 mg of 3-fluorobenzeneboronic acid. The reaction solution was stirred at 90° C. for 12 hours. Then the solvent was removed under reduced pressure. The resulting residue was extracted with water and dichloromethane. The organic layer was concentrated in vacuo and the resulting residue was separated by column chromatography (hexane/ethylacetate) to yield 120 mg of 2,2-dimethyl-4-(3-fluorophenyl)-5-{4-(methylsulfonyl)phenyl}-3(2H)-furanone as a solid. mp: 178–179° C. NMR: δ1.58 (s, 6H), 3.08 (s, 3H), 7.05 (m, 3H), 7.33 (m, 1H), 7.83 (d, J=8.7 Hz, 2H), 7.95 (d, J=8.4 Hz, 2H). IR (cm$^{-1}$): 3020, 1697, 1620, 1403, 1318, 1149, 958, 768. MS (FAB): 361 (m+1).

Alternatively, the titled compound was prepared as described in the following procedure: 3.0 g of 2,2-dimethyl-4(3-fluorophenyl)-5-{4-(methylthio)phenyl}-3(2H)-furanone (Example 166) was dissolved in 50 ml THF, 50 ml methanol and 50 ml water along with 10 g of OXONE. The reaction mixture was stirred at room temperature for 2 hours. Then the solution was concentrated in vacuo and the resulting aqueous solution was extracted with 150 ml methylene chloride. The organic layer was washed with brine and then was dried over anhydrous magnesium sulfate. The magnesium sulfate was removed by filtration and the filtrate was concentrated in vacuo. The resulting residue was recrystallized from methylene chloride/hexane to afford 3.3 g of 2,2-dimethyl-4-(3-fluorophenyl)-5-{4-(methylsulfonyl)phenyl}-3(2H)-furanone.

Another variation to prepare 2,2-dimethyl-4-(3-fluorophenyl)-5-{4-(methylsulfonyl)phenyl}-3(2H)-furanone was performed starting from 2-(3-fluorophenyl)-1-{4-(methylsulfonyl)phenyl}-ethanone as follows: To a stirred solution of 2-(3-fluorophenyl)-1-(4-methylsulfonylphenyl)-ethanone (1 g) in 10 ml of THF, was added 0.23 g of 95% sodium hydride at 0° C. The reaction solution was stirred for 1 hour at the same temperature. Then 0.64 g of a-bromo-isobutyric cyanide was added dropwise to the reaction mixture at 0° C. The reaction mixture was stirred for another 7 hours while being allowed to warm to room temperature. Then the reaction was quenched with 5 ml of water. The mixture was concentrated in vacuo, and was dissolved in 50 ml of water. The aqueous solution was extracted with ethylacetate (100 ml). The organic layer was washed with brine, concentrated in vacuo. Then the resulting residue was purified by column chromatography (hexane/ethylacetate) to afford 0.75 g of 2,2-dimethyl-4-(3-fluorophenyl)-5-{(methylsulfonyl)phenyl}-3(2H)-furanone.

EXAMPLE 5

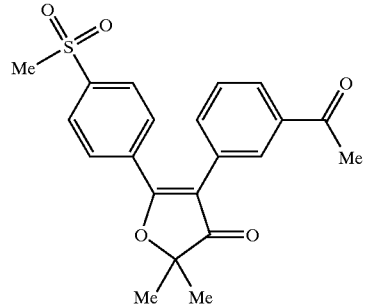

4-(3-acetylphenyl)-2,2-dimethyl-5-{4-(methylsulfonyl)phenyl}-3(2H)-furanone

To a stirred solution of 4-bromo-2,2-dimethyl-5-{4-(methylsulfonyl)phenyl}-3(2H)-furanone (170 mg) in 30 ml toluene and 10 ml ethanol, were added 25 mg of tetrakis(triphenylphosphine)palladium(0), 10 ml of saturated aqueous sodium carbonate, and 130 mg of 3-acetylbenzeneboronic acid. The reaction solution was stirred at 90° C. for 12 hours. Then the solvent was removed under reduced pressure. The resulting residue was extracted with water and dichloromethane. The organic layer was concentrated in vacuo and the resulting residue was separated by column chromatography (hexane/ethylacetate=2:1) to afford 100 mg of 4-(3-acetylphenyl)-2,2-dimethyl-5-{4-(methylsulfonyl)phenyl}-3(2H)-furanone as a solid. mp: 189–190° C. NMR: δ1.60 (s, 6H), 2.59 (s, 3H), 3.07 (s, 3H), 7.48 (m, 2H), 7.82 (d, J=8.7 Hz, 2H), 7.90 (m, 2H), 7.94 (d, J=8.4 Hz, 2H). IR (cm$^{-1}$): 1690, 1620, 1589, 1149, 958, 770.

EXAMPLE 6

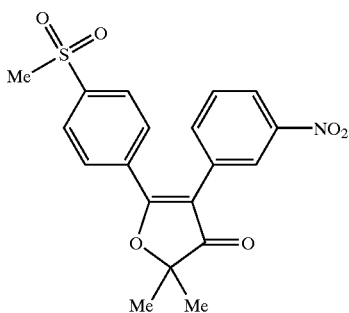

2,2-Dimethyl-5-{4-(methylsulfonyl)phenyl}-4-(3-nitrophenyl)-3(2H)-furanone

To a stirred solution of 4-bromo-2,2-dimethyl-5-{4-(methylsulfonyl)phenyl}-3(2H)-furanone (170 mg) in 30 ml toluene and 10 ml ethanol, were added 25 mg of tetrakis(triphenylphosphine)palladium(0), 10 ml of saturated aqueous sodium carbonate, and 120 mg of 3-nitrobenzeneboronic acid. The reaction solution was stirred at 90° C. for 12 hours. Then the solvent was removed under reduced pressure. The resulting residue was extracted with water and dichloromethane (50 ml×3). The organic layer was concentrated in vacuo and the resulting residue was separated by column chromatography (hexane/ethylacetate) to afford 100 mg of 2,2-dimethyl-5-{4-(methylsulfonyl)phenyl}-4-(3-nitrophenyl)-3(2H)-furanone as a solid. mp: 158–159° C. NMR: δ1.61 (s, 6H), 3.09 (s, 3H), 7.57 (t, J=7.8 Hz, 1H), 7.64 (m, 1 H), 7.81 (d, J=9.0 Hz, 2H), 7.98 (d, J=8.7 Hz, 2H), 8.19 (m, 2H). IR (cm$^{-1}$): 2982, 1697, 1529, 1403, 1349, 1150, 959, 770.

EXAMPLE 7

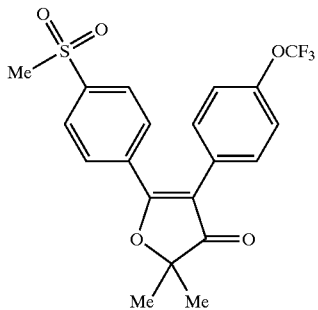

2,2-Dimethyl-5-{4-(methylsulfonyl)phenyl}-4-{4-(trifluoromethoxy)phenyl}-3(2H)-furanone To a stirred solution of 4-bromo-2,2-dimethyl-5-{4-(methylsulfonyl)phenyl}-3(2H)-furanone (150 mg) in 15 ml toluene and 5 ml ethanol, were added 30 mg of tetrakis(triphenylphosphine)palladium(0), 5 ml of saturated aqueous sodium carbonate, and 100 mg of 4-(trifluoromethoxy)benzeneboronic acid. The reaction solution was stirred at 90° C. for 24 hours. Then the solvent was removed under reduced pressure. The resulting residue was extracted with water and dichloromethane. The organic layer was concentrated in vacuo and the resulting residue was separated by column chromatography (hexane/ethylacetate) to yield 60 mg of 2,2-dimethyl-5-{4-(methylsulfonyl)phenyl}-4-{4-(trifluoromethoxy)phenyl}-3(2H)-furanone as a solid. mp: 118–120° C. NMR: δ1.58 (s, 6H), 3.08 (s, 3H), 7.20–7.26 (m, 2H), 7.31–7.34 (m, 2H), 7.82–7.85 (m, 2H), 7.95–7.98 (m, 2H). IR (cm$^{-1}$): 2931, 1698, 1510, 1387, 1258, 1150, 960, 846, 770.

EXAMPLE 8

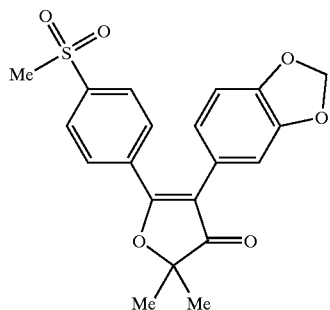

2,2-Dimethyl-4-(3,4-methylenedioxyphenyl)-5-{4-(methylsulfonyl)phenyl}-3(2H)-furanone To a stirred solution of 4-bromo-2,2-dimethyl-5-{4-(methylsulfonyl)phenyl}-3(2H)-furanone (200 mg) in 30 ml toluene and 10 ml ethanol, were added 25 mg of tetrakis(triphenylphosphine)palladium(0), 10 ml of saturated aqueous sodium carbonate, and 150 mg of (3,4-methylenedioxy)benzeneboronic acid. The reaction solution was stirred at 90° C. for 12 hours. Then the solvent was removed under reduced pressure. The resulting residue was extracted with water and dichloromethane. The organic layer was concentrated in vacuo and the resulting residue was separated by column chromatography (hexane/ethylacetate) to yield 100 mg of 2,2-dimethyl-4-(3,4-methylenedioxyphenyl)-5-{4-(methylsulfonyl)phenyl}-3(2H)-furanone as a solid. mp: 178–179° C. NMR: δ1.60 (s, 6H), 3.07 (s, 3H), 5.99 (s, 2H), 6.74 (m, 2H), 6.84 (d, J=8.7 Hz, 1H), 7.87 (d, J=8.7 Hz, 2H), 7.94 (d, J=8.7 Hz, 2H). IR (cm$^{-1}$): 1697, 1503, 1404, 1245, 1148, 959, 770.

EXAMPLE 9

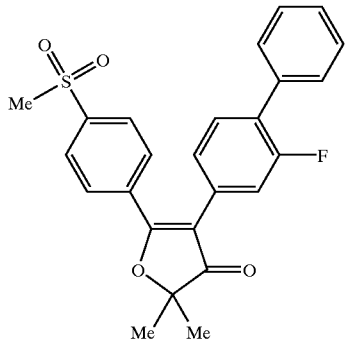

2,2-Dimethyl-4-{4-(3-fluorophenyl)phenyl}-5-{4-(methylsulfonyl)phenyl}-3(2H)-furanone 200 mg of 4-bromo-2,2-dimethyl-5-{4-(methylsulfonyl)phenyl}-3(2H)-furanone was coupled with 170 mg of {(3-fluoro-4-phenyl)benzene}boronic acid by a procedure similar to the synthetic procedure in Example 2 to yield 110 mg of 2,2-dimethyl-4-{(3-fluoro-4-phenyl)phenyl}-5-{4-(methylsulfonyl)-phenyl}-3(2H)-furanone as a solid. mp: 163–164° C. NMR: δ1.60 (s, 6H), 3.09 (s, 3H), 7.13 (m, 2H), 7.41 (m, 2H), 7.45 (m, 2H), 7.57 (m, 2H), 7.91 (d, J=8.7 Hz, 2H), 7.98 (d, J=8.7 Hz, 2H). IR (cm$^{-1}$): 3020, 1698, 1621, 1402, 1319, 1258, 1148, 957, 770.

EXAMPLE 10

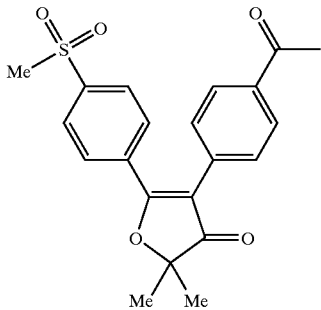

4-(4-Acetylphenyl)-2,2-dimethyl-5-{4-(methylsulfonyl)phenyl}-3(2H)-furanone 200 mg of 4-bromo-2,2-dimethyl-5-{4-(methylsulfonyl)phenyl}-3(2H)-furanone (200 mg) was coupled with 104 mg of (4-acetylbenzene)boronic acid according to a procedure similar to the synthetic procedure in Example 2 to yield 55 mg of 4-(4acetylphenyl)-2,2-dimethyl-5-{4-(methylsulfonyl)phenyl}-3(2H)-furanone as a solid. mp: 164–167° C. NMR: δ1.60 (s, 6H), 2.32 (s, 3H), 3.08 (s, 3H), 7.39–7.4 (m, 2H), 7.81–7.84 (m, 2H), 7.94–7.98 (m, 4H). IR (cm$^{-1}$): 1696, 1685, 1618, 1386, 1318, 1150, 960, 770.

EXAMPLE 11

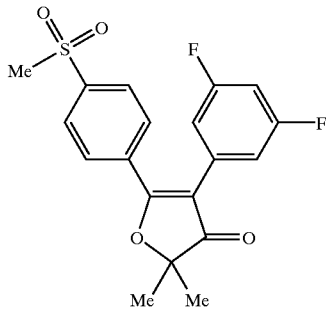

4-(3,5-Difluorophenyl)-2,2-dimethyl-5-{4-(methylsulfonyl)phenyl}-3(2H)-furanone

To a stirred solution of 4-bromo-2,2-dimethyl-5-{4-(methylsulfonyl)phenyl}-3(2H)-furanone (300 mg) in 30 ml toluene and 10 ml ethanol, were added 25 mg of tetrakis (triphenylphosphine)palladium(0), 10 ml of aqueous 2M sodium carbonate, and 200 mg of (3,5-difluorobenzene) boronic acid. The reaction solution was stirred at 90° C. for 12 hours. Then the solvent was removed under reduced pressure. The resulting residue was extracted with water and dichloromethane. The organic layer was concentrated in vacuo and the resulting residue was separated by column chromatography (hexane/ethylacetate) to give 200 mg of 4-(3,5-difluorophenyl)-2,2-dimethyl-5-{4-(methylsulfonyl) phenyl}-3(2H)-furanone as a solid. mp: 141–142° C. NMR: δ1.60 (s, 6H), 3.08 (s, 3H), 3.95 (s, 3H), 6.92 (m, 3H), 7.88 (d, J=8.7 Hz, 2H), 7.93 (d, J=8.7 Hz, 2H). IR (cm$^{-1}$): 1695, 1611, 1516, 1316, 1270, 1123, 1023, 858, 769. MS (FAB): 379 (m+1).

Alternatively, 18 g of 4-(3,5-difluorophenyl)-2,2-dimethyl-5-{4-(methylthio)-phenyl}-3(2H)-furanone (Example 173) was reacted with 45 g of OXONE in 300 ml THF, 300 ml ethanol and 300 ml water according to a procedure similar to the alternative procedure of Example 4 to afford 19.5 g of 4-(3,5-difluorophenyl)-2,2-dimethyl-5-{4-(methylsulfonyl)phenyl}-3(2H)-furanone.

EXAMPLE 12

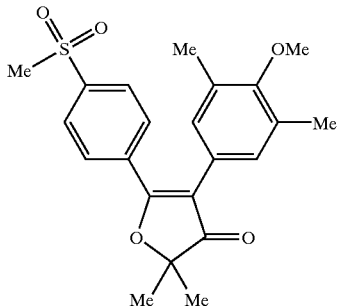

2,2-Dimethyl-4-(3,5-dimethyl-4-methoxyphenyl)-5-{4-(methylsulfonyl)phenyl}-3(2H)-furanone 300 mg of 4-bromo-2,2-dimethyl-5-{4-(methylsulfonyl) phenyl}-3(2H)-furanone was coupled with 250 mg of (3,5-dimethyl-4-methoxybenzene)boronic acid according to a procedure similar to the procedure in Example 2 to give 60 mg of 2,2-dimethyl-4-(3,5-dimethyl-4-methoxyphenyl)-5-{4-(methylsulfonyl)phenyl}-3(2H)-furanone as a solid. mp: 130–131° C. NMR: δ1.56 (s, 6H), 2.26 (s, 6H), 3.07 (s, 3H), 3.75 (s, 3H), 6.91 (s, 2H), 7.87 (d, J=8.7 Hz, 2H), 7.92 (d, J=8.7 Hz, 2H). IR (cm$^{-1}$): 2929, 1697, 1591, 1399, 1319, 1149, 1135, 771.

EXAMPLE 13

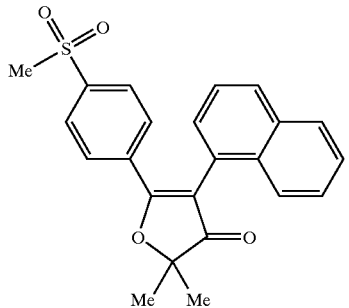

2,2-Dimethyl-5-{4-(methylsulfonyl)phenyl}-4-(1-naphthyl)-3(2H)-furanone 200 mg of 4bromo-2,2-dimethyl-5-{4-(methylsulfonyl) phenyl}-3(2H)-furanone was coupled with 114 mg of naphthalene-1-boronic acid by a procedure similar to the procedure employed for Example 2 to afford 2,2-dimethyl-5-{4-(methylsulfonyl)phenyl}-4-(1-naphthyl)-3(2H)-furanone as a solid. mp: 194–195° C. NMR: δ1.67 (s, 3H), 1.71 (s, 3H), 2.97 (s, 3H), 7.33–7.43 (m, 2H), 7.48–7.60 (m, 2H), 7.51–7.52 (m, 1H), 7.66–7.69 (m, 2H), 7.76–7.78 (m, 2H), 7.90–7.94 (m, 2H), IR (cm$^{-1}$): 1698, 1404, 1318, 1149, 1092, 772.

EXAMPLE 14

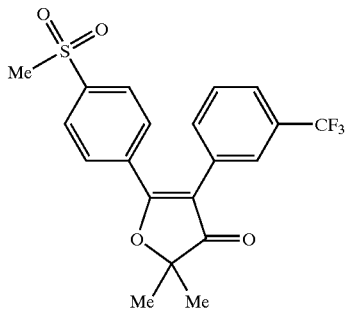

2,2-Dimethyl-5-{4-methylsulfonyl)phenyl}-4-{3-(trifluoromethyl)phenyl}-3(2H)-furanone 200 mg of 4-bromo-2,2-dimethyl-5-{4-(methylsulfonyl) phenyl}-3(2H)-furanone was coupled with 150 mg of (3-trifluoromethylbenzene)boronic acid by a procedure similar to the synthetic procedure in Example 2 to afford 100 mg of 2,2-dimethyl-5-{4-(methylsulfonyl)phenyl}-4-(3-trifluoromethylphenyl)-3(2H)-furanone as a solid. mp: 115–116° C. NMR: δ1.60 (s, 6H), 3.08 (s, 3H), 7.49 (m, 2H), 7.60 (m, 2H), 7.82 (d, J=8.7 Hz, 2H), 7.96 (d, J=9.0 Hz, 2H). IR (cm$^{-1}$): 1697, 1624, 1385, 1327, 124, 959, 770. MS (FAB): 411 (m+1).

Alternatively, 1.5 g of 2,2-dimethyl-5-{4-(methylthio) phenyl}-4-{3-trifluoromethyl)phenyl}-3(2H)-furanone (Example 169) was reacted with 4.5 g of OXONE in 50 ml THF, 50 ml ethanol and 50 ml water by following a procedure employed for the alternative synthesis of Example 4 to afford 1.28 g of the titled compound.

EXAMPLE 15

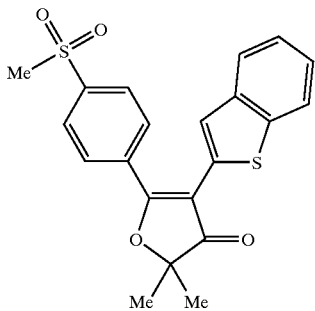

4-(2-Benzo[b]thienyl)-2,2-dimethyl-5-{4-(methylsulfonyl)phenyl}-3(2H)-furanone 200 mg of 4-bromo-2,2-dimethyl-5-{4-(methylsulfonyl) phenyl}-3(2H)-furanone was coupled with 125 mg of (2-benzo[b]thienyl)boronic acid according to a procedure similar to the procedure in Example 2 to afford 60 mg of 4-(2-benzo[b]thienyl)-2,2-dimethyl-5-{4-(methylsulfonyl) phenyl}-3(2H)-furanone as a solid. mp: 204–206° C. NMR: δ1.61 (s, 6H), 3.11 (s, 3H), 7.32~7.43 (m, 4H), 7.51~7.53 (m, 1H), 7.74~7.84 (m, 2H), 8.01 (s, 2H). IR (cm$^{-1}$): 1702, 1620, 1382, 1147, 957, 750.

EXAMPLE 16

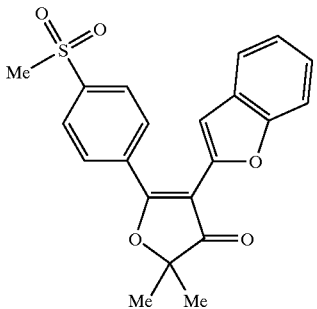

4-(2-Benzo[b]furanyl)-2,2-dimethyl-5-{4-(methylsulfonyl)phenyl}-3(2H)-furanone 200 mg of 4-bromo-2,2-dimethyl-5-{4-(methylsulfonyl) phenyl}-3(2H)-furanone was reacted with 107 mg of (2-benzo[b]furan)boronic acid by following a procedure similar to the synthetic procedure in Example 2 to afford 15 mg of 4-(2-benzo[b]furanyl)-2,2-dimethyl-5-{4-(methylsulfonyl)phenyl}-3(2H)-furanone as a solid. mp: 140–141° C. NMR: δ1.60 (s, 6H), 3.13 (s, 3H), 7.22–7.35 (m, 4H), 7.60–7.63 (m, 1H), 8.06 (m, 4H). IR (cm$^{-1}$): 1703, 1538, 1406, 1317, 1149, 958, 752.

EXAMPLE 17

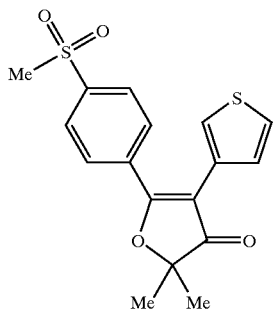

2,2-Dimethyl-5-{4-(methylsulfonyl)phenyl}4-(3-thienyl)-3(2H)-furanone 200 mg of 4-bromo-2,2-dimethyl-5-{4-(methylsulfonyl) phenyl}-3(2H)-furanone was coupled with 100 mg of thiophene-3-boronic acid according to a procedure similar to the synthetic procedure in Example 2 to yield 10 mg of 2,2-dimethyl-5-{4-(methylsulfonyl)phenyl}-4-(3-thienyl)-3 (2H)-furanone as a solid. NMR: δ1.56 (s, 6H), 3.09 (s, 3H), 6.92–6.93 (m, 1H), 7.32–7.35 (m, 1H), 7.51–7.52 (m, 1H), 7.90–7.93 (m, 2H), 7.97–8.00 (m, 2H).

EXAMPLE 18

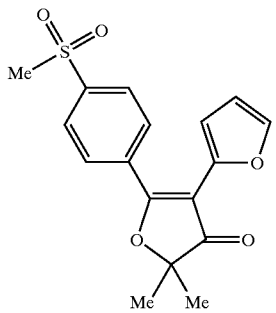

2,2-Dimethyl-4-(2-furanyl)-5-{4-(methylsulfonyl)phenyl}-3(2H)-furanone

Step 1: Preparation of 2,2-dimethyl-4-iodo-5-{4-(methylsulfonyl)phenyl}-3(2H)-furanone

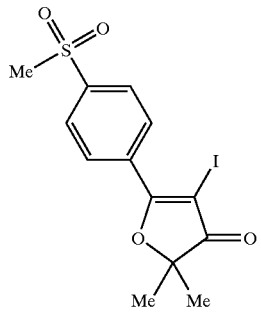

25 g of 2,2-dimethyl-5-{4-(methylsulfonyl)phenyl}-3(2H)-furanone, which was prepared by the OXONE oxidation of 2,2-dimethyl-5-{4-(methylthio)phenyl}-3(2H)-furanone by a procedure similar to Step 5 of Example 1, was dissolved in 400 ml carbon tetrachloride and 100 ml chloroform, to which were added 25 g of [bis(trifluoroacetoxyl)iodo]benzene [BTI] and 15 g of iodine. The mixture was stirred for 3 hours at room temperature and then the reaction was quenched by adding saturated aqueous sodium thiosulfate until the characteristic color of iodine disappeared. The solution was extracted with chloroform (500 ml×3) and the organic layer was concentrated in vacuo. The resulting residue was recrystallized from hexane and ethylacetate to yield 35 g of 2,2-dimethyl-4-iodo-5-{4-(methylsulfonyl)phenyl}-3(2H)-furanone. mp: 184–185° C. NMR: δ1.55 (s, 6H), 3.12 (s, 3H), 8.12 (d, J=8.7 Hz, 2H), 8.40 (d, J=8.7 Hz, 2H).

Step 2: Preparation of 2,2-dimethyl-4-(2-furanyl)-5-{4-(metylsulfonyl)phenyl}-3(2H)-furanone 250 mg of 2,2-dimethyl-4-iodo-5-{4-(methylsulfonyl)phenyl}-3(2H)-furanone was 86 mg of furan-2-boronic acid by a procedure similar to the procedure in Example 2 to afford 47 mg of 2,2-dimethyl-4-(2-furanyl)-5-{4-(methylsulfonyl)phenyl}-3(2H)-furanone as a solid. NMR: δ1.56 (s, 6H), 3.11 (s, 3H), 6.51 (m, 1H), 6.89 (d, J=3.6 Hz, 1H), 7.37 (d, J=3.6 Hz, 1H), 7.97 (m, 4H). IR (cm$^{-1}$): 2989, 1703, 1409, 1317, 2989, 1703, 1409, 1317, 1148, 959, 771.

EXAMPLE 19

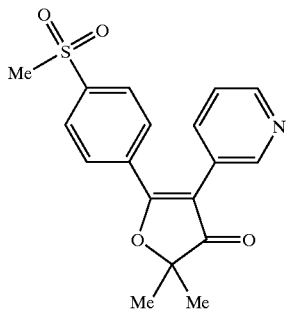

2,2-Dimethyl-5-{4-(methylsulfonyl)phenyl}-4-(3-pyridyl)-3(2H)-furanone

To a stirred solution of 4-bromo-2,2-dimethyl-5-{4-(methylsulfonyl)phenyl}-3(2H)-furanone (200 mg) in 15 ml toluene and 5 ml ethanol, were added 27 mg of tris(dibenzylideneacetone)dipalladium(0)-chloroform adduct, 17 mg of triphenyl phosphine, 5 ml of aqueous 2M sodium carbonate, and lithium 3-trimethylpyridinium boronate (200 mg). The reaction solution was stirred at 90–100° C. for 24 hours. Then the solvent was removed in vacuo. The resulting residue was extracted with water and dichloromethane (100 ml×3). The organic layer was concentrated in vacuo and the resulting residue was separated by column chromatography (hexane/ethylacetate) to afford 110 mg of 2,2-dimethyl-5-{4-(methylsulfonyl)phenyl}-4-(3-pyridyl)-3(2H)-furanone as a solid. mp: 164–166° C. NMR: δ1.60 (s, 6H), 3.09 (s, 3H), 7.38–7.42 (m, 1H), 7.76–7.79 (m, 1H), 7.80–7.83 (m, 2H), 7.96–7.99 (m, 2H), 8.42–8.49 (m, 1H), 8.56–8.61 (m, 1H). IR (cm$^{-1}$): 1698, 1386, 1316, 1149, 1061, 961, 772.

EXAMPLE 20

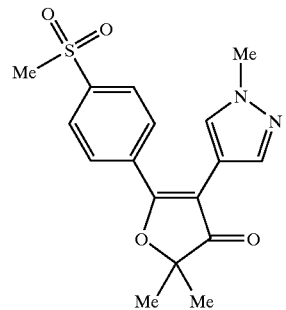

2,2-Dimethyl-4-{4-(1-N-methylpyrazolyl)}-5-{4-(methylsulfonyl)phenyl)-3(2H)-furanone To a stirred solution of 2,2-dimethyl-4-iodo-5-{4-(methylsulfonyl)phenyl}-3(2H)-furanone (445 mg) in 50 ml toluene and 15 ml ethanol, were added 25 mg of tetrakis(triphenylphosphine)palladium(0), 15 ml of aqueous 2M sodium carbonate, and 547 mg of {4-(1-N-methylpyrazolyl)}-trimethylboronate lithium salt. The reaction solution was stirred at 90° C. for 12 hours. Then the solvent was removed in vacuo. The resulting residue was extracted with water and dichloromethane (50 ml×3). The organic layer was concentrated in vacuo and the resulting residue was separated by column chromatography (hexane/ethylacetate) to give 290 mg of 2,2-dimethyl-4-{4-(1-N-methylpyrazolyl)}-5-{4-

(methylsulfonyl)phenyl}-3(2H)-furanone as a solid. mp: 114–115° C. NMR: δ1.54 (s, 6H), 3.10 (s, 3H), 3.94 (s, 3H), 7.34 (s, 1H), 7.99–8.06 (m, 4H). IR (cm$^{-1}$): 2930, 1700, 1538, 1314, 1148, 884, 771. MS(FAB): 347(m+1)

EXAMPLE 21

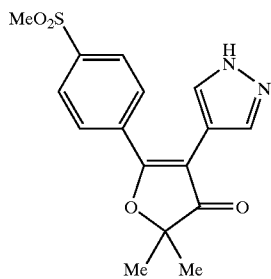

2,2-Dimethyl-5-{4-(methylsulfonyl)phenyl}-4-(4-pyrazolyl)-3(2H)-furanone

Step 1: Preparation of 4-bromo-1-N-tritylpyrazole

A mixture of 0.5 g of 4-bromopyrazole and 1.43 g of tritylchloride in 30 ml of pyridine was stirred at reflux for 18 hours. The pyridine was removed in vacuo and the resulting residue was purified by silica column chromatography (ethylacetate/hexane=1:1) to yield 1.32 g of 4-bromo-1-N-tritylpyrazole.

Step 2: Preparation of {4-(1-N-tritylpyrazolyl)}-trimethylboronate lithium salt

To a stirred solution of the 4-bromo-1-N-tritylpyrazole in 30 ml dry THF at −78° C., was added dropwise 1.4 ml of 2 M butyllithium in hexane. Then the reaction mixture was stirred for 30 minutes, followed by the addition of 0.76 ml of triisopropylborate. The reaction mixture was stirred for another hour. Then the reaction was stopped by adding 20 ml methanol. The solvent was removed in vacuo, and the resulting salt was used in the next step without further purification.

Step 3: Preparation of 2,2-dimethyl-5-{4-(methylsulfonyl)phenyl}-4-{4-(1-N-tritylpyrazol)}-3(2H)-furanone To 300 mg of 2,2-dimethyl-4-iodo-5-{4-(methylsulfonyl)phenyl}-3(2H)-furanone in 50 ml toluene and 15 ml ethanol, were added 25 mg of tetrakis(triphenylphosphine)palladium (0), 15 ml 2M aqueous sodium carbonate, and 480 mg of the crude {4-(1-N-tritylpyrazolyl)}-trimethylboronate lithium salt from the previous step. The reaction mixture was stirred at 90° C. for 12 hours. The reaction mixture was purified by a procedure similar to the purification procedure in Example 2 to yield 120 mg of 2,2-dimethyl-5-{4-(methylsulfonyl)phenyl}-4-{4-(1-N-tritylpyrazole)}-3(2H)-furanone.

Step 4: Preparation of 2,2-dimethyl-5-{4-(methylsulfonyl)phenyl}-4-(4-pyrazoyl)-3(2H)-furanone 120 mg of 2,2-dimethyl-5-{4-(methylsulfonyl)phenyl}-4-{4-(1-N-tritylpyrazolyl)}-3(2H)-furanone was stirred in 23 ml methanol for 3 hours in the presence of 36 mg of p-toluenesulfonic acid. Then the methanol was removed under reduced pressure and the resulting residue was diluted with 30 ml water. The aqueous layer was extracted with dichloromethane (30 ml×3). The organic layer was then concentrated in vacuo and the resulting residue was purified by column chromatography (hexane/ethylacetate=1:4) to afford 60 mg of 2,2-dimethyl-5-{4-(methylsulfonyl)-phenyl}-4-(4-pyrazolyl)-3(2H)-furanone. NMR: δ1.56 (s, 6H), 3.11 (s, 3H), 7.88 (s, 2H), 8.05 (m, 5H). IR (cm$^{-1}$): 3325, 1702, 1408, 1316, 1148, 913.

EXAMPLE 22

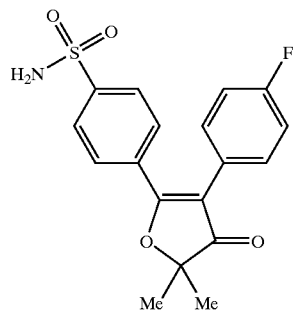

5-{4-(Aminosulfonyl)phenyl}-2,2-dimethyl-4-(4-fluorophenyl)-3(2H)-furanone

Step 1: Preparation of 2,2-dimethyl-5-{4-(methylsulfinyl)phenyl}-3(2H)-furanone

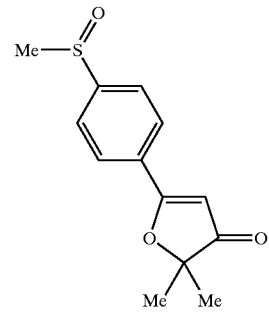

To a stirred solution of 2,2-dimethyl-5-{4-(methylthio)phenyl}-3(2H)-furanone (10 g) in 200 ml dichloromethane at 0° C., was added slowly dropwise 4.8 g of m-chloroperoxybenzoic acid (m-CPBA) dissolved in 50 ml dichloromethane. After the reaction mixture was stirred at 0° C. for another two hours, the reaction solution was concentrated in vacuo. The resulting residue was extracted with water and dichloromethane (50 ml×3), followed by washing with aqueous sodium carbonate. The organic layer was concentrated and the crude product was purified by column chromatography (hexane/ethylacetate) to obtain 7.5 g of 2,2-dimethyl-5-{4-(methylsulfinyl)phenyl}-3(2H)-furanone as a solid. mp: 108–109° C. NMR: δ1.51 (s, 6H), 2.78 (s, 3H), 6.06 (s, 1H), 7.78 (d, J=8.4 Hz, 2H), 8.02 (d, J=8.4 Hz, 2H). IR (cmu$^{-1}$): 2925, 1697, 1603, 1558, 1173, 1087, 1049.

Step 2: Preparation of 2,2-dimethyl-4-iodo-5-{4-(methylsulfinyl)phenyl}-3(2H)-furanone

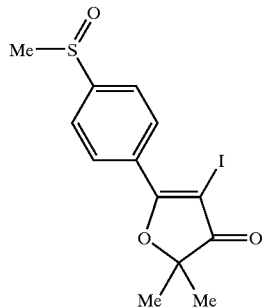

To a stirred solution of 6 g of 2,2-dimethyl-5-{4-(methylsulfinyl)phenyl}-3(2H)-furanone in 200 ml carbon tetrachloride and 100 ml chloroform, were added 5.15 g of [bis(trifluoroacetoxy)iodo]benzene (BTI) and 6.5 g of iodine. The reaction solution was stirred at room temperature. After 4 hours, the reaction was quenched by adding saturated aqueous sodium thiosulfate until the characteristic color of iodine disappeared. The quenched solution was extracted with water and dichloromethane (100 ml×3). The organic layer was concentrated in vacuo and the resulting crude product was recrystallized from hexane/ethylacetate to yield 4.5 g of 2,2-dimethyl-4-iodo-5-{4-(methylsulfinyl)phenyl}-3(2H)-furanone. NMR: δ1.53 (s, 6H), 2.79 (s, 3H), 7.81 (d, J=8.1 Hz, 2H), 8.38 (d, J=8.1 Hz, 2H). IR (cm⁻¹): 2975, 2929, 1699, 1595, 1404, 1319, 1150, 969, 766, 552.

Step 3: Preparation of 5-{4-(aminosulfonyl)phenyl}-2,2-dimethyl-4-iodo-3(2H)-furanone

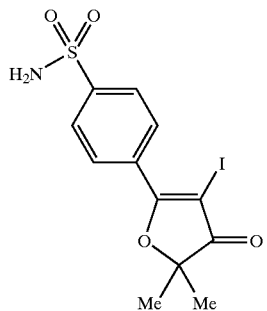

1.11 g of 2,2-dimethyl-4-iodo-5-{4-(methylsulfinyl)phenyl}-3(2H)-furanone was reacted with 30 ml trifluoroacetic anhydride (TFAA) for 2 hours at 0° C. After the volatile solvent was removed in vacuo, the resulting residue was dissolved in 50 ml of 1:1 methanol/triethylamine. The solvent was removed again in vacuo. Then the resulting residue was dissolved in 30 ml carbon tetrachloride, to which was added slowly 40 ml acetic acid saturated with chlorine at 0° C. After stirring the reaction solution at 0° C. for 20 minutes, the reaction solvent and the unreacted chlorine were removed in vacuo. The resulting residue was dissolved in 30 ml toluene and the toluene was removed again under reduced pressure. The resulting residue was reacted with 3 ml ammonia water in 40 ml THF at 0° C. for 30 minutes. The reaction solution was concentrated in vacuo and the resulting residue was diluted with 30 ml water. The aqueous solution was then extracted with dichloromethane (30 ml×3). The organic layer was concentrated under reduced pressure and was purified by column chromatography (hexane/ethylacetate=3:2) to obtain 450 mg of 5-{4-(aminosulfonyl)-phenyl}-2,2-dimethyl-4-iodo-3(2H)-furanone as a solid. mp: 179–180° C. NMR: δ1.50 (s, 6H), 5.63 (br. s, 2H), 8.05 (dd, J=9.0, 1.5 Hz, 2H), 8.29 (dd, J=9.0, 5.7 Hz, 2H). IR (cm⁻¹): 3367, 3261, 2985, 1684, 1582, 1405, 1188, 913. MS (FAB): 393 (m+1).

Step 4: Preparation of 5-{4-(aminosulfonyl)phenyl}-2,2-dimethyl-4-(4-fluorophenyl)-3(2H)-furanone To stirred solution of 100 mg of 5-{4-(aminosulfonyl)phenyl}-2,2-dimethyl-4-iodo-3(2H)-furanone dissolved in 15 ml toluene and 5 ml ethanol, were added 34 mg of tetrakis(triphenylphosphine)palladium(0), 5 ml of 2M aqueous sodium carbonate, and 80 mg of (4-fluorobenzene)boronic acid. The reaction solution was then stirred at 95° C. for 24 hours, followed by removal of the solvent in vacuo. Then the residue was extracted with 30 ml water and dichloromethane (30 ml×3). The organic layer was dried over anhydrous magnesium sulfate. Then the hydrated magnesium sulfate was filtered off and the filtrate was concentrated in vacuo. The resulting crude product was purified by column chromatography (hexane/ethylacetate=1:1) to give 40 mg of 5-{4-(aminosulfonyl)phenyl}-2,2-dimethyl-4-(4-fluorophenyl)-3(2H)-furanone as a solid. mp: 162–163° C. NMR: δ1.57 (s, 6H), 4.93 (br. s, 2H), 7.08 (d, J=8.7 Hz, 2H), 7.25 (t, J=8.7 Hz, 2H), 7.78 (d, J=8.7 Hz, 2H), 7.92 (d, J=8.7 Hz, 2H). IR (cm⁻¹): 3348, 3263, 1685, 1589, 1341, 1219, 1163.

EXAMPLE 23

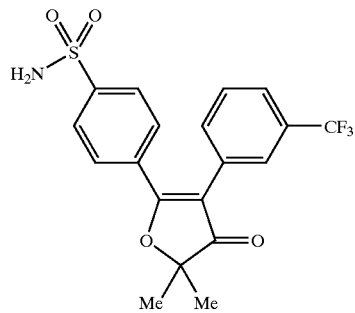

5-{4-(Aminosulfonyl)phenyl}-2,2-dimethyl-4-{3-(trifluoromethyl)phenyl}-3(2H)-furanone To a stirred solution of 100 mg of 5-{4-(aminosulfonyl)phenyl}-2,2-dimethyl-4-iodo-3(2H)-furanone dissolved in 15 ml toluene and 5 ml ethanol, were added 30 mg of tetrakis(triphenylphosphine)palladium(0), 5 ml of 2 M aqueous sodium carbonate, and 100 mg of 3-(trifluoromethyl)benzeneboronic acid. Then the mixture was stirred at 95° C. for 24 hours. The reaction mixture was purified according to a procedure similar to Step 4 of Example 22 to yield 35 mg of 5-{4-(aminosulfonyl)phenyl}2,2-dimethyl-4-{3-(trifluoromethyl)phenyl}-3(2H)-furanone. mp: 129–130° C. NMR: δ1.59 (s, 6H), 4.93 (br, s, 2H), 7.48 (m, 2H), 7.59 (m, 2H), 7.76 (d, J=8.7 Hz, 2H), 7.93 (d, J=9.0 Hz, 2H). IR (cm⁻¹): 3343, 3265, 1691, 1593, 1329, 1262.

EXAMPLE 24

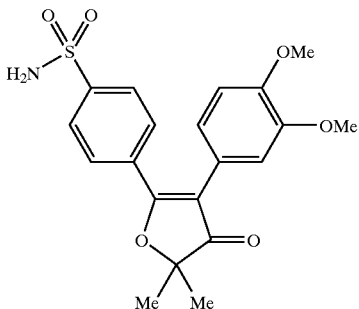

5-{4-(Aminosulfonyl)phenyl}-4-{3,4-(dimethoxy)phenyl}-2,2-dimethyl 3(2H)-furanone To a stirred solution of 150 mg of 5-{4-(aminosulfonyl)phenyl}-2,2-dimethyl-4-iodo-3(2H)-furanone dissolved in 15 ml toluene and 5 ml ethanol, were added 20 mg of tetrakis(triphenylphosphine)palladium(0), 5 ml of 2 M aqueous sodium carbonate, and 100 mg of 3,4-(dimethoxy)benzeneboronic acid. And the mixture was stirred at 95° C. for 24 hours. The reaction mixture was purified by following a procedure similar to Step 4 of Example 22 to give 60 mg of 5-{4-(aminosulfonyl)phenyl}-4-{3,4-(dimethoxy)phenyl}-2,2-dimethyl-3(2H)-furanone as a solid. mp: 213–214° C. NMR: δ1.57 (s, 6H), 3.81 (s, 3H), 3.90 (s, 3H), 4.87 (br s, 2H), 6.86 (m, 3H), 7.81 (d, J=8.4 Hz, 2H), 7.91 (d, J=8.7 Hz, 2H). IR (cm$^{-1}$): 3339, 3248, 1694, 1404, 1259, 1159, 1024, 604.

EXAMPLE 25

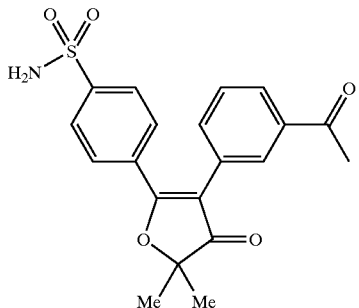

4-(3-Acetylphenyl)-5-{4-(aminosulfonyl)phenyl}-2,2-dimethyl-3(2H)-furanone 150 mg of 5-{4-(aminosulfonyl)phenyl}-2,2-dimethyl-4-iodo-3(2H)-furanone was reacted with 75 mg of (3-acetylbenzene)boronic acid by following a procedure similar to Step 4 of Example 22 to yield 40 mg of 4-(3-acetylphenyl)-5-{4-(aminosulfonyl)phenyl}-2,2-dimethyl-3(2H)-furanone as a solid. mp: 217–218° C. NMR: δ1.57 (s, 6H), 2.58 (s, 3H), 4.89 (br s, 2H), 7.48 (m, 2H), 7.78 (m, 2H), 7.91 (m, 4H). IR (cm$^{-1}$): 3340, 3233, 1682, 1558, 1162, 801, 751, 679, 654, 604. MS (FAB): 393 (m+1).

EXAMPLE 26

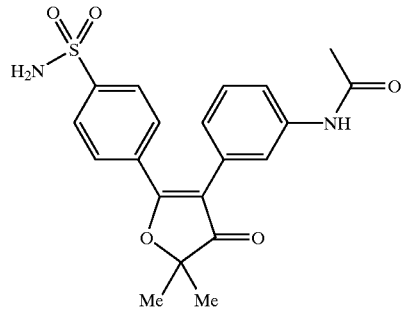

4-{3-N-(Acetylamino)phenyl}-5-{4-(aminosulfonyl)phenyl)-2,2-dimethyl-3(2H)-furanone 60 mg of 5-{4-(aminosulfonyl)phenyl}-2,2-dimethyl-4-iodo-3(2H)-furanone was reacted with 35 mg of {3-N-(acetylamino)benzene}boronic acid by following a procedure similar to Step 4 of Example 22 to give 25 mg of 4-{3-N-(acetylamino)phenyl}-5-{4-(aminosulfonyl)phenyl}-2,2-dimethyl-3(2H)-furanone as a solid. mp: 225–227° C. NMR: δ1.62 (s, 6H), 2.04 (s, 3H), 4.82 (br s, 2H), 7.4 (m, 3H), 7.53 (m, 1H), 7.68 (m, 4H). IR (cm$^{-1}$): 3325, 2926, 1698, 1558, 1437, 1119.

EXAMPLE 27

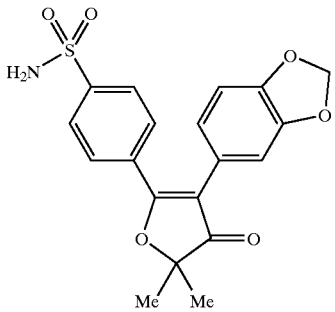

5-{4-(Aminosulfonyl)phenyl{-2,2-dimethyl-4-}3,4-(methylenedioxy)phenyl}-3(2H)-furanone 120 mg of 5-{4-(aminosulfonyl)phenyl}-2,2-dimethyl-4-iodo-3(2H)-furanone was reacted with 100 mg of 3,4-(methylenedioxy)benzeneboronic acid by following a procedure similar to Step 4 of Example 22 to yield 40 mg of 5-{4-(aminosulfonyl)phenyl}-2,2-dimethyl-4-{3,4-(methylenedioxy)phenyl}-3(2H)-furanone as a solid. mp: 178–179° C. NMR: δ1.56 (s, 6H), 4.89 (br s, 2H), 5.99 (s, 2H), 6.74 (m, 2H), 6.83 (m, 1H), 7.82 (d, J=9.0 Hz, 2H), 7.92 (d, J=9.0 Hz, 2H). IR (cm$^{-1}$): 3237, 1682, 1338, 1245, 1164.

EXAMPLE 28

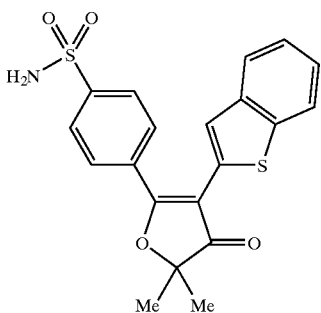

5-{4-(Aminosulfonyl)phenyl{-4(2-benzo[b]thienyl)-2,2-dimethyl-3(2H)-furanone 200 mg of 5-{4-(aminosulfonyl)phenyl}-2,2dimethyl-4-iodo-3(2H)-furanone was coupled with 109 mg of (2-benzo[b]thiophene)boronic acid by following a procedure similar to Step 4 of Example 22 to yield 45 mg of 5-{4-(aminosulfonyl)phenyl}-4-(2-benzo[b]thienyl)-2,2-dimethyl-3(2H)-furanone as a solid. mp: 120–121° C. NMR: δ1.60 (s, 3H), 4.89 (br s, 2H), 7.36 (m, 2H), 7.50 (m, 1H), 7.75 (m, 2H), 7.97 (m, 4H). IR (cm$^{-1}$): 3350, 3210, 1650, 1530, 1320, 1158, 803, 743. MS (FAB): 400 (m+1).

EXAMPLE 29

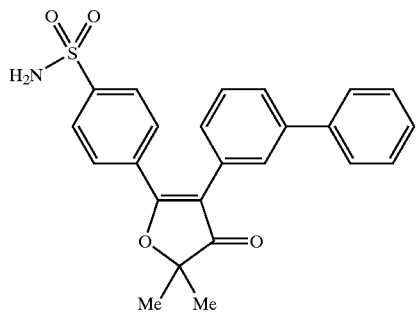

5-{4-(Aminosulfonyl)phenyl}-4-(3-biphenyl)-2,2-dimethyl-3(2H)-furanone 200 mg of 5-{4-(aminosulfonyl)phenyl}-2,2-dimethyl-4-iodo-3(2H)-furanone was reacted with 120 mg of (3-phenylbenzene)boronic acid by following a procedure similar to Step 4 of Example 22 to give 40 mg of 5-{4-(aminosulfonyl)phenyl}-4-(3-biphenyl)-2,2-dimethyl-3(2H)-furanone as a solid. mp: 160–161° C. NMR: δ1.57 (s, 6H), 4.86 (br s, 2H), 7.23 (m, 1H), 7.34 (m, 1H), 7.44 (m, 3H), 7.56 (m, 4H), 7.84 (d, J=8.7 Hz, 2H), 7.91 (d, J=8.7 Hz, 2H). IR (cm$^{-1}$): 3249, 1681, 1614, 1345, 1161.

EXAMPLE 30

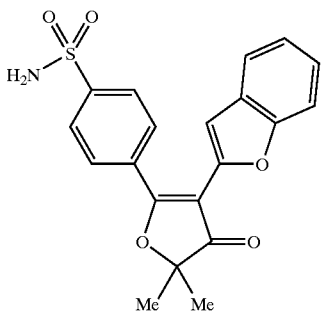

5-{4-(Aminosulfonyl)phenyl{-4-(2-benzo[b]furanyl)-2,2-dimethyl-3(2H)-furanone 200 mg of 5-{4-(aminosulfonyl)phenyl}-2,2-dimethyl-4-iodo-3(2H)-furanone was coupled with 99 mg of benzo[b]furan-2-boronic acid by following a procedure similar to Step 4 of Example 22 to give 45 mg of 5-{4-(aminosulfonyl)phenyl}-4-(2-benzo[b]furanyl)-2,2-dimethyl-3(2H)-furanone as a solid. mp: 143–145° C. NMR: δ1.60 (s, 6H), 4.92 (br s, 2H), 7.23 (m, 3H), 7.72 (m, 2H), 8.02 (m, 4H), IR (cm$^{-1}$): 3384, 3245, 1698, 1510, 1253, 1161, 793.

EXAMPLE 31

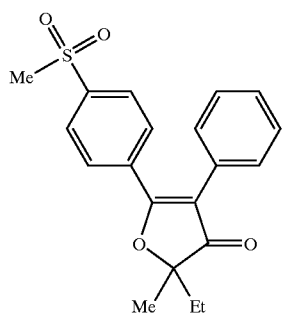

2-Ethyl-2-methyl-5-{4-(methylsulfonyl)phenyl}-4-phenyl-3(2H)-furanone

Step 1: Preparation of 4-methyl-1-{4-(methylthio)phenyl}-2-hexyn-1,4-diol

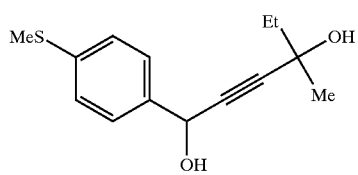

To a stirred solution of 3-methyl-1-pentyn-3-ol (23.3 g) in 150 ml anhydrous THF at −78° C. under argon, was added 130 ml of 2.5 M butyllithium in hexane dropwise over 20 minutes. The reaction solution was stirred for another 20 minutes, followed by dropwise addition 16 ml of 4-methylthiobenzaldehyde. After stirring for another 2 hours, the reaction was quenched by adding 200 ml of dilute aqueous HCl. The reaction solvent was removed in vacuo, and the resulting aqueous solution was extracted with dichloromethane (100 ml×3). The organic layer was concentrated under reduced pressure and the resulting residue was purified by column chromatography (hexane/ethylacetate=1:1) to yield 30 g of 4-methyl-1-{4-(methylthio)phenyl}-2-hexyn-1,4-diol as an oil. NMR: δ1.05 (t, J=7.5 Hz, 3H), 1.51 (s, 3H), 1.73 (m, 2H), 2.18 (s, 1H), 2.50 (s, 3H), 5.49 (s, 1,H), 7.26 (d, J=8.7 Hz, 2H), 7.45 (d, J=8.7 Hz, 2H). IR (cm$^{-1}$): 3348, 2974, 2930, 1492, 1092, 983, 795, 523.

Step 2: Preparation of 4-hydroxy-4-methyl-1-{4-(methylthio)phenyl}-2-hexyn-1-one

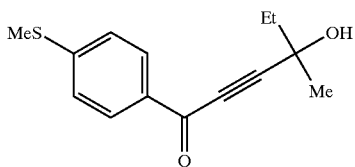

To 9.9 g of 4-methyl-1-{4-(methylthio)phenyl}-2-hexyn-1,4-diol dissolved in 200 ml dichloromethane, were added 15 g of pyridinium dichromate (PDC) and 15 g of celite. The suspension was stirred overnight at room temperature, and then the insoluble material was filtered off through Florisil. The filtrate was purified by column chromatography (hexane/ethylactate=4:1) to give 5.34 g of 4-hydroxy-4-methyl-1-{4-(methylthio)phenyl}-2-hexyn-1-one. NMR: δ1.13 (t, J=7.5 Hz, 3H), 1.62 (s, 3H), 1.85 (q, J=7.8 Hz, 2H), 2.54 (s, 3H), 7.28 (d, J=8.7 Hz, 2H), 8.01 (d, J=8.7 Hz, 2H). IR (cm$^{-1}$): 3427, 2974, 1588, 1095, 914, 745.

Step 3: Preparation of 2-ethyl-2-methyl-5-{4-(methylthio)phenyl}-3(2H)-furanone

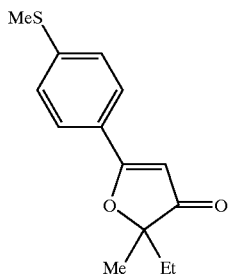

5.34 g of 4-hydroxy-4-methyl-1-{4-(methylthio)phenyl}-2-hexyn-1-one was dissolved in 200 ml ethanol, added dropwise 3 ml diethylamine diluted with 50 ml ethanol. The reaction solution was stirred at room temperature for 4 hours, and the solvent was removed in vacuo. The resulting residue was extracted with water and dichloromethane (100 ml×3). Concentration of the organic layer afforded crude 2-ethyl-2-methyl-5-{4-(methylthio)phenyl}-3(2H)-furanone, which was used in the next step without further purification.

Step 4: Preparation of 2-ethyl-2-methyl-5-{4-(methylsufonyl)phenyl}-3(2H)furanone

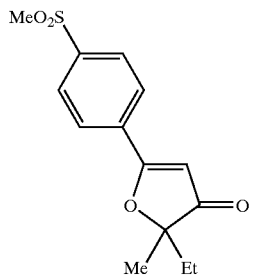

The crude product 2-ethyl-2-methyl-5-{4-(methylthio)phenyl}-3(2H)-furanone from the previous Step 3 was dissolved in 50 ml ethanol, 50 ml THF and 50 ml water, and 10 g of OXONE was added thereto. The reaction mixture was stirred overnight at room temperature. Then the insoluble materials were removed by filtration and the filtrate was concentrated in vacuo. The resulting aqueous layer was extracted with dichloromethane (100 ml×1 and 50 ml×2). The organic layer was concentrated under reduced pressure and the resulting residue was purified by column chromatography (hexane/ethylacetate=2:1) to yield 4.5 g of 2-ethyl-2-methyl-5-{4-(methylsufonyl)phenyl}-3(2H)-furanone. NMR: δ0.89 (t, J=7.2 Hz, 3H), 1.48 (s, 3H), 1.91 (q, J=7.2 Hz, 2H), 3.11 (s, 3H), 6.13 (s, 1H), 8.07 (m, 4H).

Step 5: Preparation of 4-bromo-2-ethyl-2-methy-5-{4-(methylsulfonyl)phenyl}-3(2H)-furanone

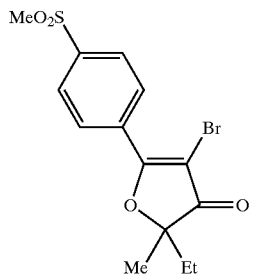

To 4.5 g of 2-ethyl-2-methyl-5-{4-(methylsufonyl)phenyl}-3(2H)-furanone dissolved in 100 ml carbon tetrachloride, were added acetic acid (3 ml) and bromine (1 ml). The reaction solution was stirred for 1 hour at room temperature. Then the reaction was quenched by adding saturated aqueous sodium thiosulfate solution until the characteristic color of bromine disappeared. The reaction solution was extracted with dichloromethane (30 ml×3) and the organic layer was concentrated in vacuo. The resulting residue was purified by column chromatographic separation (hexane/ethylacetate=1:1) to give 4 g of 4-bromo-2-ethyl-2-methy-5-{4-(methylsulfonyl)phenyl}-3(2H)-furanone. NMR: δ0.91 (t, J=7.2 Hz, 3H), 1.52 (s, 3H), 1.95 (qd, J=7.2, 3.0 Hz, 2H), 3.11 (s, 3H), 8.11 (d, J=8.7 Hz, 2H), 8.41 (d, J=8.7 Hz, 2H). IR (cm$^{-1}$): 2928, 1703, 1583, 1316, 1160, 552.

Step 6: Preparation of 2-ethyl-2-methyl-5-{4-(methylsulfonyl)phenyl}4-phenyl-3(2H)-furanone To a stirred solution of 4-bromo-2-ethyl-2-methy-5-{4-(methysulfonyl)-phenyl}-3(2H)-furanone (200 mg) in 15 ml of toluene, were added 40 mg of tetrakis(triphenylphosphine)palladium(0), 5 ml of 2 M aqueous sodium carbonate solution, and 100 mg of benzeneboronic acid. The reaction solution was stirred at reflux for 12 hours. Then the reaction solvent was evaporated under reduced pressure. The resulting residue was extracted with water and dichloromethane (30 ml×3). The organic layer was concentrated in vacuo. The resulting crude product mixture was purified by column chromatography (hexane/ethylacetate=2:1) to give 60 mg of 2-ethyl-2-methyl-5-{4-(methylsulfonyl)phenyl}-4-phenyl-3(2H)-furanone as a solid. mp: 115–117° C. NMR: δ0.96 (t, J=7.5 Hz, 3H), 1.55 (s, 3H), 1.97 (q, J=7.5 Hz, 2H), 3.07 (s, 3H), 7.37 (m, 5H), 7.85 (d, J=8.7 Hz, 2H), 7.93 (d, J=8.7 Hz, 2H). IR (cm$^{-1}$): 2928, 1697, 1620, 1403, 1318, 1149, 959, 769, 552.

EXAMPLE 32

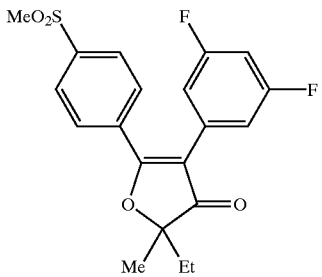

4-(3,5-Difluorophenyl)-2-ethyl-2-methyl-5-{4-(methylsulfonyl)phenyl}-3(2H)-furanone To a stirred solution of 4-bromo-2-ethyl-2-methy-5-{4-(methylsulfonyl)-phenyl}-3(2H)-furanone (200 mg) in 15 ml toluene and 5 ml ethanol, were added 34 mg of tetrakis(triphenylphosphine)palladium(0), 5 ml of 2 M aqueous sodium carbonate solution, and 110 mg of 3,5-difluorobenzeneboronic acid. Then the reaction solution was stirred at 95° C. for 12 hours. The reaction solvent was evaporated off under reduced pressure and the resulting residue was extracted with 50 ml water and dichloromethane (30 ml×3). The organic layer was concentrated in vacuo. The resulting crude product mixture was purified by column chromatography (hexane/ethylacetate=2:1) to obtain 80 mg of 4-(3,5-difluorophenyl)-2-ethyl-2-methyl-5{4-(methylsulfonyl)phenyl}-3(2H)-furanone as a solid. mp: 122–124° C. NMR: δ0.95 (t, J=7.5 Hz, 3H), 1.54 (s, 3H), 1.97 (m, 2H), 3.10 (s, 3H), 6.81 (m, 3H), 7.84 (d, J=8.7 Hz, 2H), 7.99 (d, J=8.4 Hz, 2H). IR (cm$^{-1}$): 2975, 2928, 1698, 1627, 1321, 1150, 990, 769, 552.

EXAMPLE 33

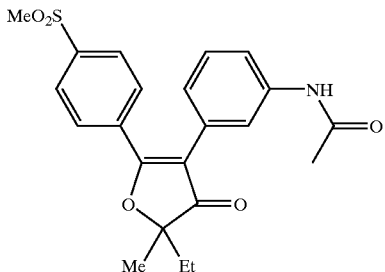

4-{3(N-Acetylamino)phenyl}-2-ethyl-2-methyl-5-}4(methylsulfonyl)phenyl}-3(2H)-furanone 200 mg of 4-bromo-2-ethyl-2-methy-5-{4-(methylsulfonyl)-phenyl}-3(2H)-furanone was coupled with 120 mg of {(3-N-acetylamino)benzene}boronic acid according to a procedure similar to the synthetic procedure in Example 32 to yield 120 mg of 4-{(3-N-acetylamino)phenyl}-2-ethyl-2-methyl-5{4-(methylsulfonyl)phenyl}-3 (2H)-furanone. mp: 56–57° C. NMR: δ0.95 (t, J=7.2, 3H), 1.54 (s, 3H), 1.95 (m, 2H), 2.07 (s, 3H), 3.07 (s, 3H), 6.92 (m, 1H), 7.33 (m, 1H), 7.56 (m, 2H), 7.85 (d, J=8.7 Hz, 2H), 7.93 (d, J=9.0 Hz, 2H), 8.00 (s, 1H). IR (cm$^{-1}$): 3312, 3077, 2928, 2881, 1695, 1619, 1553, 1318, 1149, 958, 725, 641.

EXAMPLE 34

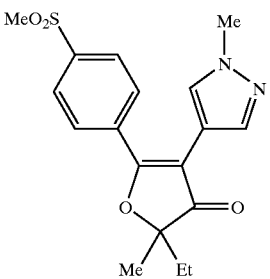

2-Ethyl-2-methyl-4-{4-(1-N-methylpyrazolyl)}-5-{4-(methylsulfonyl)phenyl}-3(2H)-furanone 210 mg of 2-ethyl-4-iodo-2-methy-5-{4-(methylsulfonyl)-phenyl}-3(2H)-furanone was reacted with 170 mg of {4-(1-N-methylpyrazolyl)}-trimethylboronate lithium salt. Then the reaction solution was stirred at 90° C. for 12 hours. The reaction solvent was evaporated off under reduced pressure and the resulting residue was diluted with 50 ml water. The aqueous solution was then extracted with dichloromethane (30 ml×3) and the organic layer was concentrated in vacuo. The resulting crude product mixture was purified by column chromatography (hexane/ethylacetate) to give 100 mg of 2-ethyl-2methyl-4-{4-(1-N-methylpyrazolyl)}-5-{4-(methylsulfonyl)phenyl}-3(2H)-furanone as a solid. mp: 78–80° C. NMR: δ0.92 (t, J=7.5 Hz, 3H), 1.59 (s, 3H). 1.93 (m, 2H), 3.10 (s, 3H), 3.93 (s, 3H), 7.38 (d, J=0.6 Hz, 1H), 7.74 (br s, 1H), 8.03 (m, 4H).

EXAMPLE 35

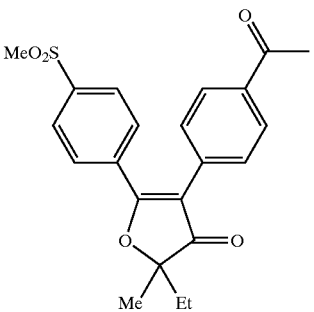

4-(4-Acetylphenyl)-2-ethyl-2-methyl-5-}4-(methylsulfonyl)phenyl)-3(2H)-furanone

Step 1: Preparation of 2-ethyl-4-iodo-2-methyl-5-{4-(methylsulfonyl)phenyl}-3(2H)-furanone To 8.88 g of 2-ethyl-2-methyl-5-{4-(methylsulfonyl)phenyl}-3(2H)-furanone in 50 ml carbon tetrachloride and 50 ml chloroform, were added [bis(trifluoroacetoxy)iodo]

benzene (6.82 g) and iodine (4 g). The reaction solution was stirred at room temperature for 4 hours. Then the reaction was quenched by adding saturated aqueous sodium thiosulfate until the characteristic color of iodine disappeared. The solution was extracted with 50 ml water and dichloromethane (100 ml×3). The organic layer was concentrated in vacuo and the resulting residue was purified by lo column chromatographic separation (hexane/ethylacetate=1:1) to yield 8.7 g of 2-ethyl-4-iodo-2-methyl-5-{4-(methylsulfonyl)phenyl}-3(2H)-furanone. NMR: δ0.89 (t, J=7.5 Hz, 3H), 1.51 (s, 3H), 1.93 (q, J=7.5 Hz, 2H), 3.11 (s, 3H), 8.11 (d, J=8.7 Hz, 2H), 8.34 (d, J=8.7 Hz, 2H). IR (cm$^{-1}$): 2928, 1701, 1552, 1314, 1148, 747, 551.

Step 2: Preparation of 4-(4-acetylphenyl)-2-ethyl-2-methyl-5-{4-(methylsulfonyl)-phenyl}-3(2H)-furanone To a stirred solution of 2-ethyl-4-iodo-2-methy-5-{4-(methylsulfonyl)phenyl}-3(2H)-furanone (200 mg) in 15 ml toluene and 5 ml ethanol, were added 34 mg of tetrakis(triphenylphosphine)palladium(0), 5 ml of 2M aqueous sodium carbonate solution and 120 mg of 4-acetylbenzeneboronic acid. Then the reaction solution was stirred at 95° C. for 12 hours. The reaction solvent was evaporated off under reduced pressure and the resulting residue was extracted with 50 ml water and dichloromethane (30 ml×3). Then the organic layer was concentrated in vacuo and the resulting crude product was purified by column chromatography (hexane/ethylacetate) to afford 120 mg of 4-(4-acetylphenyl)-2-ethyl-2-methyl-5-{4-(methylsulfonyl)phenyl}-3(2H)-furanone as a solid. mp: 147–148° C. NMR: δ0.97 (t, J=7.5 Hz, 3H), 1.56 (s, 3H), 1.99 (m, 2H), 2.62 (s, 3H), 3.08 (s, 3H), 7.39 (d, J=8.7 Hz, 2H), 7.83 (d, J=8.7 Hz, 2H), 7.97 (m, 2H). IR (cm$^{-1}$): 2929, 1684, 1410, 1317, 1149, 1016, 769, 552.

EXAMPLE 36

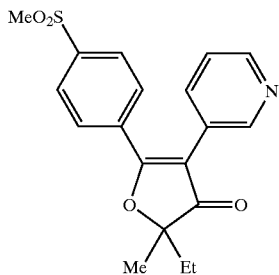

2-Ethyl-2-methyl-5-{4-(methylsulfonyl)phenyl}-4-(3-pyridyl)-3(2H)-furanone

To a stirred solution of 4-bromo-2-ethyl-2-methy-5-{4-(methylsulfonyl)-phenyl}-3(2H)-furanone (200 mg) in 15 ml toluene and 5 ml ethanol, were added 40 mg of tetrakis(triphenylphosphine)palladium(0), 5 ml of aqueous 2M sodium carbonate solution and 110 mg of (3-pyridyl)-trimethylboronate lithium salt. Then the reaction solution was stirred at 95° C. for 12 hours. The reaction solvent was evaporated off under reduced pressure and the resulting residue was diluted with 50 ml water. The aqueous solution was then extracted with dichloromethane (30 ml×3) and the organic layer was concentrated in vacuo. The resulting crude product mixture was purified by column chromatography (hexane/ethylacetate) to obtain 35 mg of 2-ethyl-2-methyl-5-{4-(methylsulfonyl)phenyl}-4-(3-pyridyl)-3(2H)-furanone. NMR: δ0.97 (t, J=7.5 Hz, 3H), 1.57 (s, 3H), 2.00 (m, 2H), 3.09 (s, 3H), 7.37 (m, 1H), 7.71 (m, 1H), 7.83 (d, J=9.0 Hz, 2H), 7.98 (d, J=8.7 Hz, 2H), 8.46 (s, 1H), 8.58 (s, 1H). IR (cm$^{-1}$): 3058, 2976, 1696, 1621, 1401, 1318, 1149, 926, 769, 726, 552.

EXAMPLE 37

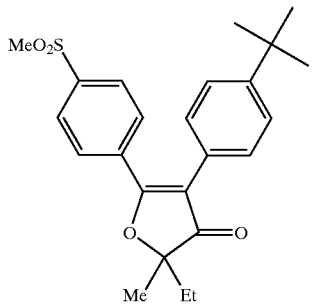

4-(4-t-Butylphenyl)-2-ethyl-2-methyl-5-{4-(methylsulfonyl)phenyl}-3(2H)-furanone 150 mg of 2-ethyl-4-iodo-2-methy-5-{4-(methylsulfonyl)phenyl}-3(2H)-furanone (150 mg) was coupled with 117 mg of (4-t-butylbenzene)boronic acid according to a procedure similar to the synthetic procedure for the Step 2 of Example 35 to afford 100 mg of 4-(4-t-butylphenyl)-2-ethyl-2-methyl-5-{4-(methylsulfonyl)-phenyl}-3(2H)-furanone. mp: 45° C. NMR: δ0.95 (t, J=7.5 Hz, 3H), 1.33 (s, 9H), 1.54 (s, 3 H), 1.96 (m, 2H), 3.08 (s, 3H), 7.38–7.41 (m, 2H), 7.86–7.95 (m, 4H). IR (cm$^{-1}$): 2967, 2871, 1696, 1594, 1320, 1149, 769, 552.

EXAMPLE 38

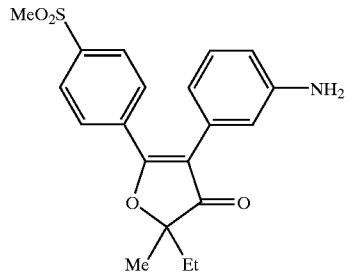

4-(3-Aminophenyl)-2-ethyl-2-methyl-5-{4-methylsulfonyl)phenyl}-3(2H)-furanone 200 mg of 2-ethyl-4-iodo-2-methy-5-{4-(methylsulfonyl)phenyl}-3(2H)-furanone was reacted with 110 mg of (3-aminobenzene)boronic acid by following a procedure similar to the synthetic procedure in Step 2 of Example 35 to afford 105 mg of 4-(3-aminophenyl)2-ethyl-2-methyl-5-{4-methylsulfonyl)phenyl}-3(2H)-furanone as a solid. mp: 77–78° C. NMR: d 0.94 (t, J=7.5 Hz, 3H), 1.53 (s, 3H), 1.96 (m, 2H), 3.07 (s, 3H), 6.57 (m, 2H), 7.14 (m, 1H), 7.91 (m, 4H). IR (cm$^{-1}$): 3457, 3370, 2926, 1692, 1620, 1403, 1317, 1148, 959, 854, 769, 552.

EXAMPLE 39

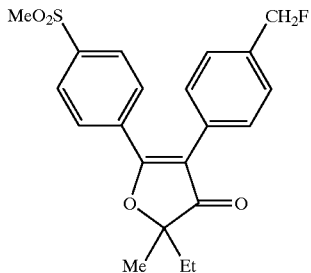

2-Ethyl-4-{4-(fluoromethyl)phenyl}-2-methyl-5-{4-(methylsulfonyl)phenyl}-3(2H)-furanone 200 mg of 2-ethyl-4-iodo-2-methy-5-{4-(methylsulfonyl)phenyl}-3(2H)-furanone was coupled with 110 mg of {4-(fluoromethyl)benzene}boronic acid according to a procedure similar to the procedure for the Step 2 of Example 35 to obtain 70 mg of 2-ethyl-4-{4-(fluoromethyl)phenyl}-2-methyl-5-{4-(methylsulfonyl)-phenyl}-3(2H)-furanone. NMR: δ0.96 (dt, J=7.5, 2.1 Hz, 3H), 1.55 (s, 3H), 1.97 (m, 2H), 3.07 (s, 3H), 5.41 (d, J=23.9 Hz, 2H), 7.37 (m, 4H), 7.85 (m, 2H), 7.93 (m, 2H). IR (cm$^{-1}$): 2974, 2929, 1697, 1319, 1150, 769, 552.

EXAMPLE 41

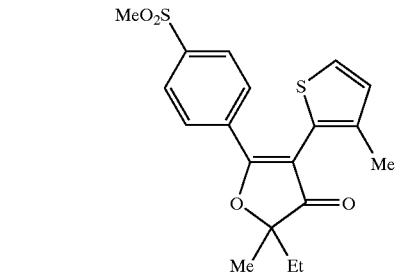

2-Ethyl-2-methyl-5-{4-(methylsulfonyl)phenyl}-4-{2-(3-methylthienyl)}-3(2H)-furanone 200 mg of 2-ethyl-4-iodo-2-methyl-5-4-(methylsulfonyl)phenyl}-3(2H)-furanone was reacted with 100 mg of {2-(3-methylthiophene)}-trimethylboronate lithium salt by following a procedure similar to the synthetic procedure in Example 36 to yield 150 mg of 2-ethyl-2-methyl-5-{4-(methylsulfonyl)phenyl}-4-{2-(3-methylthienyl)}-3(2H)-furanone NMR: δ0.95 (t, J=7.5 Hz, 3H), 1.55 (s, 3H), 1.96 (s, 3H), 1.99 (m, 2H), 3.06 (s, 3H), 6.80 (d, J=5.1 Hz, 1H), 7.36 (d, J=5.1 Hz, 1H), 7.91 (m, 4H). IR (cm$^{-1}$): 2974, 2926, 1701, 1618, 1318, 1149, 770, 729, 552.

EXAMPLE 40

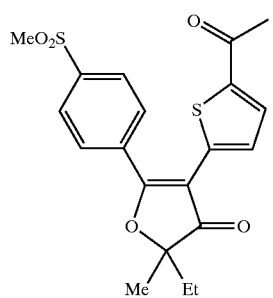

4-{5-(2-Acetylthienyl)}-2-ethyl-2-methyl-5-{4-(methylsulfonyl)phenyl}-3(2H)-furanone 200 mg of 2-ethyl-4-iodo-2-methy-5-{4-(methylsulfonyl)phenyl}-3(2H)-furanone was reacted with 100 mg of (2-acetylthiophene)-5-boronic acid by a procedure similar to the synthetic procedure in Step 2 of Example 35 to afford 70 mg of 4-{5-(2-acetylthienyl)}-2-ethyl-2-methyl-5-{4-(methylsulfonyl)phenyl}-3(2H)-furanone. NMR: δ0.95 (t, J=7.2 Hz, 3H), 1.56 (s, 3H), 1.95 (m, 2H), 2.55 (s, 3H), 3.13 (s, 3H), 7.21 (d, J=4.2 Hz, 1H), 7.95 (d, J=4.2 Hz, 1H), 7.85 (d, J=8.1 Hz, 2H), 8.08 (d, J=8.1 Hz, 2H). IR (cm$^{-1}$): 2926, 1690, 1315, 1150, 772, 552.

EXAMPLE 42

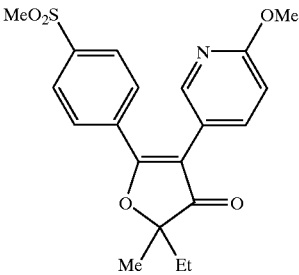

2-Ethyl-4-{3-(6-methoxypyridyl)}-2-methyl-5-{4-(methylsulfonyl)phenyl}-3(2H)-furanone 150 mg of 2-ethyl-4-iodo-2-methy-5-{4-(methylsulfonyl)phenyl}-3(2H)-furanone was coupled with 98 mg of {3-(6-methoxypyridine)}trimethylboronate lithium salt according to a procedure similar to the synthetic procedure in Example 36 to yield 100 mg of 2-ethyl-4-{3-(6-methoxypyridyl)}-2-methyl-5-{4-(methylsulfonyl)phenyl}-3(2H)-furanone as a solid. mp: 61° C. NMR: δ0.95 (t, J=7.5 Hz, 3H), 1.55 (s. 3H), 1.95 (m, 2H), 3.08 (s, 3H), 3.95 (s, 3H), 6.78 (d, J=8.4 Hz, 1H), 7.53 (dd, J=8.4, 2.4 Hz, 1H), 7.85–7.88 (m, 2H), 7.95–7.98 (m, 2H), 8.04 (d, J=2.4 Hz, 1H). IR (cm$^{-1}$): 2977, 2929, 1695, 1591, 1500, 1318, 1287, 1149, 1021, 769, 552.

EXAMPLE 43

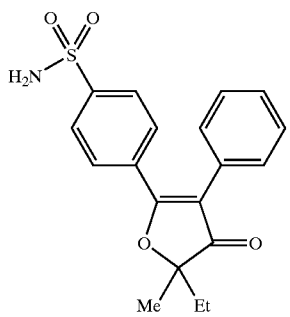

5-{4(Aminosulfonyl)phenyl}-2-ethyl-2-methyl-4-phenyl-3(2H)-furanone

Step 1: Preparation of 2-ethyl-2-methyl-5-{4-(methylsulfinyl)phenyl}-3(2H)-furanone

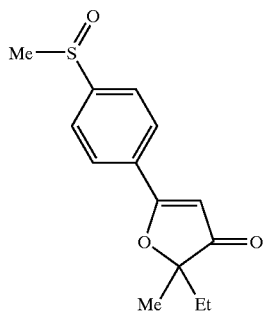

To a stirred solution of 2-ethyl-2-methyl-5-{(4-methylthio)phenyl}-3(2H)-furanone (6.0 g) in 50 ml dichloromethane, was added dropwise at 0° C. 5.9 g of 70% m-chloroperoxybenzoic acid dissolved in 100 ml dichloromethane. The reaction solution was stirred at 0° C. for 2 hours. Then the solvent was removed in vacuo, and the resulting residue was extracted with 100 ml water and dichloromethane (50 ml×2). The organic layer was concentrated under reduced pressure and the resulting crude product was purified by column chromatography (hexane/ethylacetate=2: 1) to afford 4.5 g of 2-ethyl-2-methyl-5-{4-(methylsulfinyl)phenyl}-3(2H)-furanone. NMR: δ0.89 (t, J=7.5 Hz, 3H), 1.48 (s, 3H), 1.91 (m, 2H), 2.78 (s, 3H), 6.13 (s, 1H), 8.07 (m, 4H).

Step 2: Preparation of 2-ethyl-4-iodo-2-methyl-5-{4-(methylsulfinyl)phenyl}-3(2H)-furanone

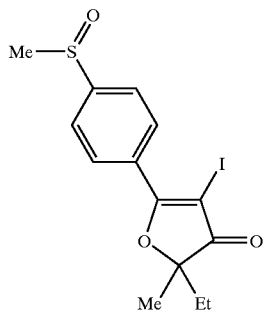

8.2 g of 2-ethyl-2-methyl-5-{4-(methylsulfinyl)phenyl}-3(2H)-furanone in 200 ml carbon tetrachloride and 200 ml chloroform was mixed with 6.8 g of [bis(trifluoroacetoxy)iodo]benzene (BTI) and 4.1 g of iodine. The mixture was stirred at room temperature for 6 hours, followed by quenching the reaction by adding saturated aqueous sodium thiosulfate until the characteristic color of iodine disappeared. The quenched solution was extracted with 300 ml water and dichloromethane (200 ml×3). The organic layer was concentrated in vacuo and the resulting residue was purified by column chromatography (hexane/ethylacetate=1:1) to give 10.0 g of 2-ethyl-4-iodo-2-methyl-5-{4-(methylsulfinyl)phenyl}-3(2H)-furanone. NMR: δ0.89 (t, J=7.5 Hz, 3H), 1.51 (s, 3H), 1.93 (m, 2H), 2.73 (s, 3H), 7.81 (d, J=8.7 Hz, 2H), 8.38 (d, J=8.7 Hz, 2H).

Step 3: Preparation of 5-{4-(aminosulfonyl)phenyl}-2-ethyl-4-iodo-2-methyl-3(2H)-furanone

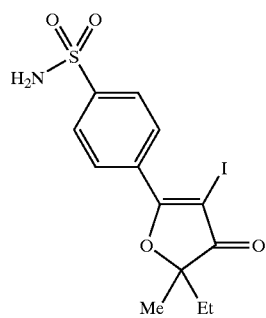

8.0 g of 2-ethyl-4-iodo-2-methyl-5-{4-(methylsulfinyl)phenyl}-3(2H)-furanone was stirred in 50 ml trifluoroacetic anhydride (TFAA) at 0° C. for 3 hours. Then the volatile material was removed in vacuo, which was followed by treatment with 30 ml of 1:1 methanol and triethylamine. The solvent was removed under reduced pressure. The same procedure of the treatment with methanolic triethylamine and the solvent removal was repeated three times. Then the resulting residue was dissolved in 100 ml carbon tetrachloride at 0° C., to which was added dropwise 5 ml of acetic acid saturated with chlorine. The reaction solution was stirred at 0° C. for 1 hour. The volatile materials including the unreacted chlorine were evaporated off under reduced pressure. The resulting residue was mixed with 100 ml THF and 20 ml ammonia water and the solution was stirred at room temperature for 2 hours. Then the solvent was removed in vacuo and the resulting residue was subjected to extraction with aqueous ammonium acetate and ethylacetate. The ethylacetate layer was concentrated in vacuo and the resulting crude product was purified by column chromatography (hexane/ethylacetate=1:1) to obtain 2.0 g of 5-{4-(aminosulfonyl)phenyl}-2-ethyl-4-iodo-2-methyl-3 (2H)-furanone. NMR: δ0.90 (t, J=7.5 Hz, 3H), 1.51 (s, 3H), 1.93 (m, 2H), 5.10 (br s, 2H), 8.08 (d, J=8.7 Hz, 2H), 8.33 (d, J=8.7 Hz, 2H).

Step 4: Preparation of 5-{4-(aminosulfonyl)phenyl}-2-ethyl-2-methyl-4-phenyl-3(2H)-furanone 100 mg of 5-{4-(aminosulfonyl)phenyl}-2-ethyl-4-iodo-2-methyl-3(2H)-furanone was reacted with 90 mg of benzeneboronic acid by following a procedure similar to Step 2 of Example 35 to give 30 mg of 5-{4-(aminosulfonyl)phenyl}-2-ethyl-2-methyl-4-phenyl-3(2H)-furanone as a solid. mp: 153–154° C. NMR: δ0.95 (t, J=7.5 Hz, 3H), 1.54 (s, 3H), 1.97 (m, 2H), 4.89 (br s, 2H), 7.26 (m, 2H), 7.36 (m, 3H), 7.79 (d, J=8.7 Hz, 2H), 7.90 (d, J=8.7 Hz, 2H). IR (cm$^{-1}$): 3340, 3256, 1684, 1616, 1392, 1342, 1161.

EXAMPLE 44

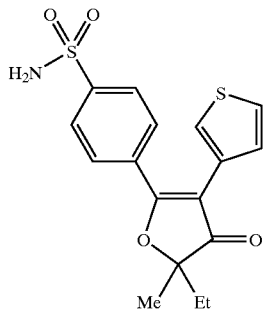

5-{4-(Aminosulfonyl)phenyl}-2-ethyl-2-methyl-4-(3-thienyl)-3(2H)-furanone 100 mg of 5-{4-(aminosulfonyl)phenyl}-2-ethyl-4-iodo-2-methyl-3(2H)-furanone was reacted with 70 mg of (3-thiophene)boronic acid by following a procedure similar to the procedure in Step 2 of Example 35 to yield 20 mg of 5-{4-(aminosulfonyl)phenyl}-2-ethyl-2-methyl-4-(3-thienyl)-3(2H)-furanone as a solid. mp: 120–121° C. NMR: δ0.93 (t, J=7.5 Hz, 3H), 1.52 (s, 3H), 1.95 (m, 2H), 5.08 (br s, 2H), 6.91 (dd, J=5.1, 1.8 Hz, 1H), 7.31 (dd, J=7.1, 3.0 Hz, 1H), 7.49 (dd, J=3.0, 1.8 Hz, 1H), 7.86 (d, J=8.7 Hz, 2H), 7.96 (d, J=8.7 Hz, 2H). IR (cm$^{-1}$): 3345, 3252, 1682, 1616, 1343, 1158. MS (FAB) 364 (m+1).

EXAMPLE 45

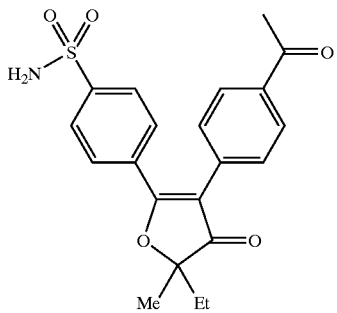

4-(4-Acetylphenyl)-5-{4-(aminosulfonyl)phenyl}-2-ethyl-2-methyl-3(2H)-furanone 100 mg of 5-{4-(aminosulfonyl)phenyl}-2-ethyl-4-iodo-2-methyl-3(2H)-furanone was reacted with 70 mg of (4-acetylbenzene)boronic acid by following a procedure similar to the procedure in Step 2 of Example 35 to yield 15 mg of 4-(4-acetylphenyl)-5-{4-(aminosulfonyl)phenyl}-2-ethyl-2-methyl-3(2H)-furanone as a solid. mp: 154–155° C. NMR: δ0.96 (t, J=7.5 Hz, 3H), 1.56 (s, 3H), 1.98 (q, J=7.5 Hz, 2H), 2.62 (s, 3H), 4.95 (br s, 2H), 7.39 (d, J=8.7 Hz, 2H), 7.77 (d, J=8.7 Hz, 2H), 7.93 (d, J=8.7 Hz, 2H), 7.95 (d, J=8.7 Hz, 2H). IR (cm$^{-1}$): 3227, 1681, 1614, 1344, 1219, 1161. MS (FAB): 400 (m+1).

EXAMPLE 46

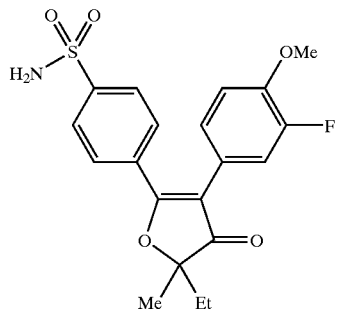

5-{4-(Aminosulfonyl)phenyl}-2-ethyl-4-(3-fluoro-4-methoxyphenyl)-2-methyl-3(2H)-furanone 100 mg of 5-{4-(aminosulfonyl)phenyl}-2-ethyl-4-iodo-2-methyl-3(2H)-furanone was reacted with 80 mg of 3-fluoro-4-methoxybenzeneboronic acid by following a procedure similar to the procedure for the Step 2 of Example 35 to give 25 mg of 5-{4-(aminosulfonyl)phenyl}-2-ethyl-4-(3-fluoro-4-methoxyphenyl)-2-methyl-3(2H)-furanone as a solid. mp: 113–114° C. NMR: δ0.94 (t, J=7.5 Hz, 3H), 1.53 (s, 3H), 1.95 (q, J=7.5 Hz, 2H), 3.91 (s, 3H), 4.96 (br s, 2H), 6.99 (m, 3H), 7.80 (d, J=8.4 Hz, 2H), 7.93 (d, J=8.7 Hz, 2H). IR (cm$^{-1}$): 3259, 1689, 1608, 1517, 1270, 1159. MS (FAB): 406 (m+1).

EXAMPLE 47

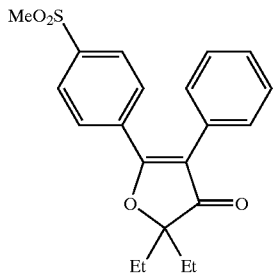

2,2-Diethyl-5-{4-(methylsulfonyl)phenyl}-4-phenyl-3(2H)-furanone

Step 1: Preparation of 4-ethyl-1-{4-(methylthio)phenyl}-2-hexyn-1,4-diol

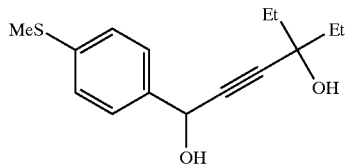

To a stirred solution of 3-ethyl-1-pentyn-3-ol (7.7 ml) in 300 ml anhydrous THF, was added dropwise 100 ml of 1.4 M methyllithium in hexane at −78° C. under argon. The mixture was further stirred for 30 minutes, followed by dropwise addition of 4-(methylthio)benzaldehyde (9.3 ml). The reaction mixture was stirred for another 12 hours, during which the cold bath was removed such that the reaction temperature reached room temperature slowly.

Then the reaction was quenched by adding dilute aqueous HCl. The solvent was removed in vacuo and the resulting residue was extracted with brine and dichloromethane (150 ml×3). The organic layer was concentrated under reduced pressure and the resulting crude product was purified by recrystallization from hexane and ethylacetate (4:1) to give 11.8 g of 4-ethyl-1-{4-(methylthio)phenyl}-2-hexyn-1,4-diol as a low-melting solid. mp: 64–65° C. NMR: δ1.04 (t, J=7.5 Hz, 6H), 1.70 (q, J=7.5 Hz, 4H), 2.49 (s, 3H), 5.47 (s, 1H), 7.26 (d, J=8.4 Hz, 2H), 7.45 (d, J=8.4 Hz, 2H). IR (cm$^{-1}$): 3368, 2970, 2207, 1637, 1589, 1262, 1093.

Step 2: Preparation of 4-ethyl-4-hydroxy-1-{4-(methylthio)phenyl}-2-hexyn-1-one

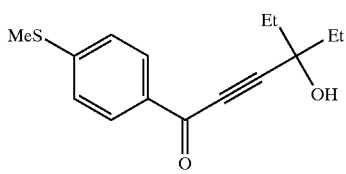

To a stirred suspension of celite (20 g) and 4-ethyl-1-{4-(methylthio)phenyl}-2-hexyn-1,4-diol (11 g) in 300 ml dichloromethane, was added 25 g of pyridinium dichromate at 0° C. Then the reaction mixture was stirred for 12 hours at room temperature. The insoluble and metallic substances were removed by filtration through Florisil. The filtrate was extracted with dilute aqueous HCl and dichloromethane (150 ml×3). The organic layer was then washed with brine and dried over anhydrous magnesium sulfate. The organic layer was concentrated in vacuo and the resulting crude product was recrystallized from 5:1 hexane and ethylacetate to yield 7.8 g of 4-ethyl-4-hydroxy-1-{4-(methylthio)phenyl}-2-hexyn-1-one as a low-melting solid. mp: 49–50° C. NMR: δ1.12 (t, J=7.5 Hz, 6H), 1.83 (q, J=7.5 Hz, 4H), 2.15 (br s, 1H), 2.54 (s, 3H), 7.28 (d, J=8.7 Hz, 2H), 8.02 (d, J=8.7 Hz, 2H). IR (cm$^{-1}$): 3432, 2970, 2208, 1636, 1588, 1285, 1095.

Step 3: Preparation of 2,2-diethyl-5-{4-(methylthio)phenyl}-3(2H)-furanone

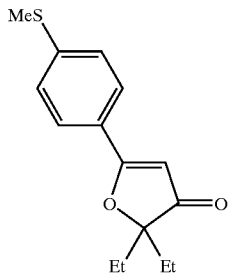

A solution 10 g of 4-ethyl-4-hydroxy-1-{4-(methylthio)phenyl}-2-hexyn-1-one in 300 ml methanol was stirred in the presence of 4 ml diethylamine at room temperature for 12 hours. Then the solvent was removed in vacuo and the resulting residue was extracted with dilute aqueous HCl and dichloromethane (50 ml×3). The organic layer was washed with brine and then concentrated under reduced pressure to yield 5.6 g of 2,2-diethyl-5-{4-(methylthio)phenyl}-3(2H)-furanone. The crude product was used for the next step without further purification. NMR: δ0.85 (t, J=7.5 Hz, 6H), 1.88 (q, J=7.5 Hz, 4H), 2.54 (s, 3H), 5.96 (s, 1H), 7.31 (d, J=9.0 Hz, 2H), 7.75 (d, J=9.0 Hz, 2H). IR (cm$^{-1}$): 2971, 1690, 1597, 1487, 1408, 1364, 1162, 1095.

Step 4: Preparation of 2,2-diethyl-5-{4-(methylsulfonyl)phenyl}3(2H)-furanone

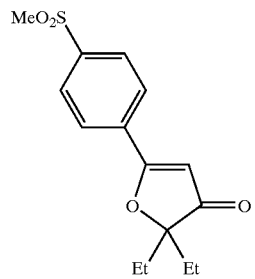

To a stirred solution of the crude 2,2-diethyl-5-{4-(methylthio)phenyl}-3(2H)-furanone (5.6 g) obtained in the previous step in 50 ml TBF and 50 ml methanol, was added dropwise 20 g of OXONE dissolved in 50 ml water at 0° C. Then the mixture was then stirred at room temperature for 14 hours. The insoluble materials were filtered off and the filtrate was concentrated in vacuo. The resulting residue was extracted with water and ethylacetate (150 ml×2). The ethylacetate layer was concentrated and the resulting crude product was purified by column chromatography (hexane/ethylacetate=2:1) to give 4.5 g of 2,2-diethyl-5-{4-(methylsulfonyl)phenyl}-3(2H)-furanone as a solid. mp: 109–110° C. NMR: 0.86 (t, J=7.5 Hz, 6H), 1.91 (q, J=7.5 Hz, 4H), 3.10 (s, 3H), 6.14 (s, 1H), 8.04 (d, J=9.0 Hz, 2H), 8.09 (d, J=9.0 Hz, 2H). IR (cm$^{-1}$): 2973, 1695, 1588, 1561, 1408, 1315, 1152.

Step 5: Preparation of 4-bromo-2,2-diethyl-5-{4-(methylsulfonyl)phenyl}-3(2H)-furanone

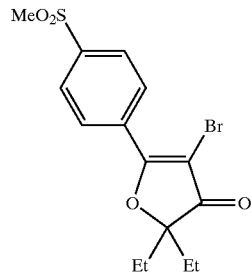

To a stirred solution of 2,2-diethyl-5-{4-(methylsulfonyl)phenyl}-3(2H)-furanone (4.5 g) in 200 ml chloroform with 3 ml acetic acid, was added dropwise 1.5 ml bromine at 0° C. The solution was then allowed to warm to room temperature and was stirred for another 4 hours. The reaction was quenched by adding saturated aqueous sodium thiosulfate until the characteristic color of bromine disappeared. The reaction mixture was then extracted with dichloromethane (100 ml×2) and the organic layer was dried over anhydrous magnesium sulfate. After the magnesium sulfate was removed by filtration, the filtrate was concentrated under reduced pressure. The resulting crude product was purified by recrystallization from hexane and ethylacetate to afford 4.5 g of 4-bromo-2,2-diethyl-5-{4-(methylsulfonyl)phenyl}-3(2H)-furanone. mp: 130–131° C. NMR: δ0.88 (t, J=7.5 Hz, 6H), 1.95 (q, J=7.5 Hz, 4H), 3.11 (s, 3H), 8.12 (d, J=8.7 Hz, 2H), 8.42 (d, J=8.7 Hz, 2H). IR (cm$^{-1}$): 2973, 1705, 1583, 1558, 1315, 1160, 1084.

Step 6: Preparation of 2,2-diethyl-5-{4-(methylsulfonyl)phenyl}-4-phenyl-3(2H)-furanone To a stirred solution of 4-bromo-2,2-diethyl-2-5-{4-(methylsulfonyl)phenyl}-3(2H)-furanone (300 mg) in 25 ml toluene and 10 ml ethanol, were added 40 mg of tetrakis(triphenylphosphine)palladium(0), 10 ml of aqueous 2M sodium carbonate solution and 140 mg of benzeneboronic acid. Then the reaction solution was stirred at 95° C. for 12 hours. The reaction solvent was evaporated off under reduced pressure and the resulting residue was extracted with 50 ml water and dichloromethane (30 ml×3). The organic layer was concentrated in vacuo and the resulting crude product mixture was purified by column chromatography (hexane/ethylacetate) to give 130 mg of 2,2-diethyl-5-{4-(methylsulfonyl)phenyl}-4-phenyl-3(2H)-furanone as a solid. mp: 139–140° C. NMR: δ0.93 (t, J=7.5 Hz, 6H), 1.99 (q, J=7.5 Hz, 4H), 3.07 (s, 3H), 7.24 (m, 2H), 7.37 (m, 3H), 7.86 (d, J=8.7 Hz, 2H), 7.93 (d, J=8.7 Hz, 2H). IR (cm$^{-1}$): 2972, 1695, 1621, 1403, 1318, 1149.

EXAMPLE 48

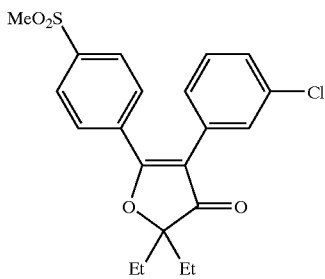

4-(3-Chlorophenyl)-2,2-diethyl-5-{4-(methylsulfonyl)phenyl}-3(2H)-furanone 300 mg of 4-bromo-2,2-diethyl-2-5-{4-(methylsulfonyl)phenyl}-3(2H)-furanone was reacted with 160 mg of (3-chlorobenzene)boronic acid according to a procedure similar to the synthetic procedure of Step 6 of Example 47 to afford 160 mg of 4-(3-chlorophenyl}-2,2-diethyl-5-{4-(methylsulfonyl)phenyl}-3(2H)-furanone as a solid mp: 131–132° C. NMR: δ0.93 (t, J=7.5 Hz, 6H), 1.98 (q, J=7.5 Hz, 4H), 3.08 (s, 3H), 7.12 (m, 1H), 7.30 (m, 3H), 7.85 (d, J=8.4 Hz, 2H), 7.95 (d, J=8.4 Hz, 2H). IR (cm$^{-1}$): 2973, 1695, 1620, 1403, 1318, 1150.

EXAMPLE 49

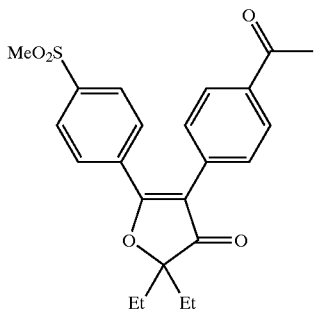

4-(4-Acetylphenyl)-2,2-diethyl-5-{4-(methylsulfonyl)phenyl}-3(2H)-furanone 300 mg of 4-bromo-2,2-diethyl-2-5-{4-(methylsulfonyl)phenyl}-3(2H)-furanone was coupled with 160 mg of (4-acetylbenzene)boronic acid according to a procedure similar to the procedure of Step 6 of Example 47 to afford 80 mg of 4-(4-acetylphenyl)-2,2-diethyl-5-{4-(methylsulfonyl)phenyl}-3(2H)-furanone as a foamy material. NMR: δ0.94 (t, J=7.5 Hz, 6H), 2.00 (q, J=7.5 Hz, 4H), 2.62 (s, 3H), 3.11 (s, 3H), 7.39 (d, J=8.4 Hz, 2H), 7.86 (d, J=8.4 Hz, 2H),7.97(dd, J=8.4, 1.5 Hz, 4H). IR (cm$^{-1}$): 2973, 1693, 1617, 1410, 1317, 1151.

EXAMPLE 50

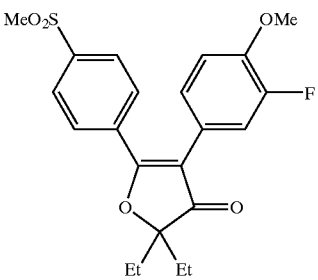

2,2-Diethyl-4-(3-fluoro-4-methoxyphenyl)-5-{4-(methylsulfonyl)phenyl}-3(2H)-furanone 300 mg of 4-bromo-2,2-diethyl-2-5-{4-(methylsulfonyl)phenyl}-3(2H)-furanone was reacted with 180 mg of (3-fluoro-4-methoxybenzene)boronic acid by following a procedure similar to the synthetic procedure of Step 6 of Example 47 to yield 100 mg of 2,2-diethyl-4-(3-fluoro-4-methoxyphenyl)-5-{4-(methylsulfonyl)-phenyl}-3(2H)-furanone as a solid. mp: 183–184° C. NMR: δ0.92 (t, J=7.5 Hz, 6H), 1.97 (q, J=7.5 Hz, 4H), 3.09 (s, 3H), 3.92 (s, 3H), 6.99 (m, 3H), 7.87 (d, J=8.7 Hz, 2H), 7.96 (d, J=9.0 Hz, 2H). IR (cm$^{-1}$): 2972, 1694, 1518, 1317, 1149.

EXAMPLE 51

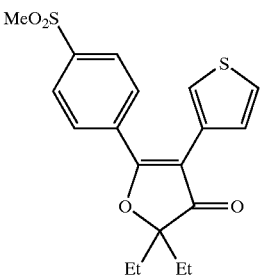

2,2-Diethyl-5-{4-(methylsulfonyl)phenyl}-4-(3-thienyl)-3(2H)-furanone 300 mg of 4-bromo-2,2-diethyl-2-5-{4-(methylsulfonyl)phenyl}-3(2H)-furanone was coupled with 130 mg of thiophene-3-boronic acid according to a procedure similar to the procedure of Step 6 of Example 47 to yield 80 mg of 2,2-diethyl-5-{4-(methylsulfonyl)phenyl}-4-(3-thienyl)-3(2H)-furanone as a foamy material. NMR: δ0.94 (t, J=7.5

Hz, 6H), 1.98 (q, J=7.5 Hz, 4H), 3.10 (s, 3H), 6.91 (dd, J=5.4, 1.5 Hz, 1H), 7.33 (dd, J=5.1, 3.0 Hz, 1H), 7.50 (dd, J=3.0, 1.2 Hz, 1H), 7.93 (d, J=8.7 Hz, 2H), 8.00 (d, J=8.7 Hz, 2H). IR (cm$^{-1}$): 2971, 1693, 1311, 1149.

EXAMPLE 52

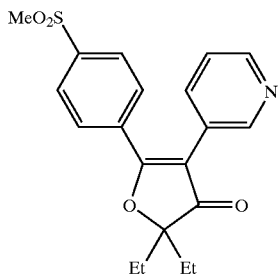

2,2-Diethyl-5-{4-(methylsulfonyl)phenyl}-4-(3-pyridyl)-3(2H)-furanone

To a stirred solution of 4-bromo-2,2-diethyl-2-5-{4-(methylsulfonyl)phenyl}-3(2H)-furanone (300 mg) in 25 ml toluene and 10 ml ethanol, were added 40 mg of tetrakis (triphenylphosphine)palladium(0), 10 ml of aqueous 2M sodium carbonate solution and 130 mg of (3-pyridyl)-trimethylboronate lithium salt. Then the reaction solution was stirred at 95° C. for 12 hours. The reaction solvent was evaporated off under reduced pressure and the resulting residue was extracted with 50 ml water and dichloromethane (30 ml×3). Then the organic layer was concentrated in vacuo. The resulting crude product mixture was purified by column chromatography (hexane/ethylacetate) to yield 30 mg of 2,2-diethyl-5-{4-(methylsulfonyl)phenyl}-4-(3-pyridyl)-3(2H)-furanone as a foamy material. NMR: δ0.94 (t, J=7.5 Hz, 6H), 2.00 (q, J=7.5 Hz, 4H), 3.09 (s, 3H), 7.36 (m, 1H), 7.54 (m, 1H), 7.84 (d, J=9.0 Hz, 2H), 7.98 (d, J=8.7 Hz, 2H), 8.44 (d, J=1.8 Hz, 1H), 8.58 (dd, J=4.8, 1.8 Hz, 1H). IR (cm$^{31\ 1}$): 2972, 1695, 1621, 1400, 1316, 1239, 1140.

EXAMPLE 53

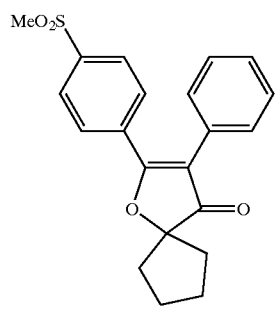

2-{(4-Methylsulfonyl)phenyl}-3phenyl-1-oxa-spiro [4,4]non-2-en-4-one

Step 1 preparation of 1-[3-hydroxy-3-(4-methylthiophenyl)-prop-1-ynyl]-cyclopentanol

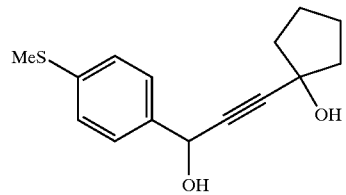

To a stirred solution of 1-ethynyl-cyclopentan-1-ol (2.0 g) in 15 ml dry THF at −78° C. under argon, was added 18 ml of 2.5 M butyllithium in hexane dropwise over 20 minutes. The reaction solution was stirred for another 20 minutes, which was followed by the addition of 4-methylthiobenzaldehyde (2.7 g) dropwlse. After stirring for another 2 hours, the reaction was quenched by adding 20 ml of dilute aqueous HCl. The reaction solvent was removed in vacuo, and the resulting aqueous solution was extracted with dichloromethane (30 ml×3). The organic layer was concentrated under reduced pressure and the resulting residue was purified by column chromatography (hexane/ethylacetate=1:1) to yield 3.48 g of 1-[3-hydroxy-3-{4-(methylthio)phenyl}-prop-1-ynyl]-cyclopentanol as a solid. mp: 118–120° C. NMR: δ0.73 (m, 4H), 1.87 (m, 4H), 2.16 (s, 1H), 2.48 (s, 3H), 2.55 (s, 1H), 5.43 (d, J=5.7 Hz, 1H), 7.24(d, J=8.4 Hz, 2H), 7.42 (d, J=8.4 Hz, 2H).

Step 2: Preparation of 3-(1-hydroxy-cyclopentyl)-1-{4-(methylthio)}-propynone

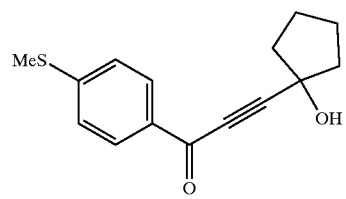

To 1.54 g of 1-[3-hydroxy-3-{4-(methylthio)phenyl}-prop-1-ynyl]-cyclopentanol in 20 ml dichloromethane, were added 3.32 g of pyridinium dichromate and 3 g of celite. The suspension was stirred overnight at room temperature and then the insoluble material was filtered off through Florisil. The filtrate was then subjected to column chromatography (hexane/ethylactate) to obtain 1.0 g of 3-(1-hydroxy-cyclopentyl)-1-{4-(methylthio)phenyl}-propynone. NMR: δ1.85 (m, 4H), 2.12 (m, 4H), 2.53 (s, 3H), 5.95 (s, 1H), 7.27 (m, 2H), 8.01 (m, 2H).

Step 3: Preparation of 2-{4-(methylthio)phenyl}-1-oxa-spiro[4,4]non-2-en-4-one

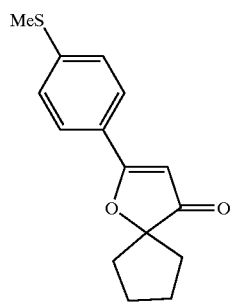

1.54 g of 3-(1-hydroxy-cyclopentyl)-1-{4-(methylthio)phenyl}-propynone was dissolved in 50 ml ethanol, added dropwise 0.75 ml diethylamine diluted with 50 ml ethanol. The reaction solution was stirred at room temperature for 4 hours, and then the solvent was removed in vacuo. The resulting residue was extracted with 20 ml water and dichloromethane (30 ml×3). Concentration of the organic layer was followed by column chromatographic separation (hexane/ethylacetate) to give 858 mg of 2-{4-(methylthio)phenyl}-1-oxa-spiro[4,4]non-2-en-4-one. NMR: δ1.89 (m, 6H), 1.92 (m, 2H), 2.47 (s, 3H), 5.89 (s, 1H), 7.24 (d, J=8.4 Hz, 2H), 7.42 (d, J=8.7 Hz, 2H).

Step 4: Preparation of 3-bromo-2-{4-(methylthio)phenyl}-1-oxa-spiro[4,4]non-2-en-4-one

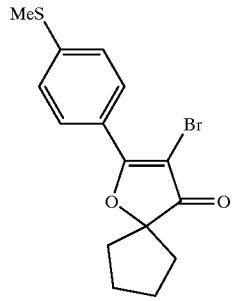

To 147 mg of 2-{4-(methylthio)phenyl}-1-oxa-spiro[4,4]non-2-en-4-one in 30 ml carbon tetrachloride, were added 1 ml bromine and 0.1 ml acetic acid. The reaction mixture was stirred for 1 hour at room temperature. Then the reaction was quenched by adding saturated aqueous sodium thiosulfate solution until the characteristic color of bromine disappeared. The quenched solution was extracted with dichloromethane (10 ml×3). The organic layer was concentrated under reduced pressure and the resulting residue was purified by column chromatography (hexane/ethylacetate) to yield 50 mg of 3-bromo-2-{4-(methylthio)phenyl}-1-oxa-spiro[4,4]non-2-en-4-one. NMR: δ1.98 (m, 4H), 2.11 (m, 4H), 2.55 (s, 3H), 7.32 (d, J=8.7 Hz, 2H), 8.13 (d, J=8.7 Hz, 2H).

Step 5: Preparation of 3-bromo-2-{4-(methylsulfonyl)phenyl}-1-oxa-spiro[4,4]non-2-en-4-one

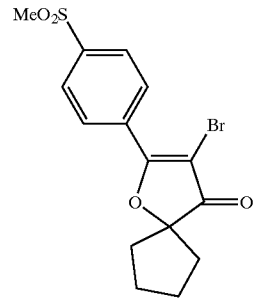

50 mg of 3-bromo-2-{4-(methylthio)phenyl}-1-oxa-spiro[4,4]non-2-en-4-one was stirred with 292 mg of OXONE at room temperature overnight in 5 ml ethanol, 5 ml THF, and 5 ml water. Then the insoluble material was filtered off and the filtrate was concentrated under reduced pressure. The resulting aqueous layer was extracted with dichloromethane and the organic layer was concentrated in vacuo. The resulting residue was purified to column chromatography (hexane/ethylacetate) to afford 68 mg of 3-bromo-2-{4-(methylsulfonyl)phenyl}-1-oxa-spiro[4,4]non-2-en-4-one as a solid. mp: 127–128° C. NMR: δ1.98 (m, 6H), 2.12 (m, 2H), 3.11 (s, 3H), 8.09 (d, J=8.7 Hz, 2H), 8.37 (d, J=8.7 Hz, 2H).

Step 6: Preparation of 2-{4-(methylsulfonyl)phenyl}-3-phenyl-1-oxa-spiro[4,4]non-2-en-4-one To a stirred solution of 3-bromo-2-(4-(methylsulfonyl)phenyl)-1-oxa-spiro[4,4]non-2-en-4-one (77 mg) in 5 ml of toluene and 15 ml ethanol, were added 15 mg of tetrakis(triphenylphosphine)palladium(0), 5 ml of 2 M aqueous sodium carbonate solution, and 27 mg of benzeneboronic acid. Then the reaction solution was stirred at 90° C. for 12 hours. The reaction solvent was evaporated off under reduced pressure and the resulting residue was extracted with 20 ml water and dichloromethane (30 ml×1). The organic layer was concentrated in vacuo and the resulting crude product mixture was purified by column chromatography (hexane/ethylacetate) to obtain 57 mg of 2-{4-(methylsulfonyl)phenyl}-3-phenyl-1-oxa-spiro[4,4]non-2-en-4-one as a solid. mp: 184-185° C. NMR: δ2.09 (m, 6H), 2.17 (m, 2H), 3.06 (s, 3H), 7.26 (m, 2H), 7,35 (m, 3H), 7.81 (d, J=8.1 Hz, 2H), 7.92 (d, J=8.1 Hz, 2H). IR (cm$^{-1}$): 2925, 1695, 1591, 1403, 1150, 771.

EXAMPLE 54

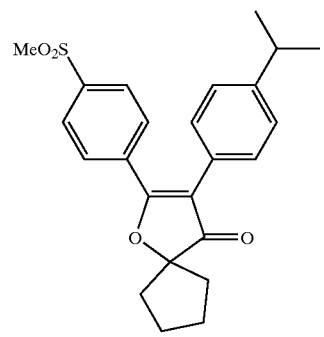

3-(4-Isopropylphenyl)-2-{4-(methylsulfonyl)phenyl}-1-oxa-spiro[4,4]non-2-en-4-one To a stirred solution of 3-bromo-2-(4-methylsulfonylphenyl)-1-oxa-spiro[4,4]non-2-en-4-one (105 mg) in 5 ml of toluene and 15 ml ethanol, were added 20 mg of tetrakis(triphenylphosphine)palladium(0), 5 ml of 2 M aqueous sodium carbonate solution, and 50 mg of 4-isopropylbenzeneboronic acid. The reaction solution was stirred at 90° C. for 12 hours. The solvent was removed under reduced pressure and the resulting residue was extracted with 20 ml water and dichloromethane (30 ml×3). The organic layer was concentrated in vacuo and the resulting crude product was purified by column chromatography (hexane/ethylacetate) to obtain 87 mg of 3-(4-isopropylphenyl)-2-{4-(methylsulfonyl)phenyl}-1-oxa-spiro[4,4]non-2-en-4-one as a solid. mp: 139–140° C. NMR: δ1.25 (s, 3H), 1.27 (s, 3H), 2.04 (m, 6H), 2.15 (m, 2H), 2.92 (m, 1H), 3.06 (s, 3H), 7.21 (m, 4H), 7.83 (d, J=8.7 Hz, 2H), 7.93 (d, J=8.7 Hz, 2H). IR (cm$^{-1}$): 2960, 1694, 1622, 1386, 1318, 1161, 768.

EXAMPLE 55

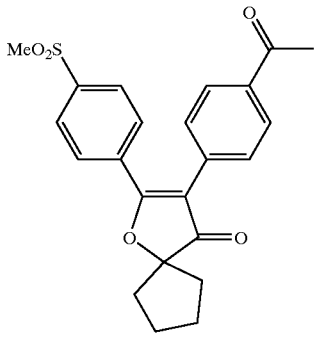

3-(4-Acetylphenyl)-2-{4-(methylsulfonyl)phenyl}-1-oxa-spiro[4,4]non-2-en-4-one 110 mg of 3-bromo-2-{4-(methylsulfonyl)phenyl}-1-oxa-spiro[4,4]non-2-en-4-one was coupled with 55 mg of (4-acetylbenzene)boronic acid by following a procedure similar to the synthetic procedure in Example 54 to give 93 mg of 3-(4-acetylphenyl)-2-{4-(methylsulfonyl)phenyl}-1-oxa-spiro[4,4]non-2-en-4-one as a solid. mp: 126–130° C. NMR: δ2.04 (m, 6H), 2.17 (m, 2H), 2.61 (s, 3H), 3.08 (s, 3H), 7.39 (d, J=8.4 Hz, 2H), 7.81 (d, J=8.4 Hz, 2H), 7.94 (m, 4H). IR (cm$^{-1}$): 2963, 1689, 1317, 1150, 771.

EXAMPLE 56

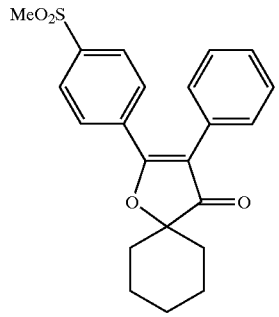

2-{4(Methylsulfonyl)phenyl}-3-phenyl-1-oxa-spiro[4,5]dec-2-en-4-one

Step 1: Preparation of 1-[3-hydroxy-3-(methylthiophenyl)-prop-1-ynyl]-cyclohexan-1-ol

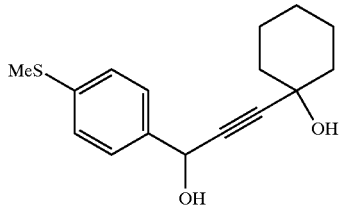

To a stirred solution of 1-ethynyl-cyclohexan-1-ol (3.2 g) in 80 ml dry THF at −78° C. and under argon, was added dropwise 35 ml of 2.5 M butyllithium in hexane over 10 minutes. The reaction solution was stirred for another 20 minutes, which was followed by the dropwise addition of 4-methylthiobenzaldehyde (3.2 ml). After stirred for another 2 hours, the reaction was quenched by adding dilute aqueous HCl. The reaction solvent was removed in vacuo, and the resulting aqueous solution was extracted with dichloromethane. The organic layer was concentrated under reduced pressure and the resulting residue was purified by column chromatography (hexane/ethylacetate) to yield 4.67 g of 1-[3-hydroxy-{4-(methylthio)phenyl}-prop-1-ynyl]-cyclohexanol. NMR: δ1.45 (m, 6H), 1.70 (m, 2H), 1.90 (m, 2H), 2.17 (d, 1H), 2.49 (s, 3H), 3.57 (s, 1H), 5.48 (d, J=6.0 Hz 1H), 7.26 (d, J=8.4 Hz, 2H), 7.46 (d, J=8.4 Hz, 2H). IR (cm$^{-1}$): 3343, 2934, 1445, 1091.

Step 2: Preparation of 3-(1-hydroxy-cyclohexyl)-1-{4-(methylthio)phenyl}-propynone

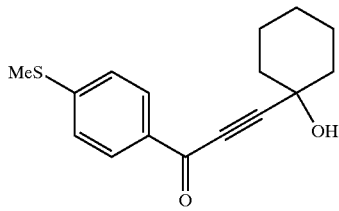

To 3.56 g of 1-[3-hydroxy-{4-(methylthio)phenyl-prop-1-ynyl]-cyclohexanol dissolved in 60 ml dichloromethane, was added 1.79 g of chromium oxide. The reaction mixture was stirred overnight at room temperature, and then the insoluble material was filtered off through Florisil. The filtrate was concentrated in vacuo and the resulting residue was purified by column chromatography (hexane/ethylactate) to obtain 1.42 g of 3-(1-hydroxy-cyclohexyl)-

1-{4-(methylthio)phenyl}-propynone. NMR: δ1.56 (m, 4H), 1.76 (m, 4H), 2.03 (m, 2H), 2.33 (s, 1H), 2.53 (s, 3H), 7.26 (d, J=8.7 Hz, 2H), 8.01 (d, J=8.7 Hz, 2H). IR (cm$^{-1}$): 3416, 2936, 1637, 1588, 1263, 1096.

Step 3: Preparation of 2-{4-(methylthio)phenyl}-1-oxa-spiro[4,5]dec-2-en-4-one

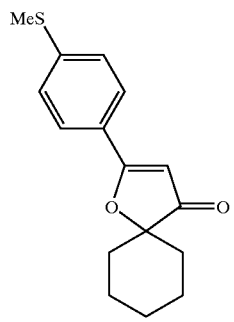

1.3 g of 3-(1-hydroxy-cyclohexyl)-1-{4-(methylthio)phenyl}-propynone was reacted with 0.6 ml diethylamine to obtain 858 mg of 2-{4methylthio)phenyl}-1-oxa-spiro[4,5]dec-2-en-4-one by following a procedure similar to the procedure in Step 3 of Example 53. NMR: δ1.62–1.82 (m, 10H), 2.54 (s, 3H), 5.92 (s, 1H), 7.30 (d, J=8.1 Hz, 2H), 7.75 (d, J=8.4 Hz, 2H). IR (cm$^{-1}$): 2933, 1686, 1588, 1408, 1095, 744.

Step 4: Preparation of 2-{4-(methylsulfonyl)phenyl}-1-oxa-spiro[4,5]dec-2-en-4-one

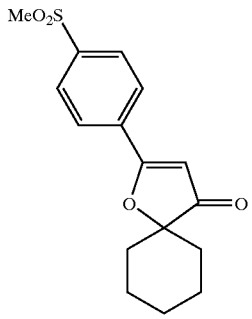

The 486 mg of 2-{4-(methylthio)phenyl}-1-oxa-spiro[4,5]dec-2-en-4-one was reacted with 1 g of OXONE by following a procedure similar to the procedure in Step 4 of Example 53 to obtain 470 mg of 2-{4-(methylsulfonyl)phenyl}-1-oxa-spiro[4,5]dec-2-en-4-one. NMR: δ1.77 (m, 10H), 3.09 (s, 3H), 6.10 (s, 1H), 8.05 (m, 4H). IR (cm$^{-1}$): 2935, 1694, 1589, 1408, 1315, 1153, 775.

Step 5: Preparation of 3-bromo-2-{4-(methylsulfonyl)phenyl}-1-oxa-spiro[4,5]dec-2-en-4-one

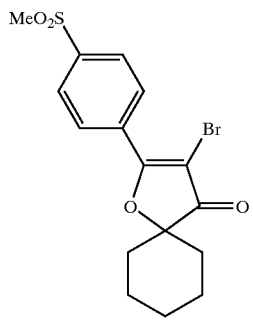

50 mg of 2-{4-(methylsulfonyl)phenyl}-1-oxa-spiro[4,5]dec-2-en-4-one was reacted with bromine (0.5 ml) in the presence of 0.1 ml acetic acid to yield 68 mg of 3-bromo-2-{4-(methylsulfonyl)phenyl}-1-oxa-spiro[4,5]dec-2-en-4-one by following a procedure similar to the procedure in Step 5 of Example 53. mp: 163–164° C. NMR: δ1.79 (m, 10H), 3.11 (s, 3H), 8.10 (d, J=8.1 Hz, 2H), 8.40 (d, J=8.1 Hz, 2H). IR (cm$^{-1}$): 2936, 1709, 1583, 1316, 1149, 912, 744.

Step 6: Preparation of 2-{4-(methylsulfonyl)phenyl}-3-phenyl-1-oxa-spiro[4,5]dec-2-en4-one To 102 mg of 3-bromo-2-{4-(methylsulfonyl)phenyl}-1-oxa-spiro[4,5]dec-2-en-4-one dissolved in 3 ml toluene and 15 ml ethanol, were added 16 mg of tetrakis(triphenylphosphin)palladium(0), 3 ml of 2 M aqueous sodium carbonate and 35 mg of benzeneboronic acid. The reaction mixture was stirred at 90° C. for 12 hours. The reaction mixture was then purified by a procedure similar to the procedure in Step 6 of Example 53 to afford 50 mg of 2-{4-(methylsulfonyl)phenyl}-3-phenyl-1-oxa-spiro[4,5]dec-2-en-4-one as a solid. mp: 126–127° C. NMR: δ1.77–1.85 (m, 10H), 3.06 (s, 3H), 7.27 (m, 2H), 7.35 (m, 3H), 7.83 (d, J=8.1 Hz, 2H), 7.94 (d. J=8.1 Hz, 2H). IR (cm$^{-1}$): 2936, 1693, 1621, 1404, 1318, 1147, 1129, 730.

EXAMPLE 57

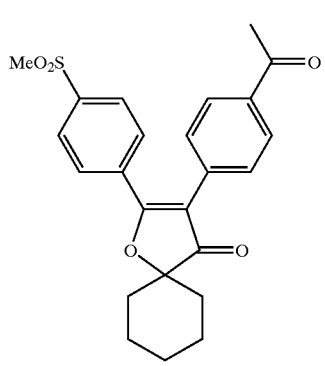

3-(4-Acetylphenyl)-2-{4-(methylsulfonyl)phenyl}-1-oxa-spiro[4,5]dec-2-2-en-4-one To 84 mg of 3-bromo-2-{4-(methylsulfonyl)phenyl}-1-oxa-spiro[4,5]dec-2-en-4-one dissolved in 3 ml toluene and 15 ml ethanol, were added 15 mg of tetrakis (triphenylphosphin)palladium(0), 3 ml of 2 M aqueous sodium carbonate and 40 mg of (4-acetylbenzene)boronic acid. The reaction mixture was stirred at 90° C. for 12 hours. The reaction mixture was then purified according to a procedure similar to Step 6 of Example 56 to obtain 35 mg of 3-(4-acetylphenyl)-2-{4-(methylsulfonyl)phenyl}-1-oxa-spiro[4,5]dec-2-en-4-one. NMR: δ1.78–1.86 (m, 10H), 2.61 (s, 3H), 3.08 (s, 3H), 7.37 (d, J=8.4 Hz, 2H), 7.84 (d, J=8.4 Hz, 2H), 7.97 (m, 4H). IR (cm$^{-1}$): 2963, 1689, 1621, 1317, 1150, 771.

Compounds of Example 58~Example 103 were synthesized by following a procedure similar to the synthetic procedure in Example 2.

EXAMPLE 58~EXAMPLE 103

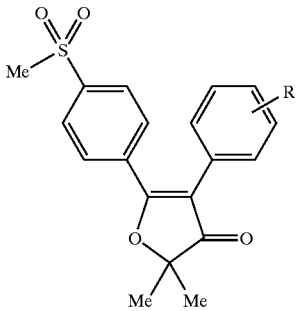

| Example | R | Melting point & spectral data |
|---|---|---|
| 58 | 4-F | mp: 154–155° C. NMR: δ 1.56(s, 6H), 3.11(s, 3H), 7.09(m, 2H), 7.30(m, 2H), 7.83(d, J=8.4Hz, 2H), 7.95(d, J=8.4Hz, 2H). IR(cm$^{-1}$): 2930, 1696, 1621, 1591, 1386, 1283, 1149, 1090, 1051, 840, 749. MS(EI): 360(m). |
| 59 | 4-Cl | Mp: 153–154° C. NMR: δ 1.57(s, 6H), 3.08(s, 3H), 7.23(d, J=8.1Hz, 2H), 7.31(d, J=8.1Hz, 2H), 7.83(d, J=8.1Hz, 2H), 7.97(d, J=8.1Hz, 2H). IR(cm$^{-1}$): 2928, 1696, 1620, 1384, 1160, 1090, 770, 551. MS(EI): 376(m). |
| 60 | 3-Cl, 4-Cl | mp: 171–173° C. NMR: δ 1.58(s, 6H), 3.09(s, 3H), 7.10(dd, J=8.4, 1.8Hz, 1H), 7.44(m, 2H), 7.83(d, J=8.7Hz, 2H), 7.98(d, J=8.7Hz, 2H). IR(cm$^{-1}$): 1693, 1620, 1317, 1150. |
| 61 | 4-Et | mp: 95–97° C. NMR: δ 1.26(t, J=7.5Hz, 3H), 1.58 (s, 6H), 2.68(q, J=7.2Hz, 2H), 3.09(s, 3H), 7.21(m, 4H), 7.90(m, 4H). IR(cm$^{-1}$): 1697, 1594, 1386, 1318, 1241, 1149, 912, 744. |
| 62 | 3-Cl | mp: 151–152° C. NMR: δ 1.58(s, 6H), 3.08(s, 3H), 7.14(m, 1H), 7.33(m, 3H), 7.83(d, J=8.7Hz, 2H), 7.95(d, J=8.4Hz, 2H). IR(cm$^{-1}$): 3020, 2982, 1698, 1619, 1384, 1240, 1150, 958, 753. |
| 63 | 3-CH$_3$ | mp: 140–141° C. NMR: δ 1.57(s, 6H), 2.35(s, 3H), 3.07(s, 3H), 7.02(d, J=7.5Hz, 1H), 7.15(m, 2H), 7.26(d, J=7.5Hz, 1H), 7.85(d, J=8.7Hz, 2H), 7.92(d, J=8.7Hz, 2H). IR(cm$^{-1}$): 2928, 1697, 1403, 1318, 1056, 956, 768. |
| 64 | 2-OMe | mp: 109–111° C. NMR: δ 1.58(s, 6H), 3.04(s, 3H), 3.54(s, 3H), 6.90–6.93(m, 1H), 7.00–7.06(m, 1H), 7.22–7.25(m, 1H), 7.40–7.42(m, 1H), 7.79–7.82(m, 2H), 7.88–7.91(m, 2H). IR(cm$^{-1}$): 3014, 1697, 1590, 1403, 1318, 1251, 1150, 960. |
| 65 | 2-F | mp: 120–122° C. NMR: δ 1.60(s, 6H), 3.06(s, 3H), 7.06–7.14(m, 1H), 7.20–7.14(m, 1H), 7.31–7.43(m, 2H), 7.80–7.83(m, 2H), 7.91–7.95(m, 2H). IR(cm$^{-1}$): 2982, 1699, 1596, 1404, 1318, 1150, 961, 761. |
| 66 | 3-NH$_2$ | mp: 186–187° C. NMR: δ 1.56(s, 6H), 3.06(s, 3H), 3.69(s, 2H), 6.57(d, J=7.5Hz, 1H), 6.66(m 2H), 7.14(t, J=7.8Hz, 1H), 7.87(d, J=9.0Hz, 2H), 7.92(d, J=8.7Hz, 2H). IR(cm$^{-1}$): 3460, 3368, 1693, 1619, 1403, 1316, 1219, 1148, 958. |
| 67 | 3-OMe, 3-OMe | mp: 169–170° C. NMR: δ 1.57(s, 6H), 3.07(s, 3H), 3.82(s, 3H), 3.91(s, 3H), 6.83(m, 3H), 7.89(d, J=9.0Hz, 2H), 7.93(d, J=8.7Hz, 2H). IR(cm$^{-1}$): 3017, 2932, 1698, 1592, 1515, 1403, 1318, 1250, 1025, 760. |
| 68 | 2-OMe, 4-OMe | mp: 107–108° C. NMR: δ 1.56(s, 6H), 3.04(s, 3H), 3.51(s, 3H), 3.85(s, 2H), 6.48(d, J=2.4Hz, 1H), 6.58 (d, J=8.4Hz, 1H), 7.15(d, J=8.7Hz, 1H), 7.89(d, J=8.7Hz, 2H), 7.93(d, J=9.0Hz, 2H). IR(cm$^{-1}$): 1699, 1403, 1318, 1150, 1072, 755. |
| 69 | 2-Cl | mp: 100–103° C. NMR: δ 1.61(s, 6H), 3.05(s, 3H), 7.25–7.27(m, 1H), 7.34–7.38(m, 2H), 7.47–7.52 (m, 1H), 7.73–7.76(m, 2H), 7.89–7.92(m, 2H). IR(cm$^{-1}$): 1699, 1403, 1318, 1150, 1072, 755. |
| 70 | 2-CH$_3$ | mp: 130–131° C. NMR: δ 1.59(s, 6H), 2.12(s, 3H), 3.04(s, 3H), 7.07–7.09(m, 1H), 7.20–7.24(m, 1H), 7.31–7.33(m, 2H), 7.73–7.76(m, 2H), 7.87–7.90(m, 2H). IR(cm$^{-1}$): 1697, 1403, 1318, 1149, 960, 754. |
| 71 | 4-CF$_3$ | mp: 144–146° C. NMR: δ 1.60(s, 6H), 3.09(s, 3H), 7.41–7.43(m, 2H), 7.63–7.65(m, 2H), 7.81–7.84(m, 2H), 7.96–7.98(m, 2H). IR(cm$^{-1}$): 1698, 1632, 1325, 1125, 1068, 959, 770. |
| 72 | 4-SCH$_3$ | mp: 137–141° C. NMR: δ 1.57(s, 6H), 2.51(s, 3H), 3.08(s, 3H), 7.17–7.22(m, 2H), 7.24–7.27(m, 2H), 7.82–7.88(m, 2H), 7.93–7.96(m, 2H). IR(cm$^{-1}$): 1698, 1316, 1149, 1092, 960, 770. |
| 73 | H | mp: 192–193° C. NMR: δ 1.58(s, 6H), 3.07(s, 3H), 7.27(m, 2H), 7.36(m, 3H), 7.84(d, J=8.7Hz, 2H), 7.93(d, J=8.4Hz, 2H). IR(cm$^{-1}$): 1697, 1503, 1404, 1245, 1148, 959, 770. |
| 74 | 2-Cl, 4-Cl | mp: 77–78° C. NMR: δ 1.60(s, 6H), 3.05(s, 3H), 7.20(d, J=8.1Hz, 1H), 7.34(dd, J=8.4, 2.4Hz, 1H), 7.51(d, J=1.8Hz, 1H), 7.74(d, J=8.7Hz, 2H), 7.94(d, J=8.7Hz, 2H). IR(cm$^{-1}$): 2929, 1701, 1623, 1404, 1318, 1150, 960, 770. |
| 75 | 3-Cl, 5-Cl | mp: 187–188° C. NMR: δ 1.58(s, 6H), 3.09(s, 3H), 7.19(d, J=1.8Hz, 2H), 7.35(t, J=1.8Hz, 1H), 7.83(d, J=8.7Hz, 2H), 7.99(d, J=8.7Hz, 2H). IR(cm$^{-1}$): 3019, 1697, 1616, 1318, 1245, 1151, 958, 770. |
| 76 | 4-t-Bu | mp: 142–143° C. NMR: δ 1.33(s, 9H), 1.57(s, 6H), 3.07(s, 3H), 7.19–7.22(m, 2H), 7.38–7.41(m, 2H), 7.86–7.95(m, 4H). IR(cm$^{-1}$): 2964, 1698, 1594, 1319, 1150, 1107, 960, 770. |
| 77 | 4-Ph | mp: 150–153° C. NMR: δ 1.60(s, 6H), 3.07(s, 3H), 7.35–7.38(m, 3H), 7.43–7.48(m, 2H), 7.61–7.64(m, 4H), 7.89–7.97(m, 4H). IR(cm$^{-1}$): 1696, 1593, 1384, 1149, 1054, 959, 755. |
| 78 | 4-Br | mp: 159–161° C. NMR: δ 1.57(s, 6H), 3.08(s, 3H), 7.15–7.18(m, 2H), 7.50–7.53(m, 2H), 7.82–7.85(m, 2H), 7.94–7.97(m, 2H). IR(cm$^{-1}$): 1697, 1620, 1383, 1318, 1150, 1012, 770. |
| 79 | 4-CHO | mp: 130–135° C. NMR: δ 1.60(s, 6H), 3.09(s, 3H), 7.47–7.50(m, 2H), 7.81–7.84(m, 2H), 7.88–7.91(m, |

-continued

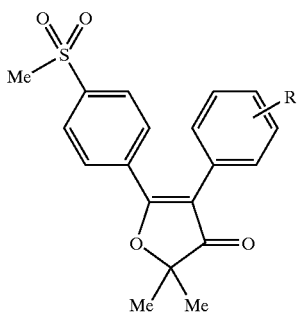

| Example | R | Melting point & spectral data |
|---|---|---|
| | | 2H), 7.95–7.98(m, 2H), 10.03(s, 1H). IR(cm$^{-1}$): 1698, 1617, 1385, 1317, 1149, 960, 770. |
| 80 | 3-F, 4-F | mp: 162° C. NMR: δ 1.58(s, 6H), 3.09(s, 3H), 6.99(m, 1H), 7.00(m, 1H), 7.16(m, 2H), 7.33(m, 1H), 7.88(d, J=9.0Hz, 2H), 7.98(d, J=8.7Hz, 2H). IR(cm$^{-1}$): 1698, 1597, 1515, 1384, 1210, 1149, 958, 770. |
| 81 | 2-F, 4-F | mp: 181–182° C. NMR: δ 1.59(s, 6H), 3.07(s, 3H), 6.87(m, 1H), 7.00(m, 1H), 7.33(m, 1H), 7.81(d, J=9.0Hz, 2H), 7.95(d, J=9.0Hz, 2H). IR(cm$^{-1}$): 1699, 1593, 1403, 1319, 1151, 1097, 972, 770. |
| 82 | 3-F, 4-OMe | mp: 144–145° C. NMR: δ 1.60(s, 6H), 3.08(s, 3H), 3.95(s, 3H), 6.92(m, 3H), 7.88(d, J=8.7Hz, 2H), 7.93(d, J=8.7Hz, 2H). IR(cm$^{-1}$): 1695, 1611, 1516, 1316, 1270, 1123, 1023, 858, 769. |
| 83 | 3-F, 4-Me | mp: 139–141° C. NMR: δ 1.57(s, 6H), 2.28(s, 3H), 3.07(s, 3H), 6.99–7.02(m, 2H), 7.13–7.16(m, 1H), 7.82–7.86(m, 2H), 7.92–7.95(m, 2H). IR(cm$^{-1}$): 1698, 1623, 1588, 1503, 1319, 1253, 1149, 756. |
| 84 | 4-iso-Pr | mp: 121–123 ° C. NMR: δ 1.26(s, 3H), 1.28(s, 3H), 2.89–2.99(m, 1H), 3.07(s, 3H), 7.18–7.26(m, 4H), 7.85–7.94(m, 4H). IR(cm$^{-1}$): 2962, 1697, 1594, 1402, 1319, 1240, 1150, 770. |
| 85 | 3-Me, 4-Me | mp: 155–156° C. NMR: δ 1.56(s, 6H), 2.25(s, 3H), 2.28(s, 3H), 3.06(s, 3H), 6.96(dd, J=7.8, 1.8Hz, 1H), 7.08(s, 1H), 7.13(d, J=7.8Hz, 1H), 7.76(d, J=9.0Hz, 1H), 7.92(d, J=9.0Hz, 2H). IR(cm$^{-1}$): 1698, 1594, 1403, 1318, 1250, 1149, 856, 770. |
| 86 | 3-iso-Pr | mp: 83–84° C. NMR: δ 1.19(s, 3H), 1.21(s, 3H), 1.58(s, 6H), 2.88(m, 1H), 3.06(s, 3H), 7.10(m, 1H), 7.21(m, 1H), 7.31(t, J=7.8Hz, 1H), 7.76(d, J=9.0Hz, 2H), 7.92(d, J=8.7Hz, 2H). IR(cm$^{-1}$): 1697, 1618, 1384, 1318, 1149, 957, 770. |
| 87 | 3-CF$_3$, 5-CF$_3$ | mp: 168° C. NMR: δ 1.61(s, 6H), 3.07(s, 3H), 7.76(s, 2H), 7.80(d, J=8.4Hz, 2H), 7.84(s, 1H), 8.00(d, J=8.4Hz, 2H). IR(cm$^{-1}$): 1701, 1593, 1405, 1321, 1250, 770. |
| 88 | 4-SEt | mp: 103–105° C. NMR: δ 1.33–1.38(t, J=7.2Hz, 3H), 1.57(s, 6H), 2.94–3.02(q, J=7.5Hz, 2H), 3.08 (s, 3H), 7.18–7.21(m, 2H), 7.29–7.32(m, 2H), 7.84–7.87(m, 2H), 7.92–7.95(m, 2H). IR(cm$^{-1}$): 1695, 1588, 1384, 1318, 1149, 770. |
| 89 | 3,4,5-tri-OMe | mp: 90–100° C. NMR: δ 1.58(s, 6H). 3.06(s, 3H), 3.76(s, 6H), 3.88(s, 3H), 7.88–7.97(m, 4H), 8.04–8.06(m, 2H). IR(cm$^{-1}$): 1693, 1584, 1391, 1321, 1125, 958. |
| 90 | 5-iso-Pr, 2-OMe | mp: 128–129° C. NMR: δ 1.22(m, 6H), 1.58(s, 6H), 3.03(s, 3H), 3.51(s, 3H), 6.82–6.85(m, 1H), 7.08(m, 1H), 7.19–7.23(m, 1H), 7.80–7.83(m, 2H), 7.87–7.90(m, 2H). IR(cm$^{-1}$): 2960, 1700, 1502, 1318, 1149, 771. |
| 91 | 3-CHO | mp: 75–80° C. NMR: δ 1.60(s, 6H), 3.08(s, 3H), 7.55–7.58(m, 2H), 7.80–7.84(m, 4H), 7.93–7.96 (m, 2H), 10.01(s, 1H). IR(cm$^{-1}$): 2929, 1696, 1621, 1589, 1403, 1149, 771. |
| 92 | 2-CHO | mp: 70–80° C. NMR: δ 1.63(s, 6H), 3.04(s, 3H), 7.61–7.62(m, 2H), 7.71–7.74(m, 2H), 7.88–7.91(m, 2H), 8.03–8.04(m, 2H), 9.94(s, 1H). IR(cm$^{-1}$): 1696, 1592, 1405, 1316, 1150, 960, 772. |
| 93 | 2-CF$_3$ | mp: 61–62° C. NMR: δ 1.59(s, 6H), 3.03(s, 3H), 7.29(m, 1H), 7.57(m, 2H), 7.68(d, J=8.7Hz, 2H), 7.87(d, J=8.7Hz, 2H). IR(cm$^{-1}$): |

-continued

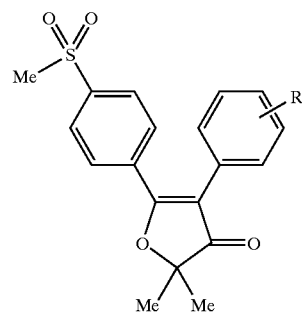

| Example | R | Melting point & spectral data |
|---|---|---|
| | | 1702, 1404, 1316, 1128. |
| 94 | 5-F, 2-CH$_3$ | mp: 159–160° C. NMR: δ 1.58(s, 6H), 2.35(s, 3H), 3.06(s, 3H), 6.96(m, 1H), 7.15(m, 2H), 7.28(m, 1H), 7.82(dd, J=8.4, 1.8Hz, 2H), 7.91(dd, J=6.6, 1.8Hz, 2H). IR(cm$^{-1}$): 1701, 1594, 1404, 1319, 1160. |
| 95 | 3-OMe | mp: 151–152° C. NMR: δ 1.58(s, 6H), 3.07(s, 3H), 3.79(s, 3H), 6.83(m, 2H), 6.90(m, 1H), 7.29(m, 1H), 7.85(d, J=8.7Hz, 2H), 7.93(d, J=8.7Hz, 2H). IR(cm$^{-1}$): 1696, 1620, 1385, 1318, 1261, 1148. |
| 96 | 4-n-Pr | mp: 99–100° C. NMR: δ 0.96(t, J=7.2Hz, 3H), 1.59 (s, 6H), 1.66(q, J=7.5Hz, 2H), 2.61(t, J=7.8Hz, 2H), 3.07(s, 3H), 7.19(s, 4H), 7.89(dd, J=8.7, 8.7Hz, 4H). IR(cm$^{-1}$): 1698, 1594, 1382, 1318, 1244, 1149. |
| 97 | 4-n-Bu | mp: 84–85° C. NMR: δ 0.83(t, J=7.5Hz. 3H), 1.26(m, 4H), 1.58(s, 6H), 2.61(t, J=7.5Hz, 2H), 3.06(s, 3H), 7.18(m, 4H), 7.87(m, 4H). IR(cm$^{-1}$): 1698, 1594, 1382, 1318, 1244, 1149. |
| 98 | 4-NMe$_2$ | NMR: δ 1.55(s, 6H), 2.98(s, 6H), 3.07(s, 3H), 6.72 (d, J=8.7Hz, 2H), 7.14(d, J=9.0Hz, 2H), 7.91(m, 4H). |
| 99 | 3-CHF$_2$ | mp: 98° C. NMR: δ 1.59(s, 6H), 3.07(s, 3H), 6.63 (t, J=56Hz, 1H), 7.26(m, 1H), 7.44(m, 3H), 7.81(m, 2H), 7.95(m, 2H). IR(cm$^{-1}$): 1699, 1622, 1403, 1318, 1150. |
| 100 | 4-Cl, 3-F | mp: 153–154° C. NMR: δ 1.57(s, 6H), 3.09(s, 3H), 7.00(m, 1H), 7.13(m, 2H), 7.39(t, J=7.8Hz, 1H), 7.84(m, 2H), 7.97(m, 2H). IR(cm$^{-1}$): 1699, 1622, 1403, 1318, 1150. |
| 101 | 4-F, 2-CH$_3$ | mp: 144–146° C. NMR: δ 1.58(s, 6H), 2.11(s, 3H), 3.06(s, 3H), 7.28(m, 1H), 7.36(m, 2H), 7.73(d, J=9.0Hz, 2H), 7.82(d, J=8.7Hz, 2H). |
| 102 | 4-CH$_2$F | mp: 132–133° C. NMR: δ 1.58(s, 6H), 3.07(s, 3H), 5.39(d, J=47.7Hz, 2H), 7.26(m, 4H), 7.85(m, 2H), 8.01(m, 2H). IR(cm$^{-1}$): 1696, 1623, 1386, 1318, 1182, 1072. |
| 103 | 2-F, 5-F | mp: 141–142° C. NMR: δ 1.59(s, 6H), 3.08(s, 3H), 7.03(m, 3H), 7.83(d, J=8.7Hz, 2H), 7.92(d, J=8.7Hz, 2H). IR(cm$^{-1}$): 1696, 1212, 913. |

EXAMPLE 104

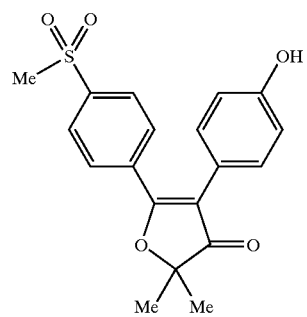

2,2-Dimethyl-4-(4-hydroxyphenyl)-5-{4-(methylsulfonyl)phenyl}-3(2H)-furanone 30 mg of 2,2-dimethyl-4-(4methoxyphenyl)-5-{4-(methylsulfonyl)phenyl}-3(2H)-furanone (Example 3) in 30 ml dichloromethane was stirred with 0.1 ml boron tribromide (1.0 M solution in $CH_2Cl_2$) at room temperature for 4 hours. And then 10 ml aqueous sodium thiosulfate was added to the reaction mixture. The mixed solution was concentrated in vacuo and was extracted with 50 ml water and dichloromethane (50 ml×3). The organic layer was concentrated under reduced pressure and was purified by column chromatography (ethylacetate) to afford 25 mg of 2,2-dimethyl-4-(4-hydroxyphenyl)-5-{4-(methylsulfonyl)phenyl}-3(2H)-furanone. mp: 150–152° C. NMR: δ1.56 (s, 6H), 2.77 (s, 1H), 3.07 (s, 3H), 6.81 (d, J=8.7 Hz, 2H), 7.14 (d, J=8.7 Hz, 2H), 7.90 (m, 4H). IR ($cm^{-1}$): 3492, 2929, 1696, 1597, 1393, 1151, 914, 744.

Compounds of Example 105 and Example 107 were prepared from the corresponding methoxy compounds by following procedures similar to the synthetic procedure of Example 104.

EXAMPLE 105~EXAMPLE 107

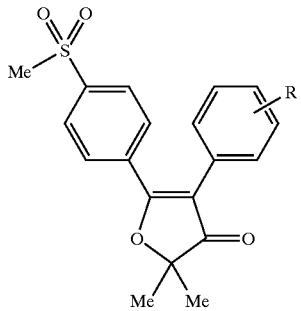

| Example | R | Melting point & spectral data |
|---|---|---|
| 105 | 2-OH | mp: 182–183° C. NMR: δ 1.62(s, 6H), 3.08(s, 3H), 6.75–6.81(m, 1H), 6.87–6.91(m, 1H), 7.04–7.08(m, 1H), 7.47(s, 1H), 7.84–7.87(m, 2H), 7.93–7.96(m, 2H). IR($cm^{-1}$): 3384, 1695, 1590, 1406, 1317, 1145, 961, 757. |
| 106 | 2-OH, 4-OMe | mp: 183–184° C. NMR: δ 1.61(s, 6H), 3.08(s, 3H), 3.80(s, 3H), 6.37(dd, J=8.7, 2.7Hz, 2H), 6.60(d, J=3.0Hz, 1H), 6.76(d, J=8.4Hz, 1H), 7.82(s, 1H), 7.87(d, J=8.7Hz, 2H), 7.95(d, J=9.0Hz, 2H). IR($cm^{-1}$): 3371, 1697, 1591, 1405, 1317, 1296, 1140, 961, 771. |
| 107 | 4-OH, 3-F | mp: 230–231° C. NMR: δ 1.57(s, 6H), 3.08(s, 3H), 6.90(m, 1H), 6.97(d, J=8.7Hz, 1H), 7.07(dd, J=11.4, J=4.8Hz, 2H), 7.85(d, J=8.7Hz, 2H), 7.95 (d, J=8.7Hz, 2H). |

EXAMPLE 108

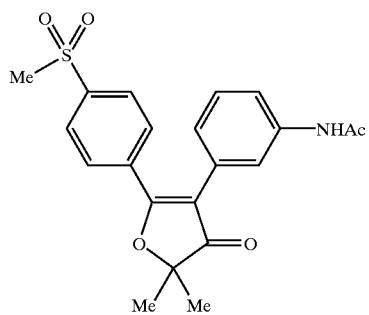

4-{3-(Acetylamino)phenyl}-2,2-dimethyl-5-{4-(methylsulfonyl)phenyl}-3(2H)-furanone To 20 mg of 4-(3-aminophenyl)-2,2-dimethyl-5-{4-(methylsulfonyl)phenyl}-3(2H)-furanone (Example 66) in 10 ml dry dichlorometane, was added 0.3 ml acetic anhydride at 0° C., and the solution was stirred at room temperature for an hour. Then the reaction mixture was concentrated in vacuo, and was extracted with water and dichloromethane. The organic layer was concentrated in vacuo and was purified by column chromatography (hexane/ethylacetate=2:1) to give 15 mg of 4-{3-N-(acetylamino)phenyl}-2,2-dimethyl-5-{4-(methylsulfonyl)phenyl}-3(2H)-furanone. mp: 217–218° C. NMR: δ1.55 (s, 6H), 2.11 (s, 3H), 3.05 (s, 3H), 6.96 (d, J=7.5 Hz, 1 ), 7.31 (d, J=8.1 Hz, 1H), 7.40 (s, 1H), 7.49 (d, J=8.1 Hz), 7.84 (d, J=8.4 Hz, 2H), 7.91 (d, J=8.4 Hz, 2H). IR ($cm^{-1}$): 3341, 1690, 1424, 1316, 1149, 959, 770.

EXAMPLE 109

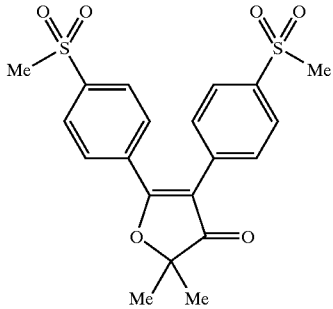

2,2-Dimethyl-4,5-di{4-(methylsulfonyl)phenyl}-3(2H)-furanone 50 mg of 2,2-dimethyl-5-{4-(methylsulfonyl)phenyl}-4-{4-(methylthio)-phenyl}-3(2H)-furanone (Example 72) in 10 ml dichloromethane and 2 ml methanol was stirred with 300 mg of OXONE at room temperature for 4 hours. The insoluble material was filtered off and the filtrate was washed with aqueous sodium bicarbonate. The organic layer was then concentrated under reduced pressure and was purified by column chromatography (ethylacetate) to give 45 mg of 2,2-dimethyl-4,5-di{4-(methylsulfonyl)phenyl}-3(2H)-furanone. mp: 245–257° C. NMR: δ1.60 (s, 6H), 3.08 (s, 3H), 3.10 (s, 3H), 7.50–7.53 (m, 2H), 7.79–7.82 (m, 2H), 7.94–8.00 (m, 4H). IR ($cm^{-1}$): 2931, 1698, 1510, 1387, 1258, 1150, 960, 846, 770.

EXAMPLE 110

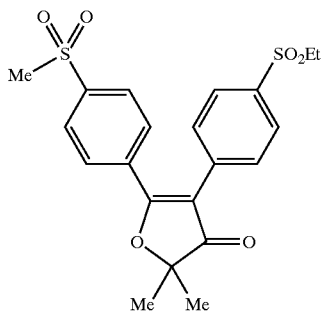

2,2-Dimethyl-4-{4-(ethylsulfonyl)phenyl}-5-{4-(methylsulfonyl)phenyl}-3(2H)-furanone 100 mg of 2,2-dimethyl-4-{4-(ethylthio)phenyl}-5-{4-(methylsulfonyl)-phenyl}-3(2H)-furanone (Example 88) in 10 ml dichloromethane, 2 ml methanol was stirred with 400 mg of OXONE at room temperature for 12 hours. The insoluble material was filtered off and the filtrate was washed with aqueous sodium bicarbonate. The organic layer was then concentrated under reduced pressure and was purified by column chromatography (ethylacetate) to give 70 mg of 2,2-dimethyl-4-{4-(ethylsulfonyl)phenyl}-5-{4-(methylsulfonyl)phenyl}-3(2H)-furanone. mp: 198–203° C. NMR: δ1.29–1.34 (t, J=7.2 Hz, 3H), 1.60 (s, 6H), 3.10 (s, 3H), 3.10–3.18 (q, J=7.5 Hz, 2H), 7.49–7.52 (m, 2H), 7.79–7.82 (m, 2H), 7.90–7.93 (m, 2H), 7.97–7.99 (m, 2H). IR (cm$^{-1}$): 1697, 1619, 1384, 1315, 1150, 960, 770.

EXAMPLE 111

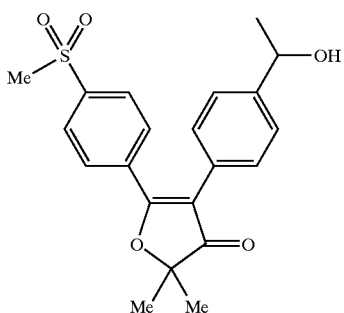

2,2-Dimethyl-4-{4-(1-hydroxyethyl)phenyl}-5-{4-(methylsulfonyl)phenyl}-3(2H)-furanone A mixture of 4-(4-acetylphenyl)-2,2-dimethyl-5-{4-(methylsulfonyl)phenyl}-3(2H)-furanone (150 mg, Example 10), sodium borohydride(35mg) and cerium(III) chloride (20 mg) in 40 ml methaol was stirred at room temperature for 12 hours, which was followed by addition of water. Then the methanol was removed in vacuo and the resulting aqueous solution was extracted with ethylacetate. The ethylacetate layer was concentrated under reduced pressure and was purified by column chromatography (hexane/ethylacetate=1:1) to obtain 100 mg of 2,2-dimethyl-4-{4-(1-hydroxyethyl)phenyl}-5-{4-(methylsulfonyl)phenyl}-3(2H)-furanone. NMR: δ1.51–1.53 (d, J=6.3 Hz, 3H), 1.58 (s, 6H), 3.07 (s, 3H), 4.90–4.97 (q, J=6.3 Hz, 1H), 7.25–7.28 (m, 2H), 7.39–7.42 (m, 2H), 7.84–7.86 (m, 2H), 7.92–7.95 (m, 2H). IR (cm$^{-1}$): 3502, 2977, 1696, 1594, 1317, 1149 960, 771.

Compounds of Example 112~Example 124 were prepared accordin to procedures similar to the procedure employed for the synthesis of Example 15.

EXAMPLE 112~EXAMPLE 124

| Example | AR | Melting point & spectral data |
|---|---|---|
| 112 | 2-Naphthyl | mp: 174–175° C. NMR: δ 1.62(s, 6H), 3.06(s, 3H), 7.24–7.28(m, 1H), 7.49–7.52(m, 2H), 7.81–7.92(m, 8H). IR(cm$^{-1}$): 1695, 1589, 1403, 1318, 1148, 957, 770. |
| 113 | 2-Thienyl | NMR: δ 1.58(s, 6H), 3.09(s, 3H), 7.05–7.07 (m, 1H), 7.11–7.13(m, 1H), 7.35–7.37(m, 1H), 7.97–7.98(m, 4H). |
| 114 | 2-(5-Acetyl)-thienyl | mp: 134–135° C. NMR: δ 1.59(s, 6H), 2.55(s, 3H), 3.12(s, 3H), 7.21(d, J=3.6Hz, 1H), 7.62(d, J=3.9Hz, 1H), 7.93(m, 2H), 8.05(m, 2H). IR (cm$^{-1}$): 2928, 1703, 1658, 1450, 1316, 1274, 1150, 771. |
| 115 | 4-Pyridyl | NMR: δ 1.60(s, 6H), 3.10(s, 3H), 7.76(m, 1H), 7.82(m, 2H), 7.80(m, 3H), 8.63(m, 2H). |
| 116 | 3-(6-Methoxy-pyridyl) | mp: 63–64° C. NMR: δ 1.58(s, 6H), 3 08(s, 3H), 3.95(s, 3H), 6.78(d, J=8.7Hz, 1H), 7.52 (m, 1H). 7.84(m, 2H), 7.95(m, 2H), 8.05(m, 1H). IR(cm$^{-1}$): 1697, 1591, 1288, 1150, 1023, 771, 552. |
| 117 | 4-(1-N-isopropyl-pyrazolyl) | mp: 143–145° C. NMR: δ 1.45(m, 6H), 1.52(s, 6H), 3.10(s, 3H), 4.32(m, 1H), 7.11(s, 1H), 7.16(s, 1H), 8.05(m, 4H). IR(cm$^{-1}$): 2981, 2931, 1698, 1561, 1409, 1315, 1152, 967, 775, 552. |
| 118 | 3-(6-Methyl-pyridyl) | mp: 100° C. NMR: δ 1.59(s, 6H), 2.59(s, 3H), 3.08(s, 3H), 7.21(d, J=8.1Hz, 1H), 7.59(m, 1H), 7.82(m, 2H), 7.95(m, 2H), 8.34(d, J=2.1Hz, 1H). |
| 119 | 2-(5-Formyl-4-methyl-thienyl) | mp: 198–199° C. NMR: δ 1.63(s, 6H), 2.62(s, 3H), 3.07(s, 3H), 7.82(m, 2H), 7.99(m, 2H), 8.18(m, 1H), 10.05(s, 1H). IR(cm$^{-1}$): 2928, 1704, 1658, 1618, 1316, 1215, 1150, 771. |
| 120 | 2-{5-(2[1,3]-Dioxalonyl)-thienyl} | mp: 118–120° C. NMR: δ 1.48(m, 2H), 1.57(s, 6H), 3.11(s, 3H), 4.02(m, 2H), 4.28(m, 2H), 5.71(s, 1H), 7.08(m, 2H), 7.98(s, 4H). IR (cm$^{-1}$): 2977, 2927, 2857, 1702, 1378, 1317, 1149, 1094, 766. |
| 121 | 2-(5-Formyl-thienyl) | mp: 168–170° C. NMR: δ 1.60(s, 6H), 3.15(s, 3H), 7.31(d, J=3.9Hz, 1H), 7.70(d, J=3.9Hz, 1H), 7.97(m, 2H), 8.07(m, 2H), 9.89(s, 1H). IR (cm$^{-1}$): 2980, 2928, 1703, 1683, 1589, 1453, 1316, 1226, 1150. |
| 122 | 2-(5-Methyl-thienyl) | mp: 141–142° C. NMR: δ 1.57(s, 6H), 2.48(s, 3H), 3.11(s, 3H), 6.70(d, J=2.7Hz, 1H), 6.91(d, J=3.6Hz, 1H), 7.81(s, 4H). IR(cm$^{-1}$): 2926, 1702, 1317, 1141, 770. |
| 123 | 2-(5-Fomyl-furanyl) | NMR: δ 1.58(s, 6H), 2.31(s, 3H), 3.11(s, 3H), 7.08(d, J=3.6Hz, 1H), 7.26(d, J=3.6Hz 2H), 7.08(s, 4H). IR(cm$^{-1}$): 1733, 1709, 1696, 1407, 1317, 1169. |
| 124 | 2-(5-Bromo-thienyl) | NMR: δ 1.57(s, 6H), 3.11(s, 3H), 6.88(d, J=3.6Hz, 1H, 7.00(d, J=3.6Hz, 1H), 7.97(m, 4H). |

Compounds of Example 125~Example 159 were prepared by procedures similar to the synthetic procedure in Step 4of Example 22.

EXAMPLE 125~EXAMPLE 159

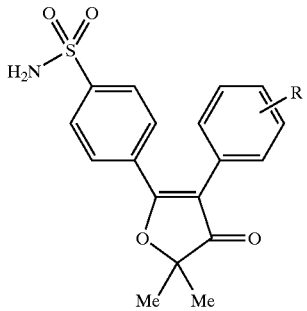

| Example | R | Melting point & spectral data |
|---|---|---|
| 125 | 3-F, 5-F | mp: 204–205° C. NMR: δ 1.57(s, 6H), 4.96 (br s, 2H), 6.78(m, 1H), 6.82(m, 2H), 7.78(d, J=8.7Hz, 2H), 7.96(d, J=8.7Hz, 2H). IR(cm⁻¹): 3267, 1686, 1218, 1160. |
| 126 | 3-Cl | mp: 194–195° C. NMR: δ 1.57(s, 6H), 4.89(br s, 2H), 7.14(m, 1H), 7.31(m, 3H), 7.78(d, J=9.0Hz, 2H), 7.93(d, J=8.4Hz, 2H). IR(cm⁻¹): 3249, 1689, 1614, 1344, 1161. |
| 127 | 3-Cl, 4-Cl | mp: 208–209° C. NMR: δ 1.57(s, 6H), 4.91(br s, 2H), 7.09(dd, J=8.4, 1.8Hz, 1H), 7.43(d, J=5.1Hz, 1H), 7.45(s, 1H), 7.78(d, J=8.4Hz, 2H), 7.95(d, J=8.7Hz, 2H). IR(cm⁻¹): 3339, 3265, 1687, 1616, 1342, 1162. |
| 128 | 3-CH₃ | Mp: 188–189° C. NMR: δ 1.57(s, 6H), 2.35(s, 3H), 4.82(br s, 2H), 7.01(m, 1H), 7.15(m, 1H), 7.25(m, 1H), 7.79(d, J=8.7Hz, 2H), 7.89(d, J=8.7Hz, 2H). IR(cm⁻¹): 3363, 3266, 1686, 1345, 1159. |
| 129 | 3-F | mp: 155–156° C. NMR: δ 1.58(s, 6H), 4.90(br s, 2H), 7.04(m, 3H), 7.30(m, 1H), 7.78(d, J=8.4Hz, 2H), 7.93(d, J=8.4Hz, 2H). IR(cm⁻¹): 3339, 3255, 1692, 1620, 1343, 1261, 1161. MS(FAB): 362(m + 1). |
| 130 | 2-F, 4-F | mp: 175–176° C. NMR: δ 1.59(s, 6H), 4.95(br s, 2H), 6.86(m, 1H), 6.98(m, 1H), 7.32(m, 1H), 7.76(d, J=9.0Hz 2H), 7.94(d, J=8.4Hz, 2H). IR(cm⁻¹): 3354, 3258, 1692, 1698, 1501, 1342, 1268, 1160, 1098. |
| 131 | 3-Me, 4-Me | mp: 175° C. NMR: δ 1.56(s, 6H), 2.24(s, 3H), 2.28(s, 3H), 5.09(br s, 2H), 6.94(d, J=7.8Hz, 1H), 7.07(d, J=7.5Hz, 1H), 7.79(d, J=8.4Hz, 2H), 7.86(d, J=8.7Hz, 2H). IR(cm⁻¹): 3349, 3258, 1689, 1620, 1550, 1345, 1160, 728. |
| 132 | 2-OMe, 4-OMe | mp: 177° C. NMR: δ 1.56(s, 6H), 3.52(s, 3H), 3.85(s, 3H), 4.87(br s, 2H), 6.49(s, 1H), 6.58(dd, J=2.4, 2.4Hz, 1H), 7.14(d, J=8.4Hz, 1H), 7.78(d, J=8.7Hz, 2H), 7.88(d, J=8.7Hz, 2H). IR(cm⁻¹): 3346, 3253, 1688, 1592, 1161, 897, 759. MS(FAB): 380(m + 1). |
| 133 | H | mp: 180–182° C. NMR: δ 1.58(s, 6H), 4.91(br s, 2H), 7.30(m, 5H), 7.78(d, J=8.7Hz, 2H), 7.89(d, J=8.4Hz, 2H). IR(cm⁻¹): 3375, 3245, 1697, 1617, 1559, 1395, 1241, 1161, 899, 752. |
| 134 | 3-Cl, 4-F | mp: 178° C. NMR: δ 1.57(s, 6H), 4.88(br s, 2H), 7.14(m, 2H), 7.39(m, 1H), 7.78(d, J=9.0Hz, 2H), 7.94(d, J=8.7Hz, 2H). IR(cm⁻¹): 3321, 3135, 1657, 1543, 1256, 1162, 912, 802. |
| 135 | 3-OMe | mp: 259–260° C. NMR: δ 1.57(s, 6H), 3.78(s, 3H), 4.90(br s, 2H), 6.86(m, 4H), 7.79(m, 2H), 7.89(m, 2H). IR(cm⁻¹): 3385, 3245, 1695, 1547, 1321, 1164, 900, 679. |
| 136 | 4-Acetyl | mp: 219–220° C. NMR: δ 1.55(s, 6H), 2.62(s, 3H), 5.00(br s, 2H), 7.26(d, J=8.7Hz, 2H), 7.75(d, J=8.7Hz, 2H), 7.78(d, J=8.7Hz, 2H), 7.95(d, J=8.7Hz, 2H). IR(cm⁻¹): 3367, 3261, 1684, 1164, 913. MS(FAB): 386(m + 1). |

-continued

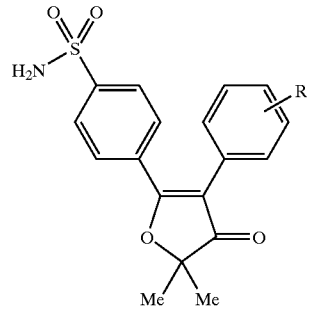

| Example | R | Melting point & spectral data |
|---|---|---|
| 137 | 2-Me | mp: 185–186° C. NMR: δ 1.58(s, 6H), 2.11(s, 3H), 4.99(br s, 2H), 7.21(m, 1H), 7.29(m, 1H), 7.30(m, 2H), 7.67(m, 2H), 7.83(m, 2H). IR(cm⁻¹): 3323, 1682, 1346, 1163, 912. |
| 138 | 3-F, 4-F | mp: 210–211° C. NMR: δ 1.58(s, 6H), 5.06(br s, 2H), 6.81(m, 1H), 7.18(m, 2H), 7.78(d, J=8.4Hz, 2H), 7.95(d, J=8.4Hz, 2H). IR(cm⁻¹): 3267, 1691, 1608, 1335, 1219, 1160. MS(FAB): 380(m + 1). |
| 139 | 4-CH₃ | mp: 163–164° C. NMR: δ 1.57(s, 6H), 2.37(s, 3H), 4.85(br, 2H), 7.18(m, 4H), 7.79(d, J=8.9Hz, 2H), 7.90(d, J=9.0Hz, 2H). IR(cm⁻¹): 3237, 1682, 1390, 1341, 1161. MS(FAB): 358(m + 1). |
| 140 | 4-Cl | mp: 230–231° C. NMR: δ 1.57(s, 6H), 4.94(br s, 2H), 7.23(d, J=8.7Hz, 2H), 7.36(d, J=8.4Hz, 2H), 7.78(d, J=8.4Hz, 2H), 7.93(d, J=8.7Hz, 2H). IR(cm⁻¹): 3333, 1685, 1387, 1342, 1219, 1161. |
| 141 | 4-SMe | mp: 96–97° C. NMR: δ 1.57(s, 6H), 2.50(s, 3H), 4.91(br s, 2H), 7.23(m, 4H), 7.81(m, 2H), 7.91(m, 2H). IR(cm⁻¹): 3374, 3228, 1683, 1339, 1161, 1094, 902, 805. MS(FAB): 390(m + 1). |
| 142 | 3-F, 4-Ph | mp: 205° C. NMR: δ 1.59(s, 6H), 5.20(br s, 2H), 7.16(m, 2H), 7.46(m, 5H), 7.86(d, J=8.7Hz, 2H), 7.97(d, J=8.7Hz, 2H). IR(cm⁻¹): 3324, 3251, 1692, 1611, 1402, 1338, 1161, 854, 728. |
| 143 | 3-Br | mp: 101–102° C. NMR: δ 1.58(s, 6H), 4.87(br s, 2H), 7.57(m, 4H), 7.84(d, J=8.4Hz, 2H), 7.94(d, J=8.4Hz, 2H). IR(cm⁻¹): 3332, 3241, 1693, 1615, 1404, 1161, 912, 726. |
| 144 | 5-iso-Pr, 2-OMe | mp: 213° C. NMR: δ 1.23(d, J=6.9Hz, 6H), 1.57(s, 6H), 2.87(m, 1H), 3.52(s, 3H), 4.85(br s, 2H), 6.84(d, J=6.9Hz, 1H), 7.07(s, 1H), 7.22(d, J=2.1Hz, 1H), 7.76(d, J=8.7Hz, 2H), 7.87(d, J=8.7Hz, 2H). IR (cm⁻¹): 3328, 3257, 1640, 1530, 1200, 1163, 1029, 746. |
| 145 | 3-iso-Pr | mp: 133° C. NMR: δ 1.21(d, J=6.9Hz, 6H), 1.57(s, 6H), 2.87(m, 1H), 4.91(br s, 2H), 7.22(m, 4H), 7.80(d, J=8.7Hz, 2H), 7.90(d, J=8.7Hz, 2H). IR(cm⁻¹): 3370, 3258, 1611, 1247, 1161, 918, 801, 605. MS(FAB): 386 (m + 1). |
| 146 | 4-SEt | mp: 185° C. NMR: δ 1.35(t, J=7.5Hz, 3H), 1.57(s, 6H), 2.97(m, 2H), 5.01(br s, 2H), 7.22(m, 4H), 7.80(d, J=8.7Hz, 2H), 7.91(d, J=8.7Hz, 2H). IR(cm⁻¹): 3354, 3257, 2927, 1695, 1682, 1587, 1343, 1161, 902. |
| 147 | 2-OMe | mp: 137° C. NMR: δ 1.57(s, 6H), 3.54(s, 3H), 5.08(br s, 2H), 6.92(d, J=8.4Hz, 1H), 7.02(t, J=8.7Hz, 1H), 7.22(d, J=8.7Hz, 1H), 7.35(t, J=7.5Hz, 1H), 7.74(d, J=8.7Hz, 2H), 7.86(d, J=8.7Hz, 2H). IR(cm⁻¹): 3335, 3252, 2929, 1685, 1588, 1404, 1161, 902, 845. |
| 148 | 4-n-Bu | mp: 107–108° C. NMR: δ 0.94(t, J=7.5Hz, 3H), 1.37(m, 2H), 1.56(s, 6H), 1.63(m, 2H), 2.62(t, J=7.5Hz, 2H), 4.94(br s, 2H), 7.18(s, 4H), 7.80(d, J=8.4Hz, 2H), 7.89(d, J=8.4Hz, 2H). IR(cm⁻¹): 3341, 3241, 2929, 1682, 1593, 1342, 1160. |
| 149 | 3-Cl, 5-Cl | mp: 209–210° C. NMR: δ 1.57(s, 6H), 4.90(br s, 2H), 7.19(d, J=1.8Hz, 2H), 7.34(t, J=1.8Hz, 1H), 7.78(d, J=8.7 Hz, 2H), 7.96(d, J=9.0Hz, 2H). IR (cm⁻¹): 3352, 3266, 1698, 1558, 1457, 1165, 899, 807. |

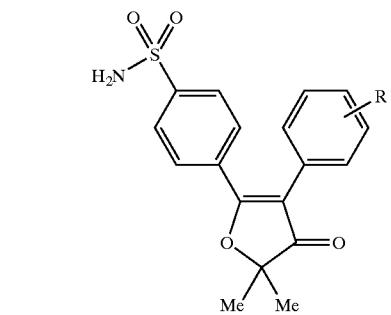

| Example | R | Melting point & spectral data |
|---|---|---|
| 150 | 3,4,5-tri-OMe | mp: 171–172° C. NMR: δ 1.57(s, 6H), 3.77(s, 6H), 3.87(s, 3H), 4.88(br s, 2H), 6.48(s, 2H), 7.84(d, J=9.0Hz, 2H), 7.93(d, J=8.7Hz, 2H). IR(cm⁻¹): 3341, 1686, 1586, 1344, 1161. |
| 151 | 4-OH | mp: 164–165° C. NMR: δ 1.51(s, 6H), 5.13(br s, 2H), 6.06(s, 1H), 6.85(m, 2H), 7.08(m, 2H), 7.96(m, 2H), 8.04(m, 2H). IR(cm⁻¹): 3352, 3266, 1698, 1558, 1457, 1165, 899, 807. |
| 152 | 4-F, 3-OMe | mp: 168–170° C. NMR: δ 1.56(s, 6H), 3.92(s, 3H), 4.90(br s, 2H), 6.96(m, 3H), 7.79(m, 2H), 7.93(m, 2H). IR(cm⁻¹): 3352, 3245, 1697, 1519, 1271, 1024, 912, 729. |
| 153 | 4-OMe, 3-Me, 5-Me | mp: 180–181° C. NMR: δ 1.55(s, 6H), 2.26(s, 6H), 3.74(s, 3H), 4.91(br s, 2H), 6.81(m, 1H), 7.53(m, 1H), 7.83(m, 2H), 7.91(m, 2H). IR(cm⁻¹): 3325, 1701, 1458, 1287, 1127. MS(FAB): 372 (m + 1) |
| 154 | 4-Et | mp: 133–135° C. NMR: δ 1.25(t, J=7.8Hz, 3H), 1.56(s, 6H), 2.67(q, J=7.8Hz, 3H), 4.92(br s, 2H), 7.20(m, 4H), 7.79(m, 2H), 7.88(m, 2H). IR(cm⁻¹): 3362, 3259, 2930, 1697, 1594, 1389, 1343, 1161. |
| 155 | 2-F | mp: 188–189° C. NMR: δ 1.58(s, 6H), 5.07(br s, 2H), 7.08(m, 1H),7.21(dt, J=75, 0.9Hz, 1H), 7.35 (m, 2H), 7.75(d, J=8.7Hz, 2H), 8.01(d, J=8.7Hz, 2H). IR(cm⁻¹): 3365, 3257, 1685, 1525, 1339, 1165, 795, 679. |
| 156 | 3-NH₂ | mp: 217–218° C. NMR: δ 1.59(s, 6H), 5.00(br s, 2H), 6.90(m, 1H), 7.05(m, 3H), 7.76(m, 2H), 7.93 (m, 2H). IR(cm⁻¹): 3311, 3222, 1695, 1489, 1422, 1344, 1161. |
| 157 | 2-F, 5-F | mp: 182–183° C. NMR: δ 1.56(s, 6H), 5.14(br s, 2H), 7.43(m, 2H), 7.70(m, 1H), 7.81(m, 2H), 7.87 (m, 2H). IR(cm⁻¹): 3362, 3259, 2965, 1697, 1559, 1387, 1162. |
| 158 | 3–NO₂ | mp: 233–234° C. NMR: δ 1.61(s, 6H), 5.09(br s, 2H), 7.56(m, 1H), 7.63(m, 1H), 7.76(d, J=8.7Hz, 2H), 7.95(d, J=8.7Hz, 2H), 8.17(m, 2H). IR(cm⁻¹): 3365, 3255, 1690, 1594, 1529, 1348, 1161. |
| 159 | 5-F, 2-Me | mp: 186–187° C. NMR: δ 1.58(s, 6H), 2.35(s, 3H), 5.04(br s, 2H), 6.97(m, 1H), 7.13(m, 2H), 7.77(d, J=8.7Hz, 2H), 7.90(d, J=8.7Hz, 2H). IR(cm⁻¹): 3386, 3237, 1691, 1406, 1219, 1160. |

Compounds of Example 160~Example 165 were prepared by procedures similar to the synthetic procedure of Example 28.

EXAMPLE 160~EXAMPLE 165

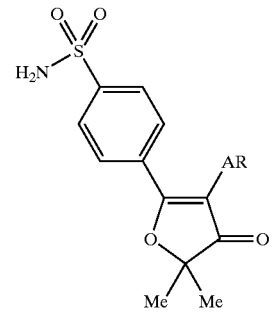

| Example | AR | Melting point & spectral data |
|---|---|---|
| 160 | 2-Furanyl | mp: 156–157° C. NMR: δ 1.56(s, 6H), 4.90(br s, 2H), 6.51(m, 1H), 6.87(m, 1H), 7.37(m, 1H), 7.93(m, 2H), 8.01(d, J=9.0Hz, 2H). IR (cm⁻¹): 3365, 3257, 1685, 1525, 1339, 1165, 795, 729. |
| 161 | 3-Thienyl | mp: 155–156° C. NMR: δ 1.56(s, 6H), 4.94(br s, 2H), 6.93(m, 1H), 7.32(m, 1H), 7.51(m, 1H), 7.86(m, 2H), 7.96(m, 2H). IR(cm⁻¹): 3353, 3254, 3105, 1695, 1616, 1343, 1158, 912, 729. |
| 162 | 2-Naphthyl | mp: 178–180° C. NMR: δ 1.62(s, 6H), 4.85(br s, 2H), 7.26(m, 2H), 7.50(m, 2H), 7.83(m, 3H), 7.85(m, 4H). IR(cm⁻¹): 3345, 3252, 1674, 1558, 1160, 801, 743, 679. MS(FAB): 393(m + 1) |
| 163 | 1-Naphthyl | mp: 200–201° C. NMR: δ 1.66(s, 3H), 1.70(s, 3H), 4.76(br s, 2H), 7.38(m, 2H), 7.52(m, 3H), 7.62(m, 2H), 7.74(m, 2H), 7.92(m, 2H). IR (cm⁻¹): 3363, 3278, 1683, 1615, 1558, 1339, 1190, 1095, 912, 739. |
| 164 | 4-(1-N-Methyl-pyrazolyl) | NMR: δ 1.53(s, 6H), 3.92(s, 3H), 5.12(br s, 2H), 7.36(s, 1H), 7.73(s, 1H), 7.98(s, 4H). |
| 165 | 3-Pyridyl | mp: 205–206° C. NMR: δ 1.60(s, 6H), 4.89 (br s, 2H), 7.36(m, 1H), 7.72(m, 1H), 7.77(d, J=8.7Hz, 2H), 7.94(d, J=8.7Hz, 2H), 8.46(d, J=1.2Hz, 1H), 8.57(dd, J=3.3, 1.5Hz, 1H). |

EXAMPLE 166

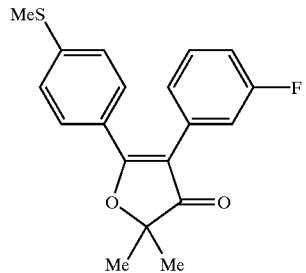

2,2-Dimethyl-4-(3-fluorophenyl)-5-{4-(methylthio)phenyl}-3(2H)-furanone

Step 1: Preparation of 2-(3-fluorophenyl)-1-{4-(methylthio)phenyl}-ethanone

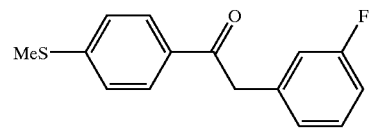

To a stirred solution of 68 ml thioanisole in 600 ml dichloromethane at 0° C., were added slowly in a series aluminum chloride (77.3 g) and (3-fluorophenyl)acetyl chloride (100 g). The reaction mixture was stirred for an hour, after which 1 L of aqueous HCl was added slowly to the reaction mixture. The quenched mixture was stirred for another hour, which was followed by extraction with methylene chloride. The organic layer was washed with brine and then was dried over anhydrous magnesium sulfate. The magnesium sulfate was filtered off and the filtrate was concentrated in vacuo. The resulting residue was purified by recrystallization from hexane/dichloromethane to yield 142.9 g of 2-(3-fluorophenyl)-1-{4-(methylthio)-phenyl}-ethanone. mp: 94.5–95.5° C. NMR: δ2.52 (s, 3H), 4.23 (s, 2H), 6.95–7.05 (m, 3H),7.25–7.30 (m, 3H), 7.92 (d, J=8.7 Hz, 2H).

Step 2: Preparation of 2,2-dimethyl-4-(3-fluorophenyl)-5-{4-(methylthio)phenyl}-3(2H)-furanone To a stirred solution of 2-(3-fluorophenyl)-1-{4-(methylthio)phenyl}-ethan-1-one (100 g) in 1 L dry THF, was added portion-wise 26 g of 95 % sodium hydride at 0° C. The reaction solution was stirred at the same temperature for 1 hour. Then 69 g of α-bromo-isobutyryl cyanide diluted in 25 ml dry THF was added dropwise to the stirred solution at 0° C. The reaction mixture was stirred overnight while allowing to warm gradually to room temperature. The solution was concentrated in vacuo, to which was added 50 ml water. The aqueous solution was extracted with ethylacetate (1 L). The organic layer was concentrated in vacuo and purified by column chromatography (hexane/ethylacetate= 6:1) to give 102 g of 2,2-dimethyl-4-(3-fluorophenyl)-5-{4-(methylthio)phenyl}-3(2H)-furanone. mp: 106° C. NMR: δ1.55 (s, 6H), 2.50 (s. 3H), 6.97–7.11 (m, 3H), 7.18 (d, J=9.0 Hz, 2H), 7.26–7.36 (m, 1H), 7.55 (d, J=9.0 Hz, 2H).

Compounds of Example 167~Example 173 were prepared by following procedures similar to the procedure used for the synthesis of Example 166.

EXAMPLE 167~EXAMPLE 173

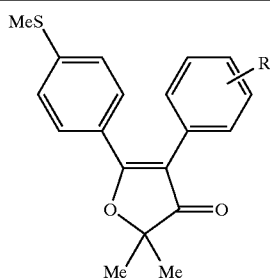

| Example | R | Melting point & spectral data |
|---|---|---|
| 167 | H | mp: 109–110° C. NMR: δ 1.55(s, 6H), 2.49(s, 3H), 7.16(d, J=8.7Hz, 2H), 7.27–7.55(m, 5H), 7.56(d, J=8.7Hz, 2H). IR(cm⁻¹): 2979, 1693, 1612, 1388, 1237, 1170, 1094, 829, 750. |
| 168 | 3-Cl | Oil. NMR: δ 1.55(s, 6H), 2.49(s, 3H), 7.15–7.22 (m, 3H), 7.27–7.31(m, 2H), 7.33–7.36(m, 1H), 7.54 (d, J=8.7Hz, 2H). |
| 169 | 3-CF$_3$ | NMR: δ 1.56(s, 6H), 2.49(s, 3H), 7.18(d, J=9.0Hz, 2H), 7.51–7.62(m, 6H). |
| 170 | 4-NO$_2$ | NMR: δ 1.57(s, 6H), 2.51(s, 3H), 7.21(d, J=8.7Hz, 2H), 7.53(d, J=8.7Hz, 2H), 7.54(d, J=9.0Hz, 2H), 8.21(d, J=8.7Hz, 2H). |
| 171 | 4-OMe | mp: 119–117° C. NMR: δ 1.54(s, 6H), 2.49(s, 3H), 3.83(s, 3H), 6.91(d, J=9.0Hz, 2H), 7.16(d, J=8.7Hz, 2H), 7.23(d, J=9.0Hz, 2H), 7.53(d, J=8.7Hz, 2H). |
| 172 | 2-F, 5-F | mp: 90.5–91° C. NMR: δ 1.56(s, 6H), 2.49(s, 3H), 7.01–7.06(m, 3H), 7.17(d, J=8.7Hz, 2H), 7.53(d, J=8.4Hz, 2H). |
| 173 | 3-F, 5-F | mp: 122–123° C. NMR: δ 1.55(s, 6H), 2.51(s, 3H), 6.71–6.78(m, 1H), 6.84–6.92(m, 2H), 7.21(d, J=8.7Hz, 2H), 7.55(d, J=9.0Hz, 2H). |

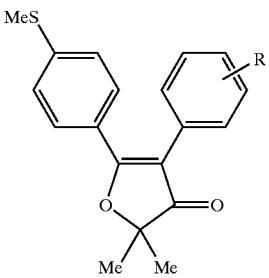

EXAMPLE 174

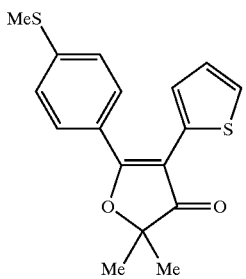

2,2-Dimethyl-5-{4-(methylthio)phenyl}-4-(2-thienyl)-3(2H)-furanone 2,2-Dimethyl-5-{4-(methylthio)phenyl}-4-(2-thienyl)-3 (2H)-furanone was prepared according to a procedure similar to the synthetic procedure in Example 166. mp: 113~114° C. NMR; δ1.55 (s, 6H), 2.51 (s, 3H), 7.05 (dd, J=5.1, 3.9 Hz, 1H), 7.11 (dd, J=3.6, 1.2 Hz, 1H), 7.22 (d, J=8.4 Hz, 2H), 7.33 (d, J=5.1 Hz, 1H), 7.68 (d, J=9.0 Hz, 2H).

EXAMPLE 175

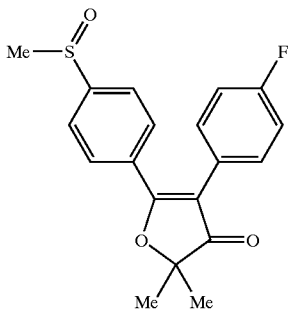

2,2-Dimethyl-4-(fluorophenyl)-5-{4-(methylsulfinyl)phenyl}-3(2H)-furanone

Step 1: Preparation of 4-bromo-2,2-dimethyl-5-{4-(methylsulfinyl)phenyl}-3(2H)-furanone

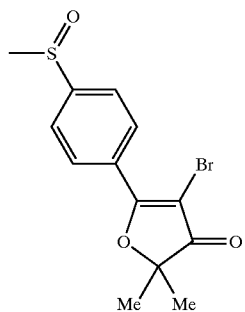

To a solution of 2,2-dimethyl-5-{4-(methylsulfinyl)phenyl}-3(2H)-furanone (135 mg) in 25 ml of $CCl_4$, were added 1 ml acetic acid and 0.1 ml bromine. The reaction mixture was stirred at room temperature for 2.5 hr. Then the reaction was quenched by adding 10 ml of saturated aqueous sodium thiosulfate. The volatile materials were removed in vacuo, which was followed by extraction with dichloromethane (50 ml×3). The organic layer was dried over anhydrous magnesium sulfate and the magnesium sulfate was filtered off. The filtrate was concentrated in vacuo and the crude product was purified by column chromatography (hexane/ethylacetate=1:1) to give 68 mg of 4-bromo-2,2-dimethyl-5-{4-(methylsulfinyl)phenyl}-3(2H)-furanone. mp: 117–118° C. NMR: δ1.55 (s, 6H), 2.79 (s, 3H), 7.81 (d, J=8.2 Hz, 2H), 8.38 (d, J=8.2 Hz, 2H). IR ($cm^{-1}$): 1706, 1601,1555, 1191, 1052.

Step 2: Preparation of 2,2-dimethyl-4-(4-fluorophenyl)-5-{4-(methylsulfinyl)phenyl}-3(2H)-furanone To 53 mg of 4-bromo-2,2-dimethyl-5-{4-(methylsulfinyl)phenyl}-3(2H)-furanone in 30 ml of benzene, were added 25 mg of $Pd(Ph_3)_4$, 25.4 mg of (4-fluorobenzene)boronic acid and 0.22 ml of 2 M aqueous sodium carbonate. The reaction mixture was stirred at 80–90° C. for 12 hours. Then the reaction mixture was concentrated under reduced pressure. The resulting residue was extracted with $CH_2Cl_2$ and brine and the organic layer was dried over anhydrous $MgSO_4$. The organic layer was evaporated off in vacuo and the crude product was purified by column chromatography (hexane/ethylacetate) to yield 15 mg of 2,2-dimethyl-4-(4-fluorophenyl)-5-{4-(methylsulfinyl)phenyl}-3(2H)-furanone. mp: 134–136° C. NMR: δ1.57 (s, 6H), 2.75 (s, 3H), 7.08 (m, 2H) 7.27 (m, 2H), 7.65 (d, J=8.2 Hz, 2H), 7.80 (d, J=8.2 Hz, 2H). IR ($cm^{-1}$): 2925, 2854, 1695, 1618, 1590, 1237, 1051, 758.

EXAMPLE 176

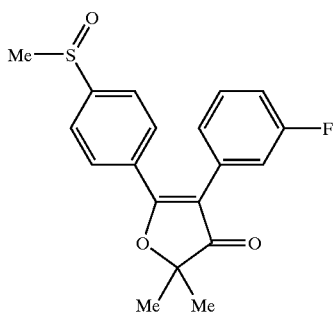

2,2-dimethyl-4-(3-fluorophenyl)-5-{4-(methylsulfinyl)phenyl}-3(2H)-furanone

To a stirred solution of 2,2-dimethyl-4-(3-fluorophenyl)-5-{4-(methylthio)phenyl}-3(2H)-furanone (2.0 g, Example 166) in 50 ml dichloromethane, was added 1.5 g of m-chloroperoxybenzoic acid at 0° C. The reaction solution was stirred at the same temperature for one and half hours, after which 30 ml 5% aqueous sodium bicarbonate was added and the solution was stirred for another 10 minutes. Then the reaction mixture was concentrated in vacuo, and the resulting residue was extracted with 50 ml water and dichloromethane (30 ml×3). The organic layer was concentrated in vacuo and was purified by column chromatography (hexane/ethylacetate=1:1) to give 1.3 g of 2,2-dimethyl-4-(3-fluorophenyl)-5-{4-(methylsulfinyl)phenyl}-3(2H)-furanone. mp: 143–144° C. NMR: δ1.58 (s, 6H), 2.76(s, 3H), 7.26–7.08 (m, 3H), 7.30–7.38 (m, 1H), 7.65 (d, J=8.2 Hz, 2H), 7.80 (d, J=8.2 Hz, 2H).

EXAMPLE 177

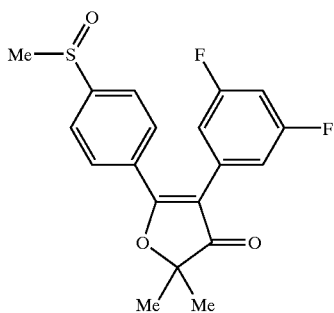

4-(3,5-Difluorophenyl)-2,2-dimethyl-5-{4-(methylsulfinyl)phenyl}-3(2H)-furanone 4-(3,5-Difluorophenyl)-2,2-dimethyl-5-{4-(methylsulfinyl)phenyl}-3(2H)-furanone was prepared by following a procedure similar to the synthetic procedure in Example 176. mp: 133–134° C. NMR: δ1.57 (s, 6H), 2.77 (s, 3H), 6.75–6.87 (m, 3H), 7.69 (d, J=8.2 Hz, 2H), 7.80 (d, J=8.2 Hz, 2H).

EXAMPLE 178

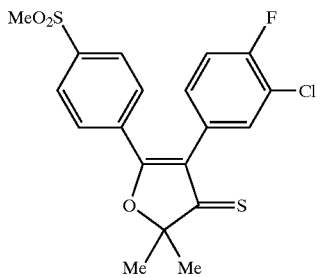

4-(3-Chloro-4-fluorophenyl)-2,2-dimethyl-5-{4 (methylsulfonyl)phenyl}-3(2H)-furan-3-thione 90 mg of 4-(3-chloro-4-fluorophenyl)-2,2-dimethyl-5-{4-(methylsulfonyl)-phenyl}-3(2H)-furanone (Example 2) in 30 ml toluene was stirred at reflux for 12 hours in the presence of 60 mg of Lawesson's reagent, Then the solvent was removed in vacuo and the resulting residue was extracted with 50 ml water and ethylacetate (50 ml×3). The organic layer was concentrated under reduced pressure and was purified by column chromatography (hexane/ ethylacetate=4:1) to give 30 mg of 4-(3-chloro-4-fluorophenyl)-2,2-dimethyl-5-{4-(methylsulfonyl)phenyl}-3(2H1)-furan-3-thione as a solid. mp: 165–166° C. NMR: δ1.71 (s, 6H), 3.07 (s, 3H), 7.12 (m, 1H), 7.21 (d, 1H), 7.36 (dd, 1H), 7.81 (d, J=8.4 Hz, 2H), 7.95 (d, J=8.4 Hz, 2H). IR (cm$^{-1}$): 1580, 1553, 1502, 1319, 1261, 1154, 957, 760.

Compounds of Example 179~Example 181 were prepared according to procedures similar to the synthetic procedure in Example 178.

EXAMPLE 179~EXAMPLE 181

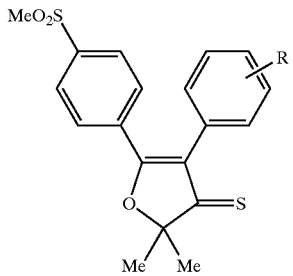

| Example | R | Melting point & spectral data |
|---|---|---|
| 179 | 4-F | NMR: δ 1.69(s, 6H), 3.12(s, 3H), 7.23(m, 2H), 7.48 (m, 1H), 7.36(dd, J=8.4, 2.4Hz, 1H), 8.11(d, J=8.1Hz, 2H), 8.48(d, J=8.4Hz, 2H). |
| 180 | 3-F | mp: 106–107° C. NMR: δ 1.70(s, 6H), 3.07(s, 3H), 7.01(m, 2H), 7.12(m, 1H), 7.40(m, 1H), 7.79(d, J=8.1Hz, 2H), 7.92(d, J=8.1Hz, 2H). IR(cm$^{-1}$); 1616, 1584, 1397, 1319, 1255, 1154, 957. |
| 181 | 3-F, 5-F | mp: 126–127° C. NMR: δ 1.72(s, 6H), 3.08(s, 3H), 6.84(m, 3H), 7.80(d, J=8.7Hz, 2H), 7.95(d, J=8.7Hz, 2H). IR(cm$^{-1}$): 1624, 1593, 1391, 1323, 1284, 1120, 988. |

EXAMPLE 182

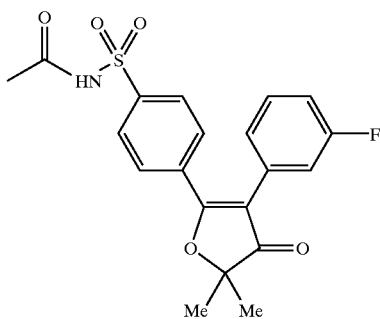

5-[{4-{(Acetylamino)sulfonyl}phenyl]-2,2-dimethyl-4-(3-fluorophenyl)-3(2H)-furanone 360 mg of 5-{4-(aminosulfonyl)phenyl}-2,2-dimethyl-4-(3-fluorophenyl)-3(2H)-furanone (Example 129) in 30 ml in dichloromethane was reacted with 0.8 ml acetic anhydride in the presence of 0.5 ml triethylamine and 50 mg of 4-(N,N-dimethylamino)pyridine at room temperature for 12 hours. The reaction mixture was concentrated in vacuo, which was followed by extraction with 30 ml water and dichloromethane (30 ml×3). The organic layer was concentrated under reduced pressure and then was purified by column chromatography (hexane/ethylacetate 2:1) to afford 397 mg of 5-[4-{(acetylamino)sulfonyl}phenyl]-2,2-dimethyl-4-(3-fluoro-phenyl)-3(2H)-furanone as a solid. mp: 178–179° C. NMR: δ1.57 (s, 6H), 2.08 (s, 3H), 7.05 (m, 3H), 7.34 (m, 1H), 7.82 (d, J=8.4 Hz, 2H), 8.05 (d, J=8.4 Hz, 2H), 8.20 (br s, 1H). IR (cm$^{-1}$): 3238, 3198, 1431, 1261, 1159.

EXAMPLE 183

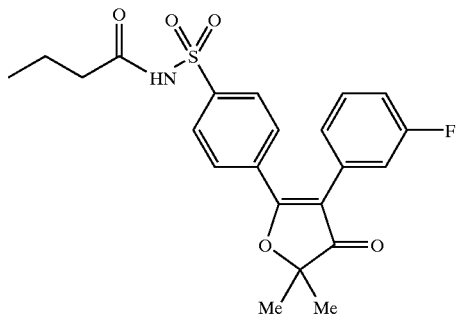

5-[4-{(n-Butyrylamino)sulfonyl}phenyl]-2,2-dimethyl-4-(3-fluorophenyl)-3(2H)-furanone 360 mg of 5-{4-(aminosulfonyl)phenyl}-2,2-dimethyl-4-(3-fluorophenyl)-3(2H)-furanone (Example 129) in 30 ml dichloromethane was reacted with 0.8 ml butyric anhydride in the presence of 0.5 ml triethylamine and 50 mg of 4-(N,N-dimethylamino)pyridine at room temperature for 12 hours. The reaction mixture was concentrated in vacuo, which was followed by extraction with 30 ml water and dichloromethane (30 ml×3). The organic layer was concentrated under reduced pressure and then was purified by column chromatography hexane/ethylacetate 2:1) to afford 363 mg of 5-[4-{(n-butyrylamino)sulfonyl}phenyl]-2,2-dimethyl-4-(3-fluorophenyl)-3(2H)-furanone as a solid. mp: 188–189° C. NMR: δ0.89 (t, J=7.5 Hz, 3H), 1.58 (s, 6H), 1.60 (m, 2H), 2.24 (t, J=7.5 Hz, 2H), 7.05 (m, 3H), 7.34 (m, 1H), 7.82 (d, J=8.4 Hz, 2H), 8.06 (d, J=8.4 Hz, 2H), 8.19 (br s, 1H). IR (cm⁻¹): 3195, 3140, 1698, 1435, 1350, 1190.

EXAMPLE 184

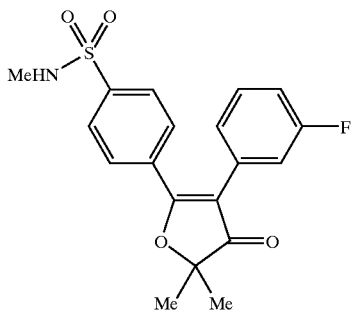

2,2-Dimethyl-5-{4-(N-methylaminosulfonyl)phenyl}-4-(3-fluorophenyl)-3(2H)-furanone 500 mg of 2,2-dimethyl-5-{4-(methylsulfinyl)phenyl}-4-(3-fluorophenyl)-3(2H)-furanone (Example 166) was stirred in 15 ml trifluroacetic anhydride for an hour at 0° C. and then the solvent was removed in vacuo. The resulting residue was dissolved in 10 ml 1:1 methanol/triethylamine and was stirred at 0° C. for an hour. The solution was concentrated under reduced pressure. Then the resulting residue was stirred in 15 ml dichloromethane, to which was added 5 ml acetic acid saturated with chlorine. After the solution was stirred for 30 minutes at 0° C., the solvent and the unreacted chlorine was removed in vacuo. The resulting residue was dissolved in 5 ml toluene and the toluene was evaporated off in vacuo. The resulting residue was dissolved in 20 ml THF and reacted with 1 ml of 40% aqueous methylamine for 2 hours at 0° C. The reaction solution was concentrated in vacuo, which was followed by extraction with 30 ml water and dichloromethane (30 ml×3). The organic layer was washed with brine and concentrated under reduce pressure. The resulting residue was purified by column chromatography (hexane/ethylacetate=3:2) to give 155 mg of 2,2-dimethyl-5-{4-(N-methylaminosulfonyl)phenyl}-4-(3-fluorophenyl)-3(2H)-furanone as a solid. mp: 176–177° C. NMR: δ1.58 (s, 6H), 2.70 (d, J=5.1 Hz, 3H), 4.35 (q, J=5.4 Hz, 1H), 7.04 (m, 3H), 7.33 (m, 1H), 7.89 (d, J=8.7 Hz, 2H), 7.86 (d, J=8.7 Hz, 2H). IR (cm⁻¹): 3285, 1696, 1402, 1388, 1261, 1160.

EXAMPLE 185

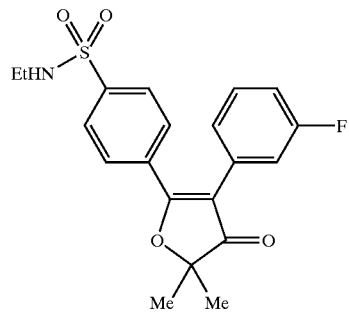

2,2-Dimethyl-5-{4-(N-ethylaminosulfonyl)phenyl}-4-(3-fluorophenyl)-3(2H)-furanone By following the procedure in Example 184 except using 70% aqueous ethylamine, the titled compound was obtained. mp: 113–114° C. NMR: δ1.13 (t, J=7.2 Hz, 3H), 1.57 (s, 6H), 3.06 (m, 2H), 4.34 (t, J 6.0 Hz, 1H), 7.03 (m, 3H), 7.32 (m, 1H), 7.78 (d, J=8.7 Hz, 2H), 7.86 (d, J=9.0 Hz, 2H). IR (cm⁻¹): 3271, 1694, 1619, 1592, 1387, 1260, 1159.

Compounds of Example 186~Example 218 were prepared by a procedure similar to the synthetic procedure in Step 6 of Example 31.

EXAMPLE 186~EXAMPLE 218

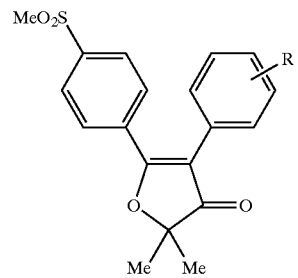

| Example | R | Melting point & spectral data |
|---|---|---|
| 186 | 4-F | mp: 111–114° C. NMR: δ 0.95(t, J=7.2Hz, 3H), 1.54(s, 3H), 1.97(m, 2H), 3.08(s, 3H), 7.09(m, 2H), 7.24(m, 2H), 7.84(d, J=8.1Hz, 2H), 7.95(d, J=8.7Hz, 2H). IR(cm⁻¹): 2972, 1696, 1591, 1511, 1318, 1149, 913, 745, 551 |
| 187 | 3-F | mp: 107–108° C. NMR: δ 0.95(t, J=7.2Hz, 3H), 1.55(s, 3H), 1.97(m, 2H), 3.08(s, 3H), 7.04(m, 2H), 7.35(m, 2H), 7.84(d, J=8.7Hz, 2H), 7.96(d, J=8.4Hz, 2H). IR(cm⁻¹): 2926, 1698, 1403, 1319, 1149, 961, 850, 769, 552 |
| 188 | 2-F | mp: 108–109° C. NMR: δ 0.96(t, J=7.2Hz, 3H), 1.56(s, 3H), 1.99(m, 2H), 3.06(s, 3H), 7.10(m, 1H), 7.28(m, 3H), 7.83(d, J=8.4Hz, 2H), 7.94(d, J=8.7Hz, 2H). IR(cm⁻¹): 2975, 2929, 1699, 1595, 1404, 1319, 1150, 969, 766, 552. |
| 189 | 3-F, 4-F | mp: 106–108° C. NMR: δ 0.94(t, J=7.5Hz, 3H), 1.54(s, 3H), 1.97(m, 2H), 3.09(s, 3H), 7.00(m, 1H), 7.16(m, 2H), 7.83(d, J=8.4Hz, 2H), 7.973(d, J=8.4Hz, 2H). IR(cm⁻¹): 2931, 1698, 1597, 1518, 1277, 1160, 959, 868, 770, 552. |
| 190 | 3-Cl, 4-F | mp: 145–146° C. NMR: δ 0.95(t, J=7.5Hz, 3H), 1.54(s, 3H), 1.97(m, 2H), 3.09(s, 3H), 7.13(m, 2H), 7.37(m, 1H), 7.84(d, J=8.7Hz, 2H), 7.97(d, J=8.7Hz, 2H). IR(cm⁻¹): 2974, 1696, 1622, 1502, 1319, 1252, 1150, 956, 766, 726, 552. |
| 191 | 4-OMe | mp: 130–133° C. NMR: δ 0.94(t, J=7.5Hz, 3H), 1.55(s, 3H), 1.97(m, 2H), 3.07(s, 3H), 3.83(s, 3H), 6.93(d, J=9.0Hz, 2H), 7.19(d, J=8.7Hz, 2H), 7.90(m, 4H). IR(cm⁻¹): 2929, 1694, 1593, 1613, 1317, 1148, 913, 744, 552. |
| 192 | 4-Me | mp: 48–49° C. NMR: δ 0.95(t, J=7.5Hz, 3H), 1.54(s, 3H), 1.96(m, 2H), 2.38(s, 3H), 3.07(s, 3H), 7.17(m, 4H), 7.89(m, 4H). IR(cm⁻¹): 2974, 2927, 1696, 1624, 1514, 1402, 1318, 1149, 958, 769, 552. |
| 193 | 3-Me | mp: 48–49° C. NMR: δ 0.95(t, J=7.5Hz, 3H), 1.54(s, 3H), 1.97(m, 2H), 2.35(s, 3H), 3.07(s, 3H), 7.00(m, 1H), 7.14(m, 2H), 7.26(m, 1H), 7.85(d, J=8.7Hz, 2H), 7.92(d, J=8.4Hz, 2H). IR(cm⁻¹): 2974, 2928, 1696, 1621, 1403, 1319, 1149, 957, 768, 552. |
| 194 | 3-CF₃ | mp: 45–46° C. NMR: δ 0.97(t, J=7.2Hz, 3H), 1.56(s, 3H), 1.99(m, 2H), 3.08(s, 3H), 7.53(m, 4H), 7.83(d, J=8.1Hz, 2H), 7.96(d, J=8.1Hz, 2H). IR (cm⁻¹): 2977, 2932, 1696, 1625, 1594, 1404, 1326, 1232, 1151, 1091, 958, 912, 769, 701, 552. |

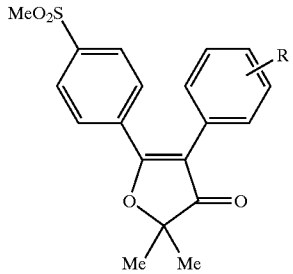
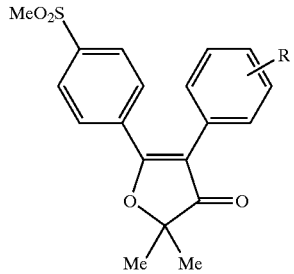

| Example | R | Melting point & spectral data |
|---|---|---|
| 195 | 3-Cl | mp: 94–95° C. NMR: δ 0.95(t, J=7.5Hz, 3H), 1.54(s, 3H), 1.98(m, 2H), 3.08(s, 3H), 7.13(m, 1H), 7.30(m, 3H), 7.84(d, J=8.7Hz, 2H), 7.96(d, J=8.7Hz, 2H). IR(cm$^{-1}$): 2975, 2930, 1699, 1620, 1403, 1319, 1150, 958, 742, 552. |
| 196 | 3-Acetyl | mp: 135–136° C. NMR: δ 0.97(t, J=7.2Hz, 3H), 1.54(s, 3H), 1.98(m, 2H), 2.58(s, 3H), 3.07(s, 3H), 7.48(m, 3H), 7.82(d, J=8.7Hz, 2H), 7.88(m, 1H), 7.94(d, J=9.0Hz, 2H). IR(cm$^{-1}$): 2927, 1694, 1590, 1318, 1149, 959, 801, 771, 552. |
| 197 | 3,4-methylenedioxy | mp: 160–163° C. NMR: δ 0.94(t, J=7.5Hz, 3H), 1.53(s, 3H), 1.96(m, 2H), 3.08(s, 3H), 6.00(s, 2H), 6.73(m, 2H), 6.84(m, 1H), 7.88(d, J=8.4Hz, 2H), 7.95(d, J=8.4Hz, 2H). IR(cm$^{-1}$): 2922, 2851, 1696, 1596, 1507, 1438, 1404, 1318, 1243, 1149, 1035, 958, 769, 552. |
| 198 | 4-Cl, 3-CF$_3$ | mp: 168–170° C. NMR: δ 0.96(t, J=7.2Hz, 3H), 1.56(s, 3H), 1.98(m, 2H), 3.09(s, 3H), 7.37(m, 1H), 7.51(m, 1H), 7.64(m, 1H), 7.82(d, J=8.7Hz, 2H), 7.99(d, J=8.4Hz, 2H). IR(cm$^{-1}$):2929, 1697, 1624, 1592, 1317, 1149, 913, 744, 552. |
| 199 | 4-Et | mp: 45° C. NMR: δ 0.95(t, J=6.9Hz, 3H), 1.26(t, J=7.8Hz, 3H), 1.53(s, 3H), 1.96(q, J=6.9Hz, 2H), 2.67(q, J=7.8Hz, 2H), 3.07(s, 3H), 7.15–2.26(m, 4H), 7.85–7.94(m, 4H). IR(cm$^{-1}$): 1693, 1594, 1319, 1149, 913, 745, 552. |
| 200 | 3-OMe | NMR: δ 0.95(t, J=7.5Hz, 3H), 1.54(s, 3H), 1.98(m, 2H), 3.07(s, 3H), 3.78(s, 3H), 6.85(m, 3H), 7.28(m, 1H), 7.86(d, J=8.7Hz, 2H), 7.93(d, J=8.4Hz, 2H). IR(cm$^{-1}$): 2931, 2838, 1696, 1621, 1403, 1318, 1149, 1036, 957, 769, 552. |
| 201 | 3-iso-Pr | NMR: δ 0.96(t, J=7.5Hz, 3H), 1.19(s, 3H), 1.21(s, 3H), 1.54(s, 3H), 1.97(m, 2H), 2.87(m, 1H), 3.06(s, 3H), 7.09(m, 2H), 7.26(m, 2H), 7.89(m, 4H). IR(cm$^{-1}$): 2964, 2928, 1696, 1620, 1402, 1319, 1149, 958, 771, 552. |
| 202 | 4-n-Pr | NMR: δ 0.96(m, 6H), 1.53(s, 3H), 1.66(m, 2H), 1.95(m, 2H), 2.61(t, J=7.5Hz, 2H), 3.07(s, 3H), 7.18(m, 4H), 7.89(m, 4H). IR(cm$^{-1}$): 2966, 2930, 1697, 1510, 1401, 1319, 1149, 958, 769, 552. |
| 203 | 4-n-Bu | NMR: δ 0.94(m, 6H), 1.38(m, 2H), 1.53(s, 3H), 1.62(m, 2H) 1.96(m, 2H), 2.63(m, 2H), 3.07(s, 3H), 7.18(m, 4H), 7.86(d, J=8.4Hz, 2H), 7.93(d, J=8.4Hz, 2H). IR(cm$^{-1}$): 2969, 2929, 1697, 1622, 1594, 1401, 1319, 1149, 958, 769, 552. |
| 204 | 3-Me, 4-Me | mp: 124–126° C. NMR: δ 0.95(t, J=7.5Hz, 3H), 1.53(s, 3H), 1.96(m, 2H), 2.25(s, 3H), 2.28(s, 3H), 3.06(s, 3H), 6.93(m, 1H), 7.06(m, 1H), 7.13(m, 1H), 7.90(m, 4H). IR(cm$^{-1}$): 2973, 2926, 1696, 1624, 1404, 1319, 1149, 959, 769, 552. |
| 205 | 3-Cl, 4-Cl | mp: 120–123° C. NMR: δ 0.95(t, J=7.5Hz, 3H), 1.54(s, 3H), 1.97(m, 2H), 3.09(s, 3H), 7.08(m, 1H), 7.44(m, 2H), 7.84(d, J=8.7Hz, 2H), 7.98(d, J=9.0Hz, 2H). IR(cm$^{-1}$): 2875, 2930, 1696, 1620, 1406, 1319, 1150, 957, 769, 730, 552. |
| 206 | 3-CHF$_2$ | mp: 110–111° C. NMR: δ 0.96(t, J=7.5Hz, 3H), 1.56(s, 3H), 1.98(m, 2H), 3.07(s, 3H), 6.63(t, J=56.4Hz, 1H), 7.36(m, 1H), 7.47(m, 3H), 7.83(d, J=8.4Hz, 2H), 7.95(d, J=8.7Hz, 2H). IR(cm$^{-1}$): 2976, 2931, 1697, 1624, 1594, 1319, 1150, 1028, 769, 552. |
| 207 | 4-Cl | mp: 62–63° C. NMR: δ 0.95(t, J=7.5Hz, 3H), 1.54(s, 3H), 1.95–1.99(m, 2H), 3.08(s, 3H), 7.20–7.23(m, 2H), 7.35–7.38(m, 2H), 7.83–7.86(m, 2H), 7.94–7.97(m, 2H). IR(cm$^{-1}$): 1696, 1588, 1319, 1150, 1090, 968, 769, 552. |
| 208 | 4-CF$_3$ | mp: 56–57° C. NMR: δ 0.96(t, J=7.5Hz, 3H), 1.56(s, 3H), 1.97–2.01(m, 2H), 3.09(s, 3H), 7.40–7.42(m, 2H), 7.63–7.65(m, 2H), 7.82–7.85(m, 2H), 7.96–7.99(m, 2H). IR(cm$^{-1}$): 2978, 2932, 1696, 1623, 1326, 1151, 1071, 846, 771, 552. |
| 209 | 4-OCF$_3$ | mp: 89–90° C. NMR: δ 0.95(t, J=7.5Hz, 3H), 1.55(s, 3H), 1.95–2.00(m, 2H), 3.09(s, 3H), 7.25–7.33(m, 4H), 7.83–7.86(m, 2H), 7.95–7.98(m, 2H). IR(cm$^{-1}$): 2976, 2931, 1697, 1567, 1259, 1150, 769, 552. |
| 210 | 4-Cl, 3-F | mp: 58–59° C. NMR: δ 0.95(t, J=7.5Hz, 3H), 1.55(s, 3H), 1.98(m, 2H), 3.10(s, 3H), 6.99(m, 1H), 7.14(m, 1H), 7.40(m, 1H), 7.85(d, J=8.7Hz, 2H), 7.99(d, J=8.7Hz, 2H). IR(cm$^{-1}$): 2930, 1715, 1698, 1622, 1403, 1319, 1150, 1074, 959, 858, 768, 552. |
| 211 | 4-F, 2-Me | NMR: δ 0.96(t, J=7.5Hz, 3H), 1.54(s, 3H), 1.99(m, 2H), 2.11(d, J=2.1Hz, 3H), 3.04(s, 3H), 7.00(m, 3H), 7.74(d, J=8.4Hz, 2H), 7.90(d, J=8.1Hz, 2H). IR (cm$^{-1}$): 2976, 2929, 1696, 1612, 1564, 1320, 1246, 1160, 958, 769, 730, 551. |
| 212 | 5-F, 2-Me | NMR: δ 0.95(t, J=7.2Hz, 3H), 1.55(s, 3H), 1.98(m, 2H), 2.35(s, 3H), 3.06(s, 3H), 6.97(m, 1H), 7.19(m, 2H), 7.84(d, J=8.4Hz, 2H), 7.93(d, J=8.1Hz, 2H). IR(cm$^{-1}$): 2977, 2930, 1697, 1632, 1503, 1405, 1320, 1150, 958, 771, 552. |
| 213 | 3-OMe, 4-OMe | mp: 133–134° C. NMR: δ 0.96(t, J=7.2Hz, 3H), 1.54(s, 3H), 1.96(q, J=8.1Hz, 2H), 3.07(s, 3H), 3.82(s, 3H), 3.91(s, 3H), 6.80(m, 2H), 6.87(m, 1H), 7.91(m, 4H). IR(cm$^{-1}$): 2974, 2933, 1696, 1592, 1516, 1319, 1260, 1150, 1027, 770, 552. |
| 214 | 3-F, 4-OMe | mp: 158–160° C. NMR: δ 0.94(t, J=7.2Hz, 3H), 1.53(s, 3H), 1.96(m, 2H), 3.09(s, 3H), 3.92(s, 3H), 7.01(m, 3H), 7.86(d, J=8.4Hz, 2H), 7.96(m, J=8.4Hz, 2H). IR(cm$^{-1}$): 2932, 1697, 1519, 1318, 1270, 1149, 1024, 768, 552. |
| 215 | 3-CF$_3$, 5-CF$_3$ | mp: 92–93° C. NMR: δ 0.98(t, J=7.5Hz, 3H), 1.58(s, 3H), 2.01(m, 2H), 3.08(s, 3H), 7.76(s, 2H), 7.82(m, 3H), 8.01(m, 2H). IR(cm$^{-1}$): 2979, 2934, 1698, 1628, 1593, 1407, 1282, 1150, 1138, 959, 896, 772, 704, 552. |
| 216 | 3-Cl, 5-Cl | mp: 188–190° C. NMR: δ 0.95(t, J=7.5Hz, 3H), 1.54(s, 3H), 1.97(q, J=7.8Hz, 2H), 3.10(s, 3H), 7.17(m, 2H), 7.35(m, 1H), 7.84(d, J=8.7Hz, 2H), 8.00(d, J=8.1Hz, 2H). IR(cm$^{-1}$): 2974, 2931, 1696, 1596, 1559, 1319, 1150, 801, 551. |
| 217 | 4-OMe, 3,5-di-Me | mp: 58–59° C. NMR: δ 0.94(t, J=7.5Hz, 3H), 1.53(s, 3H), 1.96(m, 2H), 2.26(s, 6H), 3.07(s, 3H), 3.75(s, 3H), 6.90(s, 2H), 7.90(m, 4H). IR(cm$^{-1}$): 2974, 2930, 1688, 1622, 1591, 1330, 1149, 1014, 850, 769, 552. |
| 218 | 3,4,5-tri-OMe | mp: 137–138° C. NMR: δ 0.96.(t, J=7.2Hz, 3H), 1.54(s, 3H), 1.97(m, 2H), 3.06(s, 3H), 3.76(s, 6H), 3.87(s, 3H), 6.45(s, 2H), 7.93(m, 4H). IR(cm$^{-1}$); 2973, 2934, 1696, 1582, 1394, 1321, 1149, 1126, 770, 552. |

Compounds of Example 219~Example 226 were prepared according to procedures similar to the synthetic procedure in Example 34.

EXAMPLE 219~EXAMPLE 226

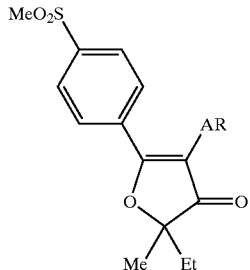

| Example | AR | Melting point & spectral data |
|---|---|---|
| 219 | 3-(6-methyl-pyridyl) | NMR: δ 0.96(t, J=7.5Hz, 3H), 1.56(s, 3H), 1.98(q, J=3.6Hz, 2H), 2.59(s, 3H), 3.08(s, 3H), 7.23(d, J=8.1Hz, 1H), 7.65(dd, J=8.1, 1.8Hz, 1H), 7.83–7.86(m, 2H), 7.95–7.98(m, 2H), 8.33(d, J=1.8Hz, 1H). IR(cm$^{-1}$): 2927, 1696, 1590, 1406, 1318, 1150, 769, 550. |
| 220 | 3-Thienyl | NMR: δ 0.94(t, J=7.5Hz, 3H), 1.53(s, 3H), 1.98(m, 2H), 3.10(s, 3H), 6.93(m, 1H), 7.31(m, 1H), 7.51(m, 1H), 7.92(d, J=8.7Hz, 2H), 7.99(d, J=9.0Hz, 2H). IR(cm$^{-1}$): 3106, 2975, 2929, 1696, 1621, 1447, 1316, 1148, 959, 852, 770, 552. |
| 221 | 2-Furanyl | mp: 138–139° C. NMR: δ 0.93(t, J=7.5Hz, 3H), 1.52(s, 3H), 1.95(m, 2H), 3.11(s, 3H), 6.51(m, 1H), 6.89(m, 1H), 7.37(m, 1H), 8.02(m, 4H). IR(cm$^{-1}$): 2976, 2930, 1701, 1642, 1545, 1409, 1317, 1149, 1090, 1069, 958, 875, 770, 730, 552. |
| 222 | 2-Benzo[b]-thienyl | mp: 68–69° C. NMR: δ 0.97(t, J=7.2Hz, 3H), 1.54(s, 3H), 1.99(m, 2H), 3.10(s, 3H), 7.33(m, 2H), 7.50(s, 1H), 7.76(m, 2H), 8.01(s, 4H). IR(cm$^{-1}$): 2925, 2866, 1701, 1620, 1457, 1317, 1148, 957, 762, 760, 551. |
| 223 | 2-Benzo[b]-furanyl | mp: 177–178° C. NMR: δ 0.96(t, J=7.5Hz, 3H), 1.54(s, 3H), 1.98(m, 2H), 3.13(s, 3H), 7.28(m, 4H), 7.60(m, 1H), 8.07(m, 4H). IR(cm$^{-1}$): 2927, 1702, 1539, 1454, 1318, 1149, 959, 766, 747, 655, 551. |
| 224 | 2-Thienyl | mp: 112–114° C. NMR: δ 0.95(t, J=7.5Hz, 3H), 1.54(s, 3H), 1.96(m, 2H), 3.10(s, 3H), 7.06(m, 1H), 7.11(m, 1H), 7.36(m, 1H), 7.99(m, 4H). IR(cm$^{-1}$): 3100, 2975, 2929, 1700, 1619, 1317, 1149, 770, 552. |
| 225 | 2-(5-Methyl-thienyl) | NMR: δ 0.93(t, J=7.5Hz, 3H), 1.52(s, 3H), 1.99(m, 2H), 2.48(s, 3H), 3.10(s, 3H), 6.70(m, 1H), 6.91(d, J=3.6Hz, 1H), 8.00(m, 4H). IR(cm$^{-1}$): 2973, 2924, 1701, 1318, 1140, 769, 551. |
| 226 | 5-Pyrimidinyl | NMR: δ 0.98(t, J=7.5Hz, 3H), 1.58(s, 3H), 2.02(m, 2H), 3.10(s, 3H), 7.83(d, J=8.7Hz, 2H), 8.02(d, J=8.7Hz, 2H), 8.70(s, 2H), 9.18(s, 1H). |

Compounds of Example 227~Example 236 were synthesized by procedures similar to the synthetic procedure in Step 4 of Example 43.

EXAMPLE 227~Example 236

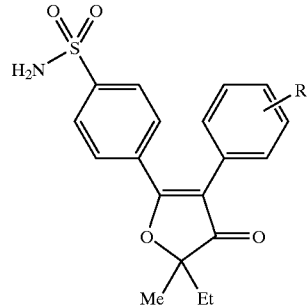

| Example | R | Melting point & spectral data |
|---|---|---|
| 227 | 4-F | mp: 129–130° C. NMR: δ 0.94(t, J=7.5Hz, 3H), 1.54(s, 3H), 1.96(m, 2H), 4.90(br s, 2H), 7.08(dd, J=9.0Hz, 8.4Hz, 2H), 7.24(dd, J=9.0, 5.7Hz, 2H), 7.78(d, J=8.4Hz, 2H), 7.92(d, J=8.4Hz, 2H). IR(cm$^{-1}$): 3339, 3261, 1682, 1619, 1511, 1343, 1161. |
| 228 | 3-F | mp: 176–177° C. NMR: δ 0.95(t, J=7.5Hz, 3H), 1.54(s, 3H), 1.97(m, 2H), 4.90(br s, 2H), 7.04(m, 3H), 7.35(m, 1H), 7.79(d, J=8.7Hz, 2H), 7.93(d, J=8.4Hz, 2H) IR(cm$^{-1}$): 3253, 1689, 1620, 1343, 1160. |
| 229 | 3-Me | mp: 115–116° C. NMR: δ 0.95(t, J=7.5Hz, 3H), 1.53(s, 3H), 1.96(m, 2H), 2.34(s, 3H), 4.97(br s, 2H), 6.99(d, J=7.2Hz, 1H), 7.13(m, 2H), 7.25(m, 1H), 7.80(d, J=8.7Hz, 2H), 7.89(d, J=9.0Hz, 2H). IR(cm$^{-1}$): 3387, 3249, 1683, 1617, 1343, 1160. |
| 230 | 3-Cl | mp: 144–145° C. NMR: δ 0.95(t, J=7.5Hz, 3H), 1.54(s, 3H), 1.97(m, 2H), 4.95(br s, 2H), 7.13(m, 1H), 7.30(m, 3H), 7.79(d, J=8.4Hz, 2H), 7.93(d, J=8.1Hz, 2H). IR(cm$^{-1}$): 3336, 3258, 1683, 1615, 1342, 1161. |
| 231 | 4-Cl | mp: 115–116° C. NMR: δ 0.94(t, J=7.5Hz, 3H), 1.54(s, 3H), 1.96(m, 2H), 4.89(br s, 2H), 7.21(d, J=8.7 Hz, 2H), 7.36(d, J=8.7Hz, 2H), 7.79(d, J=8.7Hz, 2H), 7.93(d, J=8.1Hz, 2H). IR(cm$^{-1}$): 3237, 1682, 1615, 1586, 1339, 1161. |
| 232 | 3-CF$_3$ | mp: 77–78° C. NMR: δ 0.96(t, J=7.5Hz, 3H), 1.56(s, 3H), 1.98(m, 2H), 5.06(br s, 2H), 7.47(m, 2H), 7.58(m, 2H), 7.77(d, J=9.0Hz, 2H), 7.93(d, J=8.7Hz, 2H). IR(cm$^{-1}$): 3347, 3257, 1685, 1621, 1393, 1329, 1163. |
| 233 | 4-CF$_3$ | mp: 79–80° C. NMR: δ 0.96(t, J=7.5Hz, 3H), 1.56(s, 3H), 1.98(m, 2H), 5.04(br s, 2H), 7.40(d, J=8.1Hz, 2H), 7.63(d, J=8.4Hz, 2H), 7.77(d, J=8.1Hz, 2H), 7.94(d, J=8.4Hz, 2H). IR(cm$^{-1}$): 3336, 3254, 1686, 1621, 1392, 1164. |
| 234 | 3-F, 5-F | mp: 206–207° C. NMR: δ 0.94(t, J=7.5Hz, 3H), 1.54(s, 3H), 1.97(m, 2H), 4.91(br s, 2H), 6.81(m, 3H), 7.79(d, J=8.7Hz, 2H), 7.97(d J=8.7Hz, 2H). IR(cm$^{-1}$): 3256, 1691, 1596, 1160. |
| 235 | 3-F, 4-F | mp: 157–158° C. NMR: δ 0.94(t, J=7.5Hz, 3H), 1.54(s, 3H), 1.96(m, 2H), 4.92(br s, 2H), 6.98(m, 1H), 7.15(m, 2H), 7.78(d, J=8.4Hz, 2H), 7.95(d, J=8.7Hz, 2H). IR(cm$^{-1}$): 3222, 1692, 1609, 1518, 1342, 1161. |
| 236 | 3-OMe | mp: 69–70° C. NMR: δ 0.95(t, J=7.5Hz, 3H), 1.54(s, 3H), 1.97(m, 2H), 3.78(s, 3H), 4.93(br s, 2H), 6.82(m, 2H), 6.88(m, 1H), 7.27(m, 1H), 7.79(d, J=9.0Hz, 2H), 7.90(d, J=9.0Hz, 2H). IR(cm$^{-1}$): 3339, 3253, 1692, 1617, 1344, 1259, 1161. |

EXAMPLE 237

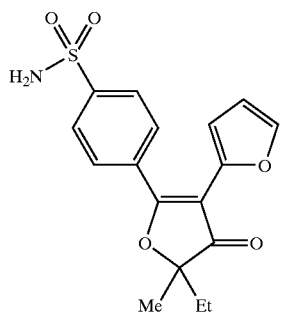

5-{4-(Aminosulfonyl)phenyl}-2-ethyl-4-(2-furanyl)-2-methyl-3(2H)-furanone

5-{4-(Aminosulfonyl)phenyl}-2-ethyl-4-iodo-2-methyl-3 (2H)-furanone was coupled with 2-furanboronic acid according to a procedure similar to the procedure in Example 44. mp: 154–155° C. NMR: δ0.92 (t, J=7.5 Hz, 3H), 1.52 (s, 3H), 1.95 (m, 2H), 5.03 (br s, 2H), 6.51 (dd, J=3.0, 1.8 Hz, 1H), 6.87 (d, J=3.0 Hz, 2H), 7.37 (d, J=1.5Hz, 1H), 7.94 (d, J=8.7 Hz, 2H), 8.02 (d, J=8.7 Hz, 2H). IR (cm$^{-1}$): 3347, 3257, 1692, 1545, 1341, 1164.

Compounds of Example 238~Example 254 were prepared by procedures similar to the synthetic procedure in Step 6 of Example 47.

EXAMPLE 238~EXAMPLE 254

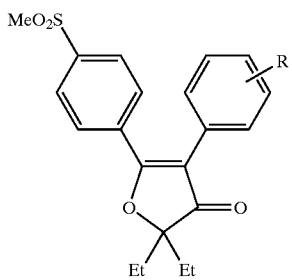

| Example | R | Melting point & spectral data |
|---|---|---|
| 238 | 3-F | Mp: 131–132° C. NMR: δ 0.93(t, J=7.5Hz, 6H), 1.99(q, J=7.5Hz, 4H), 3.08(s, 3H), 7.03(m, 3H), 7.33(m, 1H), 7.85(d, J=8.7Hz, 2H), 7.96(d, J=8.7Hz, 2H). IR(cm$^{-1}$): 2972, 1693, 1622, 1409, 1318, 1143. |
| 239 | 3-Me | Mp: 95–96° C. NMR: δ 0.93(t, J=7.5Hz, 6H), 1.98(q, J=7.5Hz, 4H), 2.35(s, 3H), 3.07(s, 3H), 6.99(m, 1H), 7.10(m, 1H), 7.16(m, 1H), 7.27(m, 1H), 7.87(d, J=8.7Hz, 2H), 7.93(d, J=8.7Hz, 2H). IR(cm$^{-1}$): 2972, 1694, 1622, 1319, 1150. |
| 240 | 3-OMe | Mp: 80–81° C. NMR: δ 0.93(t, J=7.5Hz, 6H), 1.97(q, J=7.5Hz, 4H), 3.07(s, 3H), 3.78(s, 3H), 6.89(m, 1H), 6.90(m, 2H), 7.29(m, 1H), 7.88(d, J=8.4Hz, 2H), 7.94(d, J=8.7Hz, 2H). IR(cm$^{-1}$): 2972, 1694, 1622, 1403, 1318, 1150. |
| 241 | 3-CF$_3$ | Mp: 73–74° C. NMR: δ 0.94(t, J=7.5Hz, 6H), 2.00(q, J=7.5Hz, 4H), 3.08(s, 3H), 7.48(m, 3H), 7.61(d, J=7.5Hz, 1H), 7.83(d, J=9.0Hz, 2H), 7.97(d, J=8.7Hz, 2H). IR(cm$^{-1}$): 2970, 1696, 1376, 1325, 1218, 1150. |
| 242 | 4-F | Mp: 174–175° C. NMR: δ 0.93(t, J=7.5Hz, 6H), 1.98(q, J=7.5Hz, 4H), 3.08(s, 3H), 7.08(m, 2H), 7.24(m, 2H), 7.85(d, J=8.7Hz, 2H), 7.95(d, J=8.7Hz, 2H). IR(cm$^{-1}$): 2975, 1694, 1592, 1391, 1321, 1150. |
| 243 | 4-Cl | Mp: 144–145° C. NMR: δ 0.92(t, J=7.5Hz, 6H), 1.98(q, J=7.5Hz, 4H), 3.02(s, 3H), 7.20(d, J=8.4Hz, 2H), 7.36(d, J=8.4Hz, 2H), 7.85(d, J=9.0Hz, 2H), 7.96(d, J=8.7Hz, 2H). IR(cm$^{-1}$): 2972, 1695, 1408, 1318, 1150. |
| 244 | 4-OMe | Mp: 166–167° C. NMR: δ 0.92(t, J=7.5Hz, 6H), 1.96(q, J=7.5Hz, 4H), 3.07(s, 3H), 3.83(s, 3H), 6.92(d, J=9.0Hz, 2H), 7.17(d, J=8.7Hz, 2H), 7.88(d, J=8.7Hz, 2H), 7.94(d, J=8.7Hz, 2H). IR(cm$^{-1}$): 2971, 1692, 1593, 1513, 1317, 1149. |
| 245 | 4-Me | Mp: 96–97° C. NMR: δ 0.92(t, J=7.5Hz, 6H), 1.97(q, J=7.5Hz, 4H), 2.38(s, 3H), 3.07(s, 3H), 7.13(d, J=8.1Hz, 2H), 7.29(d, J=8.1Hz, 2H), 7.86(d, J=9.0Hz, 2H), 7.93(d, J=8.7Hz, 2H). IR(cm$^{-1}$): 2971, 1693, 1594, 1401, 1317, 1149. |
| 246 | 4-CF$_3$ | Mp: 121–122° C. NMR: δ 0.94(t, J=7.5Hz, 6H), 2.00(q, J=7.5Hz, 4H), 3.09(s, 3H), 7.40(d, J=8.4Hz, 2H), 7.64(d, J=8.1Hz, 2H), 7.85(d, J=8.4Hz, 2H), 7.98(d, J=9.0Hz, 2H). IR(cm$^{-1}$): 2973, 1697, 1622, 1392, 1325, 1151. |
| 247 | 3-F, 4-F | Mp: 159–160° C. NMR: δ 0.92(t, J=7.5Hz, 6H), 1.98(q, J=7.5Hz, 4H), 3.09(s, 3H), 6.96(m, 1H), 7.15(m, 2H), 7.85(d, J=8.7Hz, 2H), 7.98(d, J=9.0Hz, 2H). IR(cm$^{-1}$): 2972, 1696, 1516, 1318, 1276, 1149. |
| 248 | 3-F, 5-F | Mp: 96–97° C. NMR: δ 0.92(t, J=7.5Hz, 6H), 1.98(q, J=7.5Hz, 4H), 3.10(s, 3H), 6.80(m, 3H), 7.85(d, J=8.7Hz, 2H), 7.80(d, J=8.4Hz, 2H). IR (cm$^{-1}$): 2972, 1697, 1318, 1150. |
| 249 | 3-OMe, 4-OMe | Mp: 130–131° C. NMR: δ 0.93(t, J=7.5Hz, 6H), 1.97(q, J=7.5Hz, 4H), 3.07(s, 3H), 3.82(s, 3H), 3.90(s, 3H), 6.77(m, 2H), 6.87(d, J=8.1Hz, 1H), 7.90(d, J=8.7Hz, 2H), 7.95(d, J=8.7Hz, 2H). IR (cm$^{-1}$): 2973, 1694, 1593, 1516, 1319, 1149. |
| 250 | 4-n-Pr | NMR: δ 0.92(t, J=7.5Hz, 6H), 0.96(t, J=7.5Hz, 3H), 1.65(m, 2H), 1.97(q, J=7.5Hz, 4H), 2.61(t, J=7.5Hz, 2H), 3.07(s, 3H), 7.15(d, J=8.1Hz, 2H), 7.20(d, J=8.4Hz, 2H), 7.87(d, J=8.4Hz, 2H), 7.93(d, J=8.7Hz, 2H). IR(cm$^{-1}$): 2969, 1694, 1594, 1318, 1150. |
| 251 | 2-F, 4-F | Mp: 165–166° C. NMR: δ 0.93(t, J=7.5Hz, 6H), 1.99(q, J=7.5Hz, 4H), 3.07(s, 3H), 6.87(m, 1H), 6.98(m, 1H), 7.27(m, 1H), 7.84(d, J=8.7Hz, 2H), 7.96(d, J=9.0Hz, 2H). IR(cm$^{-1}$): 2972, 1695, 1593, 1318, 1150. |
| 252 | 4-t-Bu | NMR: δ 0.92(t, J=7.5Hz, 6H), 1.33(s, 39H), 1.98(q, J=7.5Hz, 4H), 3.08(s, 3H), 7.18(d, J=8.7Hz, 2H), 7.39(d, J=8.4Hz, 2H), 7.89(d, J=8.7Hz, 2H), 7.94(d, J=9.0Hz, 2H). IR(cm$^{-1}$): 2965, 1694, 1502, 1318, 1250, 1149. |
| 253 | 3-Me, 4-Me | Oil. NMR: δ 0.92(t, J=7.5Hz, 6H), 1.96(q, J=7.5Hz, 4H), 2.25(s, 3H), 2.28(s, 3H), 3.06(s, 3H), 6.92(dd, J=7.8, 1.8Hz, 1H), 7.05(d, J=0.9Hz, 1H), 7.13(d, J=7.8Hz, 1H), 7.88(d, J=9.0Hz, 2H), 7.93(d, J=8.7Hz, 1H). IR(cm$^{-1}$): 2971, 1694, 1403, 1318, 1244, 1149. |
| 254 | 3-Cl, 4-F | Mp: 173–174° C. NMR: δ 0.92(t, J=7.5Hz, 6H), 1.98(q, J=7.5Hz, 4H), 3.09(s, 3H), 7.09(m, 1H), 7.16(t, J=8.7Hz, 1H), 7.36(dd, J=7.2, 2.1Hz, 1H), 7.85(d, J=8.7Hz, 2H), 7.98(d, J=8.4Hz, 2H). IR (cm$^{-1}$): 2973, 1694, 1503, 1308, 1149. |

Compounds of Example 255~Example 259 were prepared by procedures similar to the synthetic procedure in Step 6 for Example 53.

EXAMPLE 255~EXAMPLE 259

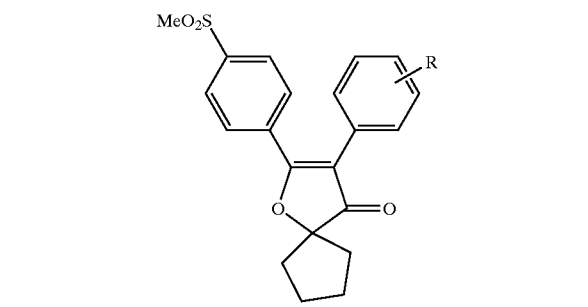

| Example | R | Melting point & spectral data |
|---|---|---|
| 255 | 3-Me | Mp: 142–143° C. NMR: δ 2.03(m, 6H), 2.10(m, 2H), 2.34(s, 3H), 3.06(s, 3H), 7.00(d, J=7.5Hz, 1H), 7.14(m, 1H), 7.26(m, 2H) 7.83(d, J=9Hz, 2H), 7.92(m, J=8.7Hz, 2H). IR(cm⁻¹): 2962, 1693, 1620, 1403, 1150, 958, 770. |
| 256 | 3-F, 5-F | mp: 127–128° C. NMR: δ 2.03(m, 6H), 2.16(m, 2H), 3.09(s, 3H), 6.80(m, 1H), 6.83(m, 2H), 7.82(d, J=8.7Hz, 2H), 7.98(d, J=8.7Hz, 2H). IR(cm⁻¹): 2962, 1702, 1626, 1591, 1393, 1287, 1197, 987. |
| 257 | 2-F | mp: 120–121° C. NMR: δ 2.05(m, 6H), 2.17(m, 2H), 3.06(s, 3H), 7.09(m, 1H), 7.24(m, 1H), 7.38(m, 1H), 7.82(m, 2H) 7.83(m, 2H). IR(cm⁻¹): 2960, 1696, 1594, 1404, 1319, 1150. |
| 258 | 4-F | mp: 109–113° C. NMR: δ 2.03(m, 6H), 2.16(m, 2H), 3.08(s, 3H), 7.08(m, 2H), 7.28(m, 2H), 7.81(m, 2H), 7.85(m, 2H). IR(cm⁻¹): 2960, 1696, 1594, 1404, 1319, 1150. |
| 259 | 3-F | mp: 158–160° C. NMR: δ 2.03(m, 8H), 2.17(m, 2H), 3.08(s, 3H), 7.06(d, J=8.4Hz, 2H), 7.35(d, J=8.4Hz, 2H), 7.82(d, J=8.4Hz, 2H), 7.95(m, 2H). IR(cm⁻¹): 2961, 1695, 1621, 1403, 1318, 1151, 770. |

EXAMPLE 260

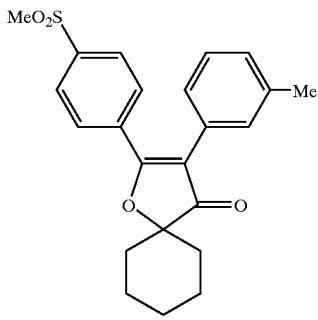

3-(3-Methylphenyl)-2-{4-(methylsulfonyl)phenyl}-1-oxa-spiro[4,5]dec-2-en-4-one 3-(3-Methylphenyl)-2-{4-(methylsulfonyl)phenyl}-1-oxa-spiro[4,5]dec-2-en-4-one was prepared by a procedure similar to the synthetic procedure in Step 6 of Example 56. mp: 154–155° C. NMR: δ1.82 (m, 10H), 2.34 (s, 3H), 3.06 (s, 3H), 6.99 (d, J=8.4 Hz, 1H), 7.13 (m, 2H), 7.25 (m, 1H), 7.86 (m, 2H), 7.93 (d, J=8.7 Hz, 2H). IR (cm⁻¹): 2934, 1693, 1621, 1403, 1147, 1129, 716.

EXAMPLE 261

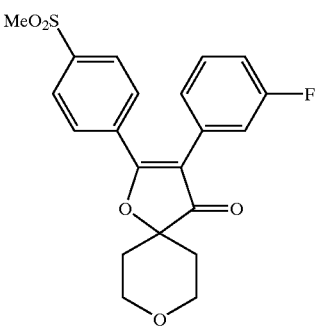

3-(3-Fluorophenyl)-2-{4-(methylsulfonyl)phenyl}-1,8-dioxa-spiro[4,5]dec-2-en-4-one Step 1 Preparation of 4-ethynyl-4-hydroxy-tetrahydro-(4H)-pyran

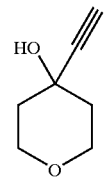

To 29.8 g of cerium(III) chloride, which was dried for 2 hours at 140° C. and 0.1 torr, was added dry 200 ml THF under argon. The suspension was stirred for 2 hours and then was cooled to −78° C. To the stirred cerium chloride solution, was added dropwise 48 ml of 25% lithium acetylide/ethylene diamine in toluene over 30 minutes, which was followed by dropwise addition of 10 g of tetrhydro-(4H)-pyran-4-one in 100 ml THF [Tetrahedron Lett. 25, 4233 (1984)]. Then the reaction mixture was slowly warmed to room temperature and was stirred for 18 hours. The reaction was quenched by adding a minimum amount of aqueous saturated ammonium chloride, and the resulting insoluble material was filtered off through celite. The filtrate was concentrated in vacuo and the resulting residue was extracted with brine and 200 ml ethylacetate. The organic layer was dried over anhydrous magnesium sulfate and the magnesium sulfate was filtered off. Then 2.6 g of 4-ethynyl-4-hydroxy-tetrahydro-(4H)-pyran was obtained from the filtrate upon concentration. NMR: δ1.77–1.86 (m, 2H), 1.91–1.99 (m. 2H), 2.51 (t, J=6.0 Hz, 1H), 2.55 (s, 1H), 3.62–3.70 (m, 2H), 3.87–4.00 (m, 2H). IR (cm⁻¹): 3388, 2960, 2865, 2109, 1717, 1338, 1085, 840.

Step 2 Preparation of 1-{4-(methylthio)phenyl}-4,4-{tetrahydro-(4H)-pyranylidenyl}-2-butyn-1,4-diol

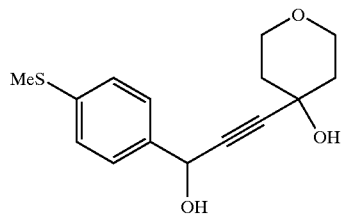

To a stirred solution of 4-ethynyl-4-hydroxy-tetrahydro-(4H)-pyran (2 g) in 90 ml dry THF, was added slowly 21.8 ml of 1.6 M butyllithium in hexane at −78° C. The mixture was stirred for 50 minutes, which was followed by addition of p-(methylthio)benzaldehyde (2.41 g). Then the reaction solution was allowed to warm slowly to room temperature and was stirred for 2 hours. The reaction was stopped by adding 100 ml ice/water, which was followed by extraction with 100 ml methylene chloride. The organic layer was dried over anhydrous magnesium sulfate and the magnesium sulfate was filtered off. The filtrate was concentrated under reduced pressure, and the resulting crude product was purified by column chromatography (hexane/ethylacetate) to yield 2.3 g of 1-{4-(methylthio)phenyl}-4,4-{tetrahydro-(4H)-pyranylidenyl}-2-butyn-1,4-diol. NMR: δ1.79–1.88 (m, 2H), 2.20–2.35 (m, 2H), 2.50 (s, 3H), 3.61–3.70 (m, 2H), 3.83–3.88 (m, 2H), 4.40 (s, 1H), 5.49 (d, J=6Hz, 1H), 5.80 (s, 1H), 7.27 (d, J=8.4 Hz, 2H), 7.45 (d, J=8.4 Hz, 2H). IR (cm$^{-1}$): 3370, 2975, 2863, 2209, 1633, 1426, 1180, 743.

Step 3: Preparation of 4-hydroxy-1-{4-(methylthio)phenyl}-4,4-{4-tetrahydro-(4H)-pyranylidenyl}-2-butyn-1-one

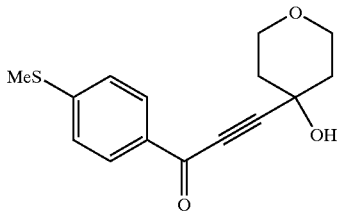

A mixture of pyridinium dichromate (4.7 g) and 2.3 g of 1-{4-(methylthio)-phenyl}-4,4-{4-tetrahydro-(4H)-pyranylidenyl}-2-butyn-1,4-diol in 120 ml dichloromethane was stirred for 22 hours at room temperature, which was followed by addition of 40 ml ether. The reaction mixture was then filtered through Florisil and the filtrate was concentrated in vacuo. The crude product was purified by column chromatography (hexane/ethylacetate) to give 1.2 g of 4-hydroxy-1-{4-(methylthio)-phenyl}-4,4-{4-tetrahydro-(4H)-pyranylidenyl}-2-butyn-1-one. NMR: δ1.93–1.99 (m, 2H), 1.98–2.15 (m, 2H), 2.52 (s, 1H), 2.54 (s, 3H), 3.70–3.78 (m, 2H), 3.93–4.00 (m, 2H), 7.29 (d, J=9.0 Hz, 2H), 8.02 (d, J=9.0 Hz , 2H). IR (cm$^{-1}$): 3400, 2957, 2862, 2208, 1568, 1263, 840.

Step 4: Preparation of 2-{4-(methylthio)phenyl}-1,8-dioxa-spiro[4,5]dec-2-en-4-one

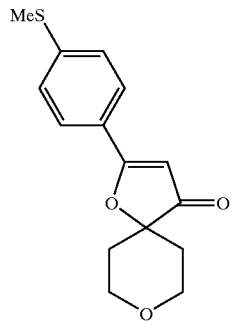

To 1.20 g of 4-hydroxy-1-{4-(methylthio)phenyl}-4,4-{4-tetrahydro-(4H)-pyranylidenyl}-2-butyn-1-one in 170 ml ethanol, was added dropwise 0.48 g of diethylamine diluted in 60 ml ethanol. The mixture was stirred for an hour at room temperature, which was followed by concentration under reduced pressure. The resulting residue was extracted with water and dichloromethane (100 ml×2) and the organic layer was dried over anhydrous magnesium sulfate. The magnesium sulfate was removed by filtration and the filtrate was concentrated in vacuo. The crude product was then purified by column chromatography (hexane/ethylacetate) to give 0.6 g of 2-{4-(methylthio)phenyl}-1,8-dioxa-spiro[4,5]dec-2-en-4-one as a solid. mp: 135–138° C. NMR: δ1.58–1.63 (m, 2H), 2.07–2.18 (m, 2H), 2.55 (s, 3H), 3.81–3.91 (m, 2H), 4.04–4.10 (m, 2H), 5.97 (s, 1H), 7.32 (d, J=9.0 Hz, 2H), 7.75 (d, J=9.0 Hz, 2H). IR (cm$^{-1}$): 2954, 2860, 1691, 1598, 1583, 1468, 1096.

Step 5: Preparation of 2-{4-(methylsulfonyl)phenyl}-1,8-dioxa-spiro[4,5]dec-2-en-4-one

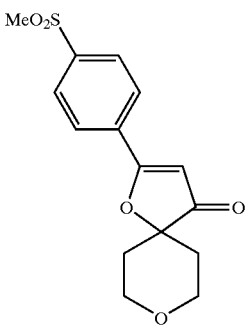

To a stirred solution of 2-{4-(methylthio)phenyl}-1,8-dioxa-spiro[4,5]dec-2-en-4-one (0.6 g) in 10 ml THF and 10 ml ethanol, was added 2.67 g of OXONE dissolved in 5 ml water. The mixture was stirred for 26 hours at room temperature. After volatile solvent was evaporated in vacuo, the aqueous solution was extracted with dichloromethane. The organic layer was concentrated under reduced pressure and the resulting crude product was purified by recrystallization from hexane/dichloromethane to give 0.55 g of 2-{4-(methylsulfonyl)phenyl}-1,8-dioxa-spiro[4,5]dec-2-en-4-one. mp: 163–165° C. NMR: δ1.58–1.70 (m, 2H), 2.09–2.20 (m, 2H), 3.11 (s, 3H), 3.82–3.92 (m, 2H), 4.04–4.14 (m, 2H), 6.16 (s, 1H), 8.05 (d, J=8.7 Hz, 2H), 8.10 (d, J=8.7 Hz, 2H). IR (cm$^{-1}$): 2862, 1694, 1314, 1152, 961.

Step 6: Preparation of 3-iodo-2-{4-(methylsulfonyl)phenyl}-1,8-dioxa-spiro[4,5]dec-2-en-4-one

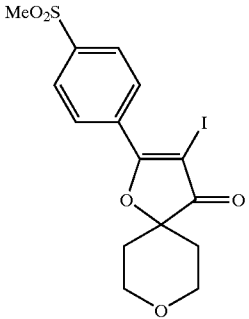

A mixed solution of 2-{4-(methylsulfonyl)phenyl}-1,8-dioxa-spiro[4,5]dec-2-en-4-one (0.55 g), [bis (trifluoroacetoxy)iodo]benzene (0.84 g) and iodine (0.45 g) in 50 ml dichloromethane was stirred for 6 hours at room temperature. Then the reaction was quenched by adding 10 ml aqueous saturated sodium thiosulfate. The organic layer was washed with brine and was concentrated under reduced pressure. The resulting crude product was purified by column chromatography (hexane/ethylacetate) to afford 0.6 g of 3-iodo-2-{4-(methylsulfonyl)phenyl}-1,8-dioxa-spiro[4,5]dec-2-en-4-one. mp: 210–213° C. NMR: δ1.60–1.72 (m, 2H), 2.11–2.44 (m, 2H), 3.12 (s, 3H), 3.80–3.90 (m, 2H), 4.04–4.14 (m, 2H), 8.21 (d, J=9 Hz, 2H), 8.41 (d, J=9 Hz, 2H). IR (cm$^{-1}$): 1690, 1580, 1146, 912, 744.

Step 7: Preparation of 3-(3-fluorophenyl)-2-{4-(methylsulfonyl)phenyl}-1,8-dioxa-spiro[4,5]dec-2-en-4-one To a stirred solution of 120 mg of 3-iodo-2-{4-(methylsulfonyl)phenyl}-1,8-dioxa-spiro[4,5]dec-2-en-4-one in 5 ml toluene and 5 ml ethanol, were added at room temperature 16 mg of tetrakis(triphenylphosphine)palladiumn(0), 0.3 ml of 2M aqueous sodium carbonate and 43 mg of 3-fluorobenzeneboronic acid. The reaction mixture was stirred at 100° C. for 3 hours. The reaction mixture was purified by a procedure similar to the method used for Example 2 to give 84 mg of 3-(3-fluorophenyl)-2-{4-(methylsulfonyl)phenyl}-1,8-dioxa-spiro[4,5]dec-2-en-one. mp: 164–166° C. NMR: δ1.70–1.75 (m, 2H), 2.15–2.26 (m, 2H), 3.09 (s, 3H), 3.84–3.94 (m, 2H), 4.08–4.14 (m, 2H), 7.02–7.10 (m, 3H), 7.31–7.40 (m, 1H), 7.86 (d, J=8.4 Hz, 2H), 7.97 (d, J=8.4 Hz, 2H). IR (cm$^{-1}$): 2862, 1694, 1623, 1430, 1318, 1148, 1103, 770.

Compounds of Example 262 and Example 263 were prepared by following procedures similar to the synthetic procedure in Step 7 of Example 261.

EXAMPLE 262 and EXAMPLE 263

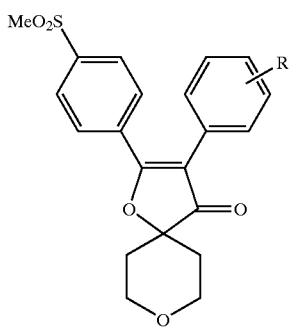

| Example | R | Melting point & spectral data |
|---|---|---|
| 262 | H | mp: 169–171° C. NMR: δ 1.65–1.75(m, 2H), 2.10–2.26(m, 2H), 3.07(s, 3H), 3.81–3.94(m, 2H), 4.05–4.14(m, 2H), 7.25–7.40(m, 5H), 7.86(d, J=8.4Hz, 2H), 7.95(d, J=8.4Hz, 2H). IR(cm$^{-1}$): 2860, 1690, 1317, 1146, 730. |
| 263 | 3-Cl | mp: 96–99° C. NMR: δ 1.66–1.75(m, 2H), 2.15–2.26(m, 2H), 3.09(s, 3H), 3.84–3.93(m, 2H), 4.07–4.15(m, 2H), 7.12–7.15(m, 1H), 7.31(7.35(m, 3H), 7.85(d, J=8.7Hz, 2H), 7.98(d, J=8.7Hz, 2H). IR (cm$^{-1}$): 2861, 1692, 1317, 1147, 1102, 732. |

EXAMPLE 264

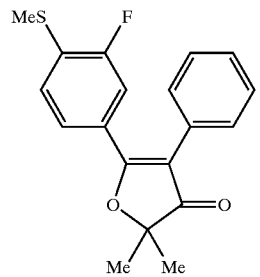

2,2-Dimethyl-5-{3-fluoro-4-(methylthio)phenyl}-4-phenyl-3(2H)-furanone

Step 1: Preparation of 1-{3-fluoro-4-(methylthio)phenyl}-2-phenyl-ethan-1-one

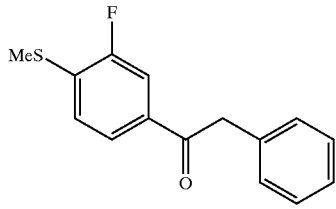

To a stirred solution of 1.5 ml 2-fluorothioanisole in 50 ml dichloromethane, were added at 0° C. 1.2 g of aluminum chloride and 1 ml of phenylacetyl chloride. The reaction mixture was stirred for 12 hours at the room temperature. Then the reaction was quenched by adding appropriate amount of ice and aqueous HCl in one portion. The quenched mixture was extracted with dichloromethane (50 ml×3) and the organic layer was washed with brine. The organic layer was dried over anhydrous magnesium sulfate, which was followed by removal of the magnesium sulfate by filtration. Then the filtrate was concentrated in vacuo and was purified by recrystallization from methanol to yield 1.8 g of 1-{3-fluoro-4-(methylthio)phenyl}-2-phenyl-ethan-1-one. mp: 71–72° C. NMR: δ2.50 (s, 3H), 4.22 (s, 2H), 7.20–7.33 (m, 6H), 7.64 (m, 1H), 7.77 (m, 1H). Step 2: Preparation of 2,2-dimethyl-5-{3-fluoro-4-(methylthio)phenyl}-4-phenyl-3(2H)-furanone To a stirred solution of 1-{3-fluoro-4-(methylthio)phenyl}-2-phenyl-ethan-1-one (1.68 g) in 100 ml dry THF, was added portion-wise at 0° C. 60% oil dispersion of sodium hydride (270 mg). The reaction solution was stirred at the same temperature for 1 hour. Then 1.2 ml of α-bromo-isobutyryl cyanide diluted in 25 ml dry THF was added dropwise to the stirred solution at 0° C. The reaction mixture was stirred overnight while warming gradually to room temperature. The solution was concentrated in vacuo, to which was added 50 ml water. The aqueous solution was extracted with dichloromethane (50 ml×3). The organic layer was concentrated in vacuo and purified by column chromatography (hexane/ethylacetate=6:1) to give 1.21 g of 2,2-dimethyl-5-{3-fluoro-4-(methylthio)phenyl}-4-phenyl-3(2H)-furanone. NMR: δ1.55 (s, 6H), 2.48 (s, 3H), 7.26–7.39 (m, 7H), 7.67 (m, 1H), 7.81 (m, 1H). IR (cm$^{-1}$): 1696, 1421, 1388, 1238.

Compounds of Example 265~Example 272 were synthesized by following procedures similar to a series of procedures employed in the synthesis of Example 264.

EXAMPLE 265~EXAMPLE 272

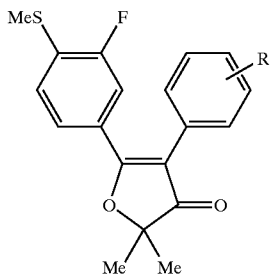

| Example | R | Melting point & spectral data |
|---|---|---|
| 265 | 2-F | NMR: δ 1.57(s, 6H), 2.48(s, 3H), 7.12(m, 2H), 7.25(m, 1H), 7.34(m, 4H). IR(cm⁻¹): 1700, 1600, 1391, 1215, 1160. |
| 266 | 4-F | NMR: δ 1.54(s, 6H), 2.49(s, 3H), 6.90(d, J=10.8, Hz, 1H), 6.99(t, J=8.7Hz, 2H), 7.02(dd, J=8.4, 1.8Hz, 1H), 7.26(m, 2H), 7.40(m, 1H). IR(cm⁻¹): 1699, 1618, 1388, 1147, 1049. |
| 267 | 2-Cl | NMR: δ 1.58(s, 6H), 2.46(s, 3H), 7.09(t, J=7.8Hz, 1H), 7.26(m, 3H), 7.34(m, 2H), 7.49(m, 1H). IR (cm⁻¹): 1694, 1616, 1426, 1384, 1299, 1234, 1155. |
| 268 | 3-Cl | NMR: δ 1.55(s, 6H), 2.49(s, 3H), 7.43(t, J=8.1Hz, 2H), 7.59(m, 2H), 7.34(m, 2H), 7.49(m, 1H). |
| 269 | 3-Cl, 4-Cl | NMR: δ 1.55(s, 6H), 2.50(s, 3H), 7.15(dd, J=8.1, 1.5Hz, 2H), 7.36(m, 2H), 7.43(m, 1H), 7.46(m, 1H). IR(cm⁻¹): 1694, 1611, 1369, 1298, 1218, 1154, 1052. |
| 270 | 2-F, 6-F | NMR: δ 1.58(s, 6H), 2.47(s, 3H), 6.85(m, 2H), 6.99(m, 1H), 7.26(m, 2H), 7.56(m, 1H). IR(cm⁻¹): 1707, 1612, 1468, 1383, 1002. |
| 271 | 3-F, 5-F | mp: 77–78° C. NMR: δ 1.55(s, 6H), 2.51(s, 3H), 6.77(m, 1H), 6.87(m, 2H), 7.16(dd, J=8.4, 7.5Hz, 1H), 7.34(m, 1H), 7.36(m, 1H). IR(cm⁻¹): 1697, 1623, 1427, 1386, 1312, 1204, 1119. |
| 272 | 4-NO₂ | mp: 107–108° C. NMR: δ 1.58(s, 6H), 2.50(s, 3H), 7.15(dd, J=8.7, 7.2Hz, 1H), 7.32(m, 1H), 7.35(m, 1H), 7.53(J=9.0Hz, 2H), 8.27(d, J=9.0Hz, 2H). IR(cm⁻¹): 1696, 1608, 1517, 1427, 1382, 1345, 1219, 1152. |

EXAMPLE 273

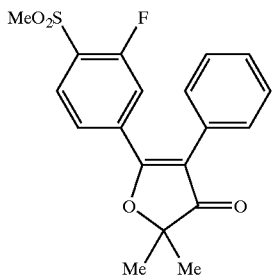

2,2-dimethyl-5-{3-fluoro-4-(methylthio)phenyl}-4-phenyl-3(2H)-furanone

To 2,2-dimethyl-5-{3-fluoro-4-(methylthio)phenyl}-4-phenyl-3((2H)-furanone (1.21 g: Example 264) dissolved in 150 ml 1:1:1 methanol/THF/water, was added 2.77 g of OXONE. The mixture was stirred at room temperature for four hours. Then the volatile solvent was removed in vacuo and the resulting solution was diluted with 50 ml water. The aqueous solution was extracted with dichloromethane (30 ml×3). The organic layer was concentrated under reduced pressure and was purified by column chromatography (hexane/ethylacetate=4:1) to afford 520 mg of 2,2-dimethyl-5-{3-(methylsulfonyl)phenyl}-4-phenyl-3(2H)-furanone as a solid. mp: 190–191° C. NMR: δ1.55 (s, 6H), 3.23 (s, 3H), 7.26 (m, 2H), 7.38 (m, 3H), 7.56 (m, 2H), 7.92 (m, 1H). IR (cm⁻¹): 1700, 1427, 1324, 1160, 1147. MS (FAB): 361 (m+1).

Compounds of Example 274~Example 287 were synthesized by procedures similar to the procedure in Example 273.

EXAMPLE 274~EXAMPLE 287

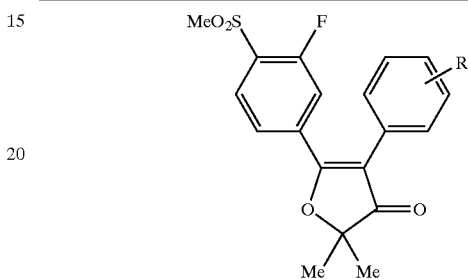

| Example | R | Melting point & spectral data |
|---|---|---|
| 274 | 2-F | mp: 135–136° C. NMR: δ 1.58(s, 6H), 3.22(s, 3H), 7.10(m, 1H), 7.24(m, 1H), 7.38(m, 2H), 7.54(m, 2H), 7.92(dd, J=8.4, 7.2Hz, 1H). IR(cm⁻¹): 1701, 1600, 1387, 1325, 1146. |
| 275 | 3-F | mp: 182–183° C. NMR: δ 1.57(s, 6H), 3.24(s, 3H), 7.02(m, 3H), 7.36(m, 1H), 7.55(m, 1H), 7.56(m, 1H), 8.00(dd, J=8.1, 7.2Hz, 1H). IR(cm⁻¹): 1700, 1601, 1385, 1323, 1160. MS(FAB): 379(m + 1) |
| 276 | 4-F | mp: 160–161° C. NMR: δ 1.50(s, 6H), 3.17(s, 3H), 7.03(t, J=8.7Hz, 2H), 7.18(t, J=8.4Hz, 2H), 7.49(m, 2H), 7.87(t, J=7.8Hz, 1H). IR(cm⁻¹): 1700, 1323, 1159, 1147. |
| 277 | 2-Cl | mp: 122–123° C. NMR: δ 1.60(s, 6H), 3.22(s, 3H), 7.25(m, 1H), 7.38(m, 2H), 7.45(m, 1H), 7.49(m, 2H), 7.91(dd, J=6.3, 1.5Hz, 1H). IR(cm⁻¹): 1705, 1611, 1429, 1384, 1325, 1150, 1072. |
| 278 | 3-Cl | mp: 108–109° C. NMR: δ 1.58(s, 6H), 3.25(s, 3H), 7.13(m, 1H), 7.32(m, 3H), 7.56(m, 2H), 7.95(t, J=7.8Hz, 1H). IR(cm⁻¹): 1704, 1695, 1567, 1490, 1384, 1325, 1219, 1159. MS(FAB): 395(m + 1) |
| 279 | 4-Cl | mp: 130–131° C. NMR: δ 1.57(s, 6H), 3.25(s, 3H), 7.23(m, 2H), 7.39(d, J=8.4Hz, 2H), 7.57(m, 2H), 7.95(d, J=6.9Hz, 1H). IR(cm⁻¹): 1700, 1694, 1610, 1495, 1406, 1323, 1247, 1159. |
| 280 | 3-Cl, 4-Cl | mp: 149–150° C. NMR: δ 1.57(s, 6H), 3.26(s, 3H), 7.09(dd, J=8.7, 2.1Hz, 1H), 7.46(m, 2H), 7.57(m, 2H), 7.98(dt, J=7.5, 1.5Hz, 1H). IR(cm⁻¹): 1705, 1486, 1324, 1159, 1072, 974. |
| 281 | 2-F, 4-F | mp: 183–184° C. NMR: δ 1.58(s, 6H), 3.24(s, 3H), 6.89(m, 1H), 7.02(m, 1H), 7.44(m, 1H), 7.53(m, 1H), 7.55(m, 1H), 7.96(dd, J=8.4, 7.2Hz, 1H). IR (cm⁻¹): 1702, 1600, 1507, 1386, 1324, 1160, 1146. |
| 282 | 2-F, 5-F | mp: 140–141° C. NMR: δ 1.59(s, 6H), 3.24(s, 3H), 7.08(m, 3H), 7.53(m, 1H), 7.56(m, 1H), 7.96(dd, J=8.1, 7.2Hz, 1H). IR(cm⁻¹): 1705, 1604, 1498, 1426, 1324, 1161, 1138. |
| 283 | 2-F, 6-F | mp: 113–115° C. NMR: δ 1.60(s, 6H), 3.23(s, 3H), 7.00(m, 2H), 7.40(m, 1H), 7.55(d, J=9.6Hz, 2H), 7.94(dd, J=7.5, 7.2Hz, 1H). IR(cm⁻¹): 1700, 1604, 1467, 1325, 1146. |
| 284 | 3-F, 4-F | mp: 158–159° C. NMR: δ 1.57(s, 6H), 3.26(s, 3H), 7.00(m, 1H), 7.18(m, 2H), 7.55(m, 1H), 7.56(m, 1H), 7.98(dd, J=8.4, 7.2Hz, 1H). IR(cm⁻¹): 1702, 1604, 1517, 1324, 1283, 1160, 1137. |
| 285 | 3-F, 5-F | mp: 163–164° C. NMR: δ 1.57(s, 6H), 3.26(s, 3H), 6.84(m, 3H), 7.55(m, 1H), 7.56(m, 1H), 7.99(dd, J=8.1, 7.2Hz, 1H). IR(cm⁻¹): 1720, 1592, 1388, 1322, 1218, 1160, 1137. MS(FAB): 397(m + 1). |
| 286 | 4-CF₃ | mp: 134–135° C. NMR: δ 1.59(s, 6H), 3.25(s, 3H), |

-continued

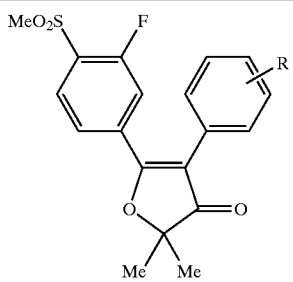

| Example | R | Melting point & spectral data |
|---|---|---|
| 287 | 4-NO₂ | 7.42(d, 2H), 7.53(m, 1H), 7.56(m, 1H), 7.66(d, 2H), 7.97(dd, J=8.4, 7.2Hz, 1H). IR(cm⁻¹): 1702, 1603, 1386, 1325, 1162, 1069. mp: 173–174° C. NMR: δ 1.60(s, 6H), 3.26(s, 3H), 7.49(d, J=8.1Hz, 2H), 7.52(m, 1H), 7.56(m, 1H), 7.99(dd, J=7.8, 7.2Hz, 1H), 8.26(d, J=8.1Hz, 2H). IR(cm⁻¹): 1701, 1605, 1518, 1324, 1220, 1160, 1140. |

EXAMPLE 288

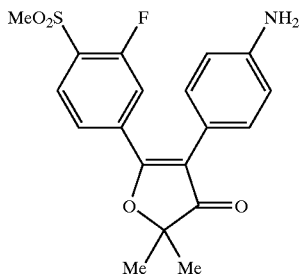

4-(aminophenyl)-2,2-dimethyl-5-{3-fluoro-4-(methylsulfonyl)phenyl}-3(2H)-furanone To 200 mg of 2,2-dimethyl-4-(4-nitrophenyl)-5-{3-fluoro-4-(methylsulfonyl)-phenyl}-3(2H)-furanone (Example 287) in 7 ml ethanol and 1 ml water, were added 0.5 ml concentrated HCl and 0.2 g of iron powder. The mixture was stirred for 12 hours at 70° C. After the reaction mixture was cooled to room temperature, the unreacted iron was filtered off. The filtrate was concentrated in vacuo and the residue was neutralized with 1 N aqueous sodium hydroxide, which was followed by extraction with 30 ml dichloromethane. The organic layer was concentrated under reduced pressure and was purified by column chromatography (hexane/ethylacetate=1:1) to afford 102 mg of 4-(4-aminophenyl)-2,2-dimethyl-5-{3-fluoro-4-(methylsulfonyl)phenyl}-3(2H)-furanone as a solid. mp: 199–200° C. NMR: δ1.54 (s, 6H), 3.24 (s, 3H), 3.80 (br s, 2H), 6.71 (d, J=8.7 Hz, 2H), 7.06 (d, J=8.7 Hz, 2H), 7.61 (dd, J=10.5, 1.8 Hz, 1H), 7.64 (dd, J=8.4, 1.8 Hz, 1H), 7.92 (dd, J=8.1, 7.2 Hz, 1H). IR (cm⁻¹): 3468, 3374, 1694, 1517, 1386, 1320, 1159, 1147.

EXAMPLE 289

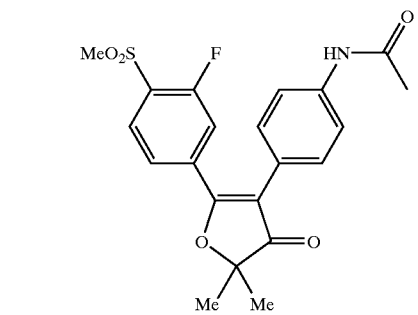

4-{4-N-(Acetylamino)phenyl}-2,2-dimethyl-5-{3-fluoro-4-(methylsulfonyl)phenyl)-phenyl}-3(2H)-furanone 60 mg of 4-(4-aminophenyl)-2,2-dimethyl-5-{3-fluoro-4-(methylsulfonyl)-phenyl}-3(2H)-furanone (Example 288) was reacted at room temperature for 12 hours with 0.2 ml acetic anhydride in 10 ml dichloromethane and 0.5 ml triethylamine in the presence of 10 mg of N,N-dimethylaminopyridine. The solvent was evaporated off in vacuo and the residue was extracted with 30 ml water and 30 ml dichloromethane. The organic layer was concentrated in vacuo and was purified by column chromatography (hexane/ethylacetate=1:1) to afford 38 mg of 4-{4-N-(acetylamino)-phenyl}-2,2-dimethyl-5-{3-fluoro-4-(methylsulfonyl)phenyl}-3(2H)-furanone as a solid. mp: 170–171° C. NMR: δ1.57 (s, 6H), 2.21 (s, 3H), 3.25 (s, 3H), 7.23 (d, J=9.9 Hz, 2H), 7.56 (m, 3H), 7.60 (dd, J=8.4, 1.8 Hz, 1H), 7.93 (dd, J=7.8, 7.2 Hz, 1H). IR (cm⁻¹): 3335, 1697, 1596, 1524, 1319, 1159, 1147.

EXAMPLE 290

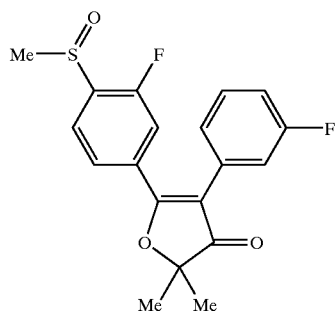

2,2-Dimethyl-5-{3-fluoro-4-(methylsulfinyl)phenyl)-4-(3-fluorophenyl)-3(2H)-furanone To a stirred solution of (2,2-dimethyl)-5-{3-fluoro-4-(methylthio)phenyl}-4-(3-fluorophenyl)-3(2H)-furanone (1.6 g) in 50 ml dichloromethane, which was prepared by a procedure similar to the procedure employed for Example 264, 1.25 g of m-chloroperoxybenzoic acid at 0° C. The reaction solution was stirred for one and half hours at the temperature, after which 30 ml 5% aqueous sodium bicarbonate was added and the solution was stirred for another 10 minutes. Then the reaction mixture was concentrated in vacuo, and the resulting residue was extracted with 50 ml water and dichloromethane (30 ml×3). The organic layer was concentrated in vacuo and was purified by column chromatography (hexane/ethylacetate=1:1) to give 1.6 g of 2,2-dimethyl-5-{3-fluoro-4-(methylsulfinyl)phenyl}-4-(3-fluorophenyl)-3(2H)-furanone as a solid. mp: 148–149° C. NMR: δ1.58 (s, 6H), 2.87 (s, 3H), 7.06 (m, 3H), 7.36(m, 1H), 7.42 (dd, J=10.5, 1.8 Hz, 1H), 7.66 (dd, J=8.4, 1.8 Hz, 1H), 7.87 (dd, J=8.1. 6.9 Hz, 1H). IR (cm⁻¹): 1700, 1623, 1420, 1261, 1216, 1192, 1135, 1077.

Compounds of Example 291~Example 299 were synthesized by following procedures similar to the procedure employed for the synthesis of Example 290.

EXAMPLE 291~EXAMPLE 299

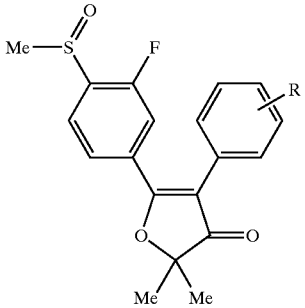

| Example | R | Melting point & spectral data |
|---|---|---|
| 291 | H | Mp: 149–150°C. NMR: δ1.57(s, 6H), 2.85(s, 3H), 7.26–7.44(m, 6H), 7.68(m, 1H), 7.83(dd, J=8.4, 6.9Hz, 1H). IR(cm$^{-1}$): 1699, 1414, 1150, 1079, 1062. |
| 292 | 2-F | NMR: δ1.58(s, 6H), 2.85(s, 3H), 7.10(m, 1H), 7.24(m, 1H), 7.40(m, 3H), 7.62(dd, J=8.1, 1.5Hz, 1H), 7.84(dd, J=8.1, 7.4Hz, 1H). IR(cm$^{-1}$): 1700, 1598, 1419, 1385, 1078. |
| 293 | 4-F | NMR: δ1.57(s, 6H), 2.86(s, 3H), 7.10(t, J=8.4Hz, 2H), 7.25(m, 1H), 7.39(m, 2H), 7.66(dd, J=8.1, 1.8Hz, 1H), 7.86(m, 1H). IR(cm$^{-1}$): 1698, 1511, 1423, 1383, 1236. |
| 294 | 2-Cl | NMR: δ1.60(s, 6H), 2.89(s, 3H), 7.26(m, 1H), 7.37(m, 3H), 7.53(m, 2H), 7.78(m, 1H). IR(cm$^{-1}$): 1703, 1625, 1565, 1469, 1384, 1153, 1077. |
| 295 | 3-Cl | NMR: δ1.57(s, 6H), 2.87(s, 3H), 7.15(m, 1H), 7.33(m, 2H), 7.42(m, 1H), 7.65(dd, J=8.1, 1.5Hz, 1H), 7.87(m, 3H). IR(cm$^{-1}$): 1702, 1621, 1566, 1412, 1382, 1240, 1151, 1078. |
| 296 | 3-Cl, 4-Cl | NMR: δ1.57(s, 6H), 2.88(s, 3H), 7.12(dd, J=8.4, 2.1 Hz, 1H), 7.44(m, 3H), 7.66(d, J=8.4Hz, 1H), 7.90(t, J=7.8Hz, 1H). IR(cm$^{-1}$)1703, 1622, 1564, 1485, 1371, 1215, 1151. |
| 297 | 2-F, 5-F | mp: 141–142°C. NMR: δ1.59(s, 6H), 2.86(s, 3H), 7.08 (m, 3H), 7.42(dd, J=10.8, 1.5Hz, 1H), 7.62(dd, J=8.4, 1.8Hz, 1H), 7.87(dd, J=8.1, 7.2Hz, 1H). IR(cm$^{-1}$): 1704, 1602, 1497, 1422, 1381, 1213. |
| 298 | 2-F, 6-F | mp: 90–92°C. NMR: δ1.60(s, 6H), 2.85(s,3H), 7.00(m, 2H), 7.42(m, 1H), 7.46(m, 1H), 7.63(m, 1H), 7.86(m, 1H). IR(cm$^{-1}$): 1707, 1486, 1384, 1148, 1080, 1003. |
| 299 | 3-F, 5-F | mp: 138–139°C. NMR: δ1.57(s, 6H), 2.88(s, 3H), 6.84 (m, 3H), 7.41(dd,J=10.5, 1.8Hz, 1H), 7.65(dd, J=8.4, 1.2Hz, 1H), 7.90(dd, J=8.1, 6.9Hz, 1H). IR(cm$^{-1}$): 2985, 1702, 1593, 1386, 1213, 1137, 1078. |

EXAMPLE 300

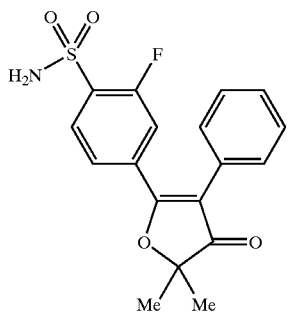

5-{4(Aminosulfonyl)-3-fluorophenyl}-2,2-dimethyl-4-phenyl-3(2H)-furanone 220 mg of 2,2-dimethyl-5-{3-fluoro-4-(methylsulfinyl)phenyl}-4-phenyl-3(2H)-furanone (Example 291) was stirred for 2 hours at 0° C. in 30 ml trifluoroacetic anhydride. The volatile material was removed in vacuo. And 30 ml of 1:1 methanol and triethylamine was added to the resulting residue. The solution was then concentrated under reduced pressure. To the resulting residue dissolved in 30 ml dichloromethane, was slowly added 5 ml acetic acid saturated with chlorine. The reaction mixture was stirred at room temperature for 5 minutes, which was followed by the removal of volatile materials in vacuo. The resulting residue was dissolved in 30 ml toluene, which was concentrated again in vacuo. The residue was diluted with 30 ml THF and then reacted with 3 ml aqueous ammonia at room temperature overnight. The reaction solution was concentrated under reduced pressure, and the resulting residue was extracted with 30 ml water and dichloromethane (30 ml×3). The organic layer was concentrated in vacuo and then was purified by column chromatography (hexane/ethylacetate=3:2) to yield 65 mg of 5-{4-(aminosulfonyl)-3-fluorophenyl}-2,2-dimethyl-4-phenyl-3(2H)-furanone. NMR: δ1.57 (s, 6H), 5.11 (br s, 21H), 7.27 (m, 2H), 7.40 (m, 3H), 7.52 (m, 2H), 7.86 (dd, J=8.1, 6.9 Hz, 1H). IR (cm$^{-1}$): 3404, 3227, 1685, 1560, 1356, 1150. MS (FAB): 362 (m+1).

Compounds of Example 301 Example 313 were prepared by a procedure similar to the procedure used for the synthesis of Example 300.

EXAMPLE 301~EXAMPLE 313

| Example | R | Melting point & spectral data |
|---|---|---|
| 301 | 2-F | mp: 86–87°C. NMR: δ1.58(s, 6H), 5.20(br s, 2H), 7.11 (m, 1H), 7.25(m, 1H), 7.36(m, 2H), 7.52(m, 2H), 7.86 (dd, J=8.1, 7.2Hz, 1H). IR(cm$^{-1}$): 3367, 3272, 1697, 1598, 1352, 1173. |
| 302 | 3-F | mp: 178–179°C. NMR: δ1.57(s, 6H), 5.20(br s, 2H), 7.04(m, 3H), 7.36(m, 1H), 7.50(m, 1H), 7.53(m, 1H), 7.89(dd, J=8.4, 6.9Hz, 1H). IR(cm$^{-1}$): 3347, 3261, 1689, 1563, 1427, 1351, 1262, 1172. MS(FAB): 380(m+1). |
| 303 | 4-F | mp: 190–192°C. NMR: δ1.57(s, 6H), 5.19(br s, 2H), 7.10(m, 2H), 7.25(t, J=8.1Hz, 2H), 7.50(m, 1H), 7.53(m, 1H), 7.89(dd, J=8.4, 7.2Hz, 1H). IR(cm$^{-1}$): 3410, 3282, 1687, 1510, 1237, 1173, 1150. |
| 304 | 2-Cl | mp: 122–123°C. NMR: δ1.60(s, 6H), 5.07(br s, 2H), 7.25(m, 2H), 7.37(m, 2H), 7.42(m, 1H), 7.47(m, 1H), 7.86(dd, J=8.4Hz, 1H). IR(cm$^{-1}$): 1692, 1623, 1611, 1565, 1428, 1353, 1224. |
| 305 | 3-Cl | mp: 164–165°C. NMR: δ1.57(s, 6H), 5.11(br s, 2H), 7.13(m, 1H), 7.33(m, 3H), 7.52(m, 2H), 7.90(t, J=7.8Hz, 1H). IR(cm$^{-1}$): 1692, 1608, 1566, 1353, 1174, 1079. |
| 306 | 4-Cl | mp: 204–205°C. NMR: δ1.56(s, 6H), 5.10(br s, 2H), 7.23(d, J=8.4Hz, 2H), 7.38(d, J=8.1Hz, 2H), 7.53(d, J=9.3Hz, 2H), 7.90(m, 1H). IR(cm$^{-1}$): 1689, 1620, 1495, 1410, 1351, 1172 |
| 307 | 3-Cl, 4-Cl | mp: 200–201°C. NMR: δ1.57(s, 6H), 5.14(br s, 2H), 7.09(dd, J=8.1, 1.8Hz, 1H), 7.46(m, 2H), 7.52(m, 2H), 7.92(t, J=7.8Hz, 1H). IR(cm$^{-1}$): 1697, 1615, 1481, 1352, |

-continued

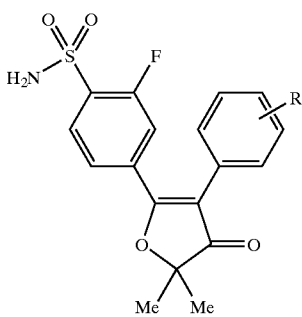

| Example | R | Melting point & spectral data |
|---|---|---|
| 308 | 2-F, 4-F | mp: 184–185°C. NMR: δ1.58(s, 6H), 5.10(br s, 2H), 6.88(m, 1H), 7.01(m, 1H), 7.34(m, 1H), 7.49(m, 1H), 7.50(m, 1H), 7.90(dd, J=8.1, 7.2Hz, 1H). IR(cm$^{-1}$): 3368, 3265, 1692, 1597, 13521219, 1173, 1149, 1292, 1153. |
| 309 | 2-F, 5-F | mp: 172–173°C. NMR: δ1.59(s, 6H), 5.16(br s, 2H), 7.08(m, 3H), 7.50(m, 2H), 7.89(dd, J=7.8, 7.2Hz, 1H). IR(cm$^{-1}$): 3350, 3264, 1698, 1602, 1499, 1426, 1217, 1174. |
| 310 | 2-F, 6-F | mp: 186–188°C. NMR: δ1.59(s, 6H), 5.15(br s, 2H), 6.98(m, 2H), 7.39(m, 1H), 7.49(m, 2H), 7.87(dd, J=8.7, 7.2Hz, 1H). IR(cm$^{-1}$): 3348, 3260, 1702, 1602, 1467, 1275. |
| 311 | 3-F, 4-F | mp: 199–200°C. NMR: δ1.57(s, 6H), 5.10(br s, 2H), 7.00(m, 1H), 7.17(m, 1H), 7.50(m, 1H), 7.53(m, 2H), 7.92(dd, J=7.5, 7.2Hz, 1H). IR(cm$^{-1}$): 3238, 1703, 1603, 1410, 1351, 1219, 1172. |
| 312 | 3-F, 5-F | mp: 198–199°C. NMR: δ1.57(s, 6H), 5.20(br s, 2H), 6.82(m, 3H), 7.50(m, 1H), 7.53(m, 1H), 7.93(dd, J=7.8, 7.2Hz, 1H). IR(cm$^{-1}$): 3255, 1697, 1594, 1391, 1219, 1172. |
| 313 | 4-NO$_2$ | mp: 222–223°C. NMR: δ1.60(s, 6H), 5.13(br s, 2H), 7.48(m, 1H), 7.49(d, J=8.1Hz, 2H), 7.51(m, 1H), 7.94(dd, J=8.1, 7.2Hz, 1H), 8.25(d, J=8.1Hz, 2H). IR(cm$^{-1}$): 3268, 1703, 1603, 1515, 1347, 1219. |

EXAMPLE 314

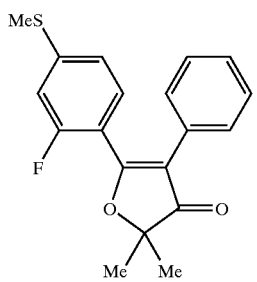

2,2-Dimethyl-5-{2-fluoro-4-(methylthio)phenyl}-4-phenyl-3(2H)-furanone

1-{2-Fluoro-4-(methylthio)phenyl}-2-phenyl-ethan-1-one (675 mg), which was prepared by a procedure similar to Step 1 in Example 264, was dissolved in 50 ml dry THF, to which was added 120 mg of sodium hydride. The reaction mixture was stirred for an hour at 0° C., which was followed by dropwise addition of 0.35 ml α-bromoisobutyryl cyanide diluted with 20 ml THF. The reaction mixture was allowed to warm to room temperature and was stirred overnight. The reaction solvent was removed in vacuo and the resulting residue was extracted with 50 ml water and dichloromethane (30 ml×3). The organic layer was concentrated under reduced pressure and was purified by column chromatography (hexane/ethylacetate=6:1) to yield 353 mg of 2,2-dimethyl-5-{2-fluoro-4-(methylthio)phenyl}-4-phenyl-3(2H)-furanone. NMR: δ1.54 (s, 6H), 2.49 (s, 3H), 6.90 (dd, J=10.8, 1.8 Hz, 1H), 7.00 (dd, J=8.4, 1.8 Hz, 1H), 7.22–7.29 (m, 5H), 7.40 (dd, J=8.4, 7.2 Hz, 1H). IR (cm$^{-1}$): 1699, 1610, 1388, 1175, 1049.

Compounds of Example 315~Example 320 were synthesized by procedures similar to the procedure in synthesis of Example 314.

EXAMPLE 315~EXAMPLE 320

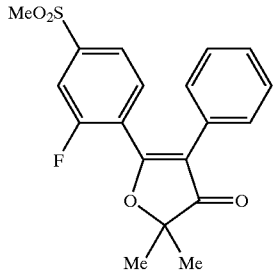

| Example | R | Melting point & spectral data |
|---|---|---|
| 315 | 3-Cl | NMR: δ1.55(s, 6H), 2.51(s, 3H), 6.91(m, 1H), 7.04(m, 1H), 7.136(m, 1H), 7.21(m, 3H), 7.43(m, 1H). IR(cm$^{-1}$): 1696, 1615, 1381, 1217, 1148 |
| 316 | 3-F | NMR: δ1.55(s, 6H), 2.51(s, 3H), 6.94(m, 4H), 7.06(m, 1H), 7.26(m, 1H), 7.43(dd, J=8.4, 6.9Hz, 1H). IR(cm$^{-1}$): 2928, 1697, 1618, 1388, 1216, 1194, 1080. |
| 317 | 4-F | NMR: δ1.55(s, 6H), 2.51(s, 3H), 6.90(dd, J=8.1, 1.8 Hz, 1H), 6.95–7.05(m, 3H), 7.25(m, 1H), 7.42(dd, J=8.1, 7.2Hz, 2H). IR(cm$^{-1}$): 1698, 1592, 1381, 1223, 1045. |
| 318 | 2-F, 5-F | NMR δ1.57(s, 6H), 2.49(s, 3H), 6.86–7.11(m, 5H), 7.47 (dd, J=8.1, 7.5Hz, 1H). |
| 319 | 3-F, 5-F | Mp: 122–123°C. NMR: δ1.56(s, 6H), 2.53(s, 3H), 6.69 (m, 1H), 6.85(m, 2H), 6.94(dd, J=11.4, 2.1Hz, 1H), 7.08 (dd, J=8.4, 1.8Hz, 1H), 7.46(dd, J=8.4, 7.2Hz, 1H). IR(cm$^{-1}$)1699, 1611, 1383, 1206, 1119 |
| 320 | 2-F, 6-F | NMR: δ1.58(s, 6H), 2.47(s, 3H), 6.90(m, 2H), 7.11(m, 1H), 7.37(m, 3H). IR(cm$^{-1}$): 1702, 1603, 1466, 1385, 1153. |

EXAMPLE 321

2,2-Dimethyl-5-{2-fluoro-4-(methylsulfonyl)phenyl)}-4-phenyl-3(2H)-furanone 305 mg of 2,2-dimethyl-5-{2-fluoro-4-(methylthio) phenyl}-4-phenyl-3(2H)-furanone (Example 314) was dissolved in 30 ml methanol, 20 ml TBF and 20 ml water, to which 1.4 g of OXONE was added. The reaction mixture was stirred overnight at room temperature. Then the solvent was removed in vacuo and the resulting residue was extracted with 50 ml water and dichloromethane (30 ml×3). The organic layer was concentrated under reduced pressure and then was purified by column chromatography (hexane/acetate=3:2) to obtain 70 mg of 2,2-dimethyl-5-{2-fluoro-4-(methylsulfonyl)phenyl}-4-phenyl-3(2H)-furanone as a solid. mp: 175–176° C. NMR: δ1.57 (s, 6H), 3.10 (s, 3H), 7.22 (m, 2H), 7.28 (m, 3H), 7.75 (dd, J=8.7, 1.8 Hz, 1H), 7.77 (m, 2H). IR (cm$^{-1}$): 1702, 1408, 1321, 1147. MS (FAB): 361 (m+1).

Compounds of Example 322 Example 326 were prepared by procedures similar to the synthetic procedure for Example 321.

EXAMPLE 322~EXAMPLE 326

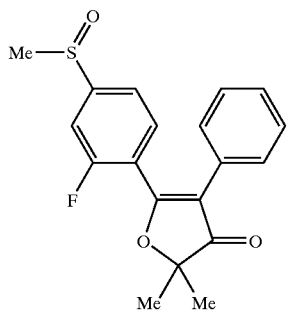

| Example | R | Melting point & spectral data |
|---|---|---|
| 322 | 3-Cl | mp: 139–140°C. NMR δ1.58(s, 6H), 3.12(s, 3H), 7.05 (m, 1H), 7.25(m, 3H), 7.77(m, 3H). IR(cm$^{-1}$): 1701, 1409, 1320, 1232, 1117, 966 |
| 323 | 3-F | mp: 157–158°C. NMR: δ1.58(s, 6H), 3.12(s, 3H), 6.97 (m, 3H), 7.26(m, 1H), 7.43(m, 1H), 7.71(dd, J=9.0, 1.8 Hz, 1H), 7.796(m, 1H). IR(cm$^{-1}$): 1701, 1577, 1433, 1308, 1117. |
| 324 | 4-F | mp: 150–152°C. NMR: δ1.59(s, 6H), 3.11(s, 3H), 7.02(t, J=9.0Hz, 2H), 7.23(m, 2H), 7.71(dd, J=10.0, 1.5Hz, 1H), 7.79(d, J=5.7Hz, 1H), 7.81(d, J=1.5Hz, 1H). |
| 325 | 2-F, 5-F | mp: 150–151°C. NMR: δ1.60(s, 6H), 3.11(s, 3H), 6.96 (m, 2H), 7.15(m, 1H), 7.69(dd, J=8.7, 1.8Hz, 1H), 7.81 (d, J=3.0Hz, 2H). IR(cm$^{-1}$)1707, 1499, 1321, 1227. |
| 326 | 3-F, 5-F | mp: 118–119°C. NMR: δ1.57(s, 6H), 3.13(s, 3H), 6.77 (m, 3H), 7.75(m, 1H), 7.82(m, 1H), 7.85(m, 1H). IR (cm$^{-1}$): 1703, 1626, 1408, 1326, 1121. |

EXAMPLE 327

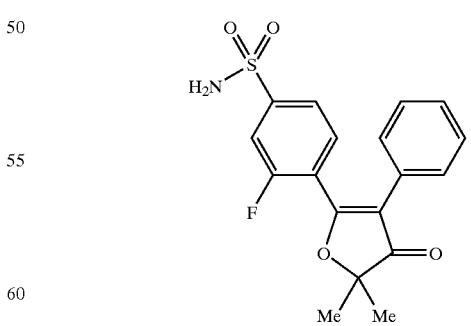

2,2-Dimethyl-5-{2-fluoro-4-(methylsulfinyl)phenyl}-4-phenyl-3(2H)-furanone

To 241 mg of 2,2-dimethyl-5-{2-fluoro-4-(methylthio)phenyl}-4-phenyl-3(2H)-furanone (Example 314) dissolved in 50 ml dichloromethane, was added 138 mg of 70% m-chloroperoxybenzoic acid. The mixture was stirred at 0° C. for 1.5 hours, which was followed by addition of 30 ml 5% aqueous sodium bicarbonate. Then the mixture was stirred for 10 minutes and the volatile material was removed in vacuo. The resulting residue was extracted with 50 ml water and dichloromethane (30 ml×3). The organic layer was concentrated under reduced pressure, and then was purified by column chromatographic separation (hexane/ethylacetate=1:1) to afford 187 mg of 2,2-dimethyl-5-{2-fluoro-4-(methylsulfinyl)phenyl}-4-phenyl-3(2H)-furanone as a solid. mp: 149–150° C. NMR: δ1.55 (s, 6H), 2.78 (s, 3H), 7.26 (m, 5H), 7.47 (m, 2H), 7.69 (dd, J=8.4, 6.6 Hz, 2H). IR (cm$^{-1}$): 1700, 1621, 1380, 1223, 1161, 1075.

Compounds of Example 328~Example 331 were synthesized according to a procedure similar to the synthetic procedure employed for Example 327.

EXAMPLE 328~EXAMPLE 331

| Example | R | Melting point & spectral data |
|---|---|---|
| 328 | 3-F | mp: 125–126° C. NMR: δ 1.54 (s, 6H), 2.79 (s, 3H), 7.01 (m, 3H), 7.25 (m, 2H), 7.49 (m, 1H), 7.78 (m, 1H). IR (cm$^{-1}$): 1701, 1577, 1433, 1308, 1117. |
| 329 | 4-F | NMR: δ 1.57 (s, 6H), 2.79 (s, 3H), 6.99 (t, J=8.7 Hz, 2H), 7.22 (dd, J=9.0, 5.4 Hz, 2H), 7.46 (d, J=8.4 Hz, 2H), 7.70 (dd, J=8.1, 6.0 Hz, 1H). IR (cm$^{-1}$): 1700, 1625, 1593, 1512, 1386, 1224. |
| 330 | 3-F, 5-F | mp: 114–115° C. NMR: δ 1.57 (s, 6H), 2.80 (s, 3H), 6.78 (m, 1H), 6.82 (m, 2H), 7.49 (m, 2H), 7.73 (dd, J=8.7, 6.0 Hz, 1H). IR (cm$^{-1}$): 1702, 1582, 1390, 1314, 1120. |
| 331 | 2-F, 6-F | NMR: δ 1.62 (s, 6H), 2.77 (s, 3H), 7.00 (m, 2H), 7.42 (m, 2H), 7.63 (dd, J=8.1, 1.5 Hz, 1H), 7.86 (dd, J=8.6, 7.2 Hz, 1H). IR (cm$^{-1}$): 1707, 1606, 1384. |

EXAMPLE 332

5-{4-(Aminosulfonyl)-2-fluorophenyl}-2,2-dimethyl-4-phenyl-3(2H)-furanone 154 mg of 2,2-dimethyl-5-{2-fluoro-4-(methylsulfinyl)phenyl}-4-phenyl-3(2H)-furanone (Example 327) was stirred in 30 ml trifluoroacetic anhydride at 0° C. for 2 hours. Then the volatile material was removed in vacuo, to which was added 50 ml of 1:1 methanol and triethylamine. The solution was stirred for 20 minutes at 0° C. and the solvent was removed under reduced pressure. The resulting residue was dissolved in 40 ml dichloromethane, which was followed by dropwise addition of 15 ml acetic acid saturated with chlorine. The reaction solution was stirred for 20 minutes at 0° C. Then the solvent and unreacted chlorine were removed in vacuo. The resulting residue was dissolved in 30 ml toluene and the toluene was evaporated off under reduced pressure. Then the resulting residue was dissolved in 40 ml THF and reacted with 5 ml ammonia water by stirring overnight. The solvent was removed in vacuo and the resulting residue was extracted with 30 ml water and dichloromethane (30 ml×3). The organic layer was concentrated in vacuo and was then purified by column chromatography (hexane/ethylacetate=3:2) to give 42 mg of 5-{4-(aminosulfonyl)-2-fluorophenyl}-2,2-dimethyl-4-phenyl-3(2H)-furanone as a solid. mp: 79–81° C. NMR: δ1.58 (s, 6H), 5.01 (br s, 2), 7.20–7.31 (m, 5H), 7.69–7.76 (m, 3H). IR (cm$^{-1}$): 3340, 3274, 1591, 1526, 1328. MS (FAB): 362 (m+1).

Compounds of Example 333~Example 335 were prepared by procedures similar to the method used for Example 332.

EXAMPLE 333~EXAMPLE 335

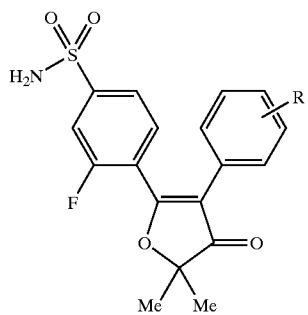

| Example | R | Melting point & spectral data |
|---|---|---|
| 333 | 3-F | mp: 168–170°C. NMR: δ1.55(s, 6H), 5.28(br s, 2H), 6.95(m, 3H), 7.25(m, 1H), 7.65(m, 2H), 7.75(m, 1H). IR (cm$^{-1}$): 3344, 3261, 1695, 1626, 1407, 1349. MS(FAB): 380(m+1). |
| 334 | 4-F | mp: 95–97°C. NMR: δ1.57(s, 6H), 5.11(br s, 2H), 7.02 (m, 2H), 7.18(m, 2H), 7.76(m, 3H). IR(cm$^{-1}$): 3366, 3268, 1700, 1625, 1511, 1230, 1164. MS(FAB): 380(m+1). |
| 335 | 3-F, 5-F | mp: 185–187°C. NMR: δ1.57(s, 6H), 5.10(br s, 2H), 6.77(m, 3H), 7.71(m, 2H), 7.80(m, 1H). IR(cm$^{-1}$): 3327, 3249, 1698, 1624, 1316, 1161. MS(FAB): 398(m+1) |

EXAMPLE 336

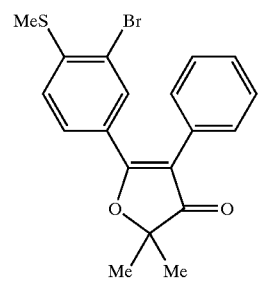

5-{3-Bromo-4-(methylthio)phenyl}-2,2-dimethyl-4-phenyl-3(2H)-furanone

To a stirred solution of 1-{3-bromo4(methylthio)phenyl}-2-phenyl-ethan-1-one (1.54 g) in 50 ml THF, was added 232 mg of 60% oil dispersion of sodium hydride. The mixture was stirred for 1 hour at 0° C., which was followed by dropwise addition of 1.1 ml α-bromoisobutyryl cyanide diluted in 20 ml THF. The reaction mixture was then slowly warmed to room temperature and was stirred overnight. The solvent was removed in vacuo and the resulting residue was extracted with 50 ml water and dichloromethane (30 ml×3). The organic layer was concentrated under reduced pressure and was purified by column chromatography (hexane/ethylacetate=6:1) to yield 1.1 g of 5-{3-bromo-4-(methylthio)phenyl}-2,2-dimethyl-4-phenyl-3(2H)-furanone. NMR: δ1.55 (s, 6H), 2.47 (s, 3H), 6.99 (d, J=8.7 Hz, 1H), 7.32 (m, 5H), 7.48 (dd, J=8.7, 2.1 Hz, 1H), 7.88 (d, J=1.8 Hz, 1H).

Compounds of Example 337~Example 340 were prepared by procedures similar to the procedures of Example 336.

EXAMPLE 337~EXAMPLE 340

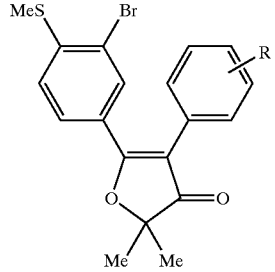

| Example | R | Melting point & spectral data |
|---|---|---|
| 337 | 3-Cl | NMR: δ1.55(s, 6H), 2.49(s, 3H), 7.02(d, J=8.7Hz, 1H), 7.18(m, 1H), 7.32(m, 3H), 7.46(dd, J=7.2, 1.8Hz, 1H), 7.88(d, J=2.1Hz, 1H). IR(cm$^{-1}$): 1695, 1609, 1389, 1239. |
| 338 | 3-F | mp: 108–109°C. NMR: δ1.55(s, 6H), 2.47(s, 3H), 7.06 (m, 4H), 7.34(m, 1H), 7.49(dd, J=7.2, 1.8Hz, 1H), 7.87 (d, J=1.8Hz, 1H). IR(cm$^{-1}$): 2983, 1696, 1599, 1391, 1258, 1195. |
| 339 | 2-F, 5-F | NMR: δ1.57(s, 6H), 2.47(s, 3H), 7.04(m, 4H), 7.44(dd, J=8.7, 1.8Hz, 1H), 7.86(d,J=1.5Hz, 1H). IR(cm$^{-1}$) 1699, 1595, 1417, 1250. |
| 340 | 3-F, 5-F | mp: 115–116°C. NMR: δ1.55(s, 6H), 2.50(s, 3H), 6.79 (m, 1H), 6.86(m, 2H), 7.05(d, J=8.4, 1H), 7.47(dd, J= 8.4, 1.8Hz, 1H), 7.87(d, J=1.8Hz, 1H). IR(cm$^{-1}$): 2925, 1689, 1604, 1391, 1120. |

EXAMPLE 341

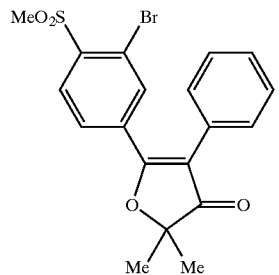

5-{3-Bromo-4-(methylsulfonyl)phenyl}-2,2-dimethyl-4-phenyl-3(2H)-furanone 350 mg of 5-{3-bromo-4-(methylthio)phenyl}-2,2-dimethyl-4-phenyl-3(2H)-furanone (Example 336), dissolved in 50 ml methanol, 50 ml THF and 50 ml water, was reacted with 1.5 g of OXONE by stirring at room temperature for 15 hours. Then the solvent was removed in vacuo and the resulting residue was extracted with 50 ml water and dichloromethane (30 ml×3). The organic layer was concentrated under reduced pressure and was purified by column chromatography (hexane/ethylacetate=3:2) to yield 173 mg of 5-{3-bromo-4-(methylsulfonyl)phenyl}-2,2-dimethyl-4-phenyl-3(2H)-furanone as a solid. mp: 154–155° C. NMR: δ1.58 (s, 6H), 3.29 (s, 3H), 7.26 (m, 3H), 7.38 (m, 2H), 8.07 (d, J=1.8 Hz, 1H), 8.10 (d, J=8.1 Hz, 2H). IR (cm$^{-1}$): 1698, 1585, 1318, 1150.

Compounds of Example 342~Example 345 were synthesized by following procedures similar to the method employed for Example 341.

EXAMPLE 342~EXAMPLE 345

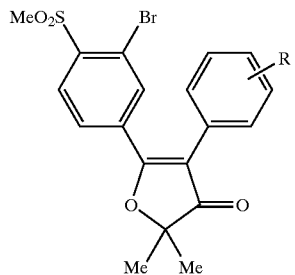

| Example | R | Melting point & spectral data |
|---|---|---|
| 342 | 3-Cl | NMR: δ1.59(s, 6H), 3.32(s, 3H), 7.14(m, 3H), 7.35(m, 1H), 7.69(dd, J=8.4, 1.8Hz, 1H), 8.08(d, J=1.8Hz, 1H), 8.16(d, J=8.4Hz, 1H). IR(cm$^{-1}$): 1700, 1388, 1320, 1151. |
| 343 | 3-F | mp: 133–134°C. NMR: δ1.57(d, 6H), 3.30(s, 3H), 7.03 (m, 3H), 7.33(m, 1H), 7.69(dd, J=8.4, 1.8Hz, 1H), 8.05 (d, J=1.5Hz, 1H), 8.14(d, J=8.4Hz, 1H). IR(cm$^{-1}$): 2931, 1700, 1586, 1390, 1312, 1151. MS(FAB): 441(m+ 2), 439(m). |
| 344 | 2-F, 5-F | NMR: δ1.59(s, 6H), 3.30(s, 3H), 7.09(m, 3H), 7.68(dd, J=8.4, 1.8Hz, 1H), 8.06(d, J=1.8Hz, 1H), 8.16(d, J=8.4Hz, 1H). IR(cm$^{-1}$): 1704, 1495, 1387, 1151. |
| 345 | 3-F, 5-F | mp: 194–195°C. NMR: δ1.58(s, 6H), 3.32(s, 3H), 6.83 (m, 3H), 7.70(dd, J=8.4, 1.8Hz, 1H), 8.06(d, J=1.8Hz, 1H), 8.18(d, J=8.1Hz, 1H). IR(cm$^{-1}$): 1702, 1627, 1377, 1120. |

EXAMPLE 346

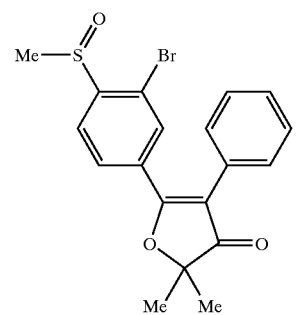

5-{3-Bromo-4-(methylsulfinyl)phenyl}-2,2-dimethyl-4-phenyl-3(2H)-furanone 391 mg of 5-{3-bromo-4-(methylthio)phenyl}-2,2-dimethyl-4-phenyl-3(2H)-furanone (Example 336) dissolved in 50 ml dichloromethane was stirred at 0° C. for 50 minutes in the presence of 183 mg of 70% m-chloroperoxybenzoic acid. Then 10 ml 5% aqueous sodium hydroxide was added to the reaction mixture and the mixed solution was stirred for another 10 minutes. The dichloromethane was removed in vacuo and the resulting residue was extracted with 50 ml water and dichloromethane (30 ml×3). The organic layer was then concentrated under reduced pressure and was purified by column chromatography (hexane/ethylacetate=1:1) to give 310 mg of 5-(3-bromo-4-(methylsulfinyl)phenyl}-2,2-dimethyl-4-phenyl-3 (2H)-furanone. NMR: δ1.58 (s, 6H), 2.84 (s, 3H), 7.30 (m, 2H), 7.38 (m, 3H), 7.78 (dd, J=8.4, 1.8 Hz, 1H), 7.88 (d, J=5.4 Hz, 1H), 7.90 (d, J=2.7 Hz, 1H). IR (cm$^{-1}$): 1698, 1619, 1388, 1064.

Compounds of Example 347~Example 350 were prepared according to procedures similar to the procedure described for Example 346.

EXAMPLE 347~EXAMPLE 350

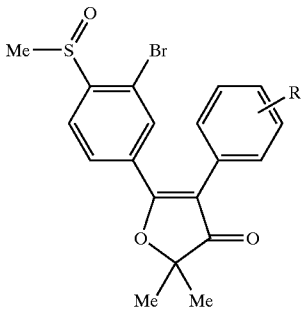

| Example | R | Melting point & spectral data |
|---|---|---|
| 347 | 3-Cl | NMR: δ1.58(s, 6H), 2.84(s, 3H), 7.15(m, 3H), 7.32(m, 1H), 7.76(dd, J=8.4, 1.8Hz, 1H), 7.88(d, J=1.5Hz, 1H), 7.93(d, J=7.8Hz, 1H). IR(cm$^{-1}$): 1708, 1496, 1417, 1386, 1065, 1194, 1080. |
| 348 | 3-F | NMR: δ1.56(s, 6H), 2.85(s, 3H), 7.05(m, 3H), 7.34(m, 1H), 7.76(dd, J=8.1, 1.8Hz, 1H), 7.87(d, J=1.8Hz, 1H), 7.91(dd, J=8.4Hz, 1H). IR(cm$^{-1}$): 2981, 1699, 1389, 1261, 1063. |
| 349 | 2-F, | NMR: δ1.59(s, 6H), 2.85(s, 3H), 7.08(m, 3H), 7.74(dd, |

131
-continued

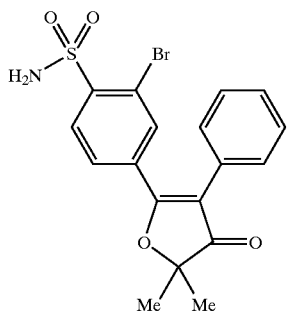

| Example | R | Melting point & spectral data |
|---|---|---|
| | 5-F | J=8.4, 1.5Hz, 1H), 7.88(d, J=1.8Hz, 1H), 7.93(d, J= 8.4Hz, 1H). IR(cm⁻¹)1708, 1496, 1417, 1386, 1065. |
| 350 | 3-F, 5-F | mp: 177–179°C. NMR: δ1.56(s, 6H), 2.86(s, 3H), 6.82 (m, 3H), 7.78(m, 1H), 7.82(s, 1H), 7.92(d, J=8.4Hz, 1H). IR(cm⁻¹): 1702, 1626, 1390, 1303, 1120. |

EXAMPLE 351

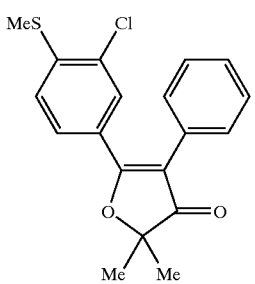

5-{4-(Aminosulfonyl)-3-bromophenyl}-2,2-dimethyl-4-phenyl-3(2H)-furanone 287 mg of 5-{3-bromo-4-(methylsulfinyl)phenyl}-2,2-dimethyl-4-phenyl-3(2H)-furanone (Example 346) in 40 ml trifluoroacetic anhydride was stirred at 0° C. for an hour. Then the solvent was removed in vacuo, and the resulting residue was dissolved in 50 ml 1:1 methanol and triethylamine. The solution was then stirred at 0° C. for an hour, which was followed by removal of the solvent in vacuo. The resulting residue was stirred in 30 ml dichloromethane, to which was added dropwise 15 ml acetic acid saturated with chlorine. The reaction solution was stirred at 0° C. for 30 minutes. Then acetic acid and the unreacted chlorine were evaporated off under reduced pressure. The resulting residue was stirred overnight in 30 ml THF and 5 ml ammonia water. The reaction mixture was then concentrated in vacuo and was subjected to extraction with 30 ml water and dichloromethane (30 ml×3). The organic layer was concentrated in vacuo and was purified by column chromatography (hexane/ ethylacetate=3:2) to obtain 89 mg of 5-{4-(aminosulfonyl)-3-bromophenyl}-2,2-dimethyl-4-phenyl-3(2H)-furanone as a solid. mp: 128–132° C. NMR: δ1.63 (s, 6H), 5.32 (br s, 2H), 7.12 (m, 2H), 7.40 (m, 3H), 7.69 (m, 1H), 7.98 (m, 2H). IR (cm⁻¹): 3400, 3282, 1686, 1556, 1171.

Compounds Example 352 and Example 353 were prepared by procedures similar to the procedure for Example 351.

132
EXAMPLE 352 and EXAMPLE 353

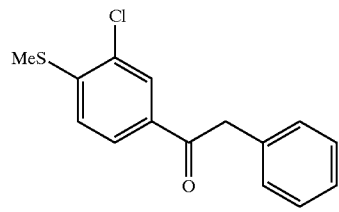

| Example | R | Melting point & spectral data |
|---|---|---|
| 352 | 3-F | mp: 151–153°C. NMR: δ1.55(s, 6H), 5.30(br s, 2H), 7.05(m, 3H), 7.36(m, 1H), 7.73(m, 1H), 7.92(m, 2H). |
| 353 | 2-F, 5-F | NMR: δ1.59(s, 6H), 5.26(br s, 2H), 7.08(m, 3H), 7.42 (m, 1H), 7.81(m, 1H), 8.08(m, 1H). IR(cm⁻¹): 3357, 1499, 1335, 1171. |

EXAMPLE 354

5-{3-Chloro-4-(methylthio)phenyl}-2,2-dimethyl-4-phenyl-3(2H)-furanone

Step 1: Preparation of 1-{3-chloro-4-(methylthio) phenyl}-2-phenyl-ethanone

To a stirred solution of 2-chlorothioanisole (3.0 g) in 120 ml dichloromethane, were added slowly first 2.8 g of aluminum chloride and 3.0 g of phenylacetyl chloride at 0° C. The reaction mixture was stirred at the temperature for 12 hours. Then the reaction solution was poured onto ice and aqueous hydrochloric acid. The quenched solution was stirred for 30 minutes and extracted with dichloromethane (80 ml×3). The organic layer was washed with brine and was dried over anhydrous magnesium sulfate. After the magnesium sulfate was removed by filtration, the filtrate was concentrated in vacuo. The resulting residue was recrystallized from hexane and dichloromethane to give 3.6 g of 1-{3-chloro-4-(methylthio)phenyl}-2-phenyl-ethanone. mp:

101–102° C. NMR: δ2.51 (s, 3H), 4.22 (s, 2H), 7.17 (d, J=8.4 Hz, 1H), 7.25 (m, 3H), 7.32 (m, 2H), 7.87 (J=8.4, 1.8 Hz, 1H), 7.97 (d, J 1.8 Hz, 1H).

Step 2: Preparation of 5-{3-chloro-4-methylthio)phenyl}-2,2-dimethyl-4-phenyl-3(2H)-furanone 3.6 g of 1-{3-chloro-4-(methylthio)phenyl}-2-phenyl-ethanone in 100 ml dry THF was stirred at 0° C. for 20 minutes in the presence of 60% oil dispersion of sodium hydride (1.5 g), which was followed by dropwise addition of α-bromoisobutyryl cyanide (3.0 ml) diluted in 50 ml THF. The reaction solution was allowed to warm slowly to room temperature and was stirred overnight. Then the solvent was removed in vacuo, which was followed by extraction with 30 ml water and diethylether (50 ml×3). The organic layer was concentrated under reduced pressure and was purified by column chromatography (hexane/ethylacetate=8:1) to yield 3.2 g of 5-{3-chloro-4-(methylthio)phenyl}-2,2-dimethyl-4-phenyl-3(2H)-furanone. NMR: δ1.52 (s, 6H), 2.45 (s, 3H), 7.17 (d, J=8.4 Hz, 1H), 7.25 (m, 3H), 7.32 (m, 2H), 7.87 (dd, J=8.4, 1.8 Hz, 1H), 7.97 (d, J=1.8 Hz, 1H). IR (cm$^{-1}$): 1694, 1613, 1592, 1389, 1252, 1145, 1128.

Compounds of Example 355 and Example 356 were prepared by procedures similar to the procedures employed for Example 354.

EXAMPLE 355 and Example 356

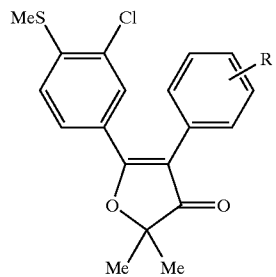

| Example | R | Melting point & spectral data |
|---|---|---|
| 355 | 3-F | NMR: δ1.55(s, 6H), 2.49(s, 3H), 7.05(m, 3H), 7.06(d, J=8.4Hz, 1H), 7.34(m, 1H), 7.44(dd, J=8.4, 1.8Hz, 1H), 7.69(d, J=1.8Hz, 1H). IR(cm$^{-1}$): 1695, 1616, 1599, 1431, 1386, 1257, 1194, 1129. |
| 356 | 3-F, 5-F | NMR: δ1.57(s, 6H), 2.51(s, 3H), 6.88(m, 3H), 7.09(d, J=8.4Hz, 1H), 7.44(dd, J=8.4, 1.8Hz, 1H), 7.69(d, J=1.8Hz, 1H). IR(cm$^{-1}$): 1698, 1623, 1593, 1391, 1309, 1120. |

EXAMPLE 357

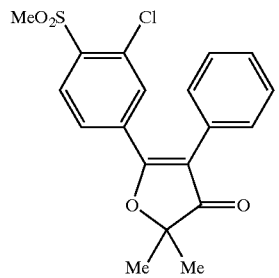

5-{3-Chloro-4(methylsulfonyl)phenyl}-2,2-dimethyl-4-phenyl-3(2H)-furanone 1.2 g of 5-{3-chloro-4-(methylthio)phenyl}-2,2-dimethyl-4-phenyl-3(2H)-furanone (Example 354) was dissolved in 150 ml of 1:1:1 methanol/THF/water, to which was added 2.8 g of OXONE. The reaction mixture was stirred at room temperature for 6 hours. The reaction mixture was concentrated in vacuo and the resulting residue was extracted with 50 ml water and ethylacetate (100 ml×3). The organic layer was concentrated in vacuo and was purified by column chromatography hexane/ethylacetate=3:1) to give 1.1 g of 5-{3-chloro-4-(methylsulfonyl)phenyl}-2,2-dimethyl-4-phenyl-3(2H)-furanone as a solid. mp: 174–175° C. NMR: δ1.58 (s, 6H), 3.28 (s, 3H), 7.27 (m, 3H), 7.39 (m, 2H), 7.66 (dd, J=8.4, 1.8 Hz, 1H), 7.86 (d, J=1.8 Hz, 1H), 8.09 (d, J=8.4 Hz, 1H). IR (cm$^{-1}$): 1700, 1587, 1391, 1321, 1241, 1152.

Compounds of Example 358~Example 362 were prepared according to the procedures similar to the procedure in Example 357.

EXAMPLE 358~EXAMPLE 362

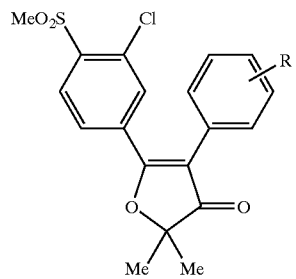

| Example | R | Melting point & spectral data |
|---|---|---|
| 358 | 3-Cl | mp: 188–189°C. NMR: δ1.58(s, 6H), 3.30(s, 3H), 7.14 (m, 1H), 7.34(m, 3H), 7.65(dd, J=8.4, 1.8Hz, 1H), 7.87 (d, J=1.5Hz, 1H), 8.12(d, J=8.4Hz, 1H). IR(cm$^{-1}$): 1700, 1620, 1585, 1388, 1321, 1241, 1162. |
| 359 | 3-F | mp: 163–164°C. NMR: δ1.58(s, 6H), 3.29(s, 3H), 7.04 (m, 3H), 7.35(m, 1H), 7.66(dd, J=8.4, 1.5Hz, 1H), 7.86 (d, 1.5Hz, 1H), 8.12(d, J=8.4Hz, 1H). IR(cm$^{-1}$): 1701, 1587, 1390, 1321, 1262, 1152. MS(FAB): 395(m+1). |
| 360 | 4-F | mp: 173–174°C. NMR: δ1.57(s, 6H), 3.29(s, 3H), 7.11 (m, 2H), 7.26(m, 2H), 7.66(dd, J=8.1, 1.5Hz, 1H), 7.85 (d, J=1.8Hz, 1H), 8.12(d, J=8.4Hz, 1H). IR(cm$^{-1}$): 1698, 1587, 1509, 1388, 1321, 1239, 1162. |
| 361 | 3-F, 4-F | mp: 150–151°C. NMR: δ1.57(s, 6H), 3.30(s, 3H), 6.99 (m, 1H), 7.17(m, 2H), 7.66(dd, J=8.4, 1.8Hz, 1H), 7.86 (d, J=1.5Hz, 1H), 8.15(d, J=8.4Hz, 1H). IR(cm$^{-1}$): 1701, 1515, 1393, 1321, 1280, 1152. |
| 362 | 3-F, 5-F | mp: 200–201°C. NMR: δ1.58(s, 6H), 3.31(s, 3H), 6.84 (m, 3H), 7.67(dd, J=8.1, 1.5Hz, 1H), 7.86(d, J=1.5Hz, 1H), 8.16(d, J=8.1Hz, 1H). IR(cm$^{-1}$): 1702, 1591, 1391, 1320, 1218, 1153, 1120. |

EXAMPLE 363

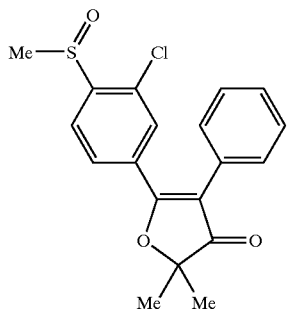

5-{3-Chloro-4-(methylsulfinyl)phenyl}-2,2-dimethyl-4-phenyl-3(2H)-furanone

To a stirred solution 3.5 g of 5-{3-chloro-4-(methylthio)phenyl}-2,2-dimethyl-4-phenyl-3(2H)-furanone (Example 354) in 80 ml dichloromethane, was added 2.5 g of 70% m-chloroperoxybenzoic acid, and the reaction mixture was stirred at 0° C. for 2 hours. Then 40 ml 5% aqueous sodium bicarbonate was added to the solution and the solution was stirred for 10 minutes. The solution was extracted with dichloromethane (50 ml×3). The organic layer was concentrated in vacuo and was purified by column chromatography (hexane/ethylacetate=1:1) to give 2.43 g of 5-{3-chloro-4-(methylsulfinyl)phenyl}-2,2-dimethyl-4-phenyl-3(2H)-furanone as a solid. mp: 120–121° C. NMR: δ1.57 (s, 6H), 2.84 (s, 3H), 7.30 (m, 3H), 7.38 (m, 2H), 7.72 (s, 1H), 7.74 (d, J=8.1 Hz, 1H), 7.91 (d, J=8.1 Hz, 1H). IR (cm$^{-1}$): 1699, 1619, 1319, 1239, 1169, 1145, 1068.

Compounds of Example 364~Example 366 were synthesized by employing procedures similar to the method in Example 363.

EXAMPLE 364~EXAMPLE 366

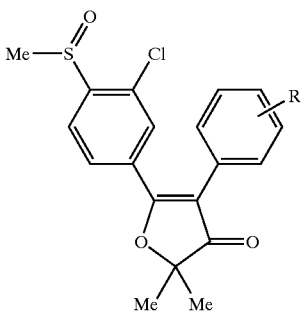

| Example | R | Melting point & spectral data |
|---|---|---|
| 364 | 3-Cl | mp: 141–142°C. NMR: δ1.57(s, 6H), 2.86(s, 3H), 7.16 (m, 1H), 7.33(m, 3H), 7.72(d, J=1.2Hz, 1H), 7.73(dd, J=8.1, 1.2Hz, 1H), 7.94(d, J=8.1Hz, 1H). IR(cm$^{-1}$): 1700, 1618, 1387, 1239, 1146, 1067. |
| 365 | 3-F | mp: 52–53°C. NMR: δ1.58(s, 6H), 2.86(s, 3H), 7.06(m, 3H), 7.35(m, 1H), 7.71(d, J=1.2Hz, 1H), 7.74(dd, J=8.1, 1.5Hz, 1H), 7.94(d, J=7.8Hz, 1H). IR(cm$^{-1}$): 1701, 1622, 1389, 1309, 1147, 1067. |
| 366 | 3-F, 5-F | mp: 123–124°C. NMR: δ1.58(s, 6H), 2.88(s, 3H), 6.85 (m, 3H), 7.71(d, J=1.5Hz, 1H), 7.74(dd, J=8.1, 1.5Hz, 1H), 7.98(d, J=1.8Hz, 1H). IR(cm$^{-1}$): 1702, 1625, 1591, 1391, 1309, 1119, 1067. |

EXAMPLE 367

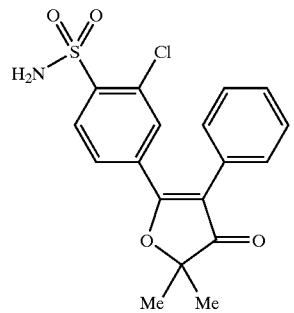

5-{4-(Aminosulfonyl)-3-chlorophenyl}-2,2-dimethyl-4-phenyl-3(2H)-furanone 1.2 g of 5-{3-chloro-4-(methylsulfinyl)phenyl}-2,2-dimethyl-4-phenyl-3(2H)-furanone (Example 363) was stirred in 30 ml trifluoroacetic anhydride at 0° C. for 2 hours. Then the solvent was removed under reduced pressure, which was followed by addition of 30 ml of 1:1 methanol/triethylamine to the resulting residue. The mixed solution was stirred at 0° C. for an hour, and the solvent was removed in vacuo. The resulting residue was dissolved, to which was added 30 ml acetic acid saturated with chlorine. The reaction mixture was stirred at 0° C. for 30 minutes. Then the solvent and the unreacted chlorine were evaporated off under reduced pressure, and the resulting residue was stirred overnight in 30 ml THF and 3 ml ammonia water. The reaction mixture was concentrated in vacuo, and the resulting residue was extracted with 30 ml water and dichloromethane (30 ml×3). The organic layer was washed with brine and then the organic layer was concentrated under reduced pressure. The resulting residue was purified by column chromatography (hexane/ethylacetate=3:2) to afford 512 mg of 5-{4-(aminosulfonyl)-3-chlorophenyl}-2,2-dimethyl-4-phenyl-3(2H)-furanone as a solid. mp: 193–194° C. NMR: δ1.58 (s, 6H), 5.14 (br s, 2H), 7.26 (m, 3H), 7.39 (m, 2H), 7.62 (dd, J=8.4, 1.8 Hz, 1H), 7.84 (d, J=1.8 Hz, 1H), 8.04 (d, J=8.1 Hz, 1H). IR (cm$^{-1}$): 3379, 3263, 1691, 1586, 1347, 1219, 1156.

Compounds of Example 368~Example 371 were prepared by procedures similar to the procedure adopted for Example 367.

EXAMPLE 368~EXAMPLE 371

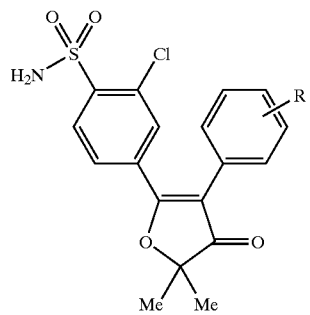

| Example | R | Melting point & spectral data |
|---|---|---|
| 368 | 3-Cl | mp: 162–163°C. NMR: δ1.57(s, 6H), 5.18(br s, 2H), 7.13(m, 1H), 7.33(m, 3H), 7.60(dd, J=8.4, 1.8Hz, 1H), 7.85(d, J=1.5Hz, 1H), 8.07(d, J=8.4Hz, 1H). |

-continued

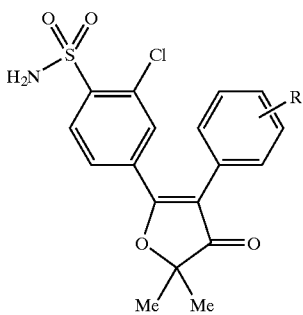

| Example | R | Melting point & spectral data |
|---|---|---|
| 369 | 3-F | IR(cm⁻¹): 3384, 3264, 1695, 1617, 1391, 1351, 1241, 1166.<br>mp: 149–150°C. NMR: δ1.57(s, 6H), 5.15(br s, 2H), 7.04(m, 3H), 7.36(m, 1H), 7.61(dd, J=8.4, 1.8Hz, 1H), 7.83(d, J=1.5Hz, 1H), 8.07(d, J=8.4Hz, 1H). IR(cm⁻¹): 3377, 3265, 1692, 1587, 1393, 1349, 1261, 1165. |
| 370 | 3-F, 4-F | mp: 216–217°C. NMR: δ1.57(s, 6H), 5.18(br s, 2H), 6.99(m, 1H), 7.17(m, 2H), 7.61(dd, J=8.4, 1.8, 1H), 7.84(d, J=1.5Hz, 1H), 8.10(d, J=8.1Hz, 1H). IR(cm⁻¹): 3401, 3264, 1687, 1515, 1396, 1220, 1165. |
| 371 | 3-F, 5-F | mp: 173–174°C. NMR: δ1.58(s, 6H), 5.19(br s, 2H), 6.84(m, 3H), 7.61(dd, J=8.4, 1.8Hz, 1H), 7.84(d, J=1.8Hz, 1H), 8.11(d, J=8.1Hz, 1H). IR(cm⁻¹): 3370, 3265, 1692, 1625, 1393, 1309, 1165, 1119. |

EXAMPLE 372

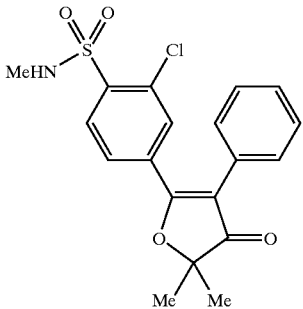

5-{3-Chloro-4-(N-methylaminosulfonyl)phenyl}-2,2-dimethyl-4-phenyl-3(2H)-furanone 200 mg of 2,2-dimethyl-5-{3-chloro-4-(methylsulfinyl)phenyl}-4-phenyl-3(2H)-furanone (Example 363) was stirred in 10 ml trifluoroacetic anhydride for an hour at 0° C. and then the solvent was removed in vacuo. The resulting residue was dissolved in 10 ml 1:1 methanol/triethylamine and was stirred for an hour at 0° C. The solution was concentrated under reduced pressure. Then the resulting residue was stirred in 15 ml dichloromethane, to which was added 5 ml acetic acid saturated with chlorine. After the solution was stirred for 30 minutes at 0° C., the solvent and the unreacted chlorine were removed in vacuo. The resulting residue was dissolved in 5 ml toluene and the toluene was evaporated off in vacuo. The resulting residue was dissolved in 20 ml THF and reacted with 1 ml of 40% aqueous methylamine for 2 hours at 0° C. The reaction solution was concentrated in vacuo, which was followed by extraction with 30 ml water and dichloromethane (30 ml×3). The organic layer was washed with brine and concentrated under reduce pressure. The resulting residue was purified by column chromatography (hexane/ethylacetate=3:2) to give 62 mg of 5-{3-chloro-4-(N-methylaminosulfonyl)phenyl}-2,2-dimethyl-4-phenyl-3(2H)-furanone as a solid. mp: 136–137° C. NMR: δ1.58 (s, 6H), 2.66 (d, J=5.4 Hz, 3H), 4.94 (q, J=5.4 Hz, 1H), 7.28 (m, 2H), 7.39 (m, 3H), 7.63 (dd, J=8.4, 1.8 Hz, 1H), 7.84 (d, J=1.8 Hz, 1H), 8.03 (d, J=8.4 Hz, 1H). IR (cm⁻¹): 3315, 1697, 1587, 1394, 1336, 1242, 1164.

EXAMPLE 373

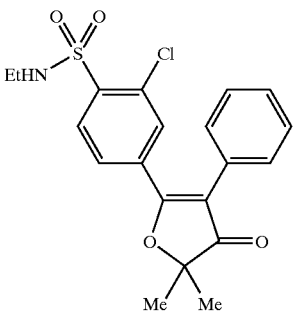

5-{3-Chloro-4-(N-ethylaminosulfonyl)phenyl}-2,2-dimethyl-4-phenyl-3(2H)-furanone By following the procedure in Example 372 except using 70% aqueous ethylamine, the titled compound was obtained. mp: 72–73° C. NMR: δ1.11 (t, J=7.2 Hz, 3H), 1.57 (s, 6H), 3.02 (m, 2H), 4.93 (t, J=6.0 Hz, 1H), 7.28 (m, 2H), 7.39 (m, 3H), 7.62 (dd, J=8.4, 1.8 Hz, 1H), 7.83 (d, J=1.8 Hz, 1H), 8.03 (d, J=8.1 Hz, 1H). IR (cm⁻¹):3300, 1698, 1618, 1587, 1393, 1337, 1241, 1163.

EXAMPLE 374

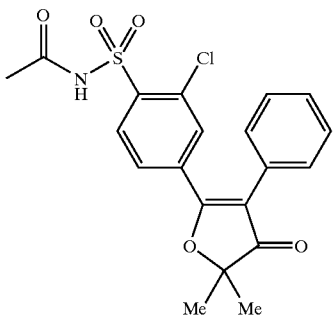

5-[4{(Acetylamino)sulfonyl}-3-chlorophenyl]-2,2-dimethyl-4-phenyl-3(2H)-furanone 150 mg of 5-{4-(aminosulfonyl)-3-chlorophenyl}-2,2-dimethyl-4-phenyl-3(2furanone (Example 367) in 10 ml dichloromethane was reacted with 0.3 ml acetic anhydride in the presence of 0.5 ml triethylamine and 15 mg of 4-(N,N-dimethylamino)pyridine at room temperature for 12 hours. The reaction mixture was concentrated in vacuo, which was followed by extraction with 30 ml water and dichloromethane (30 ml×3). The organic layer was concentrated under reduced pressure and then was purified by column chromatography (hexane/ethylacetate 2:1) to afford 113 mg of 5-[4-{(acetylamino)sulfonyl}-3-chlorophenyl]-2,2-dimethyl-4-phenyl-3(2H)-furanone as a solid. mp: 194–195°

C. NMR: δ1.57 (s, 6H), 2.10 (s, 3H), 7.27 (m, 2H), 7.40 (m, 3H), 7.68 (dd, J=8.4, 1.8 Hz, 1H), 7.85 (d, J=1.5 Hz, 1H), 8.18 (d, J=8.1 Hz, 1H), 8.45 (br s, 1H). IR (cm$^{-1}$): 3195, 3104, 1698, 1377, 1164.

EXAMPLE 375

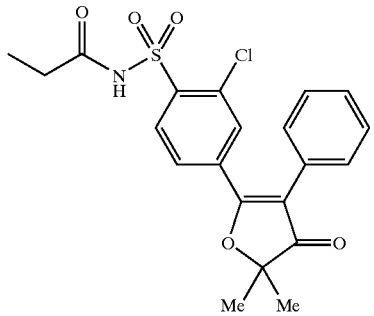

5-[3-Chloro-4-{(propionylamino)sulfonyl}phenyl]-2,2-dimethyl-4-phenyl-3(2H)-furanone 150 mg of 5-{4-(aminosulfonyl)-3-chlorophenyl}-2,2-dimethyl-4-phenyl-3(2H)-furanone (Example 367) was reacted with propionic anhydride to give 132 mg of 5-[3chloro-4-{(propionylamino)sulfonyl}phenyl]-2,2-dimethyl-4-phenyl-3(2H)-furanone according to a procedure similar to the procedure of Example 374. mp: 191–192° C. NMR: δ1.09 (t, J=7.5 Hz, 3H), 1.57 (s, 6H), 2.32 (q=7.5 Hz, 2H), 7.27 (m, 2H), 7.39 (m, 3H), 7.68 (dd, J=8.4, 1.8 Hz, 1H), 7.84 (d, J=1.5 Hz, 1H), 8.20 (d, J=8.4 Hz, 1H), 8.37 (br s, 1H). IR (cm$^{-1}$): 3204, 3105, 1699, 1458, 1396, 1164.

EXAMPLE 376

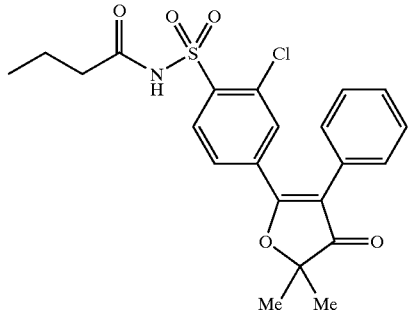

5-[4-{(n-Butyrylamino)sulfonyl}-3-chlorophenyl]-2,2-dimethyl-4-phenyl-3(2H)-furanone 150 mg of 5-{4-(aminosulfonyl)-3-chlorophenyl}-2,2-dimethyl-4-phenyl-3(2H)-furanone (Example 367) was reacted with butyric anhydride to give 124 mg of 5-[3-chloro-4-{(n-butrylamino)sulfonyl}phenyl]-2,2-dimethyl-4-phenyl-3(2H)-furanone according to a procedure similar to the procedure of Example 374. mp: 119–120° C. NMR: δ0.89 (t, J=7.5 Hz, 3H), 1.57 (s, 6H), 1.59 (m, 2H), 2.27 (t, J=7.5 Hz, 2H), 7.28 (m, 2H), 7.40 (m, 3H), 7.69 (dd, J=8.4, 1.8 Hz, 1H), 7.83 (d, J=1.8 Hz, 1H), 8.20 (d, J=8.4 Hz, 1H), 8.48 (br s, 1H). IR (cm$^{-1}$): 3191, 3105, 1698, 1684, 1453, 1242, 1187.

EXAMPLE 377

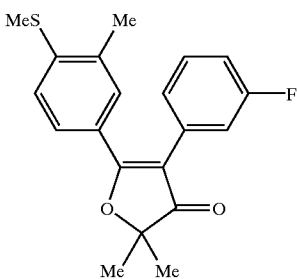

2,2-Dimethyl-4-(3-fluorophenyl)-5-{3-methyl-4-(methylthio)phenyl}-3(2H)-furanone.

437 mg of 1-{3-methyl-4-(methylthio)phenyl}-2-(3-fluorophenyl)-ethanone in 50 ml dry THF was stirred with 67 mg of 60% oil dispersion of sodium hydride for an hour at 0° C., which was followed by dropwise addition of 0.8 ml α-bromoisobutyryl cyanide diluted with 25 ml THF. The reaction solution was slowly warmed to room temperature and was stirred overnight. Then the solvent was removed in vacuo and the resulting residue was extracted with 50 ml water and dichloromethane (50 ml×3). The organic layer was concentrated in vacuo and was purified by column chromatography (hexane/ethylacetate=6:1) to yield 312 mg of 2,2-dimethyl-4-(3-fluorophenyl)-5-{3-methyl-4-(methylthio)phenyl}-3(2H)-furanone. NMR: δ1.55 (s, 6H), 2.27 (s, 3H), 2.48 (s, 3H), 7.36 (m, 4H), 7.32 (m, 1H), 7.45 (m, 2H). IR 1694, 1601, 1385, 1260, 1192.

EXAMPLE 378

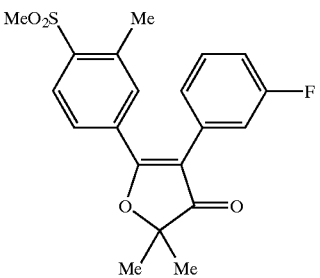

2,2-Dimethyl-4-(3-fluorophenyl)-5-{3-methyl-4-(methylsulfonyl)phenyl}-3(2H)-furanone 257 mg of 2,2-dimethyl-4-(3-fluorophenyl)-5-{3-methyl-4-(methylthio)-phenyl}-3(2H)-furanone (Example 377) in 50 ml methylenechloride was stirred with 170 mg of 70% m-chloroperoxybenzoic acid at 0° C. for an hour, which was followed by addition of 10 ml 5% aqueous sodium bicarbonate. Then the solution was stirred for another 10 minutes. The reaction mixture was concentrated in vacuo and was extracted with 50 ml water and dichloromethane (30 ml×3). The organic layer was concentrated under reduced pressure and was purified by column chromatography (hexane/ethylacetate 2:1) to afford 43 mg of 2,2-dimethyl-4-(3-fluorophenyl)-5-{3-methyl-4-(methylsulfonyl)phenyl}-3(2H)-furanone as a solid. mp: 138–139° C. NMR: δ1.57 (s, 6H), 2.68 (s, 3H), 3.09 (s, 3H), 7.03 (m, 3H), 7.28 (m, 1H), 7.58 (dd, J=8.4, 1.8 Hz, 1H), 7.63 (d, J=1.2 Hz, 1H), 8.01 (d, J=8.4 Hz, 1H). IR (cm$^{-1}$): 1698, 1589, 1387, 1312, 1262. MS (FAB): 374 (m+1).

EXAMPLE 379

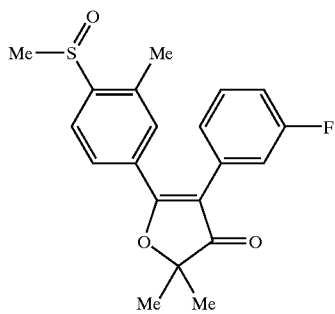

2,2-Dimethyl-4-(3-fluorophenyl)-5-{3-methyl-4-(methylsulfinyl)phenyl}-3(2H)-furanone 219 mg of 2,2-Dimethyl-4-(3-fluorophenyl)-5-{3-methyl-4-(methylsulfinyl)-phenyl}-3(2H)-furanone was obtained as a co-product during the synthesis of Example 378. NMR: δ1.56 (s, 6H), 2.32 (s, 3H), 2.70 (s, 3H), 7.04 (m, 3H), 7.31 (m, 1H), 7.49 (d, J=0.9, 1H), 7.67 (dd, J=8.1, 1.8 Hz, 1H), 7.94 (d, J=8.4, 1H). IR (cm$^{-1}$): 1697, 1384, 1259, 1204, 1072.

EXAMPLE 380

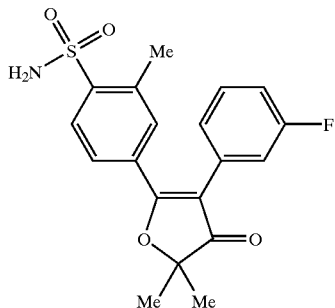

5-{4-(Aminosulfonyl)-3-methylphenyl}-2,2-dimethyl-4-(3-fluorophenyl)-3(2H)-furanone 201 mg of 2,2-dimethyl-4-(3-fluorophenyl)-5-{3-methyl-4-(methylsulfinyl)-phenyl}-3(2H)-furanone (Example 379) was converted into 76 mg of 5-{4-(aminosulfonyl)-3-methylphenyl}-2,2-dimethyl-4-(3-fluorophenyl)-3(2H)-furanone by following a procedure similar to the procedure used in Example 367. mp: 81–82° C. NMR: δ1.57 (s, 6H), 2.63 (s, 3H), 5.13 (br s, 2H), 7.03 (s, 3H), 7.27 (m, 1H), 7.45 (m, 1H), 7.61 (m, 1H), 7.96 (d, J=8.4 Hz, 1H). IR (cm$^{-1}$): 3369, 3270, 1589, 1334, 1168. MS (FAB): 375 (m+1).

EXAMPLE 381

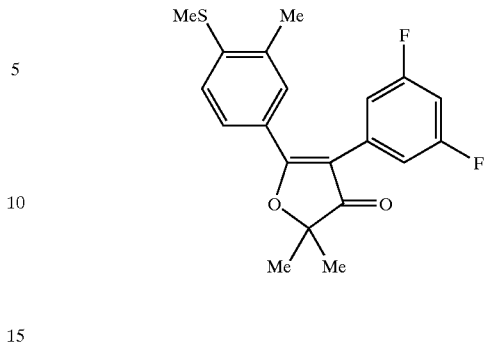

4-(3,5-Difluorophenyl)-2,2-dimethyl-5-{3-methyl-4-(methylthio)phenyl}-3(2H)-furanone 530 mg of 1-{3-methyl-4-(methylthio)phenyl}-2-(3,5-difluorophenyl)-ethanone was converted into 357 mg of 4-(3,5-difluorophenyl)-2,2-dimethyl-5-{3-methyl-4-(methylthio)phenyl}-3(2H)-furanone by following a procedure similar to the procedure of Example 377. NMR: δ1.55 (s, 6H), 2.29 (s, 3H), 2.50 (s, 3H), 6.74 (m, 1H), 6.89 (m, 2H), 7.08 (d, J=8.1 Hz, 1H), 7.40 (dd, J=8.4, 2.1 Hz, 1H), 7.45 (d, J=1.5 Hz, 1H). IR (cm$^{-1}$): 1691, 1601, 1384, 1910, 1118.

EXAMPLE 382

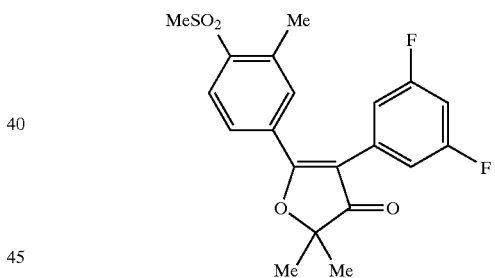

4-(3,5-Difluorophenyl)-2,2-dimethyl-5-{3-methyl-4-(methylsulfonyl)phenyl}-3(2H)-furanone 105 mg of 4-(3,5-difluorophenyl)-2,2-dimethyl-5-{3-methyl-4-(methylthio)-phenyl}-3(2H)-furanone (Example 381) was dissolved in 50 ml methanol, 30 ml THF and 50 ml water, to which was added 513 mg of OXONE. The reaction mixture was stirred at room temperature for 4 hours. Then the mixture was concentrated in vacuo, and was extracted with water 50 ml and dichloromethane (30 ml×3). Concentration of the organic layer under reduced pressure was followed by column chromatography (hexane/ethylacetate= 3:2) to give 97 mg of 4-(3,5-difluorophenyl)-2,2-dimethyl-5-{3-methyl-4-(methylsulfonyl)phenyl}-3(2H)-furanone. NMR: δ1.57 (s, 6H), 2.71 (s, 3H), 3.05 (s, 3H), 6.82 (m, 1H), 7.12 (m, 1H), 7.59 (m, 1H), 7.63 (m, 1H), 7.92 (m, 2H).

EXAMPLE 383

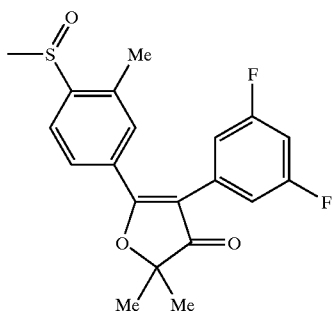

4-(3,5-Difluorophenyl)-2,2-dimethyl-5-{3-methyl-4-(methylsulfinyl)phenyl}-3(2H)-furanone To 320 mg of 4-(3,5-difluorophenyl)-2,2-dimethyl-5-{3-methyl-4-(methylthio)phenyl}-3(2H)-furanone (Example 381) in 50 ml dichloromethane, was added 172 mg of 70% m-chloroperoxybenzoic acid. The mixture was stirred at 0° C. for an hour, which was followed by addition of 30 ml 5% aqueous sodium bicarbonate. The solution was stirred for another 10 minutes. Then the mixture was concentrated in vacuo, and was extracted with 50 ml water and dichloromethane (30 ml×3). Then the organic layer was concentrated under reduced pressure and was purified by column chromatography (hexane/ethylacetate=1:1) to give 211 mg of 4-(3,5-difluorophenyl)-2,2-dimethyl-5-{3-methyl-4-(methylsulfinyl)phenyl}-3(2H)-furanone. NMR: δ1.57 (s, 6H), 2.36 (s, 3H), 2.73 (s, 3H), 6.77 (m, 1H), 6.86 (m, 2H), 7.50 (m, 1H), 7.66 (m, 1H), 7.99 (d, J=8.4 Hz, 1H). IR (cm$^{-1}$): 1698,1624,1592,1384, 1310,1206,1072,915.

EXAMPLE 384

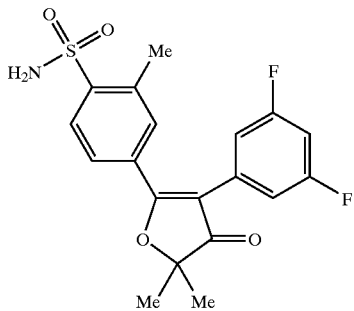

5-{4-(Aminosulfonyl)-3-methylphenyl}-4-(3-difluorophenyl)-2,2-dimethyl-3(2H)-furanone 240 mg of 4-(3,5-difluorophenyl)-2,2-dimethyl-5-{3-methyl-4-(methyl-sulfinyl)phenyl}-3(2H)-furanone was converted into 33 mg of 5-{4-(aminosulfonyl)-3-methylphenyl}-4-(3,5-difluorophenyl)-2,2-dimethyl-3(2H)-furanone by a procedure similar to the procedure used for Example 367. NMR: δ1.56 (s, 6H), 2.66 (s, 3H), 4.98 (br s, 2H), 6.85 (m, 3H), 7.41 (m, 1H), 7.80 (m, 1H), 7.92 (m, 1H).

EXAMPLE 385

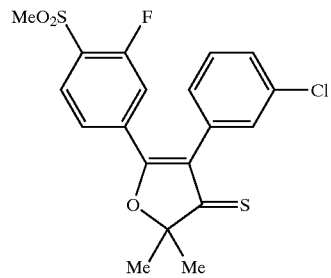

4-(3-Chlorophenyl)-2,2-dimethyl-5-{3-fluoro-4-(methylsulfonyl)phenyl}-(2H)-furan-3-thione 130 mg of 4-(3-Chlorophenyl)-2,2-dimethyl-5-{3-fluoro-4-(methylsulfonyl)-phenyl}-3(2H)-furan-3-thione (Example 278) in 20 ml toluene was stirred at reflux for 12 hours in the presence of 67 mg of Lawesson's reagent. Then the solvent was removed in vacuo and the resulting residue was extracted with 50 ml water and dichloromethane (50 ml×3). The organic layer was concentrated under reduced pressure and was purified by column chromatography (hexane/ethylacetate=4:1) to give 117 mg of 4-(3-chlorophenyl)-2,2-dimethyl-5-{3-fluoro-4-(methylsulfonyl)phenyl}-(2H)-furan-3-thione as a solid. mp: 105–106° C. NMR: δ1.71 (s, 6H), 3.24 (s, 3H), 7.12 (m, 3H), 7.41 (m, 1H), 7.52 (m, 2H), 7.92 (dd, J=7.8, 7.2 Hz, 1H). IR (cm$^{-1}$): 1604, 1557, 1324, 1273, 1209, 1145, 1047, 963.

EXAMPLE 386

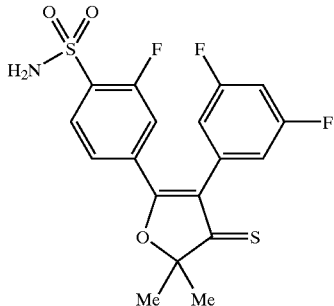

5-{4-(Aminosulfonyl)-3-fluorophenyl}-4-(3,5-difluorophenyl)-2,2-dimethyl-(2H)-furan-3-thione 140 mg of 5-{(aminosulfonyl)-3-fluorophenyl}-4-(3,5-difluorophenyl)-2,2-dimethyl-3(2H)-furanone (Example 312) was converted into 103 mg of 5-{4-(aminosulfonyl)-3-fluorophenyl}-2,2-dimethyl-4-(3,5-difluorophenyl)-(2H)-furan-3-thione by a procedure similar to the procedure employed for Example 385. mp: 153–154° C. NMR: δ1.71 (s, 6H), 5.12 (br s, 2H), 6.84 (m, 3H), 7.48 (m, 2H), 7.90 (dd, J=8.1, 8.1 Hz, 1H). IR (cm$^{-1}$): 3416, 3279, 1624, 1557, 1356, 1273, 1173, 1121, 1064.

EXAMPLE 387

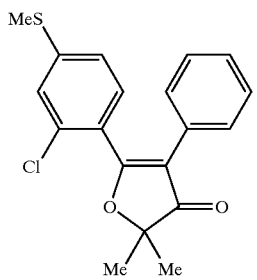

5-{2-Chloro-4-(methylthio)phenyl}-2,2-dimethyl-4-phenyl-3(2H)-furanone 3.05 g of 1-{2-chloro-4-(methylthio)phenyl}-2-phenyl-ethanone in 60 ml dry THF was stirred at 0° C. for 20 minutes in the presence of 95% oil dispersion of sodium hydride (1.0 g), which was followed by dropwise addition of α-bromoisobutyryl cyanide (2.5 ml) diluted in 50 ml THF. The reaction solution was allowed to warm slowly to room temperature and was stirred overnight. Then the solvent was removed in vacuo, which was followed by extraction with 30 ml water and diethylether (50 ml×3). The organic layer was concentrated under reduced pressure and was purified by column chromatography (hexane/ethylacetate=8:1) to yield 2.73 g of 5-{2-chloro-4-(methylthio)phenyl}-2,2-dimethyl-4-phenyl-3(2H)-furanone. NMR: δ1.56 (s, 6H), 2.48 (s, 3H), 7.10 (dd, J=8.4, 1.5 Hz, 1H), 7.24 (m, 3H), 7.26 (m, 3H), 7.37 (d, J=1.5 Hz, 1H). IR (cm$^{-1}$): 1698, 1620, 1394, 1235, 1176, 1144.

Compound of Example 388 was prepared by procedures similar to the procedures employed for Example 387.

EXAMPLE 388

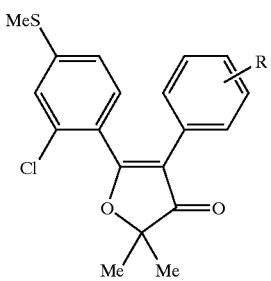

| Example | R | Melting point & spectral data |
|---|---|---|
| 388 | 3-F | NMR: δ1.56(s, 6H), 2.51(s, 3H), 6.89(m, 1H), 7.01(m, 2H), 7.14(dd, J=8.4, 1.8Hz, 1H), 7.19(m, 1H), 7.26(d, J= 3.3Hz, 1H), 7.28(d, J=1.8Hz, 1H). IR(cm$^{-1}$): 2981, 1701, 1615, 1376, 1200. |

EXAMPLE 389

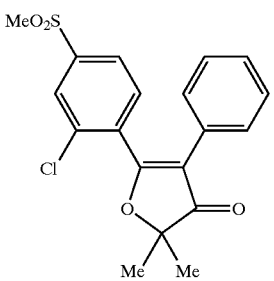

5-{2-Chloro-4(methylsulfonyl)phenyl}-2,2-dimethyl-4-phenyl-3(2H)-furanone 350 mg of 5-{2-chloro-4-(methylthio)phenyl}-2,2-dimethyl-4-phenyl-3(2H)-furanone (Example 387) was dissolved in 75 ml of 1:1:1 methanol/THF/water, to which was added 1.0 g of OXONE. The reaction mixture was stirred at room temperature for 6 hours. The reaction mixture was concentrated in vacuo and the resulting residue was extracted with 25 ml water and ethylacetate (50 ml×3). The organic layer was concentrated in vacuo and was purified by column chromatography (hexane/ethylacetate=3:1) to give 252 mg of 5-{2-chloro-4-(methylsulfonyl)phenyl}-2,2-dimethyl-4-phenyl-3(2H)-furanone as a solid. mp: 89–90° C. NMR: δ1.59 (s, 6H), 3.11 (s, 3H), 7.19 (m, 2H), 7.25 (m, 3H), 7.60 (d, J=8.1 Hz, 1H), 7.87 (dd, J=8.1, 1.8 Hz, 1H), 8.07 (d, J=1.8 Hz, 1H). IR (cm$^{-1}$): 1701, 1625, 1586, 1391, 1319, 1153.

Compound of Example 390 was prepared according to procedures similar to the procedure in Example 389.

EXAMPLE 390

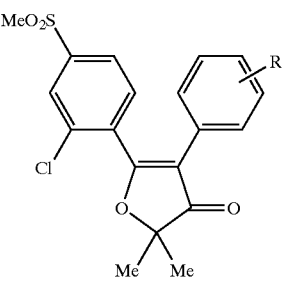

| Example | R | Melting point & spectral data |
|---|---|---|
| 390 | 3-F | mp: 97–98°C. NMR: δ1.59(s, 6H), 3.12(s, 3H), 6.88–7.02(m, 3H), 7.21(m, 1H), 7.62(d, J=7.8Hz, 1H), 7.91(dd, J=7.8, 1.8Hz, 1H), 8.08(d, J=1.8Hz, 1H). IR(cm$^{-1}$): 1702, 1626, 1392, 1319, 1262, 1154. |

EXAMPLE 391

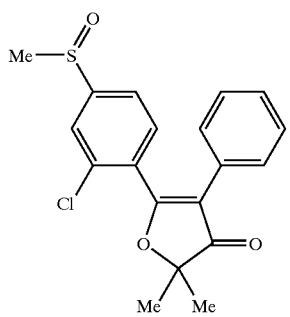

5-{2-Chloro-4-(methylsulfinyl)phenyl}-2,2-dimethyl-4-phenyl-3(2H)-furanone

To a stirred solution 2.7 g of 5-{2-chloro-4-(methylthio)phenyl}-2,2-dimethyl-4-phenyl-3(2H)-furanone (Example 387) in 80 ml dichloromethane, was added 1.94 g of 70% m-chloroperoxybenzoic acid. The reaction mixture was stirred at 0° C. for 2 hours. Then 40 ml 5% aqueous sodium bicarbonate was added to the solution and the solution was stirred for 10 minutes. The solution was extracted with dichloromethane (50 ml×3). The organic layer was concentrated in vacuo and was purified by column chromatography (hexane/ethylacetate=1:1) to give 978 mg of 5-{2-chloro-4-(methylsulfinyl)phenyl}-2,2-dimethyl-4-phenyl-3(2H)-furanone as a solid. mp: 135–136° C. NMR: δ1.59 (s, 6H), 2.78 (s, 3H), 7.22 (m, 3H), 7.25 (m, 2H), 7.54 (m, 2H), 7.79 (m, 1H). IR (cm$^{-1}$): 1698, 1623, 1392, 1242, 1145, 1063.

Compound of Example 392 was synthesized by employing procedures similar to the method for Example 391.

EXAMPLE 392

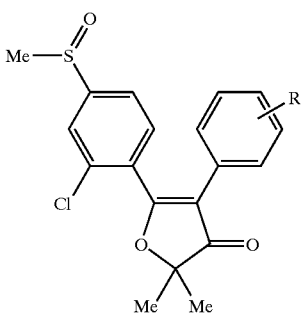

| Example | R | Melting point & spectral data |
|---|---|---|
| 392 | 3-F | Mp: 109–110° C. NMR: δ 1.59(s, 6H), 2.79(s, 3H), 6.91–7.01(m, 3H), 7.20(m, 1H), 7.57(m, 2H), 7.80(m, 1H). IR (cm$^{-1}$): 1701, 1623, 1582, 1392, 1261, 1194, 1062. |

EXAMPLE 393

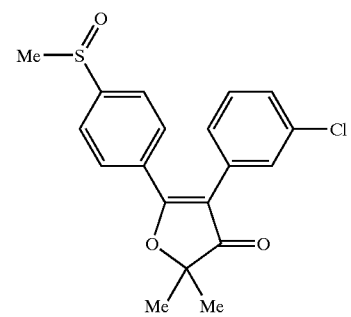

4-(3-Chlorophenyl)-2,2-dimethyl-5-{4-(methylsulfinyl)phenyl}-3(2H)-furanone

To a stirred solution of 10.98 g of 4-(3-chlorophenyl)-2,2-dimethyl-5-{4-(methylthio)phenyl}-3(2H)-furanone (Example 168) in 250 ml of dichloromethane was added dropwise 6.59 g of 70% m-chloroperoxybenzoic acid dissolved in 150 ml of dichloromethane. The reaction mixture was stirred for 1 hr at 0° C. The reaction mixture was purified following by procedure of Step 1 of Example 22 to give 6.33 g of 4-(3-chlorophenyl)-2,2-dimethyl-5-{4-(methylsulfinyl)phenyl})-3(2H)-furanone. mp: 109–110° C. NMR: δ1.57 (s, 6H), 2.75 (s, 3H), 7.17 (m, 1H), 7.31 (m, 2H) 7.65 (d, J=8.4 Hz, 2H), 7.80 (d, J=8.7 Hz, 2H).

BIOLOGICAL EVALUATION

Evaluation of in vitro COX-2 and COX-1 Activity [J. Pharmacol. Exp. Ther. 166, 96 (1969)]

Harvest of Mouse Peritoneal Macrophages

The abdominal skin of a C57BL/6 mouse was sanitized with 70% aqueous ethanol, and was removed without damaging the peritoneum. 5 ml of cold phosphate buffer solution (PBS) was then injected into the abdominal cavity. After a minute, the peritoneal fluid containing the macrophages was collected using a syringe and a needle. The collected fluid was centrifuged for 5 min at 1500 rpm to afford pellets of cells. The pellets were then dispersed in the RPMI-1640 culture medium containing 100 units/ml penicillin and 100 μg/ml streptomycin.

Evaluation of COX-2 Activity

The pellets dispersed as above were treated with 500 μM aspirin in order to knock out the activity of the COX-1 enzymes in the cells. The suspension was then diluted with the RPMI-1640 medium to contain 1×10$^6$ cells/ml. 100 μl of the suspension was added to each well of a 96-well ELISA plate. Then the plate was incubated for 2 hrs at 37° C. under 5% CO$_2$ in order to fix the macrophages onto the plate. The cells, which were not fixed onto the plate were removed by washing with PBS two times. The purity of macrophages obtained thereby was confirmed by differential counting. The RPMI-1640 medium containing 3% fetal bovine serum albumin was added to each well of the plate, which was followed by stimulation with 10 μg/ml lipopolysaccharide (LPS). Usually 5×10$^5$ cells/ml were present by this preparation. The LPS-treated suspensions were incubated for 16 hours at 37° C. under 5% CO$_2$ to induce COX-2. Then the culture medium was removed and the macrophages were washed two times with PBS. Then 130 μl RPMI-1640 culture medium was added to each well and the macrophage solutions were incubated at 37° C. for 10 minutes, which was followed by the treatment with 10 μM arachidonic acid and an appropriate amount of compounds of this invention.

The plate was incubated for another 10 minutes. The upper solution was collected using a micropipette and was subjected to determination of $PGE_2$ amount in the solution. The amount of $PGE_2$ present in the collected solution was determined either by a known radio-immuno assay or by a known enzyme-immunoassay [Methods in Enzymol. 86, 258 (1982); Methods in Enzymol. 187, 24 (1990)]. The extent of COX-2 inhibition by a compound of the present invention was calculated by assuming, that the amount of $PGE_2$ formed with the treatment of 10 µg/ml arachidonic acid was used is the maximum possible amount of $PGE_2$, and that the amount of $PGE_2$ formed without the treatment of arachidonic acid is the minimum possible amount of $PGE_2$.

Evaluation of COX-1 Activity

In the evaluation of COX-1 inhibitory activity by a compound of the present invention, the same procedures employed for evaluation of COX-2 activity were employed, except omitting the following two steps: 1) the treatment with aspirin for knockout of COX-1 activity and 2) treatment with LPS for induction of COX-2.

$IC_{50}$ data of COX-1 and COX-2 for selected compounds of the present invention were summarized in the following Table 1. $IC_{50}$ denotes a concentration of a compound, at which the enzymatic activity of COX-1 or COX-2 reaches 50% of the activity in the absence of compound treatment. In order to determine $IC_{50}$ for a compound of this invention, enzymatic activities were measured at multiple concentrations of compounds of this invention around $IC_{50}$ of the compound. Usually enzymatic activities at 4~5 concentrations were measured to calculate out $IC_{50}$ for a compound of this invention.

TABLE 1 in vitro Activities of COX-2 inhibitors.

| Example | $IC_{50}$, µg/ml COX-2 | COX-1 | Example | $IC_{50}$, µg/ml COX-2 | COX-1 |
|---|---|---|---|---|---|
| 4 | 0.02 | 5 | 214 | 0.03 | 3 |
| 5 | 0.05 | 50 | 216 | 0.03 | 20 |
| 6 | 0.05 | 5 | 225 | 0.03 | 3 |
| 10 | 0.3 | 50 | 236 | 0.0097 | 10.7 |
| 11 | 0.05 | 20 | 245 | 0.03 | 3 |
| 17 | 0.2 | 30 | 246 | 0.03 | 3 |
| 18 | 0.2 | 30 | 254 | 0.03 | 3 |
| 24 | 0.034 | 6.97 | 255 | 0.03 | 3 |
| 25 | 0.013 | 3.46 | 256 | 0.03 | 5 |
| 31 | 0.2 | 20 | 261 | 1 | 300 |
| 36 | 0.2 | 50 | 263 | 0.03 | 50 |
| 44 | 0.101 | >10 | 273 | 0.03 | 20 |
| 45 | 0.01 | 1.07 | 275 | 0.03 | 200 |
| 49 | 0.3 | 30 | 276 | 0.05 | 10 |
| 50 | 0.03 | 20 | 278 | 0.05 | 30 |
| 53 | 0.03 | 5 | 281 | 0.1 | 10 |
| 54 | 0.05 | 10 | 282 | 0.03 | 30 |
| 62 | 0.01 | 2 | 283 | 0.7 | 90 |
| 64 | 0.1 | 50 | 284 | 0.03 | 10 |
| 66 | 0.05 | 50 | 285 | 0.03 | 200 |
| 69 | 0.3 | 50 | 286 | 0.03 | 5 |
| 75 | 0.03 | 3 | 290 | 0.3 | 20 |
| 76 | 0.5 | 50 | 291 | 0.2 | 3 |
| 77 | 0.003 | 5 | 300 | 0.03 | 20 |
| 80 | 0.05 | 5 | 302 | 0.03 | 5 |
| 84 | 0.03 | 3 | 303 | 0.03 | 3 |
| 86 | 0.03 | 30 | 304 | 0.05 | 50 |
| 94 | 0.05 | 5 | 305 | 0.003 | 0.3 |
| 95 | 0.1 | 30 | 311 | 0.03 | 3 |
| 96 | 0.02 | 3 | 312 | 0.02 | 100 |
| 97 | 0.002 | 5 | 321 | 0.03 | 20 |
| 103 | 0.03 | 20 | 322 | 0.02 | 3 |
| 104 | 0.3 | 100 | 323 | 0.03 | 10 |

TABLE 1-continued in vitro Activities of COX-2 inhibitors.

| Example | $IC_{50}$, µg/ml COX-2 | COX-1 | Example | $IC_{50}$, µg/ml COX-2 | COX-1 |
|---|---|---|---|---|---|
| 105 | 0.03 | 50 | 324 | 0.03 | 3 |
| 111 | 0.3 | 50 | 325 | 0.05 | 200 |
| 113 | 0.03 | 3 | 326 | 0.03 | 20 |
| 121 | 0.2 | 30 | 332 | 0.03 | 5 |
| 122 | 0.03 | 3 | 333 | 0.003 | 10 |
| 123 | 0.3 | 50 | 334 | 0.03 | 3 |
| 126 | 0.014 | 3.82 | 335 | 0.003 | 3 |
| 127 | 0.001 | 0.12 | 340 | 10 | 30 |
| 129 | 0.0067 | 1.02 | 341 | 0.3 | 90 |
| 132 | 0.0178 | 7.42 | 342 | 0.02 | 30 |
| 135 | 0.055 | >10 | 343 | 0.03 | 50 |
| 138 | 0.0067 | 1.94 | 344 | 0.08 | 200 |
| 146 | 0.0014 | 0.83 | 345 | 0.03 | 50 |
| 149 | 0.0087 | 1.01 | 351 | 0.9 | 300 |
| 151 | 0.0188 | >10 | 357 | 0.05 | 30 |
| 155 | 0.016 | 1.8 | 358 | 0.02 | 8 |
| 157 | 0.038 | 5.15 | 359 | 0.02 | 200 |
| 160 | 0.057 | >10 | 360 | 0.009 | 3 |
| 164 | 0.03 | 100 | 361 | 0.009 | 4 |
| 167 | 3 | 50 | 362 | 0.05 | 300 |
| 168 | 0.5 | 3 | 367 | 0.06 | 8 |
| 175 | 3 | 30 | 368 | 0.02 | 7 |
| 176 | 1 | 10 | 369 | 0.02 | 50 |
| 177 | 5 | 30 | 371 | 0.02 | 200 |
| 188 | 0.3 | 30 | 372 | 0.09 | 200 |
| 193 | 0.03 | 3 | 373 | 0.3 | 600 |
| 194 | 0.05 | 20 | 378 | 0.03 | 3 |
| 195 | 0.03 | 5 | 382 | 0.08 | 200 |
| 198 | 0.03 | 3 | 384 | 0.08 | 30 |
| 200 | 0.3 | 30 | 385 | 0.03 | 0.05 |
| 201 | 0.1 | 20 | 393 | 0.3 | 5 |
| 202 | 0.03 | 3 | | | |

Evaluation of in vivo Antiinflammatary Potency

Carrageenan-induced Foot Edema in Rats (CFF)

An appropriate amount of a compound of this invention suspended in 1% methylcellulose (MC) solution was administered to male Sprague-Dawley (SD) rats weighing 150~200 g by oral gavage. The volume of the administered vehicle for a compound of this invention was controlled to be smaller than 10 ml/kg body weight of the animal. One hour later, 0.1 ml of 1% Carrageenan saline solution was directly injected into the right paw of the rats to induce edema in the paw. The paw volumes at 0 hour and at 3 hours after the injection of Carrageenan were measured by using a displacement plethysmometer (Ugo Basile, Italy). The paw volumes were used to calculate % inhibition of CFE by an amount of a compound of this invention according to the following equation. [Br. J. Pharmacol. 41, 132 (1971)]

% Inhibition of CFE=(1−Δtreated/Δcontrol)×100 wherein Δtreated=[paw volume at three hours after the Carrageenan injection−paw volume right after Carrageenan injection] for a drug-administered rat, and Δcontrol=[paw volume at three hours after the Carrageenan injection−paw volume right after Carrageenan injection] for a rat without drug administration.

CFE inhibition data for selected compounds of this invention are summarized in the following Table 2. In order to determine the inhibitory activity of a compound of this invention at a dose, usually 5 to 8 animals were used both for drug-treated group and for control group.

TABLE 2 in vivo Antiinflammatory potency of COX-2 inhibitors (CFE)

| Example | % Inhibition | Dose (oral), mg/kg body weight |
|---|---|---|
| Indomethacin | 28 | 1 |
| 4 | 36 | 3 |
| 14 | 32 | 3 |
| 20 | 36 | 3 |
| 23 | 33 | 3 |
| 84 | 25 | 3 |
| 126 | 39 | 3 |
| 129 | 47 | 3 |
| 146 | 24 | 3 |
| 155 | 35 | 3 |
| 157 | 41 | 3 |
| 164 | 29 | 3 |
| 176 | 23 | 3 |
| 177 | 37 | 3 |
| 195 | 28 | 3 |
| 255 | 31 | 3 |
| 276 | 26 | 3 |
| 278 | 27 | 3 |
| 284 | 33 | 3 |
| 302 | 27 | 3 |
| 303 | 30 | 3 |
| 308 | 32 | 3 |
| 311 | 30 | 3 |
| 312 | 31 | 3 |
| 333 | 25 | 3 |
| 334 | 37 | 3 |
| 335 | 32 | 3 |
| 343 | 25 | 3 |
| 359 | 28 | 3 |
| 361 | 41 | 3 |
| 369 | 28 | 3 |

Evaluation of Antiinflammatory Potency by Adjuvant Arthritis

Arthritis was induced in male SD rats weighing 180–200 g by subcutaneous injection of *Mycobacterium butyricum* mixed in 0.1 ml of incomplete Freund's adjuvanat into the base of the tail. The foot volumes were measured using a displacement plethysomometer 14 days after the injection of the adjuvant. Animals with paw volumes greater than the normal paw volumes (without the adjuvant treatment) by 0.37 ml were selected, and then randomized. A designated daily dose of a compound of this invention, which was suspended in 1% aqueous methylcellulose solution, was administered to the randomized rats with arthritis by oral gavage daily once beginning on day 14 after the injection of the adjuvant. The administration of the compound continued till day 22 after the injection of the adjuvant, and the paw volumes were measured on daily basis using a displacement plethysmometer. The paw volumes of 5 to 8 rats on day 22 were averaged to determine % inhibition of adjuvant arthritis (AA) by a compound of this invention according to the following equation.

% Inhibition of AA=(1−Δtreated/Δcontrol)×100 wherein Δtreated=[(paw volume at day 22)/(paw volume at day 14)−1] for a drug-administered rat, and Δcontrol=[(paw volume at day 22)/(paw volume at day 14)−1] for a rat without drug administration.

$Ed_{50}$ data for adjuvant arthritis for selected compounds of this invention were summarized in the following Table 3. $ED_{50}$ for adjuvant denotes a daily dose of a compound, at which 50% inhibition of adjuvant arthritis is achieved. $ED_{50}$ value was determined b a dose-response curve for each compound.

TABLE 3 in vivo Antiinflammatory potency of COX-2 inhibitors (AA)

| Example | Adjuvant Arthritis $ED_{50}$, mg/kg body weight |
|---|---|
| 4 | 0.07 |
| 11 | 0.03 |
| 14 | 0.06 |
| 126 | 0.03 |
| 129 | 0.02 |
| 334 | 0.09 |

Pharmacokinetic Studies in Rats

An appropriate amount of a compound suspended 1% aqueous methylcellulose solution was administered to a male SD rat by oral gavage. Blood samples were collected from the retro-orbital sinus at designated times over 24~48 hours. Plasma was separated from each blood sample by centrifugation and the plasma was stored at 4° C. until analysis. The plasma samples prepared thereby were subjected to analysis by reverse phase HPLC (high performance liquid chromatography) using an appropriate internal standard.

FIG. 1 shows a pharmacokinetic study for Example 393 orally administered to a SD rat. Detection of appreciable amounts of Example 62 in the plasma clearly indicates that the sulfoxide group of Example 393 is biotransformed into the sulfonyl group.

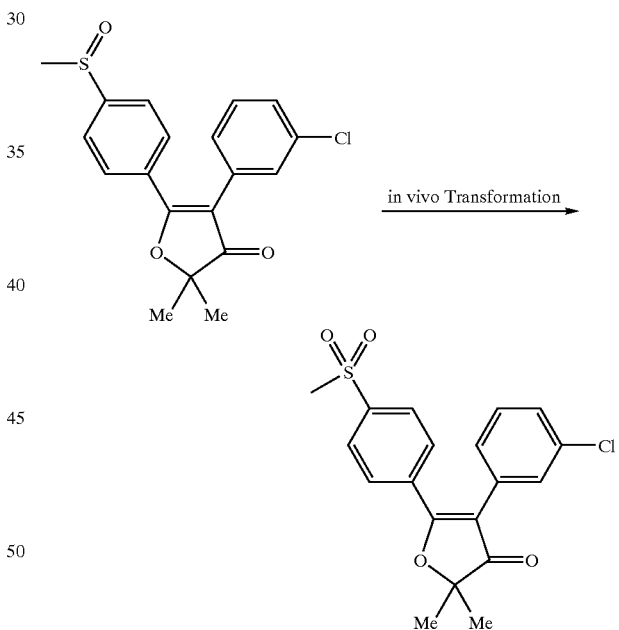

Sulfoxide compounds of this invention are inhibitors of COX-2 themselves, however, they can be transformed into the corresponding sulfones after absorption into the body as exemplified by the pharmacokinetic study for Example 393 (FIG. 1). Thus, a sulfoxide compound of this invention can be used as a prodrug for the corresponding sulfone.

Analgesic Studies

Acetic Acid-induced Writhing Test

ICR mice weighing 18~22 g were maintained in a controlled lighting environment (12 hours on/12 hours off) and fasted overnight prior analgesic testing. Mice were administered with a compound of this invention dissolved in 10:10:80 ethanol/Tween 80/saline or vehicle only by oral gavage. The administered vehicle volume was controlled to be 10 ml/kg body weight. One hour later, the animals were treated with 0.2 ml of 1.2% acetic acid by peritoneal injection. 6 minutes later, the number of abdominal constrictions was counted for a 6 minutes period. The antinociceptive activity was expressed as the reduction in the number of abdominal constrictions, compared with that of the placebo group [J. Med. Chem. 39, 4942 (1996)]. $ED_{50}$ of the mouse writhing test denotes a dose level at which the number of abdominal constrictions is half that of the placebo group. Ten animals per group were used for this study.

Carrageenan-induced Thermal Hyperalgesia Assay

Male SD rats weighing 170~220 g were fasted but with free access to water for at leat 16 hours prior to testing. The rats were administered with a compound of this invention suspended in 20 ml 0.5% methylcellulose/0.025% Tween-20, or with vehicle only. Then the rats were given 100 ml of 1% carrageenan in saline or 100 ml saline only into the plantar surface of the left hindpaw by injection. Three hours later, the nociceptive responses to thermal stimuli were assessed as follows: Rats, which were placed in a transparent plastic chamber with a glass floor, were allowed to acclimate to their environment for 10 minutes prior to the testing. The withdrawal latency period in seconds was determined for the control and the compound treated group, and a percent inhibition in the withdrawal latency was calculated to estimate the analgesic effect of the compound [Pain 32, 77 (1988)]. In this study 6 animals were used for each group.

Analgesic potency for two of compounds of this invention are presented in the following Table 4 along with that of indomethacin for comparison.

TABLE 4

Analgesic potency of COX-2 inhibitor

| Compound | $ED_{50}$, mg/kg body weight (mouse writhing) | % Inhibition at 1.0 mg/kg body weight (rat hyperalgesia) |
|---|---|---|
| Example 4 | 8.3 | 27% |
| Example 129 | 12.3 | 92% |
| Indomethacin | 7.4 | 45% |

Gastric Safety Studies

Gastric safety for compounds of this invention was evaluated as follows [Otterness et al., Laboratory Models for Testing Nonsteroidal Anti-inflammatory Drugs in *Nonsteroidal Anti-inflammatory Drugs;* ed John Wiley & Sons pp 217–227 (1985); Wiley Interscience; New York]: A designated dose of a compound of this invention suspended in 1% methylcellulose solution was administered daily once for 7 days to a male SD rat by oral gavage. The animal was sacrificed and the inner wall of the stomach was examined visually 4 hours after the last administration (the 7th day administration). The gastric safety was assessed by the "Ulcer Index" as defined as the following scores:

Score 1: apparently normal stomach.
Score 2: one or more than one ulcer site of pin-point size only.
Score 3: erosions of 2 or fewer than 2, which may be accompanied by ulcers of pin-point size (an erosion is defied by any ulcerative lesion of any dimension greater than 1 mm).
Score 4: erosions more than 2, which may be accompanied by ulcers of pin-point size.
Score 5: erosions accompanied by hemorrhage.

In evaluating the gastric safety of a compound of this invention, usually 8 animals were used. The ulcer index for a compound was calculated by averaging of the ulcer index of each animal. The following Table 5 illustrates gastric safety of some COX-2 selective inhibitors of this invention.

TABLE 5

Gastric safety of COX-2 inhibitors

| Group | Daily Dose, mg/kg body weight | Ulcer Index (1~5) |
|---|---|---|
| Placebo | — | 1.8 ± 1.0 |
| Example 4 | 30 | 1.8 ± 0.7 |
| Example 10 | 30 | 1.2 ± 0.4 |
| Example 11 | 30 | 1.8 ± 1.0 |

The above described discussion of this invention is directed primarily to preferred embodiments and practices thereof. It will be readily apparent to those skilled in the art that further changes and modifications in the actual implementation of the concepts described herein can readily be made without departing from the spirit and scope of the invention as defined by the following claims.

What is claimed is:

1. A compound of the following Formula I:

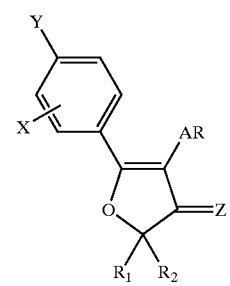

wherein

X represents halo, hydrido, or alkyl;

Y represents alkylsulfonyl, aminosulfonyl, alkylsulfinyl, (N-acylamino)-sulfonyl, (N-alkylamino)sulfonyl, or alkylthio;

Z represents oxygen or sulfur atom;

$R_1$ and $R_2$ are selected independently from lower alkyl radicals;

and AR represents a substituted or non-substituted aromatic group of 5 to 10 atoms;

or a pharmaceutically-acceptable salt thereof.

2. A compound according to claim 1, wherein

X is selected from halo, hydrido and lower alkyl;

Y is selected from (lower alkyl)sulfonyl, aminosulfonyl, (lower alkyl)sulfinyl, (lower N-acylamino)-sulfonyl, (lower N-alkylamino)sulfonyl and (lower alkyl)thio;

Z is selected from oxygen and sulfur atom; wherein $R_1$ and $R_2$ are selected independently from lower alkyl radicals;

and AR represents a substituted or non-substituted aromatic group of 5 to 10 atoms, which is selected from the group consisting of

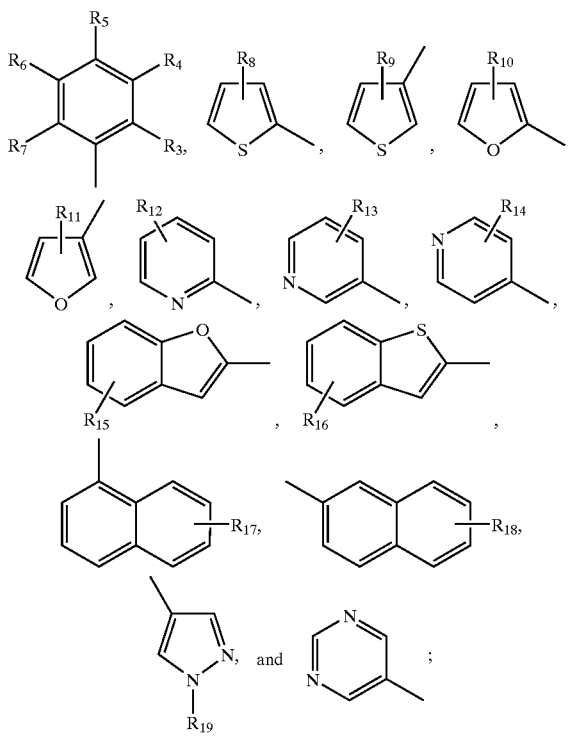

wherein, each of $R_3$ to $R_7$, if present, is independently selected from the group consisting of hydrido, halo, alkyl, haloalkyl, alkoxy, haloalkoxy, acyl, nitro, amino, N-alkylamino, N,N-dialkylamino, N-acylamino, (haloacyl)amino, formyl, cyano, azido, hydroxy, alkylthio, alkylsulfonyl, phenyl, alkoxyalkyl and hydroxyalkyl, or the adjacent two groups of $R_3$ to $R_7$ form, taken together, methylenedioxy; and wherein each of $R_8$ to $R_{19}$, if present, is selected from the group consisting of hydrido, halo, alkyl, acyl, haloalkyl, alkoxy, formyl, cyano, nitro, amino, azido and N-acylamino;

or a pharmaceutically-acceptable salt thereof.

3. A compound according to claim 1 or 2, in which

X is selected from fluoro, chloro, bromo, hydrido, methyl, ethyl and n-propyl;

Y is selected from methylsulfonyl, ethylsulfonyl, n-propylsulfonyl, aminosulfonyl, methylsulfinyl, ethylsulfinyl, n-propylsulfinyl, (N-acetylamino)sulfonyl, (N-propionylamino)sulfonyl, (N-butyrylamino)sulfonyl, (N-methylamino)sulfonyl, (N-ethylamino)sulfonyl, methylthio, ethylthio, and n-propylthio;

Z is selected from oxygen and sulfur atom; wherein $R_1$ and $R_2$ are selected independently from methyl and ethyl;

each of $R_3$ to $R_7$, if present, is independently selected from the group consisting of hydrido, fluoro, chloro, bromo, methyl, ethyl, n-propyl, iso-propyl, n-butyl, iso-butyl, t-butyl, n-pentyl, iso-pentyl, fluoromethyl, difluoromethyl, trifluoromethyl, 2-fluoroethyl, 1-fluoroethyl, 2,2-difluoroethyl, 1,2-difluoroethyl, 1,1-difluoroethyl, 2,2,2-trifluoroethyl, methoxy, ethoxy, n-propyloxy, iso-propyloxy, n-butoxy, trifluoromethoxy, difluoromethoxy, fluoromethoxy, acetyl, propionyl, n-butanoyl, iso-butanoyl, n-pentanoyl, nitro, amino, N-methylamino, N-ethylamino, N-n-propylamino, N,N-dimethylamino, N-acetylamino, N-propionylamino, N-(trifluoroacetyl)amino, formyl, hydroxy, methylthio, ethylthio, n-propylthio, methylsulfonyl, ethylsulfonyl, n-propylsulfonyl, phenyl, hydroxymethyl, 1-hydroxyethyl and 2-hydroxyethyl, or adjacent two groups of $R_3$ to $R_7$ form, taken together, methylenedioxy;

and each of $R_8$ to $R_{19}$, if present, is selected from the group consisting of hydrido, fluoro, chloro, bromo, methyl, ethyl, n-propyl, isopropyl, acetyl, propionyl, methoxy, ethoxy, iso-propyloxy, n-propyloxy and formyl;

or a pharmaceutically-acceptable salt thereof.

4. A compound according to claim 1, which is represented by the following Formula II:

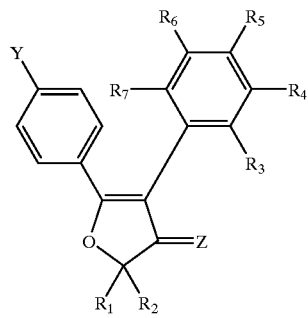

II wherein

Y represents alkylsulfonyl, aminosulfonyl, alkylsulfinyl, (N-acylamino)-sulfonyl, (N-alkylamino)sulfonyl, or alkylthio;

Z represents oxygen or sulfur atom;

$R_1$ and $R_2$ are selected independently from lower alkyl radicals;

and each of $R_3$ to $R_7$, if present, is independently selected from hydrido, halo, alkyl, haloalkyl, alkoxy, haloalkoxy, acyl, nitro, amino, N-alkylamino, N,N-dialkylamino, N-acylamino, N-(haloacyl)amino, formyl, cyano, azido, hydroxy, alkylthio, alkylsulfonyl, phenyl, alkoxyalkyl and hydroxyalkyl, or two adjacent groups of $R_3$ and $R_7$ form, taken together, methylenedioxy;

or a pharmaceutically-acceptable salt thereof.

5. A compound according to claim 4, in which

Y is selected from (lower alkyl)sulfonyl, aminosulfonyl, (lower alkyl)sulfinyl, (lower N-acylamino)sulfonyl, (lower N-alkylamino)sulfonyl, and (lower alkyl)thio;

Z is selected from oxygen and sulfur atom;

$R_1$ and $R_2$ are independently selected from methyl and ethyl radical;

and wherein each of $R_3$ to $R_7$, if present, is independently selected from hydrido, halo, lower alkyl, lower haloalkyl, lower alkoxy, lower haloalkoxy, lower acyl, nitro, amino, lower N-alkylamino, lower N,N-dialkylamino, lower N-acylamino, (lower haloacyl)amino, formyl, cyano, azido, hydroxy, lower alkylthio, lower alkylsulfonyl, phenyl, lower alkoxyalkyl and lower hydroxyalkyl, or two adjacent groups of $R_3$ to $R_7$ form, taken together, methylenedioxy;

or a pharmaceutically-acceptable salt thereof.

6. A compound according to claim 5, in which

Y is selected from methylsulfonyl, aminosulfonyl, methylsulfinyl, (N-acetylamino)sulfonyl, (N-propionylamino)sulfonyl, (N-butyrylamino)sulfonyl, (N-methylanino)sulfonyl, (N-ethylamino)sulfonyl, and methylthio;

Z is selected from oxygen and sulfur atom;

$R_1$ and $R_2$ are independently selected from methyl and ethyl radical;

and each of $R_3$ to $R_7$, if present, is independently selected from hydrido, fluoro, chloro, bromo, methyl, ethyl, n-propyl, iso-propyl, n-butyl, iso-butyl, t-butyl, n-pentyl, iso-pentyl, fluoromethyl, difluoromethyl, trifluoromethyl, 1-fluoroethyl, 2,2,2-trifluoroethyl, methoxy, trifluoromethoxy, difluoromethoxy, fluoromethoxy, acetyl, propionyl, n-butanoyl, iso-butanoyl, n-pentanoyl, nitro, amino, N,N-dimethylamino, N-acetylamino, N-propionylamino, formyl, hydroxy, methylthio, ethylthio, n-propylthio, methylsulfonyl, ethylsulfonyl, n-propylsulfonyl, phenyl, hydroxymethyl, 1-hydroxyethyl and 2-hydroxyethyl, or adjacent two groups of $R_3$ to $R_7$ form, taken together, methylenedioxy;

or a pharmaceutically-acceptable salt thereof.

7. A compound according to claim 6, which is selected from the following group of specific compounds:

2,2-Dimethyl-5-{4-(methylsulfonyl)phenyl}-4-phenyl-3(2H)-furanone;
2,2-Dimethyl-4-(2-fluorophenyl)-5-{4-(methylsulfonyl)phenyl}-3(2H)-furanone;
2,2-Dimethyl-4-(3-fluorophenyl)-5-{4-(methylsulfonyl)phenyl}-3(2H)-furanone;
2,2-Dimethyl-4-(4-fluorophenyl)-5-{4-(methylsulfonyl)phenyl}-3(2H)-furanone;
2,2-Dimethyl-4-(3-fluoro-4-phenylphenyl)-5-{4-(methylsulfonyl)phenyl}-3(2H)-furanone;
4-(2,4-Difluorophenyl)-2,2-dimethyl-5-{4-(methylsulfonyl)phenyl}-3(2H)-furanone;
4-(2,5-Difluorophenyl)-2,2-dimethyl-5-{4-(methylsulfonyl)phenyl}-3(2H)-furanone;
4-(3,4-Difluorophenyl)-2,2-dimethyl-5-{4-(methylsulfonyl)phenyl}-3(2H)-furanone;
4-(3,5-Difluorophenyl)-2,2-dimethyl-5-{4-(methylsulfonyl)phenyl}-3(2H)-furanone;
4-(2-Chlorophenyl)-2,2-dimethyl-5-{4-(methylsulfonyl)phenyl}-3(2H)-furanone;
4-(3-Chlorophenyl)-2,2-dimethyl-5-{4-(methylsulfonyl)phenyl}-3(2H)-furanone;
4-(4-Chlorophenyl)-2,2-dimethyl-5-{4-(methylsulfonyl)phenyl}-3(2H)-furanone;
4-(3-Chloro-4-fluorophenyl)-2,2-dimethyl-5-{4-(methylsulfonyl)phenyl}-3(2H)-furanone;
4-(3-Chloro-5-fluorophenyl)-2,2-dimethyl-5-{4-(methylsulfonyl)phenyl}-3(2H)-furanone;
4-(4-Chloro-3-fluorophenyl)-2,2-dimethyl-5-{4-(methylsulfonyl)phenyl}-3(2H)-furanone;
4-(2,4-Dichlorophenyl)-2,2-dimethyl-5-{4-(methylsulfonyl)phenyl}-3(2H)-furanone;
4-(3,4-Dichlorophenyl)-2,2-dimethyl-5-{4-(methylsulfonyl)phenyl}-3(2H)-furanone;
4-(3,5-Dichlorophenyl)-2,2-dimethyl-5-{4-(methylsulfonyl)phenyl}-3(2H)-furanone;
4-(4-Bromophenyl)-2,2-dimethyl-5-{4-(methylsulfonyl)phenyl}-3(2H)-furanone;
4-(3-Bromophenyl)-2,2-dimethyl-5-{4-(methylsulfonyl)phenyl}-3(2H)-furanone;
2,2-Dimethyl-4-(2-methylphenyl)-5-{4-(methylsulfonyl)phenyl}-3(2H)-furanone;
2,2-Dimethyl-4-(3-methylphenyl)-5-{4-(methylsulfonyl)phenyl}-3(2H)-furanone;
2,2-Dimethyl-4-(4-methylphenyl)-5-{4-(methylsulfonyl)phenyl}-3(2H)-furanone;
2,2-Dimethyl-4-(4-ethylphenyl)-5-{4-(methylsulfonyl)phenyl}-3(2H)-furanone;
2,2-Dimethyl-5-{4-(methylsulfonyl)phenyl}-4-(4-n-propylphenyl)-3(2H)-furanone;
2,2-Dimethyl-4-(3-iso-propylphenyl)-5-{4-(methylsulfonyl)phenyl}-3(2H)-furanone;
2,2-Dimethyl-4-(4-iso-propylphenyl)-5-{4-(methylsulfonyl)phenyl}-3(2H)-furanone;
2,2-Dimethyl-4-(3-fluoro-4-iso-propylphenyl)-5-{4-(methylsulfonyl)phenyl}-3(2H)-furanone;
4-(3-Chloro-4-iso-propylphenyl)-2,2-dimethyl-5-{4-(methylsulfonyl)phenyl}-3(2H)-furanone;
2,2-Dimethyl-4-(4-n-butylphenyl)-5-{4-(methylsulfonyl)phenyl}-3(2H)-furanone;
2,2-Dimethyl-4-(4-t-butylphenyl)-5-{4-(methylsulfonyl)phenyl}-3(2H)-furanone;
2,2-Dimethyl-4-(4-fluoro-2-methylphenyl)-5-{4-(methylsulfonyl)phenyl}-3(2H)-furanone;
2,2-Dimethyl-4-(5-fluoro-2-methylphenyl)-5-{4-(methylsulfonyl)phenyl}-3(2H)-furanone;
2,2-Dimethyl-4-(3-fluoro-4-methylphenyl)-5-{4-(methylsulfonyl)phenyl}-3(2H)-furanone;
2,2-Dimethyl-4-(2-methoxyphenyl)-5-{4-(methylsulfonyl)phenyl}-3(2H)-furanone;
2,2-Dimethyl-4-(3-methoxyphenyl)-5-{4-(methylsulfonyl)phenyl}-3(2H)-furanone;
2,2-Dimethyl-4-(4-methoxyphenyl)-5-{4-(methylsulfonyl)phenyl}-3(2H)-furanone;
2,2-Dimethyl-4-(2-hydroxyphenyl)-5-{4-(methylsulfonyl)phenyl}-3(2H)-furanone;
2,2-Dimethyl-4-(3-hydroxyphenyl)-5-{4-(methylsulfonyl)phenyl}-3(2H)-furanone;
2,2-Dimethyl-4-(4-hydroxyphenyl)-5-{4-(methylsulfonyl)phenyl}-3(2H)-furanone;
4-(2,4-Dimethoxyphenyl)-2,2-dimethyl-5-{4-(methylsulfonyl)phenyl}-3(2H)-furanone;
4-(3,4-Dimethoxyphenyl)-2,2-dimethyl-5-{4-(methylsulfonyl)phenyl}-3(2H)-furanone;
2,2-Dimethyl-4-(3,4-methylenedioxyphenyl)-5-{4-(methylsulfonyl)phenyl}-3(2H)-furanone;
2,2-Dimethyl-4-(3,5-dimethyl-4-methoxyphenyl)-5-{4-(methylsulfonyl)-phenyl}-3(2H)-furanone;
2,2-Dimethyl-4-(3,4-dimethylphenyl)-5-{4-(methylsulfonyl)phenyl}-3(2H)-furanone;
2,2-Dimethyl-4-(3-fluoro-4-methoxyphenyl)-5-{4-(methylsulfonyl)phenyl}-3(2H)-furanone;
2,2-Dimethyl-4-(3-fluoro-4-hydroxyphenyl)-5-{4-(methylsulfonyl)phenyl}-3(2H)-furanone;
2,2-Dimethyl-5-{4-(methylsulfonyl)phenyl}-4-{4-(methylthio)phenyl}-3(2H)-furanone;
2,2-Dimethyl-4-{4-(ethylthio)phenyl}-5-{4-(methylsulfonyl)phenyl}-3(2H)-furanone;
2,2-Dimethyl-4,5-di-{4-(methylsulfonyl)phenyl}-3(2H)-furanone;
2,2-Dimethyl-4-{4-(ethylsulfonyl)phenyl}-5-{4-(methylsulfonyl)phenyl}-3(2H)-furanone;
2,2-Dimethyl-4-{3-(fluoromethyl)phenyl}-5-{4-(methylsulfonyl)phenyl}-3(2H)-furanone;
2,2-Dimethyl-4-{4-(fluoromethyl)phenyl}-5-{4-(methylsulfonyl)phenyl}-3(2H)-furanone;
4-{3-(Difluoromethyl)phenyl}-2,2-dimethyl-5-{4-(methylsulfonyl)phenyl}-3(2H)-furanone;
4-{4-(Difluoromethyl)phenyl}-2,2-dimethyl-5-{4-(methylsulfonyl)phenyl}-3(2H)-furanone;
2,2-Dimethyl-5-{4-(methylsulfonyl)phenyl}-4-{2-(trifluoromethyl)phenyl}-3(2H)-furanone;

2,2-Dimethyl-5-{4-(methylsulfonyl)phenyl}-4-{3-(trifluoromethyl)phenyl}-3(2H)-furanone;
2,2-Dimethyl-4-{3-fluoro-5-(trifluoromethyl)phenyl}-5-{4-(methylsulfonyl)phenyl}-3(2H)-furanone;
4-{3-Chloro-5-(trifluoromethyl)phenyl}-2,2-dimethyl-5-{4-(methylsulfonyl)phenyl}-3(2H)-furanone;
4-{4-Acetyl-3-(trifluoromethyl)phenyl}-2,2-dimethyl-5-{4-(methylsulfonyl)phenyl}-3(2H)-furanone;
4-{3-Acetyl-5-(trifluoromethyl)phenyl}-2,2-dimethyl-5-{4-(methylsulfonyl)phenyl}-3(2H)-furanone;
2,2-Dimethyl-5-{4-(methylsulfonyl)phenyl}-4-{4-(trifluoromethyl)phenyl}-3(2H)-furanone;
2,2-Dimethyl-4-{3,5-di-(trifluoromethyl)phenyl}-5-{4-(methylsulfonyl)phenyl}-3(2H)-furanone;
4-{4-Chloro-3-(trifluoromethyl)phenyl}-2,2-dimethyl-5-{4-(methylsulfonyl)phenyl}-3(2H)-furanone;
2,2-Dimethyl-5-{4-(methylsulfonyl)phenyl}-4-(3-nitrophenyl)-3(2H)-furanone;
4-(3-Aminophenyl)-2,2-Dimethyl-5-{4-(methylsulfonyl)phenyl}-3(2H)-furanone;
2,2-Dimethyl-4-{4-(N,N-dimethylamino)phenyl}-5-{4-(methylsulfonyl)phenyl}-3(2H)-furanone;
2,2-Dimethyl-4-(2-formylphenyl)-5-{4-(methylsulfonyl)phenyl}-3(2H)-furanone;
2,2-Dimethyl-4-(3-formylphenyl)-5-{4-(methylsulfonyl)phenyl}-3(2H)-furanone;
2,2-Dimethyl-4-{4-formylphenyl}-5-{4-(methylsulfonyl)phenyl}-3(2H)-furanone;
4-{3-(Acetylamino)phenyl}-2,2-dimethyl-5-{4-(methylsulfonyl)phenyl}-3(2H)-furanone;
4-(3-Acetylphenyl)-2,2-dimethyl-5-{4-(methylsulfonyl)phenyl}-3(2H)-furanone;
4-(4-Acetylphenyl)-2,2-dimethyl-5-{4-(methylsulfonyl)phenyl}-3(2H)-furanone;
4-(4-Biphenyl)-2,2-dimethyl-5-{4-(methylsulfonyl)phenyl}-3(2H)-furanone;
2,2-Dimethyl-4-[4-(1-hydroxyethyl)phenyl]-5-{4-(methylsulfonyl)phenyl}-3(2H)-furanone;
2,2-Dimethyl-4-[4-(1-hydroxymethyl)phenyl]-5-{4-(methylsulfonyl)phenyl}-3(2H)-furanone;
2,2-Dimethyl-5-{4-(methylsulfinyl)phenyl}-4-phenyl-3(2H)-furanone;
2,2-Dimethyl-4-(3-fluorophenyl)-5-{4-(methylsulfinyl)phenyl}-3(2H)-furanone;
2,2-Dimethyl-4-(4-fluorophenyl)-5-{4-(methylsulfinyl)phenyl}-3(2H)-furanone;
2,2-Dimethyl-4-(3,5-difluorophenyl)-5-{4-(methylsulfinyl)phenyl}-3(2H)-furanone;
4-(3-Chloro-4-fluorophenyl)-2,2-dimethyl-5-{4-(methylsulfinyl)phenyl}-3(2H)-furanone;
4-(3-Chloro-5-fluorophenyl)-2,2-dimethyl-5-{4-(methylsulfinyl)phenyl}-3(2H)-furanone;
4-(3-Chlorophenyl)-2,2-dimethyl-5-{4-(methylsulfinyl)phenyl}-3(2H)-furanone;
4-(4-t-Butylphenyl)-2,2-dimethyl-5-{4-(methylsulfinyl)phenyl}-3(2H)-furanone;
2,2-Dimethyl-4-(2-fluorophenyl)-5-{4-(methylsulfinyl)phenyl}-3(2H)-furanone;
2,2-Dimethyl-4-(3-fluorophenyl)-5-{4-(methylthio)phenyl}-3(2H)-furanone;
2,2-Dimethyl-5-{4-(methylthio)phenyl}-4-phenyl-3(2H)-furanone;
4-(3-Chlorophenyl)-2,2-dimethyl-5-{4-(methylthio)phenyl}-3(2H)-furanone;
2,2-Dimethyl-5-{4-(methylthio)phenyl}-4-{3-(trifluoromethyl)phenyl}-3(2H)-furanone;
2,2-Dimethyl-5-{4-(methylsulfinyl)phenyl}-4-{3-(trifluoromethyl)phenyl}-3(2H)-furanone;
2,2-Dimethyl-4-{3-fluoro-5-(trifluoromethyl)phenyl}-5-{4-(methylsulfinyl)phenyl}-3(2H)-furanone;
4-{3-Chloro-5-(trifluoromethyl)phenyl}-2,2-dimethyl-5-{4-(methylsulfinyl)phenyl}-3(2H)-furanone;
4-{3-Acetyl-5-(trifluoromethyl)phenyl}-2,2-dimethyl-5-{4-(methylsulfinyl)phenyl}-3(2H)-furanone;
4-{4-Acetyl-3-(trifluoromethyl)phenyl}-2,2-dimethyl-5-{4-(methylsulfinyl)phenyl}-3(2H)-furanone;
2,2-Dimethyl-5-{4-(methylthio)phenyl}-4-(4-nitrophenyl)-3(2H)-furanone;
2,2-Dimethyl-4-(4-methoxyphenyl)-5-{4-(methylthio)phenyl}-3(2H)-furanone;
4-(2,5-Difluorophenyl)-2,2-dimethyl-5-{4-(methylthio)phenyl}-3(2H)-furanone;
4-(3,5-Difluorophenyl)-2,2-dimethyl-5-{4-(methylthio)phenyl}-3(2H)-furanone;
5-{4-(Aminosulfonyl)phenyl}-2,2-dimethyl-4-(4-fluorophenyl)-3(2H)-furanone;
5-{4-(Aminosulfonyl)phenyl}-4-(3,5-difluorophenyl)-2,2-dimethyl-3(2H)-furanone;
5-{4-(Aminosulfonyl)phenyl}-4-(3-chloro-5-fluorophenyl)-2,2-dimethyl-3(2H)-furanone;
5-{4-(Aminosulfonyl)phenyl}-4-(3-chlorophenyl)-2,2-dimethyl-3(2H)-furanone;
5-{4-(Aminosulfonyl)phenyl}-4-(3,4-dichlorophenyl)-2,2-dimethyl-3(2H)-furanone;
5-{4-(Aminosulfonyl)phenyl}-4-(3,5-dichlorophenyl)-2,2-dimethyl-3(2H)-furanone;
5-{4-(Aminosulfonyl)phenyl}-2,2-dimethyl-4-{3-(trifluoromethyl)phenyl}-3(2H)-furanone;
5-{4-(Aminosulfonyl)phenyl}-2,2-dimethyl-4-{3-fluoro-5-(trifluoromethyl)phenyl}-3(2H)-furanone;
5-{4-(Aminosulfonyl)phenyl}-4-{3-chloro-5-(trifluoromethyl)phenyl}-2,2-dimethyl 3(2H)-furanone;
4-{3-Acetyl-5-(trifluoromethyl)phenyl}-5-{4-(aminosulfonyl)phenyl}-2,2-dimethyl 3(2H)-furanone;
4-{4-Acetyl-5-(trifluoromethyl)phenyl}-5-{4-(aminosulfonyl)phenyl}-2,2-dimethyl 3(2H)-furanone;
5-{4-(Aminosulfonyl)phenyl}-2,2-dimethyl-4-(3-methylphenyl)-3(2H)-furanone;
5-{4-(Aminosulfonyl)phenyl}-2,2-dimethyl-4-(3-fluorophenyl)-3(2H)-furanone;
5-{4-(Aminosulfonyl)phenyl}-4-(2,4-difluorophenyl)-2,2-dimethyl-3(2H)-furanone;
5-{4-(Aminosulfonyl)phenyl}-2,2-dimethyl-4-(3,4-dimethylphenyl)-3(2H)-furanone;
5-{4-(Aminosulfonyl)phenyl}-4-(2,4-dimethoxyphenyl)-2,2-dimethyl-3(2H)-furanone;
5-{4-(Aminosulfonyl)phenyl}-4-(3,4-dimethoxyphenyl)-2,2-dimethyl-3(2H)-furanone;
4-(3-Acetylphenyl)-5-{4-(aminosulfonyl)phenyl}-2,2-dimethyl-3(2H)-furanone;
4-(3-Acetyl-5-chlorophenyl)-5-{4-(aminosulfonyl)phenyl}-2,2-dimethyl-3(2H)-furanone;
4-(3-Acetyl-4-chlorophenyl)-5-{4-(aminosulfonyl)phenyl}-2,2-dimethyl-3(2H)-furanone;
4-(3-Acetyl-4-fluorophenyl)-5-{4-(aminosulfonyl)phenyl}-2,2-dimethyl-3(2H)-furanone;
4-(3-Acetyl-5-fluorophenyl)-5-{4-(aminosulfonyl)phenyl}-2,2-dimethyl-3(2H)-furanone;
5-{4-(Aminosulfonyl)phenyl}-2,2-dimethyl-4-phenyl-3(2H)-furanone;
5-{4-(Aminosulfonyl)phenyl}-4-(3-chloro-4-fluorophenyl)-2,2-dimethyl-3(2H)-furanone;
5-{4-(Aminosulfonyl)phenyl}-2,2-dimethyl-4-(3-methoxyphenyl)-3(2H)-furanone;
4-(4-Acetylphenyl)-5-{4-(aminosulfonyl)phenyl}-2,2-dimethyl-3(2H)-furanone;

4-(4-Acetyl-3-chlorophenyl)-5-{4-(aminosulfonyl)phenyl}-2,2-dimethyl-3(2H)-furanone;

4-(4-Acetyl-3-fluorophenyl)-5-{4-(aminosulfonyl)phenyl}-2,2-dimethyl-3(2H)-furanone;

4-(4-Acetyl-3-bromophenyl)-5-{4-(aminosulfonyl)phenyl}-2,2-dimethyl-3(2H)-furanone;

4-{4-(Acetylamino)phenyl}-5-{4-(Aminosulfonyl)phenyl}-2,2-dimethyl-3(2H)-furanone;

5-{4-(Aminosulfonyl)phenyl}-2,2-dimethyl-4-(2-methylphenyl)-3(2H)-furanone;

5-{4-(Aminosulfonyl)phenyl}-4-(3,4-difluorophenyl)-2,2-dimethyl-3(2H)-furanone;

5-{4-(Aminosulfonyl)phenyl}-2,2-dimethyl-4-(4-methylphenyl)-3(2H)-furanone;

5-{4-(Aminosulfonyl)phenyl}-2,2-dimethyl-4-{3,4-(methylenedioxy)phenyl}-3(2H)-furanone;

5-{4-(Aminosulfonyl)phenyl}-4-(4-chlorophenyl)-2,2-dimethyl-3(2H)-furanone;

5-{4-(Aminosulfonyl)phenyl}-2,2-dimethyl-4-{4-(methylthio)phenyl}-3(2H)-furanone;

5-{4-(Aminosulfonyl)phenyl}-2,2-dimethyl-4-(3-fluoro-4-phenylphenyl)-3(2H)-furanone;

5-{4-(Aminosulfonyl)phenyl}-4-(4-bromophenyl)-2,2-dimethyl-3(2H)-furanone;

5-{4-(Aminosulfonyl)phenyl}-2,2-dimethyl-4-(5-iso-propyl-2-methoxyphenyl)-3(2H)-furanone;

5-{4-(Aminosulfonyl)phenyl}-2,2-dimethyl-4-(5-iso-propylphenyl)-3(2H)-furanone;

5-{4-(Aminosulfonyl)phenyl}-2,2-dimethyl-4-{4-(ethylthio)phenyl}-3(2H)-furanone;

5-{4-(Aminosulfonyl)phenyl}-2,2-dimethyl-4-(2-methoxyphenyl)-3(2H)-furanone;

5-{4-(Aminosulfonyl)phenyl}-4-(4-n-butylphenyl)-2,2-dimethyl-3(2H)-furanone;

5-{4-(Aminosulfonyl)phenyl}-4-(3,5-dichlorophenyl)-2,2-dimethyl-3(2H)-furanone;

5-{4-(Aminosulfonyl)phenyl}-2,2-dimethyl-4-(3,4,5-trimethoxyphenyl)-3(2H)-furanone;

5-{4-(Aminosulfonyl)phenyl}-2,2-dimethyl-4-(4-hydroxyphenyl)-3(2H)-furanone;

5-(4-(Aminosulfonyl)phenyl}-2,2-dimethyl-4-(4-fluoro-3-methoxyphenyl)-3(2H)-furanone;

5-{4-(Aminosulfonyl)phenyl}-2,2-dimethyl-4-(3,5-dimethyl-4-methoxyphenyl)-3(2H)-furanone;

5-{4-(Aminosulfonyl)phenyl}-2,2-dimethyl-4-(4-ethylphenyl)-3(2H)-furanone;

5-{4-(Aminosulfonyl)phenyl}-2,2-dimethyl-4-(3-phenylphenyl)-3(2H)-furanone;

5-{4-(Aminosulfonyl)phenyl}-2,2-dimethyl-4-(2-fluorophenyl)-3(2H)-furanone;

4-(3-Aminophenyl)-5-{4-(aminosulfonyl)phenyl}-2,2-dimethyl-3(2H)-furanone;

5-{4-(Aminosulfonyl)phenyl}-4-(2,5-difluorophenyl)-2,2-dimethyl-3(2H)-furanone;

5-{4-(Aminosulfonyl)phenyl}-2,2-dimethyl-4-(3-nitrophenyl)-3(2H)-furanone;

5-{4-(Aminosulfonyl)phenyl}-2,2-dimethyl-4-(5-fluoro-2-methylphenyl)-3(2H)-furanone;

2-Ethyl-2-methyl-5-{4-(methylsulfonyl)phenyl}-4-phenyl-3(2H)-furanone;

2-Ethyl-4-(4-fluorophenyl)-2-methyl-5-{4-(methylsulfonyl)phenyl}-3(2H)-furanone;

2-Ethyl-4-(3-fluorophenyl)-2-methyl-5-{4-(methylsulfonyl)phenyl}-3(2H)-furanone;

4-(3-Chlorophenyl)-2-ethyl-2-methyl-5-{4-(methylsulfonyl)phenyl}-3(2H)-furanone;

2-Ethyl-4-(2-fluorophenyl)-2-methyl-5-{4-(methylsulfonyl)phenyl}-3(2H)-furanone;

4-(4-Acetylphenyl)-2-ethyl-2-methyl-5-{4-(methylsulfonyl)phenyl}-3(2H)-furanone;

4-(4-Acetyl-3-chlorophenyl)-2-ethyl-2-methyl-5-{4-(methylsulfonyl)phenyl}-3(2H)-furanone;

4-(4-Acetyl-3-fluorophenyl)-2-ethyl-2-methyl-5-{4-(methylsulfonyl)phenyl}-3(2H)-furanone;

4-{4-Acetyl-3-(trifluoromethyl)phenyl}-2-ethyl-2-methyl-5-{4-(methylsulfonyl)-phenyl}-3(2H)-furanone;

4-(3,5-Difluorophenyl)-2-ethyl-2-methyl-5-{4-(methylsulfonyl)phenyl}-3(2H)-furanone;

4-(3,4-Difluorophenyl)-2-ethyl-2-methyl-5-{4-(methylsulfonyl)phenyl}-3(2H)-furanone;

4-(3-Chloro-4-fluorophenyl)-2-ethyl-2-methyl-5-{4-(methylsulfonyl)phenyl}-3(2H)-furanone;

4-(3-Chloro-5-fluorophenyl)-2-ethyl-2-methyl-5-{4-(methylsulfonyl)phenyl}-3(2H)-furanone;

4-(3,5-Dichlorophenyl)-2-ethyl-2-methyl-5-{4-(methylsulfonyl)phenyl}-3(2H)-furanone;

2-Ethyl-4-(4-methoxyphenyl)-2-methyl-5-{4-(methylsulfonyl)phenyl}-3(2H)-furanone;

2-Ethyl-2-methyl-4-(4-methylphenyl)-5-{4-(methylsulfonyl)phenyl}-3(2H)-furanone;

2-Ethyl-2-methyl-4-(3-methylphenyl)-5-{4-(methylsulfonyl)phenyl}-3(2H)-furanone;

2-Ethyl-2-methyl-5-{4-(methylsulfonyl)phenyl}-4-(3-trifluoromethylphenyl)-3(2H)-furanone;

4-(3-Acetylphenyl)-2-ethyl-2-methyl-5-{4-(methylsulfonyl)phenyl}-3(2H)-furanone;

4-(3-Acetyl-4-fluorophenyl)-2-ethyl-2-methyl-5-{4-(methylsulfonyl)phenyl}-3(2H)-furanone;

4-(3-Acetyl-4-chlorophenyl)-2-ethyl-2-methyl-5-{4-(methylsulfonyl)phenyl}-3(2H)-furanone;

4-{3-(Acetylamino)phenyl}-2-ethyl-2-methyl-5-{4-(methylsulfonyl)phenyl}-3(2H)-furanone;

2-Ethyl-2-methyl-4-{3,4-(methylenedioxy)phenyl}-5-{4-(methylsulfonyl)phenyl}-3(2H)-furanone;

4-{4-Chloro-3-(trifluoromethyl)phenyl}-2-ethyl-2-methyl-5-{4-(methylsulfonyl)-phenyl}-3(2H)-furanone;

4-{5-Chloro-3-(trifluoromethyl)phenyl}-2-ethyl-2-methyl-5-{4-(methylsulfonyl)-phenyl}-3(2H)-furanone;

2-Ethyl-4-{5-fluoro-3-(trifluoromethyl)phenyl}-2-ethyl-2-methyl-5-{4-(methylsulfonyl)phenyl}-3(2H)-furanone;

2-Ethyl-4-(4-ethylphenyl)-2-methyl-5-{4-(methylsulfonyl)phenyl}-3(2H)-furanone;

2-Ethyl-4-(3-methoxyphenyl)-2-methyl-5-{4-(methylsulfonyl)phenyl}-3(2H)-furanone;

2-Ethyl-4-(3-iso-propylphenyl)-2-methyl-5-{4-(methylsulfonyl)phenyl}-3(2H)-furanone;

2-Ethyl-4-(4-iso-propylphenyl)-2-methyl-5-{4-(methylsulfonyl)phenyl}-3(2H)-furanone;

2-Ethyl-4-(3-fluoro-4-iso-propylphenyl)-2-methyl-5-{4-(methylsulfonyl)phenyl}-3(2H)-furanone;

2-Ethyl-4-(5-fluoro-4-iso-propylphenyl)-2-methyl-5-{4-(methylsulfonyl)phenyl}-3(2H)-furanone;

4-(3-Chloro-4-iso-propylphenyl)-2-ethyl-2-methyl-5-{4-(methylsulfonyl)phenyl}-3(2H)-furanone;

4-(4-t-Butylphenyl)-2-ethyl-2-methyl-5-{4-(methylsulfonyl)phenyl}-3(2H)-furanone;

2-Ethyl-2-methyl-5-{4-(methylsulfonyl)phenyl}-4-(4-n-propylphenyl)-3(2H)-furanone;

4-(4-n-Butylphenyl)-2-ethyl-2-methyl-5-{4-(methylsulfonyl)phenyl}-3(2H)-furanone;

4-(3,4-Dimethylphenyl)-2-ethyl-2-methyl-5-{4-(methylsulfonyl)phenyl}-3(2H)-furanone;

4-(3,4-Dichlorophenyl)-2-ethyl-2-methyl-5-{4-(methylsulfonyl)phenyl}-3(2H)-furanone;

4-(3-Aminophenyl)-2-ethyl-2-methyl-5-{4-(methylsulfonyl)phenyl}-3(2H)-furanone;

4-{3-(Difluoromethyl)phenyl}-2-ethyl-2-methyl-5-{4-(methylsulfonyl)phenyl}-3(2H)-furanone;

2-Ethyl-4-{4-(fluoromethyl)phenyl}-2-methyl-5-{4-(methylsulfonyl)phenyl}-3(2H)-furanone;

4-(4-Chlorophenyl)-2-ethyl-2-methyl-5-{4-(methylsulfonyl)phenyl}-3(2H)-furanone;

2-Ethyl-2-methyl-5-{4-(methylsulfonyl)phenyl}-4-{4-(trifluoromethyl)phenyl}-3(2H)-furanone;

2-Ethyl-2-methyl-5-{4-(methylsulfonyl)phenyl}-4-{4-(trifluoromethoxy)phenyl}-3(2H)-furanone;

4-(4-Chloro-3-fluorophenyl)-2-ethyl-2-methyl-5-{4-(methylsulfonyl)phenyl}-3(2H)-furanone;

2-Ethyl-4-(4-fluoro-2-methylphenyl)-2-methyl-5-{4-(methylsulfonyl)phenyl}-3(2H)-furanone;

2-Ethyl-4-(5-fluoro-2-methylphenyl)-2-methyl-5-{4-(methylsulfonyl)phenyl}-3(2H)-furanone;

4-(3,4-Dimethoxyphenyl)-2-ethyl-2-methyl-5-{4-(methylsulfonyl)phenyl}-3(2H)-furanone;

4-(3,5-Dimethoxyphenyl)-2-ethyl-2-methyl-5-{4-(methylsulfonyl)phenyl}-3(2H)-furanone;

2-Ethyl-4-(5-fluoro-2-methylphenyl)-2-methyl-5-{4-(methylsulfonyl)phenyl}-3(2H)-furanone;

2-Ethyl-4-(3-fluoro-4-methoxyphenyl)-2-methyl-5-{4-(methylsulfonyl)phenyl}-3(2H)-furanone;

4-(3,5-Difluorophenyl)-2-ethyl-2-methyl-5-{4-(methylsulfonyl)phenyl}-3(2H)-furanone;

4-(3,5-Dichlorophenyl)-2-ethyl-2-methyl-5-{4-(methylsulfonyl)phenyl}-3(2H)-furanone;

4-(3,5-Dimethyl-4-methoxyphenyl)-2-ethyl-2-methyl-5-{4-(methylsulfonyl)phenyl}-3(2H)-furanone;

2-Ethyl-2-methyl-5-{4-(methylsulfonyl)phenyl}-4-(3,4,5-trimethoxyphenyl)-3(2H)-furanone;

5-{4-(Aminosulfonyl)phenyl}-2-ethyl-2-methyl-4-phenyl-3(2H)-furanone;

5-{4-(Aminosulfonyl)phenyl}-2-ethyl-4-(4-fluorophenyl)-2-methyl-3(2H)-furanone;

5-{4-(Aminosulfonyl)phenyl}-2-ethyl-4-(3-fluorophenyl)-2-methyl-3(2H)-furanone;

5-{4-(Aminosulfonyl)phenyl}-2-ethyl-2-methyl-4-(3-methylphenyl)-3(2H)-furanone;

5-{4-(Aminosulfonyl)phenyl}-4-(3-chlorophenyl)-2-ethyl-2-methyl-3(2H)-furanone;

5-{4-(Aminosulfonyl)phenyl}-4-(4-chlorophenyl)-2-ethyl-2-methyl-3(2H)-furanone;

5-(4-Aminosulfonylphenyl)-2-ethyl-2-methyl-4-{3-(trifluoromethyl)phenyl}-3(2H)-furanone;

5-(4-Aminosulfonylphenyl)-2-ethyl-2-methyl-4-{3-fluoro-5-(trifluoromethyl)phenyl}-3(2H)-furanone;

5-(4-Aminosulfonylphenyl)-4-{3-chloro-5-(trifluoromethyl)phenyl}-2-ethyl-2-methyl-3(2H)-furanone;

5-{4-(Aminosulfonyl)phenyl}-2-ethyl-2-methyl-4-{4-(trifluoromethyl)phenyl}-3(2H)-furanone;

5-{4-(Aminosulfonyl)phenyl}-4-(3,5-difluorophenyl)-2-ethyl-2-methyl-3(2H)-furanone;

5-{4-(Aminosulfonyl)phenyl}-4-(3,5-dichlorophenyl)-2-ethyl-2-methyl-3(2H)-furanone;

5-{4-(Aminosulfonyl)phenyl}-4-(3,4-difluorophenyl)-2-ethyl-2-methyl-3(2H)-furanone;

5-{4-(Aminosulfonyl)phenyl}-2-ethyl-4-(3-methoxyphenyl)-2-methyl-3(2H)-furanone;

4-(4-Acetylphenyl)-5-{4-(aminosulfonyl)phenyl}-2-ethyl-2-methyl-3(2H)-furanone;

4-(4-Acetyl-3-chlorophenyl)-5-{4-(aminosulfonyl)phenyl}-2-ethyl-2-methyl-3(2H)-furanone;

4-(4-Acetyl-3-fluorophenyl)-5-{4-(aminosulfonyl)phenyl}-2-ethyl-2-methyl-3(2H)-furanone;

4-{4-Acetyl-4-(trifluoromethyl)phenyl}-5-{4-(aminosulfonyl)phenyl}-2-ethyl-2-methyl-3(2H)-furanone;

4-{4-(Aminosulfonyl)phenyl}-2-ethyl-4-(4-fluoro-3-methoxyphenyl)-2-methyl-3(2H)-furanone;

2,2-Diethyl-5-{4-(methylsulfonyl)phenyl}-4-phenyl-3(2H)-furanone;

2,2-Diethyl-4-(3-fluorophenyl)-5-{4-(methylsulfonyl)phenyl}-3(2H)-furanone;

4-(3-Chlorophenyl)-2,2-diethyl-5-{4-(methylsulfonyl)phenyl}-3(2H)-furanone;

2,2-Diethyl-4-(3-methylphenyl)-5-{4-(methylsulfonyl)phenyl}-3(2H)-furanone;

2,2-Diethyl-4-(3-methoxyphenyl)-5-{4-(methylsulfonyl)phenyl}-3(2H)-furanone;

2,2-Diethyl-5-{4-(methylsulfonyl)phenyl}-4-{3-(trifluoromethyl)phenyl}-3(2H)-furanone;

2,2-Diethyl-4-{3-fluoro-5-(trifluoromethyl)phenyl}-5-{4-(methylsulfonyl)phenyl}-3(2H)-furanone;

4-{3-Chloro-5-(trifluoromethyl)phenyl}-2,2-diethyl-5-{4-(methylsulfonyl)phenyl}-3(2H)-furanone;

2,2-Diethyl-4-(4-fluorophenyl)-5-{4-(methylsulfonyl)phenyl}-3(2H)-furanone;

4-(4-Chlorophenyl)-2,2-diethyl-5-{4-(methylsulfonyl)phenyl}-3(2H)-furanone;

2,2-Diethyl-4-(4-methylphenyl)-5-{4-(methylsulfonyl)phenyl}-3(2H)-furanone;

2,2-Diethyl-4-(4-methoxyphenyl)-5-{4-(methylsulfonyl)phenyl}-3(2H)-furanone;

2,2-Diethyl-5-{4-(methylsulfonyl)phenyl}-4-{4-(trifluoromethyl)phenyl}-3(2H)-furanone;

4-(4-Acetyl-3-chlorophenyl)-2,2-diethyl-5-{4-(methylsulfonyl)phenyl}-3(2H)-furanone;

4-(4-Acetylphenyl)-2,2-diethyl-5-{4-(methylsulfonyl)phenyl}-3(2H)-furanone;

4-(4-Acetyl-3-fluorophenyl)-2,2-diethyl-5-{4-(methylsulfonyl)phenyl}-3(2H)-furanone;

4-(4-Acetyl-2-chlorophenyl)-2,2-diethyl-5-{4-(methylsulfonyl)phenyl}-3(2H)-furanone;

4-(4-Acetyl-2-fluorophenyl)-2,2-diethyl-5-{4-(methylsulfonyl)phenyl}-3(2H)-furanone;

2,2-Diethyl-4-(3,4-difluorophenyl)-5-{4-(methylsulfonyl)phenyl}-3(2H)-furanone;

2,2-Diethyl-4-(3,5-difluorophenyl)-5-{4-(methylsulfonyl)phenyl}-3(2H)-furanone;

2,2-Diethyl-4-(2,5-difluorophenyl)-5-{4-(methylsulfonyl)phenyl}-3(2H)-furanone;

4-(3-Chloro-5-fluorophenyl)-2,2-diethyl-5-{4-(methylsulfonyl)phenyl}-3(2H)-furanone;

2,2-Diethyl-4-(3,4-dimethoxyphenyl)-5-{4-(methylsulfonyl)phenyl}-3(2H)-furanone;

2,2-Diethyl-5-{4-(methylsulfonyl)phenyl}-4-(4-n-propylphenyl)-3(2H)-furanone;

2,2-Diethyl-4-(2,4-difluorophenyl)-5-{4-(methylsulfonyl)phenyl}-3(2H)-furanone;

4-(4-t-Butylphenyl)-2,2-diethyl-5-{4-(methylsulfonyl)phenyl}-3(2H)-furanone;

2,2-Diethyl-4-(3,4-dimethylphenyl)-5-{4-(methylsulfonyl)phenyl}-3(2H)-furanone;

2,2-Diethyl-4-(4-iso-propylphenyl)-5-{4-(methylsulfonyl)phenyl}-3(2H)-furanone;

4-(3-Acetylphenyl)-2,2-diethyl-5-{4-(methylsulfonyl)phenyl}-3(2H)-furanone;

4-(3-Chloro-4-fluorophenyl)-2,2-diethyl-5-{4-(methylsulfonyl)phenyl}-3(2H)-furanone;

2,2-Diethyl-4-(3-fluoro-4-methoxyphenyl)-5-{4-(methylsulfonyl)phenyl}-3(2H)-furanone;

4-(3-Chloro-4-fluorophenyl)-2,2-dimethyl-5-{4-(methylsulfonyl)phenyl}-(2H)-furan-3-thione;
2,2-Dimethyl-4-(4-fluorophenyl)-5-{4-(methylsulfonyl)phenyl}-(2H)-furan-3-thione;
2,2-Dimethyl-4-(3-fluorophenyl)-5-{4-(methylsulfonyl)phenyl}-(2H)-furan-3thione;
4-(3,5-Difluorophenyl)-2,2-dimethyl-5-{4-(methylsulfonyl)phenyl}-(2H)-furan-3-thione;
5-[4-{(Acetylamino)sulfonyl}phenyl]-2,2-dimethyl-4-(3-fluorophenyl)-3(2H)-furanone;
5-[4-{(Butyrylamino)sulfonyl}phenyl]-2,2-dimethyl-4-(3-fluorophenyl)-3(2H)-furanone;
2,2-Dimethyl-5-[4-{(N-methylamino)sulfonyl}phenyl]-4-(3-fluorophenyl)-3(2H)-furanone; and
2,2-Dimethyl-5-[4-{(N-ethylamino)sulfonyl}phenyl]-4-(3-fluorophenyl)-3(2H)-furanone; or
a pharmaceutically-acceptable salt thereof.

8. A compound according to claim 1, which is represented by Formula IV:

wherein
X represents halo or alkyl;
Y represents alkylsulfonyl, aminosulfonyl, alkylsulfinyl, (N-acylamino)-sulfonyl, (N-alkylamino)sulfonyl, or alkylthio;
Z represents oxygen or sulfur atom;
and each of $R_3$ to $R_7$, if present, is independently selected from hydrido, halo, alkyl, haloalkyl, alkyloxy, nitro, amino, N-acylamino, acyl, formyl, hydroxyalkyl, phenyl, and cyano, or two adjacent groups of $R_3$ to $R_7$ form, taken together, methylenedioxy;
or a pharmaceutically-acceptable salt thereof.

9. A compound according to claim 8, in which
X represents halo or lower alkyl;
Y is selected from (lower alkyl)sulfonyl, aminosulfonyl, (lower alkyl)sulfinyl, (lower N-acylamino)sulfonyl, (lower N-alkylamino)sulfonyl, and (lower alkyl)thio;
Z is selected from oxygen and sulfur atom;
and each of $R_3$ to $R_7$, if present, is independently selected from hydrido, halo, lower alkyl, lower haloalkyl, lower alkyloxy, nitro, amino, and N-(lower acyl)amino;
or a pharmaceutically acceptable salt thereof.

10. A compound according to claim 9, in which
X represents fluoro, chloro, bromo or methyl;
Y is selected from methylsulfonyl, ethylsulfonyl, aminosulfonyl, methylsulfinyl, ethylsulfinyl, (N-acetylamino)sulfonyl, (N-propionylamino)sulfonyl, (N-butyrylamino)sulfonyl, (N-methylamino)sulfonyl, (N-ethylamino)sulfonyl, methylthio, and ethylthio;
Z is selected from oxygen and sulfur atom;
and each of $R_3$ to $R_7$, if present, is independently selected from hydrido, fluoro, chloro, bromo, methyl, ethyl, iso-propyl, fluoromethyl, difluoromethyl, trifluoromethyl, methoxy, ethoxy, n-propyloxy, iso-propyloxy, n-butoxy, nitro, amino, N-acetylamino, and N-propionylamino;
or a pharmaceutically-acceptable salt thereof.

11. A compound according to claim 10, which is selected from the following group of compounds:

2,2-Dimethyl-5-{3-fluoro-4-(methylthio)phenyl}-4-phenyl-3(2H)-furanone;
2,2-Dimethyl-5-{3-fluoro-4-(methylsulfinyl)phenyl}-4-phenyl-3(2H)-furanone;
2,2-Dimethyl-5-{3-fluoro-4-(methylsulfonyl)phenyl}-4-phenyl-3(2H)-furanone;
5-{4-(Aminosulfonyl)-3-fluorophenyl}-2,2-dimethyl-4-phenyl-3(2H)-furanone;
4-(2-Chlorophenyl)-2,2-dimethyl-5-{3-fluoro-4-(methylthio)phenyl}-3(2H)-furanone;
4-(2-Chlorophenyl)-2,2-dimethyl-5-{3-fluoro-4-(methylsulfinyl)phenyl}-3(2H)-furanone;
4-(2-Chlorophenyl)-2,2-dimethyl-5-{3-fluoro-4-(methylsulfonyl)phenyl}-3(2H)-furanone;
5-{4-(Aminosulfonyl)-3-fluorophenyl}-4-(2-chlorophenyl)-2,2-dimethyl-3(2H)-furanone;
4-(3-Chlorophenyl)-2,2-dimethyl-5-{3-fluoro-4-(methylthio)phenyl}-3(2H)-furanone;
4-(3-Chlorophenyl)-2,2-dimethyl-5-{3-fluoro-4-(methylsulfinyl)phenyl}-3(2H)-furanone;
4-(3-Chlorophenyl)-2,2-dimethyl-5-{3-fluoro-4-(methylsulfonyl)phenyl}-3(2H)-furanone;
5-{4-(Aminosulfonyl)-3-fluorophenyl}-4-(3-chlorophenyl)-2,2-dimethyl-3(2H)-furanone;
4-(4-Chlorophenyl)-2,2-dimethyl-5-{3-fluoro-4-(methylthio)phenyl}-3(2H)-furanone;
4-(4-Chlorophenyl)-2,2-dimethyl-5-{3-fluoro-4-(methylsulfinyl)phenyl}-3(2H)-furanone;
4-(4-Chlorophenyl)-2,2-dimethyl-5-{3-fluoro-4-(methylsulfonyl)phenyl}-3(2H)-furanone;
5-{4-(Aminosulfonyl)-3-fluorophenyl}-4-(4-chlorophenyl)-2,2-dimethyl-3(2H)-furanone;
4-(3,4-Dichlorophenyl)-2,2-dimethyl-5-{3-fluoro-4-(methylthio)phenyl}-3(2H)-furanone;
4-(3,4-Dichlorophenyl)-2,2-dimethyl-5-{3-fluoro-4-(methylsulfinyl)phenyl}-3(2H)-furanone;
4-(3,4-Dichlorophenyl)-2,2-dimethyl-5-{3-fluoro-4-(methylsulfonyl)phenyl}-3(2H)-furanone;
5-{4-(Aminosulfonyl)-3-fluorophenyl}-4-(3,4-dichlorophenyl)-2,2-dimethyl-3(2H)-furanone;
2,2-Dimethyl-5-{3-fluoro-4-(methylthio)phenyl}-4-(2-fluorophenyl)-3(2H)-furanone;
2,2-Dimethyl-5-{3-fluoro-4-(methylsulfinyl)phenyl}-4-(2-fluorophenyl)-3(2H)-furanone;
2,2-Dimethyl-5-{3-fluoro-4-(methylsulfonyl)phenyl}-4-(2-fluorophenyl)-3(2H)-furanone;
5-{4-(Aminosulfonyl)-3-fluorophenyl}-2,2-dimethyl-4-(2-fluorophenyl)-3(2H)-furanone;
2,2-Dimethyl-5-{3-fluoro-4-(methylthio)phenyl}-4-(3-fluorophenyl)-3(2H)-furanone;
2,2-Dimethyl-5-{3-fluoro-4-(methylsulfinyl)phenyl}-4-(3-fluorophenyl)-3(2H)-furanone;
2,2-Dimethyl-5-{3-fluoro-4-(methylsulfonyl)phenyl}-4-(3-fluorophenyl)-3(2H)-furanone;
5-{4-(Aminosulfonyl)-3-fluorophenyl}-2,2-dimethyl-4-(3-fluorophenyl)-3(2H)-furanone;
2,2-Dimethyl-5-{3-fluoro-4-(methylthio)phenyl}-4-(4-fluorophenyl)-3(2H)-furanone;
2,2-Dimethyl-5-{3-fluoro-4-(methylsulfinyl)phenyl}-4-(4-fluorophenyl)-3(2H)-furanone;

2,2-Dimethyl-5-{3-fluoro-4-(methylsulfonyl)phenyl}-4-(4-fluorophenyl)-3(2H)-furanone;
5-{4-(Aminosulfonyl)-3-fluorophenyl}-2,2-dimethyl-4-(4-fluorophenyl)-3(2H)-furanone;
4-(2,4-Difluorophenyl)-2,2-dimethyl-5-{3-fluoro-4-(methylthio)phenyl}-3(2H)-furanone;
4-(2,4-Difluorophenyl)-2,2-dimethyl-5-{3-fluoro-4-(methylsulfinyl)phenyl}-3(2H)-furanone;
4-(2,4-Difluorophenyl)-2,2-dimethyl-5-{3-fluoro-4-(methylsulfonyl)phenyl}-3(2H)-furanone;
5-{4-(Aminosulfonyl)-3-fluorophenyl}-4-(2,4-difluorophenyl)-2,2-dimethyl-3(2H)-furanone;
4-(2,5-Difluorophenyl)-2,2-dimethyl-5-{3-fluoro-4-(methylthio)phenyl}-3(2H)-furanone;
4-(2,5-Difluorophenyl)-2,2-dimethyl-5-{3-fluoro-4-(methylsulfinyl)phenyl}-3(2H)-furanone;
4-(2,5-Difluorophenyl)-2,2-dimethyl-5-{3-fluoro-4-(methylsulfonyl)phenyl}-3(2H)-furanone;
5-{4-(Aminosulfonyl)-3-fluorophenyl}-4-(2,5-difluorophenyl)-2,2-dimethyl-3(2H)-furanone;
4-(2,6-Difluorophenyl)-2,2-dimethyl-5-{3-fluoro-4-(methylthio)phenyl}-3(2H)-furanone;
4-(2,6-Difluorophenyl)-2,2-dimethyl-5-{3-fluoro-4-(methylsulfinyl)phenyl}-3(2H)-furanone;
4-(2,6-Difluorophenyl)-2,2-dimethyl-5-{3-fluoro-4-(methylsulfonyl)phenyl}-3(2H)-furanone;
5-{4-(Aminosulfonyl)-3-fluorophenyl}-4-(2,6-difluorophenyl)-2,2-dimethyl-3(2H)-furanone;
4-(3,4-Difluorophenyl)-2,2-dimethyl-5-{3-fluoro-4-(methylthio)phenyl}-3(2H)-furanone;
4-(3,4-Difluorophenyl)-2,2-dimethyl-5-{3-fluoro-4-(methylsulfinyl)phenyl}-3(2H)-furanone;
4-(3,4-Difluorophenyl)-2,2-dimethyl-5-{3-fluoro-4-(methylsulfonyl)phenyl}-3(2H)-furanone;
5-{4-(Aminosulfonyl)-3-fluorophenyl}-4-(3,4-difluorophenyl)-2,2-dimethyl-3(2H)-furanone;
4-(3,5-Difluorophenyl)-2,2-dimethyl-5-{3-fluoro-4-(methylthio)phenyl}-3(2H)-furanone;
4-(3,5-Difluorophenyl)-2,2-dimethyl-5-{3-fluoro-4-(methylsulfinyl)phenyl}-3(2H)-furanone;
4-(3,5-Difluorophenyl)-2,2-dimethyl-5-{3-fluoro-4-(methylsulfonyl)phenyl}-3(2H)-furanone;
5-{4-(Aminosulfonyl)-3-fluorophenyl}-4-(3,5-difluorophenyl)-2,2-dimethyl-3(2H)-furanone;
2,2-Dimethyl-5-{3-fluoro-4-(methylthio)phenyl}-4-(2-trifluoromethylphenyl)-3(2H)-furanone;
2,2-Dimethyl-5-{3-fluoro-4-(methylsulfinyl)phenyl}-4-(2-trifluoromethylphenyl)-3(2H)-furanone;
2,2-Dimethyl-5-{3-fluoro-4-(methylsulfonyl)phenyl}-4-(2-trifluoromethylphenyl)-3(2H)-furanone;
5-{4-(Aminosulfonyl)-3-fluorophenyl}-2,2-dimethyl-4-(2-trifluoromethylphenyl)-3(2H)-furanone;
2,2-Dimethyl-5-{3-fluoro-4-(methylthio)phenyl}-4-(3-trifluoromethylphenyl)-3(2H)-furanone;
2,2-Dimethyl-5-{3-fluoro-4-(methylsulfinyl)phenyl}-4-(3-trifluoromethylphenyl)-3(2H)-furanone;
2,2-Dimethyl-5-{3-fluoro-4-(methylsulfonyl)phenyl}-4-(3-trifluoromethylphenyl)-3(2H)-furanone;
5-{4-(Aminosulfonyl)-3-fluorophenyl}-2,2-dimethyl-4-(3-trifluoromethylphenyl)-3(2H)-furanone;
2,2-Dimethyl-5-{-3-fluoro-4-(methylthio)phenyl}-4-(4-trifluoromethylphenyl)-3(2H)-furanone;
2,2-Dimethyl-5-{3-fluoro-4-(methylsulfinyl)phenyl}-4-(4-trifluoromethylphenyl)-3(2H)-furanone;
2,2-Dimethyl-5-{3-fluoro-4-(methylsulfonyl)phenyl}-4-(4-trifluoromethylphenyl)-3(2H)-furanone;
5-{4-(Aminosulfonyl)-3-fluorophenyl}-2,2-dimethyl-4-(4-trifluoromethylphenyl)-3(2H)-furanone;
2,2-Dimethyl-5-{3-fluoro-4-(methylthio)phenyl}-4-(4-nitrophenyl)-3(2H)-furanone;
2,2-Dimethyl-5-{3-fluoro-4-(methylsulfinyl)phenyl}-4-(4-nitrophenyl)-3(2H)-furanone;
2,2-Dimethyl-5-{3-fluoro-4-(methylsulfonyl)phenyl}-4-(4-nitrophenyl)-3(2H)-furanone;
5-{4-(Aminosulfonyl)-3-fluorophenyl}-2,2-dimethyl-4-(4-nitrophenyl)-3(2H)-furanone;
4-(4-Aminophenyl)-2,2-dimethyl-5-{3-fluoro-4-(methylthio)phenyl}-3(2H)-furanone;
4-(4-Aminophenyl)-2,2-dimethyl-5-{3-fluoro-4-(methylsulfinyl)phenyl}-3(2H)-furanone;
4-(4-Aminophenyl)-2,2-dimethyl-5-{3-fluoro-4-(methylsulfonyl)phenyl}-3(2H)-furanone;
4-(4-Aminophenyl)-5-{4-(aminosulfonyl)-3-fluorophenyl}-2,2-dimethyl-3(2H)-furanone;
4-{4-(Acetylamino)phenyl}-2,2-dimethyl-5-{3-fluoro-4-(methylthio)phenyl}-3(2H)-furanone;
4-{4-(Acetylamino)phenyl}-2,2-dimethyl-5-{3-fluoro-4-(methylsulfinyl)phenyl}-3(2H)-furanone;
4-{4-(Acetylamino)phenyl}-2,2-dimethyl-5-{3-fluoro-4-(methylsulfonyl)phenyl}-3(2H)-furanone;
4-{4-(Acetylamino)phenyl}-5-{4-(aminosulfonyl)-3-fluorophenyl}-2,2-dimethyl-3(2H)-furanone;
2-2-Dimethyl-5-{3-fluoro-4-(methylthio)phenyl}-4-(3-methoxyphenyl)-3(2H-furanone;
2-2-Dimethyl-5-{3-fluoro-4-(methylsulfonyl)phenyl}-4-(3-methoxyphenyl)-3(2H)-furanone;
2,2-Dimethyl-5-{2-fluoro-4-(methylthio)phenyl}-4-phenyl-3(2H)-furanone;
2,2-Dimethyl-5-{2-fluoro-4-(methylsulfinyl)phenyl}-4-phenyl-3(2H)-furanone;
2,2-Dimethyl-5-{2-fluoro-4-(methylsulfonyl)phenyl}-4-phenyl-3(2H)-furanone;
5-{4-(Aminosulfonyl)-2-fluorophenyl}-2,2-dimethyl-4-phenyl-3(2H)-furanone;
4-(2-Chlorophenyl)-2,2-dimethyl-5-{2-fluoro-4-(methylthio)phenyl}-3(2H)-furanone;
4-(2-Chlorophenyl)-2,2-dimethyl-5-{2-fluoro-4-(methylsulfinyl)phenyl}-3(2H)-furanone;
4-(2-Chlorophenyl)-2,2-dimethyl-5-{2-fluoro-4-(methylsulfonyl)phenyl}-3(2H)-furanone;
5-{4-(Aminosulfonyl)-2-fluorophenyl}-4-(2-chlorophenyl)-2,2-dimethyl-3(2H)-furanone;
4-(3-Chlorophenyl)-2,2-dimethyl-5-{2-fluoro-4-(methylthio)phenyl}-3(2H)-furanone;
4-(3-Chlorophenyl)-2,2-dimethyl-5-{2-fluoro-4-(methylsulfinyl)phenyl}-3(2H)-furanone;
4-(3-Chlorophenyl)-2,2-dimethyl-5-{2-fluoro-4-(methylsulfonyl)phenyl}-3(2H)-furanone;
5-{4-(Aminosulfonyl)-2-fluorophenyl}-4-(3-chlorophenyl)-2,2-dimethyl-3(2H)-furanone;
2,2-Dimethyl-5-{2-fluoro-4-(methylthio)phenyl}-4-(2-fluorophenyl)-3(2H)-furanone;
2,2-Dimethyl-5-{2-fluoro-4-(methylsulfinyl)phenyl}-4-(2-fluorophenyl)-3(2H)-furanone;
2,2-Dimethyl-5-{2-fluoro-4-(methylsulfonyl)phenyl}-4-(2-fluorophenyl)-3(2H)-furanone;
5-{4-(Aminosulfonyl)-2-fluorophenyl}-2,2-dimethyl-4-(2-fluorophenyl)-3(2H)-furanone;
2,2-Dimethyl-5-{2-fluoro-4-(methylthio)phenyl}-4-(3-fluorophenyl)-3(2H)-furanone;
2,2-Dimethyl-5-{2-fluoro-4-(methylsulfinyl)phenyl}-4-(3-fluorophenyl)-3(2H)-furanone;
2,2-Dimethyl-5-{2-fluoro-4-(methylsulfonyl)phenyl}-4-(3-fluorophenyl)-3(2H)-furanone;
5-{4-(Aminosulfonyl)-2-fluorophenyl}-2,2-dimethyl-4-(3-fluorophenyl)-3(2H)-furanone;

2,2-Dimethyl-5-{2-fluoro-4-(methylthio)phenyl}-4-(4-fluorophenyl)-3(2H)-furanone;

2,2-Dimethyl-5-{2-fluoro-4-(methylsulfinyl)phenyl}-4-(4-fluorophenyl)-3(2H)-furanone;

2,2-Dimethyl-5-{2-fluoro-4-(methylsulfonyl)phenyl}-4-(4-fluorophenyl)-3(2H)-furanone;

5-{4-(Aminosulfonyl)-2-fluorophenyl}-2,2-dimethyl-4-(4-fluorophenyl)-3(2H)-furanone;

4-(2,4-Difluorophenyl)-2,2-dimethyl-5-{2-fluoro-4-(methylthio)phenyl}-3(2H)-furanone;

4-(2,4-Difluorophenyl)-2,2-dimethyl-5-{2-fluoro-4-(methylsulfinyl)phenyl}-3(2H)-furanone;

4-(2,4-Difluorophenyl)-2,2-dimethyl-5-{2-fluoro-4-(methylsulfonyl)phenyl}-3(2H)-furanone;

5-{4-(Aminosulfonyl)-2-fluorophenyl}-4-(2,4-difluorophenyl)-2,2-dimethyl-3(2H)-furanone;

4-(2,5-Difluorophenyl)-2,2-dimethyl-5-{2-fluoro-4-(methylthio)phenyl}-3(2H)-furanone;

4-(2,5-Difluorophenyl)-2,2-dimethyl-5-{2-fluoro-4-(methylsulfinyl)phenyl}-3(2H)-furanone;

4-(2,5-Difluorophenyl)-2,2-dimethyl-5-{2-fluoro-4-(methylsulfonyl)phenyl}-3(2H)-furanone;

5-{4-(Aminosulfonyl)-2-fluorophenyl}-4-(2,5-difluorophenyl)-2,2-dimethyl-3(2H)-furanone;

4-(3,4-Difluorophenyl)-2,2-dimethyl-5-{2-fluoro-4-(methylthio)phenyl}-3(2H)-furanone;

4-(3,4-Difluorophenyl)-2,2-dimethyl-5-{2-fluoro-4-(methylsulfinyl)phenyl}-3(2H)-furanone;

4-(3,4-Difluorophenyl)-2,2-dimethyl-5-{2-fluoro-4-(methylsulfonyl)phenyl}-3(2H)-furanone;

5-{4-(Aminosulfonyl)-2-fluorophenyl}-4-(3,4-difluorophenyl)-2,2-dimethyl-3(2H)-furanone;

4-(3,5-Difluorophenyl)-2,2-dimethyl-5-{2-fluoro-4-(methylthio)phenyl}-3(2H)-furanone;

4-(3,5-Difluorophenyl)-2,2-dimethyl-5-{2-fluoro-4-(methylsulfinyl)phenyl}-3(2H)-furanone;

4-(3,5-Difluorophenyl)-2,2-dimethyl-5-{2-fluoro-4-(methylsulfonyl)phenyl}-3(2H)-furanone;

5-{4-(Aminosulfonyl}-2-fluorophenyl}-4-(3,5-difluorophenyl)-2,2-dimethyl-3(2H)-furanone;

2,2-Dimethyl-5-{2-fluoro-4-(methylthio)phenyl}-4-(3-trifluoromethylphenyl)-3(2H)-furanone;

2,2-Dimethyl-5-{2-fluoro-4-(methylsulfinyl)phenyl}-4-(3-trifluoromethylphenyl)-3(2H)-furanone;

2,2-Dimethyl-5-{2-fluoro-4-(methylsulfonyl)phenyl}-4-(3-trifluoromethylphenyl)-3(2H)-furanone;

5-{4-(Aminosulfonyl)-2-fluorophenyl}-2,2-dimethyl-4-(3-trifluoromethylphenyl)-3(2H)-furanone;

5-{3-Bromo-4-(methylthio)phenyl}-2,2-dimethyl-4-phenyl-3(2H)-furanone;

5-{3-Bromo-4-(methylsulfonyl)phenyl}-2,2-dimethyl-4-phenyl-3(2H)-furanone;

5-{3-Bromo-4-(methylsulfinyl)phenyl}-2,2-dimethyl-4-phenyl-3(2H)-furanone;

5-{4-(Aminosulfonyl)-3-bromophenyl}-2,2-dimethyl-4-phenyl-3(2H)-furanone;

5-{3-Bromo-4-(methylthio)phenyl}-4-(3-chlorophenyl)-2,2-dimethyl-3(2H)-furanone;

5-{3-Bromo-4-(methylsulfonyl)phenyl}-4-(3-chlorophenyl)-2,2-dimethyl-3(2H)-furanone;

5-{3-Bromo-4-(methylsulfinyl)phenyl}-4-(3-chlorophenyl)-2,2-dimethyl-3(2H)-furanone;

5-{4-(Aminosulfonyl)-3-bromophenyl}-4-(3-chlorophenyl)-2,2-dimethyl-3(2H)-furanone;

5-{3-Bromo-4-(methylthio)phenyl}-4-(4-chlorophenyl)-2,2-dimethyl-3(2H)-furanone;

5-{3-Bromo-4-(methylsulfonyl)phenyl}-4-(4-chlorophenyl)-2,2-dimethyl-3(2H)-furanone;

5-{3-Bromo-4-(methylsulfinyl)phenyl}-4-(4-chlorophenyl)-2,2-dimethyl-3(2H)-furanone;

5-{4-(Aminosulfonyl)-3-bromophenyl}-4-(4-chlorophenyl)-2,2-dimethyl-3(2H)-furanone;

5-{3-Bromo-4-(methylthio)phenyl}-2,2-dimethyl-4-(3-fluorophenyl)-3(2H)-furanone;

5-{3-Bromo-4-(methylsulfonyl)phenyl}-2,2-dimethyl-4-(3-fluorophenyl)-3(2H)-furanone;

5-{3-Bromo-4-(methylsulfinyl)phenyl}-2,2-dimethyl-4-(3-fluorophenyl)-3(2H)-furanone;

5-{4-(Aminosulfonyl)-3-bromophenyl}-2,2-dimethyl-4-(3-fluorophenyl)-3(2H)-furanone;

5-{3-Bromo-4-(methylthio)phenyl}-2,2-dimethyl-4-(4-fluorophenyl)-3(2H)-furanone;

5-{3-Bromo-4-(methylsulfonyl)phenyl}-2,2-dimethyl-4-(4-fluorophenyl)-3(2H)-furanone;

5-{3-Bromo-4-(methylsulfinyl)phenyl}-2,2-dimethyl-4-(4-fluorophenyl)-3(2H)-furanone;

5-{4-(Aminosulfonyl)-3-bromophenyl}-2,2-dimethyl-4-(4-fluorophenyl)-3(2H)-furanone;

5-{3-Bromo-4-(methylthio)phenyl}-4-(2,4-difluorophenyl)-2,2-dimethyl-3(2H)-furanone;

5-{3-Bromo-4-(methylsulfonyl)phenyl}-4-(2,4-difluorophenyl)-2,2-dimethyl-3(2H)-furanone 5-{3-Bromo-4-(methylsulfinyl)phenyl}-4-(2,4-difluorophenyl)-2,2-dimethyl-3(2H)-furanone;

5-{4-(Aminosulfonyl)-3-bromophenyl}-4-(2,4-difluorophenyl)-2,2-dimethyl-3(2H)-furanone;

5-{3-Bromo-4-(methylthio)phenyl}-4-(2,5-difluorophenyl)-2,2-dimethyl-3(2H)-furanone;

5-{3-Bromo-4-(methylsulfonyl)phenyl}-4-(2,5-difluorophenyl)-2,2-dimethyl-3(2H)-furanone 5-{3-Bromo-4-(methylsulfinyl)phenyl}-4-(2,5-difluorophenyl)-2,2-dimethyl-3(2H)-furanone;

5-{4-(Aminosulfonyl)-3-bromophenyl}-4-(2,5-difluorophenyl)-2,2-dimethyl-3(2H)-furanone;

5-{3-Bromo-4-(methylthio)phenyl}-4-(3,5-difluorophenyl)-2,2-dimethyl-3(2H)-furanone;

5-{3-Bromo-4-(methylsulfonyl)phenyl}-4-(3,5-difluorophenyl)-2,2-dimethyl-3(2H)-furanone;

5-{3-Bromo-4-(methylsulfinyl)phenyl}-4-(3,5-difluorophenyl)-2,2-dimethyl-3(2H)-furanone;

5-{4-(Aminosulfonyl)-3-bromophenyl}-4-(3,5-difluorophenyl)-2,2-dimethyl-3(2H)-furanone;

5-{3-Bromo-4-(methylthio)phenyl}-2,2-dimethyl-4-(3-trifluoromethylphenyl)-3(2H)-furanone;

5-{3-Bromo-4-(methylsulfonyl)phenyl}-2,2-dimethyl-4-(3-trifluoromethylphenyl)-3(2H)-furanone;

5-{3-Bromo-4-(methylsulfinyl)phenyl}-2,2-dimethyl-4-(3-trifluoromethylphenyl)-3(2H)-furanone;

5-{4-(Aminosulfonyl)-3-bromophenyl}-2,2-dimethyl-4-(3-trifluoromethylphenyl)-3(2H)-furanone;

5-{3-Chloro-4-(methylthio)phenyl}-2,2-dimethyl-4-phenyl-3(2H)-furanone;

5-{3-Chloro-4-(methylsulfonyl)phenyl}-2,2-dimethyl-4-phenyl-3(2H)-furanone;

5-{3-Chloro-4-(methylsulfinyl)phenyl}-2,2-dimethyl-4-phenyl-3(2H)-furanone;

5-{4-(Aminosulfonyl)-3-chlorophenyl}-2,2-dimethyl-4-phenyl-3(2H)-furanone;

5-{3-Chloro-4-(methylthio)phenyl}-4-(3-chlorophenyl)-2,2-dimethyl-3(2H)-furanone;

5-{3-Chloro-4-(methylsulfonyl)phenyl}-4-(3-chlorophenyl)-2,2-dimethyl-3(2H)-furanone;

5-{3-Chloro-4-(methylsulfinyl)phenyl}-4-(3-chlorophenyl)-2,2-dimethyl-3(2H)-furanone;

5-{4-(Aminosulfonyl)-3-chlorophenyl}-4-(3-chlorophenyl)-2,2-dimethyl-3(2H)-furanone;

5-{3-Chloro-4-(methylthio)phenyl}-4-(4-chlorophenyl)-2,2-dimethyl-3(2H)-furanone;
5-{3-Chloro-4-(methylsulfonyl)phenyl}-4-(4-chlorophenyl)-2,2-dimethyl-3(2H)-furanone;
5-{3-Chloro-4-(methylsulfinyl)phenyl}-4-(4-chlorophenyl)-2,2-dimethyl-3(2H)-furanone;
5-{4-(Aminosulfonyl)-3-chlorophenyl}-4-(4-chlorophenyl)-2,2-dimethyl-3(2H)-furanone;
5-{3-Chloro-4-(methylthio)phenyl}-4-(3-fluorophenyl)-2,2-dimethyl-3(2H)-furanone;
5-{3-Chloro-4-(methylsulfonyl)phenyl}-4-(3-fluorophenyl)-2,2-dimethyl-3(2H)-furanone;
5-{3-Chloro-4-(methylsulfinyl)phenyl}-4-(3-fluorophenyl)-2,2-dimethyl-3(2H)-furanone
5-{4-(Aminosulfonyl)-3-chlorophenyl}-4-(3-fluorophenyl)-2,2-dimethyl-3(2H)-furanone;
5-{3-Chloro-4-(methylthio)phenyl}-4-(4-fluorophenyl)-2,2-dimethyl-3(2H)-furanone;
5-{3-Chloro-4-(methylsulfonyl)phenyl}-4-(4-fluorophenyl)-2,2-dimethyl-3(2H)-furanone;
5-{3-Chloro-4-(methylsulfinyl)phenyl}-4-(4-fluorophenyl)-2,2-dimethyl-3(2H)-furanone;
5-{4-(Aminosulfonyl)-3-chlorophenyl}-4-(4-fluorophenyl)-2,2-dimethyl-3(2H)-furanone;
5-{3-Chloro-4-(methylthio)phenyl}-4-(2,4-difluorophenyl)-2,2-dimethyl-3(2H)-furanone;
5-{3-Chloro-4-(methylsulfonyl)phenyl}-4-(2,4-difluorophenyl)-2,2-dimethyl-3(2H)-furanone;
5-{3-Chloro-4-(methylsulfinyl)phenyl}-4-(2,4-difluorophenyl)-2,2-dimethyl-3(2H)-furanone;
5-{4-(Aminosulfonyl)-3-chlorophenyl}-4-(2,4-difluorophenyl)-2,2-dimethyl-3(2H)-furanone;
5-{3-Chloro-4-(methylthio)phenyl}-4-(2,5-difluorophenyl)-2,2-dimethyl-3(2H)-furanone;
5-{3-Chloro-4-(methylsulfonyl)phenyl}-4-(2,5-difluorophenyl)-2,2-dimethyl-3(2H)-furanone;
5-{3-Chloro-4-(methylsulfinyl)phenyl}-4-(2,5-difluorophenyl)-2,2-dimethyl-3(2H)-furanone;
5-{4-(Aminosulfonyl)-3-chlorophenyl}-4-(2,5-difluorophenyl)-2,2-dimethyl-3(2H)-furanone;
5-{3-Chloro-4-(methylthio)phenyl}-4-(3,4-difluorophenyl)-2,2-dimethyl-3(2H)-furanone;
5-{3-Chloro-4-(methylsulfonyl)phenyl}-4-(3,4-difluorophenyl)-2,2-dimethyl-3(2H)-furanone;
5-{3-Chloro-4-(methylsulfinyl)phenyl}-4-(3,4-difluorophenyl)-2,2-dimethyl-3(2H)-furanone;
5-{4-(Aminosulfonyl)-3-chlorophenyl}-4-(3,4-difluorophenyl)-2,2-dimethyl-3(2H)-furanone;
5-{3-Chloro-4-(methylthio)phenyl}-4-(3,5-difluorophenyl)-2,2-dimethyl-3(2H)-furanone;
5-{3-Chloro-4-(methylsulfonyl)phenyl}-4-(3,5-difluorophenyl)-2,2-dimethyl-3(2H)-furanone;
5-{3-Chloro-4-(methylsulfinyl)phenyl}-4-(3,5-difluorophenyl)-2,2-dimethyl-3(2H)-furanone;
5-{4-(Aminosulfonyl)-3-chlorophenyl}-4-(3,5-difluorophenyl)-2,2-dimethyl-3(2H)-furanone;
4-(3,5-Difluorophenyl)-2,2-dimethyl-5-{3-methyl-4-(methylthio)phenyl}-3(2H)-furanone;
4-(3,5-Difluorophenyl)-2,2-dimethyl-5-{3-methyl-4-(methylsulfinyl)phenyl}-3(2H)-furanone;
4-(3,5-Difluorophenyl)-2,2-dimethyl-5-{3-methyl-4-(methylsulfonyl)phenyl}-3(2H)-furanone;
5-{4-(Aminosulfonyl)-3-methylphenyl}-4-(3,5-difluorophenyl)-2,2-dimethyl-3(2H)-furanone;
5-{3-Chloro-4-(methylthio)phenyl}-2,2-dimethyl-4-(3-trifluoromethylphenyl)-3(2H)-furanone;
5-{3-Chloro-4-(methylsulfonyl)phenyl}-2,2-dimethyl-4-(3-trifluoromethylphenyl)-3(2H)-furanone;
5-{3-Chloro-4-(methylsulfinyl)phenyl}-2,2-dimethyl-4-(3-trifluoromethylphenyl)-3(2H)-furanone;
5-{4-(Aminosulfonyl)-3-chlorophenyl}-2,2-dimethyl-4-(3-trifluoromethylphenyl)-3(2H)-furanone;
5-{2-Chloro-4-(methylthio)phenyl}-2,2-dimethyl-4-phenyl-3(2H)-furanone;
5-{2-Chloro-4-(methylsulfinyl)phenyl}-2,2-dimethyl-4-phenyl-3(2H)-furanone;
5-{2-Chloro-4-(methylsulfonyl)phenyl}-2,2-dimethyl-4-phenyl-3(2H)-furanone;
5-{4-(Aminosulfonyl)-2-chlorophenyl}-2,2-dimethyl-4-phenyl-3(2H)-furanone;
5-{2-Chloro-4-(methylthio)phenyl}-4-(3-chlorophenyl)-2,2-dimethyl-3(2H)-furanone;
5-{2-Chloro-4-(methylsulfonyl)phenyl}-4-(3-chlorophenyl)-2,2-dimethyl-3(2H)-furanone;
5-{2-Chloro-4-(methylsulfinyl)phenyl}-4-(3-chlorophenyl)-2,2-dimethyl-3(2H)-furanone;
5-{4-(Aminosulfonyl)-2-chlorophenyl}-4-(3-chlorophenyl)-2,2-dimethyl-3(2H)-furanone;
5-{2-Chloro-4-(methylthio)phenyl}-2,2-dimethyl-4-(3-fluorophenyl)-3(2H)-furanone;
5-{2-Chloro-4-(methylsulfinyl)phenyl}-2,2-dimethyl-4-(3-fluorophenyl)-3(2H)-furanone;
5-{2-Chloro-4-(methylsulfonyl)phenyl}-2,2-dimethyl-4-(3-fluorophenyl)-3(2H)-furanone;
5-{4-(Aminosulfonyl)-2-chlorophenyl}-2,2-dimethyl-4-(3-fluorophenyl)-3(2H)-furanone;
5-{2-Chloro-4-(methylthio)phenyl}-2,2-dimethyl-4-(4-fluorophenyl)-3(2H)-furanone;
5-{2-Chloro-4-(methylsulfinyl)phenyl}-2,2-dimethyl-4-(4-fluorophenyl)-3(2H)-furanone;
5-{2-Chloro-4-(methylsulfonyl)phenyl}-2,2-dimethyl-4-(4-fluorophenyl)-3(2H)-furanone;
5-{4-(Aminosulfonyl)-2-chlorophenyl}-2,2-dimethyl-4-(4-fluorophenyl)-3(2H)-furanone;
5-{2-Chloro-4-(methylthio)phenyl}-4-(2,5-difluorophenyl)-2,2-dimethyl-3(2H)-furanone;
5-{2-Chloro-4-(methylsulfonyl)phenyl}-4-(2,5-difluorophenyl)-2,2-dimethyl-3(2H)-furanone;
5-{2-Chloro-4-(methylsulfinyl)phenyl}-4-(2,5-difluorophenyl)-2,2-dimethyl-3(2H)-furanone;
5-{4-(Aminosulfonyl)-2-chlorophenyl}-4-(2,5-difluorophenyl)-2,2-dimethyl-3(2H)-furanone;
5-{2-Chloro-4-(methylthio)phenyl}-4-(3,5-difluorophenyl)-2,2-dimethyl-3(2H)-furanone;
5-{2-Chloro-4-(methylsulfonyl)phenyl}-4-(3,5-difluorophenyl)-2,2-dimethyl-3(2H)-furanone;
5-{2-Chloro-4-(methylsulfinyl)phenyl}-4-(3,5-difluorophenyl)-2,2-dimethyl-3(2H)-furanone;
5-{4-(Aminosulfonyl)-2-chlorophenyl}-4-(3,5-difluorophenyl)-2,2-dimethyl-3(2H)-furanone;
2,2-Dimethyl-5-{3-methyl-4-(methylthio)phenyl}-4-phenyl-3(2H)-furanone
2,2-Dimethyl-5-{3-methyl-4-(methylsulfinyl)phenyl}-4-phenyl-3(2H)-furanone;
2,2-Dimethyl-5-{3-methyl-4-(methylsulfonyl)phenyl}-4-phenyl-3(2H)-furanone;
5-{4-(Aminosulfonyl)-3-methylphenyl}-2,2-dimethyl-4-phenyl-3(2H)-furanone;
2,2-Dimethyl-4-(3-fluorophenyl)-5-{3-methyl-4-(methylthio)phenyl}-3(2H)-furanone
2,2-Dimethyl-4-(3-fluorophenyl)-5-{3-methyl-4-(methylsulfinyl)phenyl}-3(2H)-furanone;
2,2-Dimethyl-4-(3-fluorophenyl)-5-{3-methyl-4-(methylsulfonyl)phenyl}-3(2H)-furanone;
5{-4-(Aminosulfonyl)-3-methylphenyl}-2,2-dimethyl-4-(3-fluorophenyl)-3(2H)-furanone;

4-(3,5-Difluorophenyl)-2,2-dimethyl-5-{3-methyl-4-(methylthio)phenyl}-3(2H)-furanone 4-(3,5-Difluorophenyl)-2,2-dimethyl-5-{3-methyl-4-(methylsulfinyl)phenyl}-3(2H)-furanone;

4-(3,5-Difluorophenyl)-2,2-dimethyl-5-{3-methyl-4-(methylsulfonyl)phenyl}-3(2H)-furanone;

5-{4-(Aminosulfonyl)-3-methylphenyl}-4-(3,5-difluorophenyl)-2,2-dimethyl-3(2H)-furanone;

5-{3-Chloro-4-(N-methylaminosulfonyl)phenyl}-2,2-dimethyl-4-phenyl-3(2H)-furanone 5-{3-Chloro-4-(N-ethylaminosulfonyl)phenyl}-2,2-dimethyl-4-phenyl-3(2H)-furanone 5-[4-{(Acetylamino)sulfonyl}-3-chlorophenyl]-2,2-dimethyl-4-phenyl-3(2H)-furanone;

5-[3-Chloro-4-{(N-n-propionylamino)sulfonyl}phenyl]-2,2-dimethyl-4-phenyl-3(2H)-furanone;

5-[3-Chloro-4-{(N-n-butyrylamino)sulfonyl}phenyl]-2,2-dimethyl-4-phenyl-3(2H)-furanone;

4-(3-Chlorophenyl)-2,2-dimethyl-5-{3-fluoro-4-(methylthio)phenyl}-(2H)-furan-3-thion 4-(3-Chlorophenyl)-2,2-dimethyl-5-{3-fluoro-4-(methylsulfonyl)phenyl}-(2H)-furan-3-thion 4-(3-Chlorophenyl)-2,2-dimethyl-5-{3-fluoro-4-(methylsulfinyl)phenyl}-(2H)-furan-3-thion 5-{4-(Aminosulfonyl)-3-fluorophenyl}-4-(3-chlorophenyl)-2,2-dimethyl-(2H)-furan-3-thion 4-(3,5-Difluorophenyl)-2,2-dimethyl-5-{3-fluoro-(4-methylthio)phenyl}-(2H)-furan-3-thione;

4-(3,5-Difluorophenyl)-2,2-dimethyl-5-{3-fluoro-(4-methylsulfonyl)phenyl}-(2H)-furan-3-thione;

4-(3,5-Difluorophenyl)-2,2-dimethyl-5-{3-fluoro-(4-methylsulfinyl)phenyl}-(2H)-furan-3-thione; and 5-{(4-Aminosulfonyl)-3-fluorophenyl}-4-(3,5-difluorophenyl)-2,2-dimethyl-(2H)-furan-3-thione;

or a pharmaceutically-acceptable salt thereof.

12. A compound according to claim 1, which is represented by Formula V:

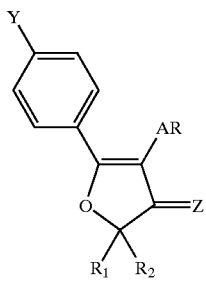

V wherein
Y represents alkylsulfonyl, aminosulfonyl, alkylsulfinyl, (N-acylamino)sulfonyl, (N-alkylamino)sulfonyl, or alkylthio;

Z represents oxygen or sulfur atom; wherein $R_1$ and $R_2$ are independently selected from methyl and ethyl radical;

and AR is a substituted or non-substituted aromatic group of 5 to 10 atoms excluding substituted or non-substituted phenyl group;

or a pharmaceutically-acceptable salt thereof.

13. A compound according to claim 12, in which
Y is selected from (lower alkyl)sulfonyl, aminosulfonyl, and (lower N-acylamino)sulfonyl;

Z is selected from oxygen and sulfur atom;

$R_1$ and $R_2$ are independently selected from methyl and ethyl radical;

and AR is selected from the following specific aromatic groups:

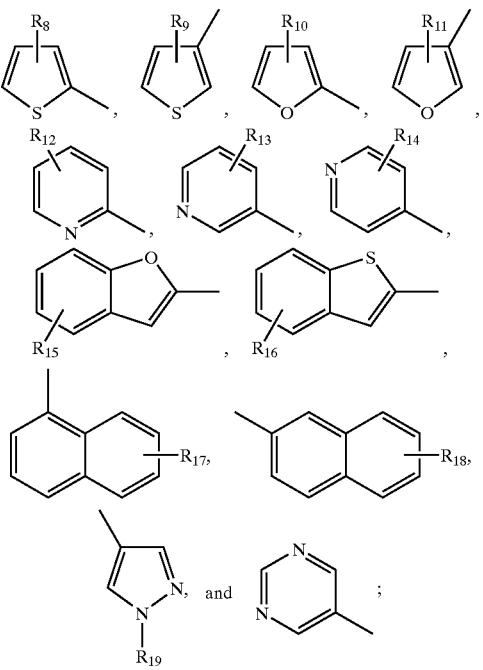

wherein, each of $R_8$ to $R_{19}$, if present, is selected from hydrido, halo, lower alkyl, lower acyl, lower haloalkyl, lower alkoxy, formyl, cyano, nitro, amino, azido, and N-acylamino;

or a pharmaceutically acceptable salt thereof.

14. A compound according to claim 13, in which
Y is selected from methylsulfonyl, ethylsulfonyl, aminosulfonyl, (N-acetylamino)sulfonyl, and (N-propionylamino)sulfonyl;

Z is selected from oxygen and sulfur atom;

$R_1$ and $R_2$ are independently selected from methyl and ethyl radical;

and each of $R_8$ to $R_{19}$, if present, is selected from hydrido, fluoro, chloro, bromo, methyl, ethyl, iso-propyl, acetyl, n-proionyl, trifluoromethyl, methoxy, ethoxy, and formyl;

or a pharmaceutically acceptable salt thereof.

15. A compound according to claim 14, which is selected from the following group of compounds:

2,2-Dimethyl-5-{4-(methylthio)phenyl}-4-(3-thienyl)-3(2H-furanone;

2,2-Dimethyl-4-{2-(3-methylthienyl)}-5-{4-(methylsulfonyl)phenyl}-3(2H-furanone;

2,2-Dimethyl-4-{2-(5-formylthienyl)}-5-{4-(methylsulfonyl)phenyl}-3(2H) furanone;

4-(2-Benzo[b]thienyl)-2,2-dimethyl-5-{4-(methylsulfonyl)phenyl}-3(2H)-furanone;

2,2-Dimethyl-5-{4-(methylsulfonyl)phenyl}-4-(1-naphthyl)-3(2H)-furanone;

2,2-Dimethyl-5-{4-(methylsulfonyl)phenyl}-4-(3-pyridyl)-3(2H)-furanone;

2,2-Dimethyl-5-{4-(methylsulfonyl)phenyl}-4-(2-pyridyl)-3(2H)-furanone;

4-(2-Benzo[b]furanyl)-2,2-dimethyl-5-{4-(methylsulfonyl)phenyl}-3(2H)-furanone;

2,2-Dimethyl-5-{4-(methylsulfonyl)phenyl}-4-(2-naphthyl)-3(2-furanone;

2,2-Dimethyl-4-{5-(2-fluorothienyl}-5-{4-(methylsulfonyl)phenyl}-3(2-furanone;
2,2-Dimethyl-4-{5-(3-fluorothienyl}-5{-(methylsulfonyl)phenyl}-3(2H)-furanone;
2,2-Dimethyl-4-{4-(2-fluorothienyl)}-5-{4-(methylsulfonyl)phenyl}-3(2-furanone;
2,2-Dimethyl-5-{4-(methylsulfonyl)phenyl}-4-(2-thienyl)-3(2-furanone;
2,2-Dimethyl-5-{4-(methylsulfonyl)phenyl}-4-(3-thienyl)-3(2-furanone;
4-{2-(5-Acetylthienyl)}-2,2-dimethyl-5-{4-(methylsulfonyl)phenyl}-3(2H)-furanone;
2,2-Dimethyl-4-(2-furanyl)-5-{4-(methylsulfonyl)phenyl}-3(2H)-furanone;
2,2-Dimethyl-4-(3-furanyl)-5-{4-(methylsulfonyl)phenyl}-3(2H)-furanone;
2,2-Dimethyl-4-{5-(3-fluorofuranyl)}-5-{4-(methylsulfonyl)phenyl}-3(2H)-furanone;
2,2-Dimethyl-4-{5-(2-fluorofuranyl)}-5-{4-(methylsulfonyl)phenyl}-3(2H)-furanone;
2,2-Dimethyl-4-{4-(2-fluorofuranyl)}-5-{4-(methylsulfonyl)phenyl}-3(2H)-furanone;
2,2-Dimethyl-4-{4-(1-N-methylpyrazolyl)}-5-{4-(methylsulfonyl)phenyl}-3(2H)-furanone;
2,2-Dimethyl-4-{4-(1-N-ethylpyrazolyl)}-5-{4-(methylsulfonyl)phenyl}-3(2H)-furanone;
2,2-Dimethyl-5-{4-(methylsulfonyl)phenyl}-4-(4-pyridyl)-3(2H)-furanone;
2,2-Dimethyl-4-{3-(6-methoxypyridyl)}-5-{4-(methylsulfonyl)phenyl}-3(2H)-furanone;
2,2-Dimethyl-4-{4-(1-N-iso-propylpyrazolyl)}-5-{4-(methylsulfonyl)phenyl}-3(2H)-furanone;
2,2-Dimethyl-5-{4-(methylsulfonyl)phenyl}-4-(5-pyrimidinyl)-3(2H)-furanone;
2,2-Dimethyl-4-{3-(6-methylpyridyl)}-5-{4-(methylsulfonyl)phenyl}-3(2H)-furanone;
2,2-Dimethyl-4-{2-(5-formyl-4-methylthienyl)}-5-{4-(methylsulfonyl)phenyl}-3(2H)-furanone;
2,2-Dimethyl-4-[2-{5-(1,3-dioxoian)-2-yl}thienyl]-5-{4-(methylsulfonyl)phenyl}-3(2H)-furanone;
4-{2-(5-Bromothienyl)}-2,2-dimethyl-5-{4-(methylsulfonyl)phenyl}-3(2H)-furanone;
2,2-Dimethyl-5-{4-(methylsulfonyl)phenyl}-4-(4-pyrazolyl)-3(2-furanone;
5-{4-(Aminosulfonyl)phenyl}-2-ethyl-2-methyl-4-(2-pyridyl)-3(2H)-furanone;
5-{4-(Aminosulfonyl)phenyl}-2-ethyl-2-methyl-4-(3-pyridyl)-3(2H)-furanone;
5-{4-(Aminosulfonyl)phenyl}-2-ethyl-2-methyl-4-(4-pyridyl)-3(2H)-furanone;
5-{4-(Aminosulfonyl)phenyl}-2-ethyl-2-methyl-4-{4-(1-N-methylpyrazolyl)}-3(2H)-furanone;
5-{4-(Aminosulfonyl)phenyl}-2-ethyl-4-{4-(1-N-ethylpyrazolyl)}-2-methyl-3(2H)-furanone;
5-{4-(Aminosulfonyl)phenyl}-2-ethyl-2-methyl-4-{4-(1-N-iso-propylpyrazolyl)}-3(2H)-furanone;
5-{4-(Aminosulfonyl)phenyl}-2-ethyl-2-methyl-4-(3-thienyl)-3(2H)-furanone;
5-{4-(Aminosulfonyl)phenyl}-2-ethyl-4-{2-(2-fluorothienyl)}-2-methyl-3(2H)-furanone;
5-{4-(Aminosulfonyl)phenyl}-2-ethyl-4-{5-(2-fluorothienyl)}-2-methyl-3(2H)-furanone;
5-{4-(Aminosulfonyl)phenyl}-2-ethyl-4-{5-(3-fluorothienyl)}-2-methyl-3(2H)-furanone;
5-{4-(Aminosulfonyl)phenyl}-2-ethyl-4-(2-furanyl)-2-methyl-3(2H)-furanone;
5-{4-(Aminosulfonyl)phenyl}-2-ethyl-4-(3-furanyl)-2-methyl-3(2H)-furanone;
5-{4-(Aminosulfonyl)phenyl}-2-ethyl-4-{5-(3-fluorofuranyl)}-2-methyl-3(2H)-furanone;
5-{4-(Aminosulfonyl)phenyl}-2-ethyl-4-{4-(2-fluorofuranyl)}-2-methyl-3(2H)-furanone;
5-{4-(Aminosulfonyl)phenyl}-2-ethyl-4-{5-(2-fluorofuranyl)}-2-methyl-3(2H)-furanone;
2,2-Diethyl-5-{4-(methylsulfonyl)phenyl}-4-(3-thienyl)-3(2H)-furanone;
2,2-Diethyl-5-{4-(methylsulfonyl)phenyl}-4-(2-thienyl)-3(2H)-furanone;
2,2-Diethyl-5-{4-(methylsulfonyl)phenyl}-4-(2-pyridyl)-3(2H)-furanone;
2,2-Diethyl-5-{4-(methylsulfonyl)phenyl}-4-(4-pyridyl)-3(2H)-furanone;
2,2-Diethyl-4-{4-(1-N-methylpyrazolyl)}-5-{4-(methylsulfonyl)phenyl}-3(2H)-furanone;
2-Ethyl-2-methyl-5-{4-(methylsulfonyl)phenyl}-4-(3-pyridyl)-3(2H)-furanone;
2-Ethyl-2-methyl-4-{4-(1-N-methylpyrazolyl)}-5-{4-(methylsulfonyl)phenyl}-3(2H)-furanone;
2-Ethyl-2-methyl-5-{4-(methylsulfonyl)phenyl}-4-(4-pyrazolyl)-3(2H)-furanone;
2-Ethyl-4-{4-(1-N-ethylpyrazoly)}-2-methyl-5-{4-(methylsulfonyl)phenyl}-3(2H)-furanone;
2-Ethyl-2-methyl-5-{4-(methylsulfonyl)phenyl}-4-{4-(1-N-iso-propylpyrazolyl)}-3(2H)-furanone;
2-Ethyl-2-methyl-4-{3-(6-methoxypyridyl)}-5-{4-(methylsulfonyl)phenyl}-3(2H)-furanone;
2-Ethyl-2-methyl-4-{3-(6-methylpyridyl)}-5-{4-(methylsulfonyl)phenyl}-3(2H)-furanone;
2-Ethyl-2-methyl-5-{4-(methylsulfonyl)phenyl}-4-(3-thienyl)-3(2H)-furanone;
2-Ethyl-2-methyl-5-{4-(methylsulfonyl)phenyl}-4-{4-(2-fluorothienyl)}-3(2H)-furanone;
2-Ethyl-4-(2-furanyl)-2-methyl-5-{4-(methylsulfonyl)phenyl}-3(2H)-furanone;
2-Ethyl-4-(3-furanyl)-2-methyl-5-{4-(methylsulfonyl)phenyl}-3(2H)-furanone;
2-Ethyl-4-{5-(3-fluorofuranyl}-2-methyl-5-{4-(methylsulfonyl)phenyl}-3(2H)-furanone;
2-Ethyl-4-{5-(2-fluorofuranyl}-2-methyl-5-{4-(methylsulfonyl)phenyl}-3(2H)-furanone;
2-Ethyl-4-{4-(2-fluorofuranyl)}-2-methyl-5-{4-(methylsulfonyl)phenyl}-3(2H)-furanone;
4-(2-Benzo[b]thienyl)-2-ethyl-2-methyl-5-{4-(methylsulfonyl)phenyl}-3(2H)-furanone;
4-(2-Benzo[b]furanyl)-2-ethyl-2-methyl-5-{4-(methylsulfonyl)phenyl}-3(2H)-furanone;
2-Ethyl-2-methyl-5-{4-(methylsulfonyl)phenyl}-4-(2-thienyl)-3(2H)-furanone;
2-Ethyl-4-{5-(2-fluorothienyl)}-2-methyl-5-{4-(methylsulfonyl)phenyl}-3(2H)-furanone;
4-{2-(5-Acetylthienyl)}-2-ethyl-2-methyl-5-{4-(methylsulfonyl)phenyl}-3(2H)-furanone;
2-Ethyl-2-methyl-5-{4-(methylsulfonyl)phenyl}-4-{2-(5-methylthienyl)}-3(2H)-furanone;
2-Ethyl-2-methyl-5-{4-(methylsulfonyl)phenyl}-4-{2-(3-methylthienyl)}-3(2H)-furanone;
5-{4-(Aminosulfonyl)phenyl}-2,2-dimethyl-4-(2-furanyl)-3(2H)-furanone;
5-{4-(Aminosulfonyl)phenyl}-2,2-dimethyl-4-(3-furanyl)-3(2H)-furanone;
5-{4-(Aminosulfonyl)phenyl}-2,2-dimethyl-4-{5-(3-fluorofuranyl)}-3(2H)-furanone;
5-{4-(Aminosulfonyl)phenyl}-2,2-dimethyl-4-{5-(2-fluorofuranyl)}-3(2H)-furanone;
5-{4-(Aminosulfonyl)phenyl}-2,2-dimethyl-4-{4-(2-fluorofuranyl)}-3(2H)-furanone;

5-{4-(Aminosulfonyl)phenyl}-2,2-dimethyl-4-(3-thienyl)-3(2H)-furanone;
5-{4-(Aminosulfonyl)phenyl}-2,2-dimethyl-4-(2-thienyl)-3(2H)-furanone;
5-{4-(Aminosulfonyl)phenyl}-2,2-dimethyl-4-{4-(2-fluorothienyl)}-3(2H)-furanone;
5-{4-(Aminosulfonyl)phenyl}-2,2-dimethyl-4-{5-(2-fluorothienyl)}-3(2H-furanone;
5-{4-(Aminosulfonyl)phenyl}-2,2-dimethyl-4-{5-(3-fluorothienyl}-3(2H)-furanone;
5-{4-(Aminosulfonyl)phenyl}-4-(2-benzo[b]thienyl)-2,2-dimethyl-3(2H)-furanone;
5-{4-(Aminosulfonyl)phenyl}-4-(2-benzo[b]furanyl)-2,2-dimethyl-3(2H)-furanone;
5-{4-(Aminosulfonyl)phenyl}-2,2 dimethyl-4-(2-naphthyl)-3(2H)-furanone;
5-{4-(Aminosulfonyl)phenyl}-2,2-dimethyl-4-(1-naphthyl)-3(2H)-furanone;
5-{4-(Aminosulfonyl)phenyl}-2,2-dimethyl-4-(2-pyridyl)-3(2H)-furanone;
5-{4-(Aminosulfonyl)phenyl}-2,2-dimethyl-4-(3-pyridyl)-3(2H)-furanone;
5-{4-(Aminosulfonyl)phenyl}-2,2-dimethyl-4-(4-pyridyl)-3(2H)-furanone;
5-{4-(Aminosulfonyl)phenyl}-2,2-dimethyl-4-{4-(1-N-methylpyrazolyl)}-3(2H)-furanone;
5-{4-(Aminosulfonyl)phenyl}-2,2-dimethyl-4-{4-(1-N-ethylpyrazolyl)}-3(2H)-furanone;
5-{4-(Aminosulfonyl)phenyl}-2,2-dimethyl-4-{4-(1-N-isopropylpyrazolyl)}-3(2H)-furanone; and
5-{4-(Aminosulfonyl)phenyl}-2,2-dimethyl-4-(4-pyrazolyl)-3(2H)-furanone;
or a pharmaceutically-acceptable salt thereof.

16. A pharmaceutical composition containing a therapeutically-effective amount of a compound of any one of claims 1–7 and 8–15 for treating an inflammatory disease.

17. A pharmaceutical composition containing a therapeutically-effective amount of a compound of any one of claims 1–7 and 8–15 for treating an inflammation-associated disease.

18. A pharmaceutical composition containing a therapeutically-effective amount of a compound of any one of claims 1–7 and 8–15 for treating a cycloozygenase-2 mediated disease.

19. A pharmaceutical composition containing a therapeutically-effective amount of a compound of any one of claims 1–7 and 8–15 for treating a disease susceptible to nonsteroidal anti-inflammatory drugs.

20. A process for the synthesis of 4,5-diaryl-2,2-dimethyl-3-(2H)-furanone compounds of Formula I, comprising reacting α-bromoisobutyryl cyanide with 1,2 diarylethanone in the presence of a base in accordance with the following reaction scheme

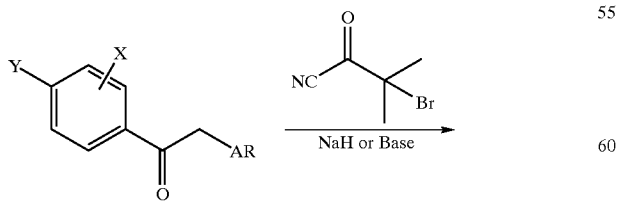

-continued

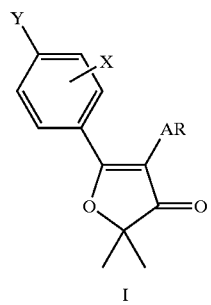

I wherein
Y is selected from alkylthio and alkysulfonyl;
X is selected from hydrido, halo and alkyl;
and AR represents a substituted or non-substituted aromatic group of 5 to 10 atoms.

21. A process for treating a cyclooxygenase-2 mediated disease which comprises administering to a person in need thereof a therapeutically effective amount of a sulfoxide compound of the Formula VI

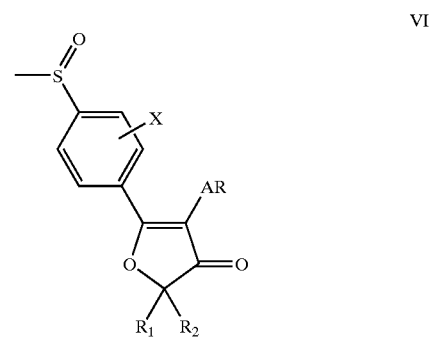

VI wherein
X represents halo, hydrido, or alkyl;
$R_1$ and $R_2$ are selected independently from lower alkyl radicals; and AR represents a substituted or non-substituted aromatic group of 5 to 10 atoms.
the sulfoxide compound being transformed after absorption into the body into the corresponding sulfone compound of the formula VII.

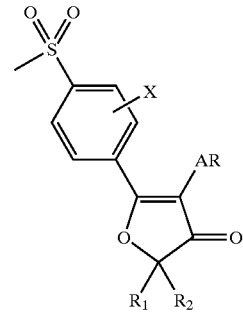

VII

* * * * *

UNITED STATES PATENT AND TRADEMARK OFFICE
CERTIFICATE OF CORRECTION

PATENT NO. : 6,492,416 B1　　　　　　　　　　　　　　　　　　　　　　Page 1 of 1
APPLICATION NO. : 09/744762
DATED : December 10, 2002
INVENTOR(S) : Song-Seok Shin et al.

It is certified that error appears in the above-identified patent and that said Letters Patent is hereby corrected as shown below:

Claim 7, Col. 164, line 4, "4-{4-(Aminosufonyl)phenyl}" should read --5-{4-(Aminosulfonyl)phenyl}--.

Claim 15, Col. 175, line 3, "-5{-(methylsulfonyl)" should read -- -5{4-(methylsulfonyl)--.

Claim 15, Col. 175, lines 2, 6, 8, 9, 43, "3(2-furanone;" should read --3(2H)-furanone;--.

Claim 18, Col. 177, line 43, "cycloozyenase-2" should read --cyclooxygenase-2--.

Claim 20, Col. 178, line 43, "atoms." should read --atoms;--.

Signed and Sealed this

Seventeenth Day of July, 2007

JON W. DUDAS
*Director of the United States Patent and Trademark Office*